US011230728B2

(12) United States Patent
Belisle et al.

(10) Patent No.: US 11,230,728 B2
(45) Date of Patent: Jan. 25, 2022

(54) DIFFERENTIATION OF LYME DISEASE AND SOUTHERN TICK-ASSOCIATED RASH ILLNESS

(71) Applicants: Colorado State University Research Foundation, Fort Collins, CO (US); The United States of America, as represented by the secretary, Department of Health and Human Services, Bethesda, MD (US); Gary P. Wormser, New York, NY (US)

(72) Inventors: John T. Belisle, Fort Collins, CO (US); Claudia R. Molins, Bethesda, MD (US); Gary P. Wormser, New York, NY (US)

(73) Assignees: Colorado State University Research Foundation, Fort Collins, CO (US); The United States of America, as represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 16/703,401

(22) Filed: Dec. 4, 2019

(65) Prior Publication Data

US 2020/0140915 A1 May 7, 2020

Related U.S. Application Data

(63) Continuation of application No. PCT/US2018/036688, filed on Jun. 8, 2018.

(60) Provisional application No. 62/516,824, filed on Jun. 18, 2017.

(51) Int. Cl.
*C12Q 1/04* (2006.01)
*G01N 33/68* (2006.01)

(52) U.S. Cl.
CPC .......... *C12Q 1/04* (2013.01); *G01N 33/6848* (2013.01); *G01N 2333/20* (2013.01); *G01N 2800/20* (2013.01); *G01N 2800/26* (2013.01)

(58) Field of Classification Search
None
See application file for complete search history.

(56) References Cited

U.S. PATENT DOCUMENTS

| 4,421,653 | A | 12/1983 | LeDain et al. |
| 6,203,798 | B1 | 3/2001 | Bergstrom et al. |
| 8,580,490 | B1 | 11/2013 | Belisle et al. |
| 9,316,652 | B2 | 4/2016 | Joosten et al. |
| 10,669,567 | B2 | 6/2020 | Belisle et al. |
| 2016/0237470 | A1* | 8/2016 | Belisle ............ C12Q 1/04 |
| 2017/0030911 | A1 | 2/2017 | Russell et al. |

FOREIGN PATENT DOCUMENTS

| WO | WO 2008/089072 A2 | 7/2008 |
| WO | WO 2013/110026 A1 | 7/2013 |

OTHER PUBLICATIONS

Molins et al. 2015 (Development of a Metabolic Biosignature for Detection of Early Lyme Disease; CID 2015:60: 17671775) (Year: 2015).*
Angel et al. Cerebrospinal fluid proteome of patients with acute lyme disease. Journal of Proteome Research, 2012, vol. 11, No. 10, pp. 4814-4822.
Ashton et al. Application of Metabolomics as an Innovative Approach for the Diagnosis of Lyme Disease. *Abstracts of the General Meeting of the American Society for Microbiology*, 2014.
European Search Report, EP16752970.0, dated Jun. 8, 2018.
Friedman J, Hastie T, Ribshirani R. Regularization Paths for Generalized Linear Models via Coordinate Descent. Journal of Statistical Software. Jan. 2010; vol. 33, Issue 1: pp. 1-22.
International Search Report and Written Opinion, PCT/US2016/018248, dated Jul. 1, 2016.
International Search Report and Written Opinion, PCT/US2018/036688, dated Oct. 24, 2018.
Jacobs et al. Proteomic analysis of lyme disease: global protein comparison of three strains of borrelia burgdorferi. Proteomics, 2005, vol. 5, No. 5, pp. 1446-1453.
Molins et al. Development of a metabolic biosignature for detection of early lyme disease. Clinical Infectious Diseases, 2015 (first published online Mar. 11, 2015), DOI: 10.1093/cid/civ815.
Molins et al. Metabolic differentiation of early lyme disease from southern tick-associated rash illness (STARI). Sci Transl Med, Aug. 16, 2017, vol. 9, pp. 1-12.
Weiner et al. Biomarkers of inflammation, immunosuppression and stress with active disease are revealed by metabolomic profiling of tuberculosis patients. PLoS One, Jul. 23, 2012, vol. 7, e40221, pp. 1-14.

* cited by examiner

*Primary Examiner* — Mary Maille Lyons
(74) *Attorney, Agent, or Firm* — Polsinelli PC

(57) ABSTRACT

The present disclosure provides a biosignature that distinguishes Lyme disease, including early Lyme disease, from STARI. The present disclosure also provides methods for detecting Lyme disease and STARI, as well as methods for treating subjects diagnosed with Lyme disease or STARI.

2 Claims, 33 Drawing Sheets

Specification includes a Sequence Listing.

Linear Discriminant

SEQUENCE LISTING

```
<160> NUMBER OF SEQ ID NOS: 15

<210> SEQ ID NO 1
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 1

Asp Phe Arg Tyr
1

<210> SEQ ID NO 2
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 2

Gln Leu Pro Lys
1

<210> SEQ ID NO 3
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 3

Arg Asp Cys Ala
1

<210> SEQ ID NO 4
<211> LENGTH: 5
<212> TYPE: PRT
<213> ORGANISM: Artificial Sequence
<220> FEATURE:
<223> OTHER INFORMATION: Synthetic Sequence
```

<400> SEQUENCE: 4

Gln Val Leu Leu Gly
1               5

<210> SEQ ID NO 5
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 5

Lys Lys Thr Thr
1

<210> SEQ ID NO 6
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 6

Ala Lys Met Asn
1

<210> SEQ ID NO 7
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 7

Asp His Phe Asp
1

<210> SEQ ID NO 8
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 8

Leu Lys Glu Pro Pro
1               5

<210> SEQ ID NO 9
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 9

Ala Ile Lys Thr
1

<210> SEQ ID NO 10
<211> LENGTH: 4
<212> TYPE: PRT
<213> ORGANISM: Artificial Sequence
<220> FEATURE:
<223> OTHER INFORMATION: Synthetic Sequence

```
<400> SEQUENCE: 10

Pro Asp Pro Leu
1

<210> SEQ ID NO 11
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 11

Pro Gln Ala Lys
1

<210> SEQ ID NO 12
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 12

His Cys Asp Thr
1

<210> SEQ ID NO 13
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 13

Gln Glu Gln Ile
1

<210> SEQ ID NO 14
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 14

Ala Leu Ala Pro Lys
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 15

Leu Ala Pro Lys Ile
1               5
```

DIFFERENTIATION OF LYME DISEASE AND SOUTHERN TICK-ASSOCIATED RASH ILLNESS

CROSS REFERENCE TO RELATED APPLICATIONS

This application is a continuation of International Application No. PCT/US2018/036688, with an international filing date of Jun. 8, 2018, which PCT application claims the benefit of U.S. provisional application No. 62/516,824, filed Jun. 8, 2017. The contents of the above-mentioned applications are hereby incorporated by reference in their entirety.

GOVERNMENTAL RIGHTS

This invention was made with government support under A1100228 and A1099094, each awarded by National Institutes of Health. The government has certain rights in the invention.

REFERENCE TO SEQUENCE LISTING

The instant application contains a Sequence Listing which has been submitted electronically in ASCII format and is hereby incorporated by reference in its entirety. Said ASCII copy, created on Apr. 27, 2021, is named "CSURF_065620-642266_ST25.txt", and is 2.58 KB in size.

FIELD OF THE INVENTION

The present disclosure relates to human disease detection tools and methods, and in particular pertains to tools and methods for detecting Lyme disease and southern tick-associated rash illness (STARI), and for distinguishing Lyme disease from STARI.

BACKGROUND OF THE INVENTION

Lyme disease is a multisystem bacterial infection that in the United States is primarily caused by infection with *Borrelia burgdorferi* sensu stricto. Over 300,000 cases of Lyme disease are estimated to occur annually in the United States, with over 3.4 million laboratory diagnostic tests performed each year. Symptoms associated with this infection include fever, chills, headache, fatigue, muscle and joint aches, and swollen lymph nodes; however, the most prominent clinical manifestation in the early stage is the presence of one or more erythema migrans (EM) skin lesions. This annular, expanding erythematous skin lesion occurs at the site of the tick bite in 70 to 80% of infected individuals and is typically 5 cm or more in diameter. Although an EM lesion is a hallmark for Lyme disease, other types of skin lesions can be confused with EM, including the rash of southern tick-associated rash illness (STARI).

A strict geographic segregation of Lyme disease and STARI does not exist, as there are regions where STARI and Lyme disease are co-prevalent. Clinically, the skin lesions of STARI and early Lyme disease are indistinguishable, and no laboratory tool or method exists for the diagnosis of STARI or differentiation of STARI from Lyme disease. The only biomarkers evaluated for differential diagnosis of early Lyme disease and STARI have been serum antibodies to *B. burgdorferi*. However, these tests have poor sensitivity for early stages of Lyme disease, and thus a lack of *B. burgdorferi* antibodies cannot be used as a reliable differential marker for STARI. Thus, there is a need for diagnostic methods to differentiate between Lyme disease and STARI, and that facilitate proper treatment, patient management and disease surveillance.

SUMMARY OF THE INVENTION

In one aspect, the present disclosure encompasses a method for analyzing a blood sample from a subject, the method comprising: (a) deproteinizing the blood sample to produce a metabolite extract; (b) performing liquid chromatography coupled to mass spectrometry on a sample of the metabolite extract; and (c) providing abundance values for each molecular feature in Table A, Table B, Table C, or Table D.

In another aspect, the present disclosure encompasses a method for classifying a subject as having Lyme disease or STARI, the method comprising: (a) deproteinizing a blood sample from a subject to produce a metabolite extract, wherein the subject has at least one symptom that is associated with Lyme disease or STARI; (b) performing liquid chromatography coupled to mass spectrometry on a sample of the metabolite extract; (c) providing abundance values for each molecular feature in Table A, Table B, Table C, or Table D; and (d) inputting the abundance values from step (c) into a classification model trained with samples of metabolite extracts derived from suitable controls, wherein the classification model produces a disease score and the disease score distinguishes subjects with Lyme disease or STARI.

In another aspect, the present disclosure encompasses a method for treating a subject with Lyme disease, the method comprising: (a) obtaining a disease score from a test; (b) diagnosing the subject with Lyme disease based on the disease score; and (c) administering a treatment to the subject with Lyme disease, wherein the test comprises measuring the amount of each molecular feature in Table A, Table B, Table C, or Table D; providing abundance values for each molecular feature measured; and inputting the abundance values into a classification model trained with samples derived from suitable controls, wherein the classification model produces a disease score and the disease score distinguishes subjects with Lyme disease from subjects with STARI, and optionally from healthy subjects. In certain examples, the test comprises (i) deproteinizing a blood sample from a subject to produce a metabolite extract; (ii) performing liquid chromatography coupled to mass spectrometry on a sample of the metabolite extract; (iii) providing abundance values for each molecular feature in Table A, Table B, Table C, or Table D; and (iv) inputting the abundance values from step (iii) into a classification model trained with samples of metabolite extracts derived from suitable controls, wherein the classification model produces a disease score and the disease score distinguishes subjects with Lyme disease. In further examples, the subject has at least one symptom of Lyme disease. In still further examples, the Lyme disease is early Lyme disease and optionally the symptom is an EM rash.

In another aspect, the present disclosure encompasses a method for treating a subject with STARI, the method comprising: (a) obtaining a disease score from a test; (b) diagnosing the subject with STARI based on the disease score; and (c) administering a treatment to the subject with STARI, wherein the test comprises measuring the amount of each molecular feature in Table A, Table B, Table C, or Table D; providing abundance values for each molecular feature measured; and inputting the abundance values into a classification model trained with samples derived from suitable controls, wherein the classification model produces a disease score and the disease score distinguishes subjects with STARI. In certain examples, the test comprises (i) deproteinizing a blood sample from a subject to produce a metabolite extract; (ii) performing liquid chromatography coupled to mass spectrometry on a sample of the metabolite extract; (iii) providing abundance values for each molecular feature in Table A, Table B, Table C, or Table D; and (iv) inputting the abundance values from step (iii) into a classification model trained with samples of metabolite extracts derived from suitable controls, wherein the classification model produces a disease score and the disease score distinguishes subjects with STARI from subjects with Lyme disease, including early Lyme disease, and optionally from healthy subjects. In further examples, the subject has at least one symptom of STARI. In still further examples, the symptom is an EM or an EM-like rash.

Other aspects and iterations of the invention are described below.

BRIEF DESCRIPTION OF THE FIGURES

FIG. 4A: Fourteen of the metabolites with level 1 or level 2 structural identifications were evaluated for abundance differences between early Lyme disease (green squares) and STARI (blue triangles) normalized to the metabolite abundance in healthy controls. Included are metabolites identified for NAE and PFAM metabolism. GP-NAE: glycerophospho-N-palmitoyl ethanolamine; Lyso PA (20:4): arachidonoyl lysophosphatidic acid; CMPF: 3-carboxy-4-methyl-5-propyl-2-furanpropanoic acid. The relative mean abundance and 95% confidence intervals are shown for each metabolite. FIG. 4B: Abundance fold change ranges (x-axis) plotted against the percent of MFs from the 261 MF early Lyme disease-STARI biosignature that have increased (light blue) or decreased (dark blue) abundances in STARI relative to healthy controls, and increased (light green) or decreased (dark green) abundances in early Lyme disease relative to healthy controls. FIG. 4C: The percent overlap of MFs between STARI and early Lyme disease that increase (dark purple) or decrease (light purple) relative to healthy controls within each abundance fold change range. An overlap of 30%, 16%, 5%, 0%, 0%, and 4% was found for MFs with increased abundance relative to healthy controls, and 12%, 13%, 0%, 7%, 0%, and 8% for MFs with decreased abundance relative to healthy controls for the MFs falling within the 1.0-1.4, 1.5-1.9, 2.0-2.4, 2.5-2.9, 3.0-3.4, and abundance fold ranges, respectively.

FIG. 5A: LASSO scores (Xβ; i.e. the linear portion of the regression model) were calculated for Test-Set data of early Lyme disease and STARI serum samples by multiplying the transformed abundances of the 38 MFs identified in the two-way LASSO model by the LASSO coefficients of the model and summing for each sample. Scores are plotted along the y-axis; serum samples are plotted randomly along the x-axis for easier viewing. FIG. 5B: An ROC curve demonstrates the level of discrimination that is achieved between early Lyme disease and STARI using the 38 MFs of the two-way LASSO classification model by depicting a true positive rate (sensitivity; early Lyme disease) versus a false positive rate (specificity; STARI) for the Test-Set samples (Table 7). The AUC was calculated to be 0.986. The diagonal line represents an AUC value of 0.5. The performance of two-tiered testing (red dot) on the same sample set (Test-Set 1) was included as a reference for the sensitivity and specificity of the current clinical laboratory test for Lyme disease. FIG. 5C: LASSO scores (Xβi) were calculated for the Test-Set data of early Lyme disease (green spheres), STARI (blue spheres), and healthy control (black spheres) serum samples by multiplying the transformed abundances of the 82 MFs identified in the three-way LASSO model by each of three LASSO coefficients used in the model. Each axis represents the sample score in the direction of one of the three sample groups. Scores are used in calculation of probabilities of class membership, with highest probability determining the predicted class. Although there is overlap, the three groups predominantly occupy distinct areas of the plot.

DETAILED DESCRIPTION

Figure 1:
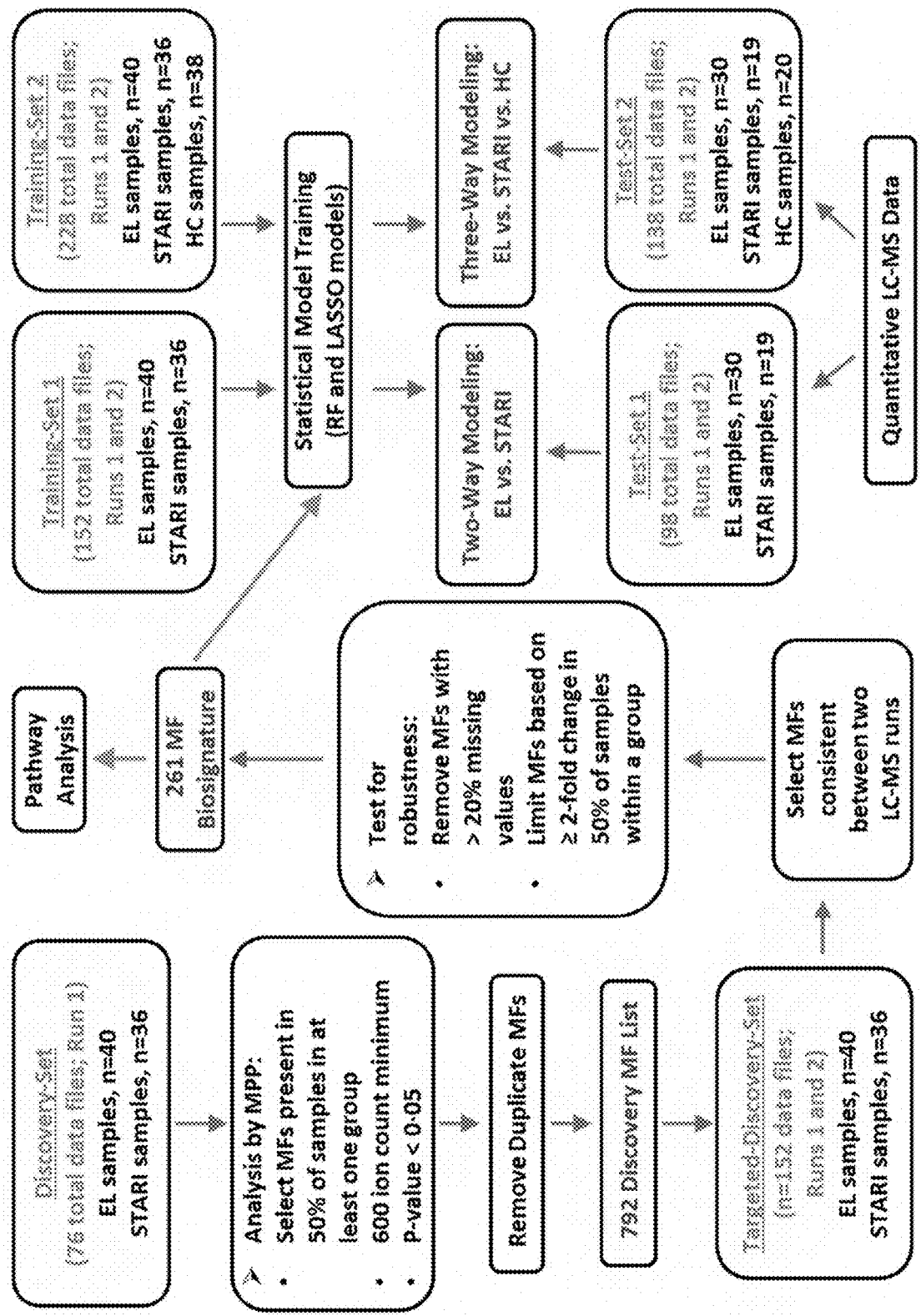
FIG. 1 is a block diagram depicting a metabolic profiling process for the identification and application of differentiating molecular features (MFs). LC-MS data from an initial Discovery-Set of early Lyme disease (EL) and STARI samples was used to identify a list of MFs that were targeted in a second LC-MS run. The data from both LC-MS runs was combined to form the Targeted-Discovery-Set. The MFs were then screened for consistency and robustness and this resulted in a final early Lyme disease-STARI biosignature of 261 MFs. This biosignature was used for downstream pathway analysis and for classification modeling. Two training-data sets along with the 261 MF biosignature list were used to train multiple classification models, random forest (RF) and least absolute shrinkage and selection operator (LASSO). Data from samples of two Test-Sets (not included for the Discovery/Training-Set data) were blindly tested against the two-way (EL vs STARI) and three-way [EL vs STARI vs healthy controls (HC)] classification models. The regression coefficients used for each MF in the LASSO two-way and three-way classification models are provided in Table 5 and Table 7, respectively.

Lyme disease is an illness caused by a *Borrelia* species (e.g., *Borrelia burgdorferi, Borrelia garinii, Borellia afzelii*, etc.) and is transmitted to humans through the bite of infected blacklegged ticks (*Ixodes* species). Lyme disease can go through several stages and may cause different symptoms, depending on how long a subject has been infected and where in the body the infection has spread. The stages of Lyme disease include Stage 1, Stage 2, and Stage 3. Stage 1 Lyme disease may also be referred to as "early localized Lyme disease" or "early Lyme disease" and usually develops about 1 day to about 4 weeks after infection. Non-limiting examples of symptoms of Stage 1 Lyme disease include erythema migrans and flu-like symptoms, such as lack of energy, headache, stiff neck, fever, chills, muscle pain, joint pain, and swollen lymph nodes. Stage 1 Lyme disease may result in one or more than one symptom. In some cases, Stage 1 Lyme disease does not result in any symptoms. Stage 2 Lyme disease may also be referred to as "early disseminated infection" and usually develops about 1 month to about 4 months after infection. Non-limiting examples of symptoms of Stage 2 Lyme disease include an erythema migrans (or additional erythema migrans rash sites), pain, weakness, numbness in the arms and/or legs, Bell's palsy (facial drooping), headaches, fainting, poor memory, reduced ability to concentrate, conjunctivitis, episodes of pain, redness and swelling in one or more large joints, rapid heartbeats (palpitations), and serious heart problems. Stage 3 Lyme disease may also be referred to as "late persistent Lyme disease" and usually develops months to years after infection. Non-limiting examples of symptoms of Stage 3 Lyme disease include arthritis, numbness and tingling in the hands, numbness and tingling in the feet, numbness and tingling in the back, tiredness, Bell's palsy (facial drooping), problems with memory, mood, sleep speaking, and heart problems (pericarditis). A subject diagnosed with Lyme disease, or suspected of having Lyme disease, may be identified on the basis of one or more symptoms, geographic location, and possibility of tick bite. Currently, several routine diagnostic tests are known for diagnosing Lyme disease. Typically these tests detect and/or quantify antibodies to one or more *Borellia* antigens, and are performed using common immunoassay methods such as enzyme-linked immunoassays (EIA or ELISA), immunofluorescence assays, or Western immunoblots. Generally, these tests are most reliable only a few weeks after an infection. Positive PCR and/or positive culture may also be used. (See, e.g., Moore et al., "Current Guidelines, Common Clinical Pitfalls, and Future Directions for Laboratory Diagnosis of Lyme Disease, United States," Emerg Infect Dis. 2016, Vol. 22, No. 7). In one example, diagnostic testing may comprise a commercially-available C6 EIA. The C6 Lyme EIA measures antibody reactivity to a synthetic peptide corresponding to the sixth invariable region of VIsE, a highly conserved surface protein of the causative *Borrelia burgdorferi* bacterium. Alternatively, or in addition, diagnostic testing may comprise using IgM and/or IgG immunoblots following a positive or equivocal first-tier assay. As used herein, a subject that is negative for antibodies to Lyme disease causing *Borrelia* species need only be negative by one method of testing.

Southern tick-associated rash illness (STARI) is an illness associated with a bite from the lone star tick, *Amblyomma americanum*. The causative agent of STARI is unknown. The rash of STARI is a red, expanding "bull's-eye" lesion that develops around the site of a lone star tick bite. The rash of STARI may be referred to as an EM rash or an EM-like rash. The rash usually appears within 7 days of tick bite and expands to a diameter of 8 centimeters (3 inches) or more. Non-limiting examples of additional symptoms associated with STARI include discomfort and/or itching at the bite site, muscle pain, joint pain, fatigue, fever, chills, and headache. A subject diagnosed with STARI, or suspected of having STARI, may be identified on the basis of one or more symptom, geographic location, and possibility of tick bite.

Complicating the clinical differentiation between Lyme disease, and in particular early Lyme disease, and STARI are shared symptoms (for example, an EM or EM-like rash), co-prevalence of STARI and Lyme disease in certain geographic regions, and poor sensitivity of common diagnostic methods for early stages Lyme disease. The present disclosure provides a biosignature that identifies Lyme disease and southern tick-associated rash illness (STARI), and distinguishes one from the other. Various aspects of the biosignature and its use are described in detail below.

I. Definitions

So that the present disclosure may be more readily understood, certain terms are first defined. Unless defined otherwise, all technical and scientific terms used herein have the same meaning as commonly understood by one of ordinary skill in the art to which examples of the disclosure pertain. Many methods and materials similar, modified, or equivalent to those described herein can be used in the practice of the examples of the present disclosure without undue experimentation, the preferred materials and methods are described herein. In describing and claiming the examples of the present disclosure, the following terminology will be used in accordance with the definitions set out below.

The term "about," as used herein, refers to variation of in the numerical quantity that can occur, for example, through typical measuring techniques and equipment, with respect to any quantifiable variable, including, but not limited to, mass, volume, time, distance, wave length, frequency, voltage, current, and electromagnetic field. Further, given solid and liquid handling procedures used in the real world, there is certain inadvertent error and variation that is likely through differences in the manufacture, source, or purity of the ingredients used to make the compositions or carry out the methods and the like. The term "about" also encompasses these variations, which can be up to ±5-10%, but can also be ±9%, 8%, 7%, 6%, 5%, 4%, 3%, 2%, 1%, etc. Whether or not modified by the term "about," the claims include equivalents to the quantities.

As used herein, the term "accuracy" refers to the ability of a test (e.g., a diagnostic test, a classification model, etc.) to correctly differentiate one type of subject (e.g., a subject with Lyme disease) from one or more different types of subjects (e.g., a subject with STARI, a healthy subject, etc.). Accuracy is equal to (true positive result)+(true negative result)/(true positive result)+(true negative result)+(false positive result)+(false negative result).

The term "biosignature" refers to a plurality of molecular features forming a distinctive pattern which is indicative of a disease or condition of an animal, preferably a human.

The term "molecular feature" refers to a small molecule metabolite in a blood sample that has a mass less than 3000 Da. The term "abundance value" refers to an amount of a molecular feature in a blood sample. The abundance value for a molecular feature may be identified via any suitable method known in the art. Molecular features are defined herein by a positive ion m/z charge ratio ±a suitable tolerance to account for instrument variability (e.g., ±15 ppm) and optionally one or more additional characteristic such as retention time or a chemical structure based on accurate mass; and abundance values for each molecular feature are obtained from a measurement of the area under the peak for the monoisotopic mass of each molecular feature determined by mass spectrometry. Given that the present disclosure identifies the molecular features (i.e., small molecule metabolites) forming each biosignature, alternative methods for measuring the amount of the metabolites may be used without departing from the scope of the invention.

As used herein, the term "ROC" means "receiver operating characteristic". A ROC analysis may be used to evaluate the diagnostic performance, or predictive ability, of a test or a method of analysis. A ROC graph is a plot of sensitivity and specificity of a test at various thresholds or cut-off values. Each point on a ROC curve represents the sensitivity and its respective specificity. A threshold value can be selected based on an ROC curve, wherein the threshold value is a point where sensitivity and specificity both have acceptable values. The threshold value can be used in applying the test for diagnostic purposes. It will be understood that if only specificity is optimized, then the test will be less likely to generate a false positive (diagnosis of the disease in more subjects who do not have the disease) at the cost of an increased likelihood that some cases of disease will not be identified (e.g., false negatives). If only sensitivity is optimized, the test will be more likely to identify most or all of the subjects with the disease, but will also diagnose the disease in more subjects who do not have the disease (e.g., false positives). A user is able to modify the parameters, and therefore select an ROC threshold value suitable for a given clinical situation, in ways that will be readily understood by those skilled in the art.

Another useful feature of the ROC curve is an area under the curve (AUC) value, which quantifies the overall ability of the test to discriminate between different sample properties, for example, to discriminate between subjects with Lyme disease and those STARI; to discriminate between subjects with STARI and healthy subjects; subjects or to discriminate between subjects with Lyme disease, STARI, and healthy subjects. A test that is no better at identifying true positives than random chance will generate a ROC curve with an AUC of 0.5. A test having perfect specificity and sensitivity (i.e., generating no false positives and no false negatives) will have an AUC of 1.00. In reality, most tests will have an AUC somewhere between these two values.

As used herein, the term "sensitivity" refers to the percentage of truly positive observations which is classified as such by a test, and indicates the proportion of subjects correctly identified as having a given condition. In other words, sensitivity is equal to (true positive result)/[(true positive result)+(false negative result)].

As used herein, the term "specificity" refers to the percentage of truly negative observations which is classified as such by a test, and indicates the proportion of subjects correctly identified as not having a given condition. Specificity is equal to (true negative result)/[(true negative result)+(false positive result).

As used herein, the term "subject" refers to a mammal, preferably a human. The mammals include, but are not limited to, humans, primates, livestock, rodents, and pets. A subject may be waiting for medical care or treatment, may be under medical care or treatment, or may have received medical care or treatment.

As used interchangeably herein, the terms "control group," "normal group," "control subject," or "healthy subject" refer to a subject, or a group of subjects, not previously diagnosed with the disease in question and/or treated for the disease in question for a therapeutically effective amount of time (e.g., 12 months or more).

As used herein, the term "blood sample" refers to a biological sample derived from blood, preferably peripheral (or circulating) blood. The blood sample can be whole blood, plasma or serum.

The terms "treat," "treating," or "treatment" as used herein, refer to the provision of medical care by a trained and licensed health professional to a subject in need thereof. The medical care may be a diagnostic test, a therapeutic treatment, and/or a prophylactic or preventative measure. The object of therapeutic and prophylactic treatment is to prevent or slow down (lessen) an undesired physiological change or disease/disorder. Beneficial or desired clinical results of therapeutic or prophylactic treatments include, but are not limited to, alleviation of symptoms, diminishment of extent of disease, stabilized (i.e., not worsening) state of disease, a delay or slowing of disease progression, amelioration or palliation of the disease state, and remission (whether partial or total), whether detectable or undetectable. "Treatment" can also mean prolonging survival as compared to expected survival if not receiving treatment. Alternatively, the medical care may be a recommendation for no intervention. For example, no medical intervention may be needed for diseases that are self-limiting. Those in need of treatment include those already with the disease, condition, or disorder as well as those prone to have the disease, condition or disorder or those in which the disease, condition or disorder is to be prevented.

II. Biosignatures

In an aspect, the present disclosure provides a biosignature that provides an accuracy of detecting Lyme disease equal to or greater than about 80%. In another aspect, the present disclosure provides a biosignature that provides an accuracy of detecting STARI disease equal to or greater than about 80%.

A method for identifying a Lyme disease biosignature and/or a STARI biosignature is detailed in the examples. Generally speaking, the method comprises: a) obtaining test blood samples and control blood samples; b) analyzing the test blood samples and control blood samples by mass spectrometry to obtain abundance values for a plurality of molecular features in the test blood samples and the control blood samples; and c) applying a statistical modeling technique to select for a plurality of molecular features that distinguish test blood samples from control blood samples with an accuracy equal to or greater than about 80%. Test blood samples are from subjects with Lyme disease and/or STARI, either of which is confirmed using known diagnostic methods as described above; and control bloods samples are from subjects confirmed to be free of Lyme, STARI, or both using known diagnostic methods for each. The molecular features that distinguish test blood samples from control blood samples comprise the biosignature for that disease.

A blood sample may be a whole blood sample, a plasma sample, or a serum sample. Any of a variety of methods generally known in the art for collecting a blood sample may be utilized. Generally speaking, the sample collection method preferably maintains the integrity of the sample such that abundance values for each molecular feature can be accurately measured. A blood sample may be used "as is", or a blood sample may be processed to remove undesirable constituents. In preferred examples, a blood sample is processed using standard techniques to remove high-molecular weight species, and thereby obtain an extract comprising small molecule metabolites. This is referred to herein as "deproteinization" or a "deproteinization step." For example, a solvent or solvent mixture (e.g., methanol or the like) may be added to a blood sample to precipitate these high-molecular weight species followed by a centrifugation step to separate the precipitate and the metabolite-containing supernatant. In another example, proteases may be the added to a blood sample. In another example, size exclusion chromatography may be used.

Analysis using mass spectrometry, preferably high resolution mass spectrometry, yields abundance measures for a plurality of molecular features. The abundance value for each molecular feature may be obtained from a measurement of the area under the peak for the monoisotopic mass of each molecular feature. Identification and extraction of molecular features involves finding and quantifying all the known and unknown compounds/metabolites down to the lowest abundance, and extracting all relevant spectral and chromatographic information. Algorithms are available to identify and extract molecular features. Such algorithms include for example the Molecular Feature Extractor (MFE) by Agilent. MFE locates ions that are covariant (rise and fall together in abundance) but the analysis is not exclusively based on chromatographic peak information. The algorithm uses the accuracy of the mass measurements to group related ions—related by charge-state envelope, isotopic distribution, and/or the presence of adducts and dimers. It assigns multiple species (ions) that are related to the same neutral molecule (for example, ions representing multiple charge states or adducts of the same neutral molecule) to a single compound that is referred to as a feature. Using this approach, the MFE algorithm can locate multiple compounds within a single chromatographic peak. Specific parameters for MFE may include a minimum ion count of 600, an absolute height of 2,000 ion counts, ion species H+ and Na+, charge state maximum 1, and compound ion count threshold of 2 or more ions. Once the molecular feature has been identified and extracted, the area under the peak for the monoisotopic mass is used to determine the abundance value for the molecular feature. The monoisotopic mass is the sum of the masses of the atoms in a molecule using the unbound, ground-state, rest mass of the principal (most abundant) isotope for each element instead of the isotopic average mass. Monoisotopic mass is typically expressed in unified atomic mass units (u), also called daltons (Da).

A molecular feature is identified as a potential molecular feature for utilization in a biosignature of the present disclosure if it is present in at least 50% of either the test blood samples or the control blood samples. For example, the molecular feature may be present in at least 50%, at least 55%, at least 60%, at least 65%, at least 70%, at least 75%, at least 80%, at least 85%, at least 90%, at least 95% or 100% of either the test blood samples or the control blood samples. Additionally, a molecular feature is identified as a potential molecular feature for utilization in a biosignature of the present disclosure if it is significantly different in abundance between the test blood samples and the control blood samples. Specifically, a molecular feature is identified as being significantly different if the difference in abundance value of the molecular feature in the test blood samples versus the abundance value of the molecular feature in the blood biological samples has a p-value is less than 0.1, preferably less than 0.05, less than 0.01, less than 0.005, or less than 0.001.

To increase the stringency of the biosignature, replicates of the test blood samples and control blood samples may be analyzed. For example, the test blood samples and control blood samples may be analyzed in duplicate. Alternatively, the test biological samples and control biological samples may be analyzed in triplicate. Additionally, the test blood samples and control blood samples may be analyzed four, five or six times. The replicate analysis is used to down-select the plurality of molecular features. The down-selection results in a biosignature with increased stringency.

Once a plurality of potential molecular features has been generated, a statistical modeling technique may be applied to select for the molecular features that provide an accuracy of disease detection that is clinically meaningful. Several statistical models are available to select the molecular features that comprise a biosignature of the present disclosure. Non-limiting examples of statistical modeling techniques include LDA, classification tree (CT) analysis, random forests, and LASSO (least absolute shrinkage and selection operator) logistic regression analysis. Various methods are known in the art for determining an optimal cut-off that maximizes sensitivity and/or specificity to serve as a threshold for discriminating samples obtained from subjects with Lyme disease or STARI. For the biosignatures in Table A, Table C, and Table D, the cut-off is determined by a data point of the highest specificity at the highest sensitivity on the ROC curve. However, the cut-off can be set as required by situational circumstances. For example, in certain clinical situations it may be desirable to minimize false-positive rates. These clinical situations may include, but are not limited to, the use of an experimental treatment (e.g., in a clinical trial) or the use of a treatment associated with serious adverse events and/or a higher than average number of side effects. Alternatively, it may be desirable to minimize false-negative rates in other clinical situations. Non-limiting examples may include treatment with a non-pharmacological intervention, the use of a treatment with a good risk-benefit profile, or treatment with an additional diagnostic agent. For the biosignatures in Table A, molecular feature stability across many samples and different LC-MS analyses was used as the cut-off.

In one example, the present disclosure provides a biosignature comprising each molecular feature in Table A, wherein the molecular features in the table are defined at least by their m/z ratio ±15 ppm, in some examples ±10 ppm, in some examples ±5 ppm (depending upon instrument variability). A biosignature comprising each molecular feature in Table A provides a 98% probability of accurately detecting a sample from a subject with Lyme disease, including early Lyme disease, and an 89% probability of accurately detecting a sample from a subject with STARI, when discriminating between a classification of Lyme disease and STARI. A skilled artisan will appreciate that in certain examples one or more molecular feature may be eliminated from the model without a clinically meaningful, negative impact on the model.

TABLE A

| MF # | Name | m/z (positive ion) | Mass | Retention Time (see examples) | Compound Predicted Formula | Predicted Chemical Structure (based on accurate mass) | Metabolite Class or Pathway |
|---|---|---|---|---|---|---|---|
| 1 | CSU/CDC-001 | 166.0852 | 165.078 | 1.86 | $C_9H_{11}NO_2$ | Phenylalanine | Phenylalanine metabolism |
| 2 | CSU/CDC-012 | 270.3156 | 269.3076 | 18.02 | $C_{18}H_{39}N$ | — | — |
| 3 | CSU/CDC-013 | 284.3314 | 283.3236 | 18.13 | $C_{19}H_{41}N$ | — | — |
| 4 | CSU/CDC-014 | 300.6407 | 599.268 | 18.27 | $C_{33}H_{37}N_5O_6$ | Asp Phe Arg Tyr (SEQ ID NO: 1) | Peptide |
| 5 | CSU/CDC-019 | 300.2892 | 299.2821 | 19.66 | $C_{18}H_{37}NO_2$ | Palmitoyl ethanolamide | N-acyl ethanolamine metabolism |
| 6 | CSU/CDC-039 | 734.5079 | 1449.9753 | 17.81 | — | — | — |
| 7 | CSU/CDC-062 | 370.1837 | 369.1757 | 19.7 | $C_{19}H_{23}N_5O_3$ | — | — |
| 8 | CSU/CDC-066 | 811.1942 | 810.1869 | 12.07 | $C_{42}H_{30}N_6O_{12}$ | — | — |
| 9 | CSU/CDC-067 | 947.7976 | 946.7936 | 14.55 | $C_{62}H_{106}O_6$ | TAG(59:7) | Triacylglycerol metabolism |
| 10 | CSU/CDC-072 | 410.2033 | 409.196 | 17.18 | — | — | — |
| 11 | CSU/CDC-075 | 1487.0005 | 1485.9987 | 18.17 | — | — | — |
| 12 | CSU/CDC-086 | 137.0463 | 136.0378 | 1.37 | $C_4H_8O_5$ | Threonate | Sugar metabolite |
| 13 | CSU/CDC-107 | 811.7965 | 810.7882 | 12.07 | — | — | — |
| 14 | CSU/CDC-132 | 616.1776 | 615.1699 | 15.43 | — | — | — |
| 15 | CSU/CDC-152 | 713.4492 | 712.4391 | 19.35 | $C_{38}H_{65}O_{10}P$ | PG(32:5) | Glycerophospholipid metabolism |
| 16 | CSU/CDC-155 | 502.3376 | 484.3039 | 19.87 | $C_{27}H_{40}N_4O_4$ | Gln Leu Pro Lys (SEQ ID NO: 2) | Peptide |
| 17 | CSU/CDC-158 | 415.3045 | 414.2978 | 20.19 | — | — | — |
| 18 | CSU/CDC-164 | 366.3729 | 365.3655 | 22.79 | — | — | — |
| 19 | CSU/CDC-166 | 333.1446 | 332.1373 | 12.89 | $C_{12}H_{20}N_4O_7$ | Glu Gln Gly | Peptide |
| 20 | CSU/CDC-205 | 241.1069 | 240.0996 | 14.7 | $C_{12}H_{16}O_5$ | 3-Carboxy-4-methyl-5-propyl-2-furanpropanoic acid (CMPF) | Fatty acid metabolism |
| 21 | CSU/CDC-211 | 464.1916 | 463.1849 | 13.05 | $C_{16}H_{29}N_7O_7S$ | Arg Asp Cys Ala (SEQ ID NO: 3) | Peptide |
| 22 | CSU/CDC-212 | 1249.2045 | 1248.1993 | 15.31 | — | — | — |
| 23 | CSU/CDC-213 | 1248.9178 | 1247.9141 | 15.3 | — | — | — |
| 24 | CSU/CDC-219 | 158.1539 | 157.1466 | 15.36 | — | — | — |
| 25 | CSU/CDC-227 | 529.3381 | 528.3296 | 16.89 | $C_{24}H_{44}N_6O_7$ | Gln Val Leu Leu Gly (SEQ ID NO: 4) | Peptide |
| 26 | CSU/CDC-229 | 282.2776 | 264.2456 | 20.56 | $C_{18}H_{32}O$ | — | — |
| 27 | CSU/CDC-235 | 190.1260 | 189.1187 | 14.12 | $C_9F_{119}NOS$ | 8-Methylthiooctanal doxime | 2-oxocarboxylic acid metabolism |

TABLE A-continued

| MF # | Name | m/z (positive ion) | Mass | Retention Time (see examples) | Compound Predicted Formula | Predicted Chemical Structure (based on accurate mass) | Metabolite Class or Pathway |
|---|---|---|---|---|---|---|---|
| 28 | CSU/CDC-238 | 382.3675 | 381.3603 | 20.23 | $C_{24}H_{47}NO_2$ | Erucicoyl ethanolamide | N-acyl ethanolamine metabolism |
| 29 | CSU/CDC-244 | 477.2968 | 476.2898 | 22.79 | $C_{31}H_{40}O_4$ | Lys Lys Thr Thr (SEQ ID NO: 5) | Peptide |
| 30 | CSU/CDC-248 | 459.3968 | 458.3904 | 19.08 | — | — | — |
| 31 | CSU/CDC-253 | 342.2635 | 341.2565 | 15.62 | $C_{19}H_{35}NO_4$ | — | — |
| 32 | CSU/CDC-254 | 529.3827 | 1022.6938 | 17.86 | — | — | — |
| 33 | CSU/CDC-258 | 459.2502 | 458.2429 | 19.02 | $C_{23}H_{39}O_7P$ | Lyso PA(20:4) | Glycerophospholipid metabolism |
| 34 | CSU/CDC-002 | 239.0919 | 238.0844 | 11.66 | $C_{12}H_{14}O_5$ | Trans-2, 3, 4-trimethoxycinnamate | Phenylpropanoid and polyketide metabolism |
| 35 | CSU/CDC-028 | 389.2174 | 388.2094 | 15.47 | $C_{19}H_{32}O_8$ | Methyl 10,12,13,15-bisepidioxy-16-hydroperoxy-8E-octadecenoate | Fatty acid metabolism |
| 36 | CSU/CDC-182 | 285.2065 | 284.1991 | 16.02 | $C_{16}H_{28}O_4$ | — | — |
| 37 | CSU/CDC-204 | 279.1693 | 278.1629 | 11.05 | $C_{15}H_{22}N_2O_3$ | Phe Leu | Dipeptide |
| 38 | CSU/CDC-247 | 714.6967 | 1427.3824 | 11.76 | — | — | — |

In one example, the present disclosure provides a biosignature comprising each molecular feature in Table B, wherein the molecular features in the table are defined at least by their m/z ratio ±15 ppm, in some examples ±10 ppm, in some examples ±5 ppm (depending upon instrument variability). The biosignature comprises each molecular feature in Table B that maintains an absolute abundance fold change of 2 or greater between Lyme disease and STARI, and maintains an abundance coefficient of variation of 0.2 or less between STARI blood samples, and maintains an abundance coefficient of variation of 0.2 or less between Lyme disease blood samples. A skilled artisan will appreciate that in certain examples one or more molecular features may be eliminated from the model without a clinically meaningful, negative impact on the model.

TABLE B

| MF # | Name | m/z (positive ion) | Mass | Retention Time (see examples) | Compound Predicted Formula | Predicted Chemical Structure (based on accurate mass) | Metabolite Class or Pathway |
|---|---|---|---|---|---|---|---|
| 1 | CSU/CDC-006 | 286.1444 | 285.1371 | 16.08 | $C_{17}H_{19}NO_3$ | Piperine | Alkaloid metabolism |
| 2 | CSU/CDC-021 | 394.3515 | 376.3171 | 20.09 | — | — | — |
| 3 | CSU/CDC-023 | 284.2943 | 283.2872 | 21.15 | $C_{18}H_{37}NO$ | Stearamide | Primary Fatty Acid Amide Metabolism |
| 4 | CSU/CDC-083 | 482.404 | 481.3976 | 19.99 | — | — | — |
| 5 | CSU/CDC-086 | 137.0463 | 136.0378 | 1.37 | $C_4H_8O_5$ | Threonate | Sugar metabolite |
| 6 | CSU/CDC-217 | 438.3787 | 420.3453 | 19.93 | — | — | — |
| 7 | CSU/CDC-219 | 158.1539 | 157.1466 | 15.36 | — | — | — |
| 8 | CSU/CDC-211 | 464.1916 | 463.1849 | 13.05 | $C_{16}H_{29}N_7O_7S$ | Arg Asp Cys Ala (SEQ ID NO: 3) | Peptide |
| 9 | CSU/CDC-240 | 441.3687 | 440.3614 | 21.26 | $C_{30}H_{48}O_2$ | 4,4-Dimethyl-14a-formyl-5a-cholesta-8,24-dien-3b-ol | Sterol metabolism |
| 10 | CSU/CDC-248 | 459.3968 | 458.3904 | 19.08 | — | — | — |

TABLE B-continued

| MF # | Name | m/z (positive ion) | Mass | Retention Time (see examples) | Compound Predicted Formula | Predicted Chemical Structure (based on accurate mass) | Metabolite Class or Pathway |
|---|---|---|---|---|---|---|---|
| 11 | CSU/CDC-258 | 459.2502 | 458.2429 | 19.02 | $C_{23}H_{39}O_7P$ | Lyso PA(20:4) | Glycerohospholipid metabolism |

In one example, the present disclosure provides a biosignature comprising each molecular feature in Table C, wherein the molecular features in the table are defined at least by their m/z ratio ±15 ppm, in some examples ±10 ppm, in some examples ±5 ppm (depending upon instrument variability). The biosignature comprising each molecular feature in Table C provides an 85% probability of accurately detecting a sample from a subject with Lyme disease, including early Lyme disease, an 92% probability of accurately detecting a sample from a subject with STARI, and a 93% probability of accurately detecting a sample from a healthy subject, when discriminating between a status (classification) of Lyme disease, STARI, and healthy. A skilled artisan will appreciate that in certain examples one or more molecular features may be eliminated from the model without a clinically meaningful, negative impact on the model.

TABLE C

| MF # | Name | m/z (positive ion) | Mass | Retention Time (see examples) | Compound Predicted Formula | Predicted Chemical Structure (based on accurate mass) | Metabolite Class or Pathway |
|---|---|---|---|---|---|---|---|
| 1 | CSU/CDC-001 | 166.0852 | 165.078 | 1.86 | $C_9H_{11}NO_2$ | Phenylalanine | Phenylalanine metabolism |
| 2 | CSU/CDC-012 | 270.3156 | 269.3076 | 18.02 | $C_{18}H_{39}N$ | — | — |
| 3 | CSU/CDC-013 | 284.3314 | 283.3236 | 18.13 | $C_{19}H_{41}N$ | — | — |
| 4 | CSU/CDC-014 | 300.6407 | 599.268 | 18.27 | $C_{33}H_{37}N_5O_6$ | Asp Phe Arg Tyr | Peptide |
| 5 | CSU/CDC-019 | 300.2892 | 299.2821 | 19.66 | $C_{18}H_{37}NO_2$ | Palmitoyl ethanolamide | N-acyl ethanolamine metabolism |
| 6 | CSU/CDC-039 | 734.5079 | 1449.9753 | 17.81 | — | — | — |
| 7 | CSU/CDC-062 | 370.1837 | 369.1757 | 19.7 | $C_{19}H_{23}N_5O_3$ | — | — |
| 8 | CSU/CDC-066 | 811.1942 | 810.1869 | 12.07 | $C_{42}H_{30}N_6O_{12}$ | — | — |
| 9 | CSU/CDC-067 | 947.7976 | 946.7936 | 14.55 | $C_{62}H_{106}O_6$ | TAG(59:7) | Triacylglycerol metabolism |
| 10 | CSU/CDC-072 | 410.2033 | 409.196 | 17.18 | — | — | — |
| 11 | CSU/CDC-075 | 1487.0005 | 1485.9987 | 18.17 | — | — | — |
| 12 | CSU/CDC-086 | 137.0463 | 136.0378 | 1.37 | $C_4H_8O_5$ | Threonate | Sugar metabolite |
| 13 | CSU/CDC-107 | 811.7965 | 810.7882 | 12.07 | — | — | — |
| 14 | CSU/CDC-132 | 616.1776 | 615.1699 | 15.43 | — | — | — |
| 15 | CSU/CDC-152 | 713.4492 | 712.4391 | 19.35 | $C_{38}H_{65}O_{10}P$ | PG(32:5) | Glycerophospholipid metabolism |
| 16 | CSU/CDC-155 | 502.3376 | 484.3039 | 19.87 | $C_{27}H_{40}N_4O_4$ | Gln Leu Pro Lys | Peptide |
| 17 | CSU/CDC-158 | 415.3045 | 414.2978 | 20.19 | — | — | — |
| 18 | CSU/CDC-164 | 366.3729 | 365.3655 | 22.79 | — | — | — |
| 19 | CSU/CDC-166 | 333.1446 | 332.1373 | 12.89 | $C_{12}H_{20}N_4O_7$ | Glu Gln Gly | Peptide |
| 20 | CSU/CDC-205 | 241.1069 | 240.0996 | 14.7 | $C_{12}H_{16}O_5$ | 3-Carboxy-4-methyl-5-propyl-2-furanpropanoic acid (CMPF) | Fatty acid metabolism |
| 21 | CSU/CDC-211 | 464.1916 | 463.1849 | 13.05 | $C_{16}H_{29}N_7O_7S$ | Arg Asp Cys Ala | Peptide |
| 22 | CSU/CDC-212 | 1249.2045 | 1248.1993 | 15.31 | — | — | — |

TABLE C-continued

| MF # | Name | m/z (positive ion) | Mass | Retention Time (see examples) | Compound Predicted Formula | Predicted Chemical Structure (based on accurate mass) | Metabolite Class or Pathway |
|---|---|---|---|---|---|---|---|
| 23 | CSU/CDC-213 | 1248.9178 | 1247.9141 | 15.3 | — | — | — |
| 24 | CSU/CDC-219 | 158.1539 | 157.1466 | 15.36 | — | — | — |
| 25 | CSU/CDC-227 | 529.3381 | 528.3296 | 16.89 | $C_{24}H_{44}N_6O_7$ | Gln Val Leu Leu Gly | Peptide |
| 26 | CSU/CDC-229 | 282.2776 | 264.2456 | 20.56 | $C_{18}H_{32}O$ | — | — |
| 27 | CSU/CDC-235 | 190.1260 | 189.1187 | 14.12 | $C_9H_{19}NOS$ | 8-Methylthio-octanaldoxime | 2-oxocarboxylic acid metabolism |
| 28 | CSU/CDC-238 | 382.3675 | 381.3603 | 20.23 | $C_{24}H_{47}NO_2$ | Erucicoyl ethanolamide | N-acyl ethanolamine metabolism |
| 29 | CSU/CDC-244 | 477.2968 | 476.2898 | 22.79 | $C_{31}H_{40}O_4$ | Lys Lys Thr Thr | Peptide |
| 30 | CSU/CDC-248 | 459.3968 | 458.3904 | 19.08 | — | — | — |
| 31 | CSU/CDC-253 | 342.2635 | 341.2565 | 15.62 | $C_{19}H_{35}NO_4$ | — | — |
| 32 | CSU/CDC-254 | 529.3827 | 1022.6938 | 17.86 | — | — | — |
| 33 | CSU/CDC-258 | 459.2502 | 458.2429 | 19.02 | $C_{23}H_{39}O_7P$ | Lyso PA(20:4) | Glycerophospholipid metabolism |
| 34 | CSU/CDC-003 | 886.4296 | 1770.8438 | 12.18 | — | — | — |
| 35 | CSU/CDC-004 | 181.0859 | 180.0788 | 14.7 | $C_{10}H_{12}O_3$ | 5'-(3'-Methoxy-4'-hydroxyphenyl)-gamma-valerolactone | Endogenous metabolite associated with microbiome |
| 36 | CSU/CDC-006 | 286.1444 | 285.1371 | 16.08 | $C_{17}H_{19}NO_3$ | Piperine | Alkaloid metabolism |
| 37 | CSU/CDC-008 | 463.2339 | 462.2248 | 16.36 | $C_{25}H_{34}O_8$ | Ala Lys Met Asn | Peptide |
| 38 | CSU/CDC-009 | 242.2844 | 241.2772 | 17.1 | $C_{16}H_{35}N$ | — | — |
| 39 | CSU/CDC-017 | 590.4237 | 589.4194 | 19.24 | — | — | — |
| 40 | CSU/CDC-026 | 553.3904 | 552.3819 | 23.38 | $C_{35}H_{52}O_5$ | Furohyperforin | Endogenous metabolite - derived from food |
| 41 | CSU/CDC-030 | 399.2364 | 398.2313 | 16.23 | — | — | — |
| 42 | CSU/CDC-042 | 580.4144 | 1158.8173 | 18.26 | — | — | — |
| 43 | CSU/CDC-052 | 704.4985 | 1372.925 | 18.7 | — | — | — |
| 44 | CSU/CDC-061 | 623.4521 | 1210.8362 | 19.55 | — | — | — |
| 45 | CSU/CDC-070 | 389.2178 | 388.2099 | 15.52 | $C_{19}H_{32}O_8$ | — | — |
| 46 | CSU/CDC-074 | 1111.6690 | 1110.6656 | 17.89 | — | — | — |
| 47 | CSU/CDC-083 | 482.4040 | 481.3976 | 19.99 | — | — | — |
| 48 | CSU/CDC-084 | 533.1929 | 532.1854 | 20.84 | $C_{23}H_{28}N_6O_9$ | Asp His Phe Asp | Peptide |
| 49 | CSU/CDC-087 | 466.3152 | 465.3085 | 14.73 | $C_{26}H_{43}NO_6$ | Glycocholic acid | Bile acid metabolism |
| 50 | CSU/CDC-091 | 683.4728 | 1347.9062 | 17.56 | — | — | — |
| 51 | CSU/CDC-095 | 227.0897 | 204.1002 | 9.68 | $C_9H_{16}O_5$ | — | — |
| 52 | CSU/CDC-098 | 183.1016 | 182.0943 | 10.89 | $C_{10}H_{14}O_3$ | — | — |
| 53 | CSU/CDC-099 | 476.3055 | 475.2993 | 11.09 | $C_{26}H_{41}N_3O_5$ | — | — |
| 54 | CSU/CDC-112 | 215.1283 | 214.1209 | 12.32 | $C_{11}H_{18}O_4$ | alpha-Carboxy-delta-decalactone | Endogenous metabolite - derived from food |

TABLE C-continued

| MF # | Name | m/z (positive ion) | Mass | Retention Time (see examples) | Compound Predicted Formula | Predicted Chemical Structure (based on accurate mass) | Metabolite Class or Pathway |
|---|---|---|---|---|---|---|---|
| 55 | CSU/CDC-115 | 519.1881 | 518.1813 | 12.33 | $C_{20}H_{30}N_4O_{12}$ | Poly-g-D-glutamate | Poly D-glutamate metabolism |
| 56 | CSU/CDC-128 | 1086.1800 | 2170.3435 | 15.38 | — | — | — |
| 57 | CSU/CDC-133 | 285.2061 | 284.1993 | 15.99 | $C_{16}H_{28}O_4$ | — | — |
| 58 | CSU/CDC-134 | 357.1363 | 356.1284 | 15.98 | $C_{20}H_{20}O_6$ | Xanthoxylol | Endogenous metabolite - derived from food |
| 59 | CSU/CDC-136 | 299.1853 | 298.1781 | 16.24 | $C_{16}H_{26}O_5$ | Tetranor-PGE1 | Prostaglandin metabolism |
| 60 | CSU/CDC-137 | 334.2580 | 333.2514 | 16.36 | — | — | — |
| 61 | CSU/CDC-138 | 317.2317 | 316.2254 | 16.63 | — | — | — |
| 62 | CSU/CDC-141 | 331.2471 | 330.2403 | 17.26 | $C_{18}H_{34}O_5$ | 11,12,13-trihydroxy-9-octadecenoic acid | Fatty acid metabolism |
| 63 | CSU/CDC-144 | 583.3480 | 582.3379 | 18.04 | $C_{27}H_{46}N_6O_8$ | Leu Lys Glu Pro Pro | Peptide |
| 64 | CSU/CDC-157 | 648.4672 | 647.4609 | 19.98 | $C_{34}H_{66}NO_8P$ | PE(29:1) | Glycerophospholipid metabolism |
| 65 | CSU/CDC-165 | 445.2880 | 854.5087 | 12.48 | $C_{45}H_{74}O_{15}$ | (3b,21b)-12-Oleanene-3,21,28-triol 28-[arabinosyl-(1->3)-arabinosyl-(1->3)-arabinoside] | Endogenous metabolite - derived from food |
| 66 | CSU/CDC-181 | 1486.7386 | 2971.4668 | 14.97 | — | — | — |
| 67 | CSU/CDC-183 | 668.4686 | 1317.8969 | 18.04 | $C_{16}H_{28}O_4$ | Omphalotin A | Endogenous metabolite - derived from food |
| 68 | CSU/CDC-184 | 454.2924 | 436.2587 | 18.1 | $C_{21}H_{41}O_7P$ | Lyso-PA(18:1) | Glycerophospholipid metabolism |
| 69 | CSU/CDC-186 | 607.9324 | 606.9246 | 19.01 | — | — | — |
| 70 | CSU/CDC-188 | 521.4202 | 503.3858 | 21.06 | — | — | — |
| 71 | CSU/CDC-193 | 176.0746 | 175.0667 | 2.31 | — | — | — |
| 72 | CSU/CDC-194 | 596.9082 | 1191.8033 | 19.1 | — | — | — |
| 73 | CSU/CDC-203 | 532.5606 | 531.5555 | 18.38 | — | — | — |
| 74 | CSU/CDC-206 | 337.1667 | 336.1599 | 20.67 | $C_{12}H_{24}N_4O_7$ | — | — |
| 75 | CSU/CDC-210 | 415.1634 | 207.0784 | 12.2 | $C_8H_9N_5O_2$ | 6-Amino-9H-purine-9-propanoic acid | Endogenous metabolite - derived from food |
| 76 | CSU/CDC-218 | 364.3407 | 346.3068 | 20.72 | — | — | — |
| 77 | CSU/CDC-222 | 989.5004 | 1976.9858 | 12.03 | — | — | — |
| 78 | CSU/CDC-224 | 819.6064 | 1635.8239 | 12.06 | — | — | — |
| 79 | CSU/CDC-237 | 286.2737 | 285.2666 | 19.08 | $C_{17}H_{35}NO_2$ | Pentadecanoyl ethanolamide | N-acyl ethanolamine metabolism |
| 80 | CSU/CDC-245 | 614.4833 | 613.4772 | 19.78 | — | — | — |
| 81 | CSU/CDC-250 | 298.2740 | 297.2668 | 16.44 | $C_{18}H_{35}NO_2$ | 3-Ketospingosine | Sphingolipid metabolism |
| 82 | CSU/CDC-252 | 1003.7020 | 1002.696 | 18.46 | — | — | — |

In one example, the present disclosure provides a biosignature comprising each molecular feature in Table D, wherein the molecular features in the table are defined at least by their m/z ratio ±15 ppm, in some examples ±10 ppm, in some examples ±5 ppm (depending upon instrument variability). The biosignature comprising each molecular feature in Table D provides an 97% probability of accurately detecting a sample from a subject with Lyme disease, including early Lyme disease, and an 89% probability of accurately detecting a sample from a subject with STARI, when discriminating between a classification of Lyme disease and STARI. The biosignature comprising each molecular feature in Table D provides an 85% probability of accurately detecting a sample from a subject with Lyme disease, including early Lyme disease, a 92% probability of accurately detecting a sample from a subject with STARI, and a 93% probability of accurately detecting a sample from a healthy subject, when discriminating between a classification of Lyme disease, STARI, and healthy. A skilled artisan will appreciate that one or more molecular features may be eliminated from the model without a clinically meaningful, negative impact on the model.

TABLE D

| MF # | Name | m/z (positive ion) | Mass | Retention Time (see examples) | Compound Predicted Formula | Predicted Chemical Structure (based on accurate mass) | Metabolite Class or Pathway |
|---|---|---|---|---|---|---|---|
| 1 | CSU/CDC-001 | 166.0852 | 165.078 | 1.86 | $C_9H_{11}NO_2$ | Phenylalanine | Phenylalanine metabolism |
| 2 | CSU/CDC-012 | 270.3156 | 269.3076 | 18.02 | $C_{18}H_{39}N$ | — | — |
| 3 | CSU/CDC-013 | 284.3314 | 283.3236 | 18.13 | $C_{19}H_{41}N$ | — | — |
| 4 | CSU/CDC-014 | 300.6407 | 599.268 | 18.27 | $C_{33}H_{37}N_5O_6$ | Asp Phe Arg Tyr | Peptide |
| 5 | CSU/CDC-019 | 300.2892 | 299.2821 | 19.66 | $C_{18}H_{37}NO_2$ | Palmitoyl ethanolamide | N-acyl ethanolamine metabolism |
| 6 | CSU/CDC-039 | 734.5079 | 1449.9753 | 17.81 | — | — | — |
| 7 | CSU/CDC-062 | 370.1837 | 369.1757 | 19.7 | $C_{19}H_{23}N_5O_3$ | — | — |
| 8 | CSU/CDC-066 | 811.1942 | 810.1869 | 12.07 | $C_{42}H_{30}N_6O_{12}$ | — | — |
| 9 | CSU/CDC-067 | 947.7976 | 946.7936 | 14.55 | $C_{62}H_{106}O_6$ | TAG(59:7) | Triacylglycerol metabolism |
| 10 | CSU/CDC-072 | 410.2033 | 409.196 | 17.18 | — | — | — |
| 11 | CSU/CDC-075 | 1487.0005 | 1485.9987 | 18.17 | — | — | — |
| 12 | CSU/CDC-086 | 137.0463 | 136.0378 | 1.37 | $C_4H_8O_5$ | Threonate | Sugar metabolite |
| 13 | CSU/CDC-107 | 811.7965 | 810.7882 | 12.07 | — | — | — |
| 14 | CSU/CDC-132 | 616.1776 | 615.1699 | 15.43 | — | — | — |
| 15 | CSU/CDC-152 | 713.4492 | 712.4391 | 19.35 | $C_{38}H_{65}O_{10}P$ | PG(32:5) | Glycerophospholipid metabolism |
| 16 | CSU/CDC-155 | 502.3376 | 484.3039 | 19.87 | $C_{27}H_{40}N_4O_4$ | Gln Leu Pro Lys | Peptide |
| 17 | CSU/CDC-158 | 415.3045 | 414.2978 | 20.19 | — | — | — |
| 18 | CSU/CDC-164 | 366.3729 | 365.3655 | 22.79 | — | — | — |
| 19 | CSU/CDC-166 | 333.1446 | 332.1373 | 12.89 | $C_{12}H_{20}N_4O_7$ | Glu Gln Gly | Peptide |
| 20 | CSU/CDC-205 | 241.1069 | 240.0996 | 14.7 | $C_{12}H_{16}O_5$ | 3-Carboxy-4-methyl-5-propyl-2-furanpropanoic acid (CMPF) | Fatty acid metabolism |
| 21 | CSU/CDC-211 | 464.1916 | 463.1849 | 13.05 | $C_{16}H_{29}N_7O_7S$ | Arg Asp Cys Ala | Peptide |
| 22 | CSU/CDC-212 | 1249.2045 | 1248.1993 | 15.31 | — | — | — |
| 23 | CSU/CDC-213 | 1248.9178 | 1247.9141 | 15.3 | — | — | — |
| 24 | CSU/CDC-219 | 158.1539 | 157.1466 | 15.36 | — | — | — |
| 25 | CSU/CDC-227 | 529.3381 | 528.3296 | 16.89 | $C_{24}H_{44}N_6O_7$ | Gln Val Leu Leu Gly | Peptide |
| 26 | CSU/CDC-229 | 282.2776 | 264.2456 | 20.56 | $C_{18}H_{32}O$ | — | — |
| 27 | CSU/CDC-235 | 190.1260 | 189.1187 | 14.12 | $C_9H_{19}NOS$ | 8-Methylthio-octanaldoxime | 2-oxocarboxylic acid metabolism |
| 28 | CSU/CDC-238 | 382.3675 | 381.3603 | 20.23 | $C_{24}H_{47}NO_2$ | Erucicoyl ethanolamide | N-acyl ethanolamine metabolism |

TABLE D-continued

| MF # | Name | m/z (positive ion) | Mass | Retention Time (see examples) | Compound Predicted Formula | Predicted Chemical Structure (based on accurate mass) | Metabolite Class or Pathway |
|---|---|---|---|---|---|---|---|
| 29 | CSU/CDC-244 | 477.2968 | 476.2898 | 22.79 | $C_{31}H_{40}O_4$ | Lys Lys Thr Thr | Peptide |
| 30 | CSU/CDC-248 | 459.3968 | 458.3904 | 19.08 | — | — | — |
| 31 | CSU/CDC-253 | 342.2635 | 341.2565 | 15.62 | $C_{19}H_{35}NO_4$ | — | — |
| 32 | CSU/CDC-254 | 529.3827 | 1022.6938 | 17.86 | — | — | — |
| 33 | CSU/CDC-258 | 459.2502 | 458.2429 | 19.02 | $C_{23}H_{39}O_7P$ | Lyso PA(20:4) | Glycerohospholipid metabolism |
| 34 | CSU/CDC-002 | 239.0919 | 238.0844 | 11.66 | $C_{12}H_{14}O_5$ | Trans-2,3,4-trimethoxycinnamate | Phenylpropanoid and polyketide metabolism |
| 35 | CSU/CDC-028 | 389.2174 | 388.2094 | 15.47 | $C_{19}H_{32}O_8$ | Methyl 10,12,13,15-bisepidioxy-16-hydroperoxy-8E-octadecenoate | Fatty acid metabolism |
| 36 | CSU/CDC-182 | 285.2065 | 284.1991 | 16.02 | $C_{16}H_{28}O_4$ | — | — |
| 37 | CSU/CDC-204 | 279.1693 | 278.1629 | 11.05 | $C_{15}H_{22}N_2O_3$ | Phe Leu | Dipeptide |
| 38 | CSU/CDC-247 | 714.6967 | 1427.3824 | 11.76 | — | — | — |
| 39 | CSU/CDC-003 | 886.4296 | 1770.8438 | 12.18 | — | — | — |
| 40 | CSU/CDC-004 | 181.0859 | 180.0788 | 14.7 | $C_{10}H_{12}O_3$ | 5'-(3'-Methoxy-4'-hydroxyphenyl)-gamma-valerolactone | Endogenous metabolite associated with microbiome |
| 41 | CSU/CDC-006 | 286.1444 | 285.1371 | 16.08 | $C_{17}H_{19}NO_3$ | Piperine | Alkaloid metabolism |
| 42 | CSU/CDC-008 | 463.2339 | 462.2248 | 16.36 | $C_{25}H_{34}O_8$ | Ala Lys Met Asn | Peptide |
| 43 | CSU/CDC-009 | 242.2844 | 241.2772 | 17.1 | $C_{16}H_{35}N$ | — | — |
| 44 | CSU/CDC-017 | 590.4237 | 589.4194 | 19.24 | — | — | — |
| 45 | CSU/CDC-026 | 553.3904 | 552.3819 | 23.38 | $C_{35}H_{52}O_5$ | Furohyperforin | Endogenous metabolite - derived from food |
| 46 | CSU/CDC-030 | 399.2364 | 398.2313 | 16.23 | — | — | — |
| 47 | CSU/CDC-042 | 580.4144 | 1158.8173 | 18.26 | — | — | — |
| 48 | CSU/CDC-052 | 704.4985 | 1372.925 | 18.7 | — | — | — |
| 49 | CSU/CDC-061 | 623.4521 | 1210.8362 | 19.55 | — | — | — |
| 50 | CSU/CDC-070 | 389.2178 | 388.2099 | 15.52 | $C_{19}H_{32}O_8$ | — | — |
| 51 | CSU/CDC-074 | 1111.6690 | 1110.6656 | 17.89 | — | — | — |
| 52 | CSU/CDC-083 | 482.4040 | 481.3976 | 19.99 | — | — | — |
| 53 | CSU/CDC-084 | 533.1929 | 532.1854 | 20.84 | $C_{23}H_{28}N_6O_9$ | Asp His Phe Asp | Peptide |
| 54 | CSU/CDC-087 | 466.3152 | 465.3085 | 14.73 | $C_{26}H_{43}NO_6$ | Glycocholic acid | Bile acid metabolism |
| 55 | CSU/CDC-091 | 683.4728 | 1347.9062 | 17.56 | — | — | — |
| 56 | CSU/CDC-095 | 227.0897 | 204.1002 | 9.68 | $C_9H_{16}O_5$ | — | — |
| 57 | CSU/CDC-098 | 183.1016 | 182.0943 | 10.89 | $C_{10}H_{14}O_3$ | — | — |
| 58 | CSU/CDC-099 | 476.3055 | 475.2993 | 11.09 | $C_{26}H_{41}N_3O_5$ | — | — |
| 59 | CSU/CDC-112 | 215.1283 | 214.1209 | 12.32 | $C_{11}H_{18}O_4$ | alpha-Carboxy-delta-decalactone | Endogenous metabolite - derived from food |

TABLE D-continued

| MF # | Name | m/z (positive ion) | Mass | Retention Time (see examples) | Compound Predicted Formula | Predicted Chemical Structure (based on accurate mass) | Metabolite Class or Pathway |
|---|---|---|---|---|---|---|---|
| 60 | CSU/CDC-115 | 519.1881 | 518.1813 | 12.33 | $C_{20}H_{30}N_4O_{12}$ | Poly-g-D-glutamate | Poly D-glutamate metabolism |
| 61 | CSU/CDC-128 | 1086.1800 | 2170.3435 | 15.38 | — | — | — |
| 62 | CSU/CDC-133 | 285.2061 | 284.1993 | 15.99 | $C_{16}H_{28}O_4$ | — | — |
| 63 | CSU/CDC-134 | 357.1363 | 356.1284 | 15.98 | $C_{20}H_{20}O_6$ | Xanthoxylol | Endogenous metabolite - derived from food |
| 64 | CSU/CDC-136 | 299.1853 | 298.1781 | 16.24 | $C_{16}H_{26}O_5$ | Tetranor-PGE1 | Prostaglandin metabolism |
| 65 | CSU/CDC-137 | 334.2580 | 333.2514 | 16.36 | — | — | — |
| 66 | CSU/CDC-138 | 317.2317 | 316.2254 | 16.63 | — | — | — |
| 67 | CSU/CDC-141 | 331.2471 | 330.2403 | 17.26 | $C_{18}H_{34}O_5$ | 11,12,13-trihydroxy-9-octadecenoic acid | Fatty acid metabolism |
| 68 | CSU/CDC-144 | 583.3480 | 582.3379 | 18.04 | $C_{27}H_{46}N_6O_8$ | Leu Lys Glu Pro Pro | Peptide |
| 69 | CSU/CDC-157 | 648.4672 | 647.4609 | 19.98 | $C_{34}H_{66}NO_8P$ | PE(29:1) | Glycerophospholipid metabolism |
| 70 | CSU/CDC-165 | 445.2880 | 854.5087 | 12.48 | $C_{45}H_{74}O_{15}$ | (3b,21b)-12-Oleanene-3,21,28-triol 28-[arabinosyl-(1->3)-arabinosyl-(1->3)-arabinoside] | Endogenous metabolite - derived from food |
| 71 | CSU/CDC-181 | 1486.7386 | 2971.4668 | 14.97 | — | — | — |
| 72 | CSU/CDC-183 | 668.4686 | 1317.8969 | 18.04 | $C_{16}H_{28}O_4$ | Omphalotin A | Endogenous metabolite - derived from food |
| 73 | CSU/CDC-184 | 454.2924 | 436.2587 | 18.1 | $C_{21}H_{41}O_7P$ | Lyso-PA(18:1) | Glycerophospholipid metabolism |
| 74 | CSU/CDC-186 | 607.9324 | 606.9246 | 19.01 | — | — | — |
| 75 | CSU/CDC-188 | 521.4202 | 503.3858 | 21.06 | — | — | — |
| 76 | CSU/CDC-193 | 176.0746 | 175.0667 | 2.31 | — | — | — |
| 77 | CSU/CDC-194 | 596.9082 | 1191.8033 | 19.1 | — | — | — |
| 78 | CSU/CDC-203 | 532.5606 | 531.5555 | 18.38 | — | — | — |
| 79 | CSU/CDC-206 | 337.1667 | 336.1599 | 20.67 | $C_{12}H_{24}N_4O_7$ | — | — |
| 80 | CSU/CDC-210 | 415.1634 | 207.0784 | 12.2 | $C_8H_9N_5O_2$ | 6-Amino-9H-purine-9-propanoic acid | Endogenous metabolite - derived from food |
| 81 | CSU/CDC-218 | 364.3407 | 346.3068 | 20.72 | — | — | — |
| 82 | CSU/CDC-222 | 989.5004 | 1976.9858 | 12.03 | — | — | — |
| 83 | CSU/CDC-224 | 819.6064 | 1635.8239 | 12.06 | — | — | — |
| 84 | CSU/CDC-237 | 286.2737 | 285.2666 | 19.08 | $C_{17}H_{35}NO_2$ | Pentadecanoyl ethanolamide | N-acyl ethanolamine metabolism |
| 85 | CSU/CDC-245 | 614.4833 | 613.4772 | 19.78 | — | — | — |
| 86 | CSU/CDC-250 | 298.2740 | 297.2668 | 16.44 | $C_{18}H_{35}NO_2$ | 3-Ketospingosine | Sphingolipid metabolism |
| 87 | CSU/CDC-252 | 1003.7020 | 1002.696 | 18.46 | — | — | — |
| 88 | CSU/CDC-005 | 223.0968 | 222.0895 | 14.69 | $C_{12}H_{14}O_4$ | — | — |
| 89 | CSU/CDC-007 | 286.1437 | 285.1364 | 16.06 | $C_{17}H_{19}NO_3$ | — | — |

TABLE D-continued

| MF # | Name | m/z (positive ion) | Mass | Retention Time (see examples) | Compound Predicted Formula | Predicted Chemical Structure (based on accurate mass) | Metabolite Class or Pathway |
|---|---|---|---|---|---|---|---|
| 90 | CSU/CDC-010 | 1112.6727 | 1111.6663 | 17.86 | — | — | — |
| 91 | CSU/CDC-011 | 454.2923 | 453.2867 | 18.08 | $C_{21}H_{44}NO_7P$ | Glycerophospho-N-Palmitoyl Ethanolamine | N-acyl ethanolamine metabolism |
| 92 | CSU/CDC-015 | 522.3580 | 521.3483 | 18.5 | $C_{26}H_{52}NO_7P$ | PC(18:1) | Glycerophospholipid metabolism |
| 93 | CSU/CDC-016 | 363.2192 | 362.2132 | 18.58 | $C_{21}H_{30}O_5$ | 4,5α-dihydrocortisone | Sterol metabolism |
| 94 | CSU/CDC-018 | 388.3939 | 387.3868 | 19.53 | — | — | — |
| 95 | CSU/CDC-020 | 256.2632 | 255.2561 | 20.08 | $C_{16}H_{33}NO$ | Palmitic amide | Primary Fatty Acid Amide Metabolism |
| 96 | CSU/CDC-021 | 394.3515 | 376.3171 | 20.09 | — | — | — |
| 97 | CSU/CDC-022 | 228.1955 | 227.1885 | 20.99 | — | — | — |
| 98 | CSU/CDC-023 | 284.2943 | 283.2872 | 21.15 | $C_{18}H_{37}NO$ | Stearamide | Primary Fatty Acid Amide Metabolism |
| 99 | CSU/CDC-024 | 338.3430 | 337.3344 | 22.14 | $C_{22}H_{43}NO$ | 13Z-Docosenamide (Erucamide) | Primary Fatty Acid Amide Metabolism |
| 100 | CSU/CDC-025 | 689.5604 | 688.5504 | 22.52 | $C_{38}H_{77}N_2O_6P$ | SM(d18:1-15:0)/ SM (d18:1/14:1-OH) | Sphingolipid metabolism |
| 101 | CSU/CDC-027 | 432.2803 | 431.2727 | 10.8 | $C_{25}H_{37}NO_5$ | Ala Ile Lys Thr | Peptide |
| 102 | CSU/CDC-029 | 385.2211 | 384.2147 | 15.84 | $C_{16}H_{28}N_6O_5$ | Lys His Thr | Peptides |
| 103 | CSU/CDC-031 | 449.3261 | 879.6122 | 17.07 | $C_{46}H_{89}NO_{12}S$ | C22-OH Sulfatide | Sphingolipid metabolism |
| 104 | CSU/CDC-032 | 467.3821 | 444.2717 | 17.1 | $C_{24}H_{40}O_8$ | 2-glyceryl-6-keto-PGF1α | Prostaglandin metabolism |
| 105 | CSU/CDC-033 | 836.5936 | 835.5845 | 17.15 | $C_{44}H_{85}NO_{11}S$ | C20 Sulfatide | Sphingolipid metabolism |
| 106 | CSU/CDC-034 | 792.5646 | 791.5581 | 17.17 | $C_{42}H_{82}NO_{10}P$ | PS(36:0) | Glycerophospholipid metabolism |
| 107 | CSU/CDC-035 | 356.2802 | 355.2722 | 17.35 | — | — | — |
| 108 | CSU/CDC-036 | 806.5798 | 805.5746 | 17.71 | $C_{43}H_{84}NO_{10}P$ | PS(37:0) | Glycerophospholipid metabolism |
| 109 | CSU/CDC-037 | 762.5582 | 761.5482 | 17.79 | $C_{41}H_{80}NO_9P$ | PS-O(35:1) | Glycerophospholipid metabolism |
| 110 | CSU/CDC-038 | 718.5308 | 700.4946 | 17.88 | $C_{39}H_{73}O_8P$ | PA(36:2) | Glycerophospholipid metabolism |
| 111 | CSU/CDC-040 | 690.4825 | 1361.924 | 17.95 | — | — | — |
| 112 | CSU/CDC-041 | 426.1798 | 425.1725 | 18.03 | — | — | — |
| 113 | CSU/CDC-043 | 741.5154 | 1481.0142 | 18.24 | $C_{83}H_{150}O_{17}P_2$ | CL(74:6) | Glycerophospholipid metabolism |
| 114 | CSU/CDC-044 | 864.6245 | 863.6166 | 18.17 | $C_{46}H_{89}NO_{11}S$ | C22 Sulfatide | Sphingolipid metabolism |
| 115 | CSU/CDC-045 | 558.4017 | 1080.7347 | 18.28 | — | — | — |
| 116 | CSU/CDC-046 | 719.5012 | 1402.9377 | 18.26 | — | — | — |
| 117 | CSU/CDC-047 | 536.3897 | 1053.7382 | 18.36 | — | — | — |
| 118 | CSU/CDC-048 | 538.8674 | 1058.696 | 18.4 | — | — | — |
| 119 | CSU/CDC-049 | 653.4619 | 1270.8593 | 18.43 | — | — | — |
| 120 | CSU/CDC-050 | 732.5450 | 714.5092 | 18.47 | $C_{40}H_{75}O_8P$ | PA(37:2) | Glycerophospholipid metabolism |
| 121 | CSU/CDC-051 | 748.5232 | 1478.0059 | 18.58 | — | — | — |
| 122 | CSU/CDC-053 | 682.4841 | 1328.9008 | 18.77 | — | — | — |
| 123 | CSU/CDC-054 | 360.3615 | 359.3555 | 18.89 | — | — | — |

TABLE D-continued

| MF # | Name | m/z (positive ion) | Mass | Retention Time (see examples) | Compound Predicted Formula | Predicted Chemical Structure (based on accurate mass) | Metabolite Class or Pathway |
|---|---|---|---|---|---|---|---|
| 124 | CSU/CDC-055 | 441.2412 | 440.2325 | 19.09 | $C_{20}H_{32}N_4O_7$ | Pro Asp Pro Leu | Peptide |
| 125 | CSU/CDC-056 | 638.4554 | 1240.847 | 18.92 | — | — | — |
| 126 | CSU/CDC-057 | 755.5311 | 1474.9941 | 18.94 | $C_{83}H_{144}O_{17}P_2$ | CL(74:9) | Glycerophospholipid metabolism |
| 127 | CSU/CDC-058 | 711.5023 | 1386.9417 | 19.09 | — | — | — |
| 128 | CSU/CDC-059 | 784.5530 | 1567.0908 | 19.27 | — | — | — |
| 129 | CSU/CDC-060 | 645.4660 | 1271.8896 | 19.36 | — | — | — |
| 130 | CSU/CDC-063 | 300.2886 | 282.2569 | 19.84 | $C_{18}H_{34}O_2$ | 13Z-octadecenoic acid | Fatty acid metabolism |
| 131 | CSU/CDC-064 | 309.0981 | 308.0913 | 2.06 | $C_{15}H_{16}O_7$ | — | — |
| 132 | CSU/CDC-065 | 561.2965 | 1120.5778 | 11.7 | $C_{54}H_{88}O_{24}$ | Camellioside D | Endogenous metabolite - derived from food |
| 133 | CSU/CDC-068 | 1106.2625 | 2209.5193 | 14.53 | — | — | — |
| 134 | CSU/CDC-069 | 371.2070 | 370.1997 | 15.52 | $C_{15}H_{26}N_6O_7$ | His Ser Lys | Peptide |
| 135 | CSU/CDC-071 | 443.2649 | 442.256 | 15.52 | $C_{19}H_{34}N_6O_6$ | Pro Gln Ala Lys | Peptide |
| 136 | CSU/CDC-073 | 850.6093 | 849.6009 | 17.63 | $C_{48}H_{84}NO_9P$ | PS-O(42:6) | Glycerophospholipid metabolism |
| 137 | CSU/CDC-076 | 697.4896 | 1358.909 | 18.32 | — | — | — |
| 138 | CSU/CDC-077 | 439.8234 | 877.6325 | 18.71 | — | — | — |
| 139 | CSU/CDC-078 | 567.8897 | 566.8818 | 18.73 | — | — | — |
| 140 | CSU/CDC-079 | 435.2506 | 434.243 | 19 | $C_{21}H_{39}O_7P$ | Lyso-PA(18:2) | Glycerophospholipid metabolism |
| 141 | CSU/CDC-080 | 834.6136 | 833.6057 | 18.83 | $C_{45}H_{88}NO_{10}P$ | PS(39:0) | Glycerophospholipid metabolism |
| 142 | CSU/CDC-081 | 534.8834 | 533.8771 | 18.82 | — | — | — |
| 143 | CSU/CDC-082 | 468.8441 | 467.8373 | 19.13 | — | — | — |
| 144 | CSU/CDC-085 | 312.3259 | 311.319 | 22.05 | — | — | — |
| 145 | CSU/CDC-088 | 228.1955 | 227.1884 | 15.22 | — | — | — |
| 146 | CSU/CDC-089 | 385.2211 | 384.2143 | 15.83 | $C_{20}H_{32}O_7$ | Lys His Thr | Peptide |
| 147 | CSU/CDC-090 | 403.2338 | 402.2253 | 15.84 | C16H30N6O6 | Lys Gln Gln | Peptide |
| 148 | CSU/CDC-092 | 675.4753 | 1348.9377 | 18.37 | — | — | — |
| 149 | CSU/CDC-093 | 682.4841 | 1345.9257 | 18.76 | — | — | — |
| 150 | CSU/CDC-094 | 762.5401 | 1506.0367 | 19.36 | — | — | — |
| 151 | CSU/CDC-177 | 189.1122 | 188.1049 | 12.27 | $C_9H_{14}O_4$ | Nonanedioic Acid | Fatty acid metabolism |
| 152 | CSU/CDC-097 | 169.0860 | 168.0786 | 9.94 | $C_9H_{12}O_3$ | 2,6-Dimethoxy-4-methylphenol | Endogenous metabolite - derived from food |
| 153 | CSU/CDC-100 | 276.1263 | 275.1196 | 11.16 | $C_{15}H_{17}NO_4$ | — | — |
| 154 | CSU/CDC-101 | 314.0672 | 313.06 | 11.56 | $C_{10}H_{12}N_5O_5P$ | — | — |
| 155 | CSU/CDC-102 | 201.1122 | 200.1047 | 11.56 | $C_{10}H_{16}O_4$ | Decenedioic acid | Fatty acid metabolism |
| 156 | CSU/CDC-103 | 115.0391 | 114.0318 | 11.57 | $C_5H_6O_3$ | 2-Hydroxy-2,4-pentadienoate | Phenylalanine metabolism |
| 157 | CSU/CDC-104 | 491.1569 | 490.1504 | 11.56 | $C_{24}H_{26}O_{11}$ | — | — |

TABLE D-continued

| MF # | Name | m/z (positive ion) | Mass | Retention Time (see examples) | Compound Predicted Formula | Predicted Chemical Structure (based on accurate mass) | Metabolite Class or Pathway |
|---|---|---|---|---|---|---|---|
| 158 | CSU/CDC-105 | 241.1054 | 218.1157 | 11.57 | $C_{10}H_{18}O_5$ | 3-Hydroxy-sebacic acid | Fatty acid metabolism |
| 159 | CSU/CDC-106 | 105.0914 | 104.0841 | 11.57 | — | — | — |
| 160 | CSU/CDC-108 | 311.1472 | 328.1391 | 12.22 | $C_{18}H_{20}N_2O_4$ | Phe Tyr | Peptide |
| 161 | CSU/CDC-109 | 271.1543 | 270.1464 | 12.24 | — | — | — |
| 162 | CSU/CDC-110 | 169.0860 | 168.0787 | 12.24 | $C_9H_{12}O_3$ | 2,6-Dimethoxy-4-methylphenol | Endogenous metabolite - derived from food |
| 163 | CSU/CDC-111 | 187.0967 | 186.0889 | 12.24 | $C_9H_{14}O_4$ | — | — |
| 164 | CSU/CDC-113 | 475.1635 | 474.1547 | 12.25 | $C_{25}H_{22}N_4O_6$ | His Cys Asp Thr | Peptide |
| 165 | CSU/CDC-114 | 129.0547 | 128.0474 | 12.33 | $C_6H_8O_3$ | (4E)-2-Oxohexenoic acid | Fatty acid metabolism |
| 166 | CSU/CDC-116 | 125.0599 | 124.0527 | 13.12 | $C_7H_8O_2$ | 4-Methylcatechol | Catechol metabolism |
| 167 | CSU/CDC-117 | 247.1550 | 246.1469 | 13.13 | $C_{12}H_{22}O_5$ | 3-Hydroxy-dodecanedioic acid | Fatty acid metabolism |
| 168 | CSU/CDC-118 | 517.2614 | 516.2544 | 13.13 | $C_{21}H_{36}N_6O_9$ | Gln Glu Gln Ile | Peptide |
| 169 | CSU/CDC-119 | 301.0739 | 300.0658 | 13.14 | $C_{16}H_{12}O_6$ | Chrysoeriol | Endogenous metabolite - derived from food |
| 170 | CSU/CDC-120 | 327.1773 | 304.1885 | 14.17 | $C_{16}H_{24}N_4O_2$ | — | — |
| 171 | CSU/CDC-121 | 387.2023 | 386.1935 | 14.51 | $C_{19}H_{30}O_8$ | Citroside A | Endogenous metabolite - derived from food |
| 172 | CSU/CDC-122 | 875.8451 | 1749.684 | 14.55 | — | — | — |
| 173 | CSU/CDC-123 | 737.5118 | 736.5056 | 14.52 | $C_{42}H_{73}O_8P$ | PA(39:5) | Glycerophospholipid metabolism |
| 174 | CSU/CDC-124 | 1274.3497 | 1273.3481 | 14.96 | — | — | — |
| 175 | CSU/CDC-125 | 1274.2092 | 1273.2 | 14.96 | — | — | — |
| 176 | CSU/CDC-126 | 1486.5728 | 2971.1328 | 14.95 | — | — | — |
| 177 | CSU/CDC-127 | 965.3818 | 964.3727 | 15.37 | — | — | — |
| 178 | CSU/CDC-129 | 1086.0562 | 2170.0908 | 15.38 | $C_{97}H_{167}N_5O_{48}$ | NeuAcalpha2-3Galbeta1-3GalNAcbeta1-4(9-OAc-NeuAcalpha2-8NeuAcalpha2-3)Galbeta1-4Glcbeta-Cer(d18:1/18:0) | Sphingolipid metabolism |
| 179 | CSU/CDC-130 | 1086.4344 | 2169.8474 | 15.39 | — | — | — |
| 180 | CSU/CDC-131 | 1240.7800 | 1239.7712 | 15.38 | — | — | — |
| 181 | CSU/CDC-135 | 317.1956 | 316.1885 | 16.24 | $C_{12}H_{24}N_6O_4$ | Arg Ala Ala | Peptide |
| 182 | CSU/CDC-139 | 299.2219 | 298.2148 | 16.64 | $C_{17}H_{30}O_4$ | 8E-Heptadecenedioic acid | Fatty acid metabolism |
| 183 | CSU/CDC-140 | 748.5408 | 747.5317 | 17.23 | $C_{40}H_{78}NO_9P$ | PS-O(34:1) | Glycerophospholipid metabolism |
| 184 | CSU/CDC-142 | 712.4935 | 1422.9749 | 17.82 | $C_{79}H_{140}O_{17}P_2$ | CL(70:7) | Glycerophospholipid metabolism |
| 185 | CSU/CDC-143 | 674.5013 | 673.4957 | 17.99 | $C_{37}H_{72}NO_7P$ | PE-P(32:1) | Glycerophospholipid metabolism |
| 186 | CSU/CDC-145 | 677.9537 | 676.9478 | 18.36 | — | — | — |

TABLE D-continued

| MF # | Name | m/z (positive ion) | Mass | Retention Time (see examples) | Compound Predicted Formula | Predicted Chemical Structure (based on accurate mass) | Metabolite Class or Pathway |
|---|---|---|---|---|---|---|---|
| 187 | CSU/CDC-146 | 531.3522 | 530.3457 | 18.4 | $C_{35}H_{46}O_4$ | — | — |
| 188 | CSU/CDC-147 | 585.2733 | 584.2649 | 18.39 | $C_{33}H_{36}N_4O_6$ | 15,16-Dihydrobiliverdin | Bilirubin breakdown products - Porphyrin metabolism |
| 189 | CSU/CDC-148 | 513.3431 | 512.3352 | 18.4 | — | — | — |
| 190 | CSU/CDC-149 | 611.9156 | 610.9073 | 18.59 | — | — | — |
| 191 | CSU/CDC-150 | 549.0538 | 531.0181 | 18.38 | — | — | — |
| 192 | CSU/CDC-151 | 755.5311 | 1509.0457 | 18.93 | — | — | — |
| 193 | CSU/CDC-153 | 599.4146 | 598.4079 | 19.59 | $C_{40}H_{54}O_4$ | Isomytiloxanthin | Isoflavinoid |
| 194 | CSU/CDC-154 | 762.5029 | 761.4919 | 19.66 | $C_{43}H_{72}NO_8P$ | PE(38:7) | Glycerophospholipid metabolism |
| 195 | CSU/CDC-156 | 741.4805 | 740.4698 | 19.96 | $C_{40}H_{69}O_{10}P$ | PG(34:5) | Glycerophospholipid metabolism |
| 196 | CSU/CDC-159 | 516.3532 | 498.3199 | 20.27 | $C_{23}H_{42}N_6O_6$ | Ala Leu Ala Pro Lys | Peptide |
| 197 | CSU/CDC-160 | 769.5099 | 768.5018 | 20.53 | $C_{42}H_{73}O_{10}P$ | PG(36:5) | Glycerophospholipid metabolism |
| 198 | CSU/CDC-161 | 862.5881 | 861.5818 | 20.86 | — | — | — |
| 199 | CSU/CDC-162 | 837.5358 | 836.5274 | 21.11 | $C_{53}H_{72}O_8$ | Amitenone | Endogenous metabolite - derived from food |
| 200 | CSU/CDC-163 | 558.3995 | 540.367 | 21.44 | $C_{26}H_{48}N_6O_6$ | Leu Ala Pro Lys Ile | Peptide |
| 201 | CSU/CDC-167 | 1105.9305 | 2209.8462 | 14.53 | — | — | — |
| 202 | CSU/CDC-168 | 329.1049 | 328.0976 | 14.61 | $C_{18}H_{16}O_6$ | 2-Oxo-3-phenylpropanoic acid | Phenylalanine metabolism |
| 203 | CSU/CDC-169 | 1241.2053 | 1240.2 | 15.38 | — | — | — |
| 204 | CSU/CDC-170 | 1088.6731 | 1087.6676 | 17.85 | — | — | — |
| 205 | CSU/CDC-171 | 667.4391 | 666.4323 | 20.35 | $C_{37}H_{63}O_8P$ | PA(24:5) | Glycerophospholipid metabolism |
| 206 | CSU/CDC-172 | 133.0497 | 132.0423 | 11.57 | $C_5H_8O_4$ | 2-Acetolactic acid | Pantothenate and CoA Biosynthesis Pathway |
| 207 | CSU/CDC-173 | 259.1540 | 258.1469 | 11.75 | — | — | — |
| 208 | CSU/CDC-174 | 311.1472 | 288.1574 | 12.23 | $C_{10}H_{20}N_6O_4$ | Asn Arg | Dipeptide |
| 209 | CSU/CDC-175 | 147.0652 | 146.0579 | 12.33 | $C_6H_{10}O_4$ | α-Ketopantoic acid | Pantothenate and CoA Biosynthesis Pathway |
| 210 | CSU/CDC-176 | 169.0860 | 168.0788 | 12.29 | $C_9H_{12}O_3$ | Epoxyoxophorone | Endogenous metabolite - derived from food |
| 211 | CSU/CDC-096 | 187.0965 | 186.0894 | 9.93 | $C_9H_{14}O_4$ | 5-Butyltetrahydro-2-oxo-3-furancarboxylic acid | Endogenous metabolite - derived from food |
| 212 | CSU/CDC-178 | 139.1116 | 138.1044 | 12.95 | $C_9H_{14}O_4$ | 3,6-Nonadienal | Endogenous metabolite - derived from food |
| 213 | CSU/CDC-179 | 515.2811 | 514.2745 | 13.14 | $C_{26}H_{42}O_{10}$ | Cofaryloside | Endogenous metabolite - derived from food |

TABLE D-continued

| MF # | Name | m/z (positive ion) | Mass | Retention Time (see examples) | Compound Predicted Formula | Predicted Chemical Structure (based on accurate mass) | Metabolite Class or Pathway |
|---|---|---|---|---|---|---|---|
| 214 | CSU/CDC-180 | 283.1522 | 282.1444 | 13.93 | $C_{25}H_{42}N_2O_7S$ | Epidihydrophaseic acid | Endogenous metabolite - derived from food |
| 215 | CSU/CDC-185 | 706.9750 | 705.9684 | 18.7 | — | — | — |
| 216 | CSU/CDC-187 | 834.5575 | 833.5502 | 20.32 | — | — | — |
| 217 | CSU/CDC-189 | 683.4727 | 1364.9294 | 17.54 | — | — | — |
| 218 | CSU/CDC-190 | 728.9890 | 1455.9633 | 18.63 | — | — | — |
| 219 | CSU/CDC-191 | 726.5104 | 1451.0035 | 18.64 | $C_{81}H_{144}O_{17}P_2$ | CL(72:7) | Glycerophospholipid metabolism |
| 220 | CSU/CDC-192 | 633.9280 | 632.9206 | 18.47 | — | — | — |
| 221 | CSU/CDC-195 | 209.0784 | 208.0713 | 9.92 | $C_{17}H_{24}O_3$ | Benzylsuccinate | Phenylpropanoic acid metabolism |
| 222 | CSU/CDC-196 | 792.5483 | 1566.055 | 18.46 | — | — | — |
| 223 | CSU/CDC-197 | 618.9221 | 1218.8083 | 19.02 | — | — | — |
| 224 | CSU/CDC-198 | 549.0543 | 531.0189 | 18.37 | — | — | — |
| 225 | CSU/CDC-199 | 553.7262 | 552.7188 | 18.74 | — | — | — |
| 226 | CSU/CDC-200 | 756.0320 | 755.0266 | 18.95 | — | — | — |
| 227 | CSU/CDC-201 | 639.6307 | 638.6205 | 19.58 | — | — | — |
| 228 | CSU/CDC-202 | 753.4414 | 730.4513 | 19.37 | $C_{42}H_{67}O_8P$ | PA(39:8) | Glycerophospholipid metabolism |
| 229 | CSU/CDC-207 | 328.3204 | 327.3148 | 20.72 | $C_{20}H_{41}NO_2$ | Stearoyl ethanolamide | N-acyl ethanolamine metabolism |
| 230 | CSU/CDC-208 | 514.3718 | 1009.7122 | 18.42 | $C_{56}H_{99}NO_{14}$ | 3-O-acetyl-sphingosine-2,3,4,6-tetra-O-acetyl-GalCer(d18:1/h22:0) | Sphingolipid metabolism |
| 231 | CSU/CDC-209 | 630.4594 | 1241.8737 | 19.95 | — | — | — |
| 232 | CSU/CDC-214 | 244.2270 | 243.22 | 17.17 | $C_{14}H_{29}NO_2$ | Lauroyl ethanolamide | N-acyl ethanolamine metabolism |
| 233 | CSU/CDC-215 | 463.3426 | 924.6699 | 18.08 | — | — | — |
| 234 | CSU/CDC-216 | 468.3892 | 450.3553 | 19.17 | $C_{31}H_{46}O_2$ | — | — |
| 235 | CSU/CDC-217 | 438.3787 | 420.3453 | 19.93 | — | — | — |
| 236 | CSU/CDC-220 | 792.0006 | 790.995 | 12.04 | — | — | — |
| 237 | CSU/CDC-221 | 792.2025 | 791.1947 | 12.04 | — | — | — |
| 238 | CSU/CDC-223 | 791.6016 | 790.594 | 12.04 | — | — | — |
| 239 | CSU/CDC-225 | 1115.5593 | 2228.1028 | 14.95 | — | — | — |
| 240 | CSU/CDC-226 | 1486.9176 | 2970.7976 | 14.96 | — | — | — |
| 241 | CSU/CDC-228 | 430.3161 | 412.2845 | 20.23 | $C_{23}H_{40}O_6$ | — | — |
| 242 | CSU/CDC-230 | 297.2793 | 296.2734 | 20.66 | $C_{19}H_{36}O_2$ | Methyl oleate | Oleic acid ester |
| 243 | CSU/CDC-231 | 714.3655 | 1426.718 | 11.73 | — | — | — |
| 244 | CSU/CDC-232 | 714.5306 | 1427.0479 | 11.76 | — | — | — |
| 245 | CSU/CDC-233 | 989.7499 | 1977.4865 | 12.03 | — | — | — |
| 246 | CSU/CDC-234 | 221.0744 | 220.0672 | 13.7 | $C_7H_{12}N_2O_6$ | L-beta-aspartyl-L-serine | Peptide |

TABLE D-continued

| MF # | Name | m/z (positive ion) | Mass | Retention Time (see examples) | Compound Predicted Formula | Predicted Chemical Structure (based on accurate mass) | Metabolite Class or Pathway |
|---|---|---|---|---|---|---|---|
| 247 | CSU/CDC-236 | 313.2734 | 312.2663 | 18.91 | $C_{19}H_{36}O_3$ | 2-oxo-nonadecanoic acid | Fatty acid metabolism |
| 248 | CSU/CDC-239 | 337.2712 | 314.282 | 20.66 | $C_{19}H_{38}O_3$ | 2-Hydroxy-nonadecanoic acid | Fatty acid metabolism |
| 249 | CSU/CDC-240 | 441.3687 | 440.3614 | 21.26 | $C_{30}H_{48}O_2$ | 4,4-Dimethyl-14a-formyl-5a-cholesta-8,24-dien-3b-ol | Sterol metabolism |
| 250 | CSU/CDC-241 | 425.3735 | 424.3666 | 21.5 | $C_{30}H_{48}O$ | Butyrospermone | Sterol metabolism |
| 251 | CSU/CDC-242 | 356.3517 | 355.3448 | 21.67 | $C_{22}H_{45}NO_2$ | Eicosanoyl ethanolamide | N-acyl ethanolamine metabolism |
| 252 | CSU/CDC-243 | 393.2970 | 370.3082 | 22.46 | $C_{22}H_{42}O_4$ | — | — |
| 253 | CSU/CDC-246 | 167.9935 | 166.9861 | 13.2 | $C_7H_5NS_2$ | — | — |
| 254 | CSU/CDC-249 | 677.6170 | 676.6095 | 20.71 | $C_{47}H_{80}O_2$ | Cholesterol ester (20:2) | Sterol metabolism |
| 255 | CSU/CDC-251 | 460.2695 | 459.2627 | 16.87 | $C_{26}H_{37}NO_6$ | — | — |
| 256 | CSU/CDC-255 | 630.4765 | 612.4417 | 18.11 | — | — | — |
| 257 | CSU/CDC-256 | 514.3734 | 1026.7281 | 18.41 | — | — | — |
| 258 | CSU/CDC-257 | 667.4754 | 1315.916 | 19.28 | — | — | — |
| 259 | CSU/CDC-259 | 516.8549 | 1031.6945 | 18.43 | — | — | — |
| 260 | CSU/CDC-260 | 740.5242 | 1479.0334 | 19.4 | $C_{83}H_{148}O_{17}P_2$ | CL(74:7) | Glycerohospholipid metabolism |
| 261 | CSU/CDC-261 | 1104.0614 | 2206.1096 | 15.2 | — | — | — |

III. Methods for Analyzing a Blood Sample from a Subject

In another aspect, the present disclosure provides a method for analyzing a blood sample from a subject. The method comprises performing liquid chromatography coupled to mass spectrometry on a blood sample, and providing abundance values for each molecular feature in Table A, Table B, Table C, or Table D. Preferably, the method further comprises deproteinizing a blood sample from a subject to produce a metabolite extract and then performing liquid chromatography coupled to mass spectrometry on a sample of the metabolite extract. The method may comprise providing abundance values for each molecular feature in Table A or Table C. The method may comprise providing abundance values for each molecular feature in Table B or Table D. The method may comprise providing abundance values for each molecular feature in Table A, Table B, or Table D. The method may comprise providing abundance values for each molecular feature in Table C or Table D.

A subject may be a human or a non-human mammal including, but not limited to, a livestock animal, a companion animal, a lab animal, or a zoological animal. A subject may be a rodent, e.g., a mouse, a rat, a guinea pig, etc. A subject may also be a livestock animal. Non-limiting examples of suitable livestock animals may include pigs, cows, horses, goats, sheep, llamas and alpacas. Alternatively, a subject may be a companion animal. Non-limiting examples of companion animals may include pets such as dogs, cats, rabbits, and birds. A subject may be a zoological animal. As used herein, a "zoological animal" refers to an animal that may be found in a zoo. Such animals may include non-human primates, large cats, wolves, and bears. In preferred examples, a subject is human.

Methods of the present disclosure for analyzing a blood sample may be used to monitor the progression or resolution of Lyme disease or STARI. A skilled artisan will also appreciate that infection with *Borrelia* species that cause Lyme disease, or with the causative agent(s) of STARI, likely commences prior to diagnosis or the onset of symptoms associated with the disease. For at least these reasons, a suitable blood sample may be from a subject that may or may not have a symptom associated with Lyme disease or STARI. Non-limiting examples of symptoms associated with Lyme disease and STARI are described above. A subject may have at least one symptom associated with Lyme disease, at least one symptom associated with STARI, or at least one symptom associated with Lyme disease and STARI. As a non-limiting example, a subject can have an erythema migrans (EM) rash or an EM-like rash. Alternatively, a subject may not have a symptom of Lyme disease or STARI but may be at risk of having Lyme disease or STARI. Non-limiting examples of risk factors for Lyme disease or STARI include living in or visiting a region endemic for Lyme disease or STARI, spending time in wooded or grassy areas, camping, fishing, gardening, hiking, hunting and/or picnicking in a region endemic for Lyme disease or STARI, and not removing tick(s) promptly or properly. In each of the above examples, suitable subjects, whether or not they have a symptom associated with Lyme disease or STARI at the time a blood sample is obtained, may or may not have received (or be receiving) treatment for Lyme disease, STARI, or another disease with symptoms similar to Lyme disease or STARI.

A blood sample may be a whole blood sample, a plasma sample, or a serum sample. Any of a variety of methods generally known in the art for collecting a blood sample may be utilized. Generally speaking, the sample collection method preferably maintains the integrity of the sample such that abundance values for each molecular feature in Table A, Table B, Table C, or Table D can be accurately measured according to the disclosure. A blood sample may be used "as is", or a blood sample may be processed to remove undesirable constituents. In preferred examples, a blood sample is processed using standard techniques to remove high-molecular weight species, and thereby obtain an extract comprising small molecule metabolites. This is referred to herein as "deproteinization" or a "deproteinization step." For example, a solvent or solvent mixture (e.g., methanol or the like) may be added to a blood sample to precipitate these high-molecular weight species followed by a centrifugation step to separate the precipitate and the metabolite-containing supernatant. In another example, proteases may be the added to a blood sample. In another example, size exclusion chromatography may be used.

A single blood sample may be obtained from a subject. Alternatively, the molecular features may be detected in blood samples obtained over time from a subject. As such, more than one blood sample may be collected from a subject over time. For instance, 2, 3, 4, 5, 6, 7, 8, 9, 10, 11, 12, 13, 14, 15, 16 or more blood samples may be collected from a subject over time. For example, 2, 3, 4, 5, or 6 blood samples are collected from a subject over time. Alternatively, 6, 7, 8, 9, or 10 blood samples are collected from a subject over time. Further, 10, 11, 12, 13, or 14 blood samples are collected from a subject over time. Still further, 14, 15, 16 or more blood samples are collected from a subject over time. The blood samples collected from the subject over time may be used to monitor Lyme disease or STARI in a subject. Alternatively, the blood samples collected from the subject over time may be used to monitor response to treatment in a subject.

When more than one sample is collected from a subject over time, blood samples may be collected 0.5, 1, 2, 3, 4, 5, 6, 7, 8, 9, 10, 11, 12 or more days apart. For example, blood samples may be collected 0.5, 1, 2, 3, or 4 days apart. Alternatively, blood samples may be collected 4, 5, 6, or 7 days apart. Further, blood samples may be collected 7, 8, 9, or 10 days apart. Still further, blood samples may be collected 10, 11, 12 or more days apart.

Once a sample is obtained, it is processed in vitro to measure abundance values for each molecular feature in Table A, Table B, Table C, or Table D. All suitable methods for measuring the abundance value for each of the molecular features known to one of skill in the art are contemplated within the scope of the invention. For example, mass spectrometry may be used to measure abundance values for each molecular feature in Table A, Table B, Table C, or Table D. The abundance values may be determined through direct infusion into the mass spectrometer. Alternatively, techniques coupling a chromatographic step with a mass spectrometry step may be used. The chromatographic step may be liquid chromatography. In certain examples, the abundance value for each of the molecular features may be determined utilizing liquid chromatography followed by mass spectrometry (LC-MS). In some examples, the liquid chromatography is high performance liquid chromatography (HPLC). Non-limiting examples of HPLC include partition chromatography, normal phase chromatography, displacement chromatography, reversed phase chromatography, size exclusion chromatography, ion exchange chromatography, bioaffinity chromatography, aqueous normal phase chromatography or ultrafast liquid chromatography. As used herein "mass spectrometry" describes methods of ionization coupled with mass selectors. Non-limiting examples of methods of ionization include matrix-assisted laser desorption/ionization (MALDI), electrospray ionization (ESI), and atmospheric pressure chemical ionization (ACPI). Non-limiting examples of mass selectors include quadropole, time of flight (TOF), and ion trap. Further, the mass selectors may be used in combination such as quadropole-TOF or triple quadropole.

In one example, an aliquot of a serum metabolite extract may be applied to a Poroshell 120, EC-C8, 2.1×100 mm, 2.7 μm LC Column (Agilent Technologies, Palo Alto, Calif.), and metabolites may be eluted with a nonlinear gradient of acetonitrile in formic acid (e.g., 0.1%) at a flow rate of 250 μl/min with an Agilent 1200 series LC system. The eluent may be introduced directly into an Agilent 6520 quadropole time of flight mass (Q-TOF) spectrometer and MS may be performed as previously described (27, 50). LC-MS and LC-MS/MS data may be collected under the following parameters: gas temperature, 310° C.; drying gas at 10 liters per min; nebulizer at 45 lb per in$^2$; capillary voltage, 4,000 V; fragmentation energy, 120 V; skimmer, 65 V; and octapole RF setting, 750 V. The positive-ion MS data for the mass range of 75 to 1,700 Da may be acquired at a rate of 2 scans per sec in both centroid and profile modes in 4-GHz high-resolution mode. Positive-ion reference masses may be used to ensure mass accuracy. To monitor instrument performance, quality control samples having a metabolite extract of healthy control serum may be analyzed in duplicate at the beginning of each analysis day and every 20 samples during the analysis day. In view of the specifics disclosed in this example, a skilled artisan will be able to optimize conditions as needed when using alternative equipment or approaches.

IV. Methods for Classifying a Subject as Having Lyme Disease or STARI

In another aspect, the present disclosure provides a method for classifying a subject as having Lyme disease or STARI. The method comprises analyzing a blood sample from a subject as described in Section III to provide abundance values for each molecular feature in Table A, Table B, Table C, or Table D; and comparing the abundance values to a reference set of abundance values. The statistical significance of any difference between the abundance values measured in the subject's blood sample as compared to the abundance values from the reference set is then determined. If the difference is statistically significant then a subject may be classified as having Lyme disease or STARI; if the difference is not statistically significant then a subject may be classified as not having Lyme disease or STARI. For instance, when using p-values, the abundance value of a molecular feature in a test blood sample is identified as being significantly different from the abundance value of the molecular feature in the reference set when the p-value is less than 0.1, preferably less than 0.05, less than 0.01, less than 0.005, or less than 0.001. Abundance values for the molecular features from the reference set may be determined before, after, or at the same time, as the abundance values for the molecular features from the subject's blood sample. Alternatively, abundance values for the molecular features from a reference set stored in a database may be used.

Any suitable reference set known in the art may be used; alternatively a new reference set may be generated. A suitable reference set comprises the abundance values for each of the molecular feature in Table A, Table B, Table C, or Table D in blood sample(s) obtained from control subjects known to be positive for Lyme disease, known to be positive for STARI, known to be negative for Lyme disease, known to be negative for STARI, known to be negative for Lyme disease and STARI, healthy subjects, or any combination thereof. Further, control subjects known to be negative for Lyme disease and/or STARI may also be known to be suffering from a disease with overlapping symptoms, may exhibit serologic cross-reactivity with Lyme disease, and/or may be suffering for another spirochetal infection. A subject suffering from a disease with overlapping symptoms may have one or more of the symptoms of Lyme disease described above. Non-limiting examples of diseases with overlapping symptoms include tick-bite hypersensitivity reactions, certain cutaneous fungal infections and bacterial cellulitis with non-Lyme EM-like lesions, syphilis, fibromyalgia, lupus, mixed connective tissue disorders (MCTD), chronic fatigue syndrome (CFS), rheumatoid arthritis, depression, mononucleosis, multiple sclerosis, sarcoidosis, endocarditis, colitis, Crohn's disease, early ALS, early Alzheimers disease, encephalitis, Fifth's disease, gastroesophageal reflux disease, infectious arthritis, interstitial cystis, irritable bowel syndrome, juvenile arthritis, Ménières syndrome, osteoarthritis, prostatitis, psoriatic arthritis, psychiatric disorders (bipolar, depression, etc.), Raynaud's syndrome, reactive arthritis, scleroderma, Sjogren's syndrome, sleep disorders, and thyroid disease. Specifically, a disease with overlapping symptoms is selected from the group consisting of syphilis and fibromyalgia. Further, the disclosure provides a method of correctly distinguishing a subject with early Lyme disease from a subject exhibiting serologic cross-reactivity with Lyme disease. A 2-tier serology-based assay is frequently used to diagnose Lyme disease. However, such an assay suffers from poor sensitivity in subjects with early Lyme disease. Non-limiting examples of diseases that exhibit serologic cross-reactivity with Lyme disease include infectious mononucleosis, syphilis, periodontal disease caused by *Treponema denticola*, granulocytic anaplasmosis, Epstein-Barr virus infection, malaria, *Helicobacter pylori* infections, bacterial endocarditis, rheumatoid arthritis, multiple sclerosis, infections caused by other spirochetes, and lupus. Specifically, a disease with serologic cross-reactivity is selected from the group consisting of infectious mononucleosis and syphilis. Non-limiting examples of other spirochetal infections include syphilis, severe periodontitis, leptospirosis, relapsing fever, rate-bite fever, bejel, yaws, pinta, and intestinal spirochaetosis. Specifically, another spirochetal infection is selected from the group consisting of syphilis and severe periodontitis.

In one example, a method for classifying a subject as having Lyme disease comprises: (a) deproteinizing a blood sample from a subject to produce a metabolite extract; (b) performing liquid chromatography coupled to mass spectrometry on a sample of the metabolite extract; (c) providing abundance values for each molecular feature in Table A, Table B, Table C, or Table D; and (d) inputting the abundance values from step (c) into a classification model trained with samples of metabolite extracts derived from suitable controls, wherein the classification model produces a disease score and the disease score distinguishes subjects with Lyme disease. In one example, the subject has at least one symptom associated with Lyme disease. In a specific example, the subject has an erythema migrans rash or an EM-like rash. In another example, the subject does not have a symptom of Lyme disease but is at risk of having Lyme disease. In each of the above examples, the subject may or may not have received (or be receiving) treatment for Lyme disease, STARI, or another disease with symptoms similar to Lyme disease or STARI.

In another example, a method for classifying a subject as having STARI comprises: (a) deproteinizing a blood sample from a subject to produce a metabolite extract; (b) performing liquid chromatography coupled to mass spectrometry on a sample of the metabolite extract; (c) providing abundance values for each molecular feature in Table A, Table B, Table C, or Table D; and (d) inputting the abundance values from step (c) into a classification model trained with samples of metabolite extracts derived from suitable controls, wherein the classification model produces a disease score and the disease score distinguishes subjects with STARI. In one example, the subject has at least one symptom associated with STARI. In a specific example, the subject has an erythema migrans rash or an EM-like rash. In another example, the subject does not have a symptom of STARI but is at risk of having STARI. In each of the above examples, the subject may or may not have received (or be receiving) treatment for Lyme disease, STARI, or another disease with symptoms similar to Lyme disease or STARI.

In another example, a method for classifying a subject as having Lyme disease or STARI comprises: (a) deproteinizing a blood sample from a subject to produce a metabolite extract; (b) performing liquid chromatography coupled to mass spectrometry on a sample of the metabolite extract; (c) providing abundance values for each molecular feature in Table A, Table B, Table C, or Table D; and (d) inputting the abundance values from step (c) into a classification model trained with samples of metabolite extracts derived from suitable controls, wherein the classification model produces a disease score and the disease score distinguishes subjects with Lyme disease from subjects STARI, and optionally further distinguishes healthy subjects. In one example, the subject has at least one symptom associated with Lyme disease and/or at least one symptom associated with STARI. In a specific example, the subject has an erythema migrans rash or an EM-like rash. In another example, the subject does not have a symptom of Lyme disease or STARI but is at risk of having Lyme disease or STARI. In each of the above examples, the subject may or may not have received (or be receiving) treatment for Lyme disease, STARI, or another disease with symptoms similar to Lyme disease or STARI.

In each of the above examples, the classification model has been trained with samples derived from suitable controls. Any suitable classification system known in the art may be used, provided the model produced therefrom has an accuracy of at least 80% for detecting a sample from a subject with Lyme disease, including early Lyme disease, and/or an accuracy of at least 80% for detecting a sample from a subject with STARI. For example, a classification model may have an accuracy of about 80%, about 85%, about 90%, about 95%, or greater for detecting a sample from a subject with Lyme disease, including early Lyme disease, and/or an accuracy of about 80%, about 85%, about 90%, about 95%, or greater for detecting a sample from a subject with STARI. Non-limiting examples of suitable classification models include LASSO, RF, ridge regression, elastic net, linear discriminant analysis, logistic regression, support vector machines, CT, and kernel estimation. In various examples, the model has a sensitivity from about 0.8 to about 1, and/or a specificity from about 0.8 to about 1. In certain examples, area under the ROC curve may be used to evaluate the suitability of a model, and an AUC ROC value of about 0.8 or greater indicates the model has a suitable accuracy.

The classification model produces a disease score and the disease score distinguishes: (i) samples from subjects with Lyme disease from samples from subjects with STARI, or (ii) distinguishes samples from subjects with Lyme disease from samples from control subjects, or (iii) distinguishes samples from subjects with STARI from samples from control subjects, or (iv) distinguishes samples from subjects with Lyme disease, samples from subjects with STARI and samples from control subjects from one another. As a non-limiting example, LASSO scores for a subject's sample may be calculated by multiplying the respective regression coefficients resulting from LASSO analysis by the transformed abundance of each MF in the biosignature and summing for each sample. In a further example, the sample score may be transformed into probabilities for each sample being classified to each sample group. As another non-limiting example, the transformed abundances of all MFs are used to classify the sample into one of the sample groups in each classification tree developed in an RF model, where the levels of chosen MFs are used sequentially to classify the samples, and the final classification is determined by majority votes among all such classification trees in the RF model. Scores from alternative classification models may be calculated as is known in the art.

In one example, abundance values are provided for each molecular feature in Table A, Table B, or Table D; the suitable controls comprise a blood sample known to be positive for Lyme disease and a blood sample known to be positive for STARI; and the classification model has an accuracy of at least 80%, at least 85%, at least 90%, or at least 95% for detecting a sample from a subject with Lyme disease and an accuracy of at least 80% or at least 85% for detecting a sample from a subject with STARI. Alternatively, abundance values are provided for each molecular feature in Table A, Table B, or Table D; the suitable controls include a blood sample known to be positive for Lyme disease, a blood sample known to be positive for STARI, and a blood sample known to be negative for both Lyme disease and STARI; and the classification model has an accuracy of at least 80%, at least 85%, or at least 90%, even more preferably at least 95% for detecting a sample from a subject with Lyme disease and an accuracy of at least 80% or at least 85% for detecting a sample from a subject with STARI. In still another alternative, abundance values are provided for each molecular feature in Table C or Table D; the suitable controls include a blood sample known to be positive for Lyme disease, a blood sample known to be positive for STARI, and a blood sample known to be negative for both Lyme disease and STARI; and the classification model has an accuracy of at least 80%, preferably at least 85% for detecting a sample from a subject with Lyme disease; an accuracy of at least 80%, at least 85%, or at least 90% for detecting a sample from a subject with STARI; and an accuracy of at least 80%, at least 85%, at least 90%, or at least 95% for detecting a sample from a healthy subject.

V. Methods for Treating a Subject as Having Lyme Disease or STARI

Another aspect of the disclosure is a method for treating a subject based on the subject's classification as having Lyme disease or STARI as described in Section IV. Treatment may be with a non-pharmacological treatment, a pharmacological treatment, or an additional diagnostic test.

In one example, the method comprises (a) obtaining a disease score from a test; (b) diagnosing the subject with Lyme disease based on the disease score; and (c) administering a treatment to the subject with Lyme disease, wherein the test comprises measuring the amount of each molecular feature in Table A, Table B, Table C, or Table D; providing abundance values for each molecular feature measured; and inputting the abundance values into a classification model trained with samples derived from suitable controls, wherein the classification model produces a disease score and the disease score distinguishes subjects with Lyme disease from subjects with STARI, and optionally from healthy subjects. In some examples, the test is a method of Section IV. In further examples, the test comprises (i) deproteinizing a blood sample from a subject to produce a metabolite extract; (ii) performing liquid chromatography coupled to mass spectrometry on a sample of the metabolite extract; (iii) providing abundance values for each molecular feature in Table A, Table B, Table C or Table D; and (iv) inputting the abundance values from step (iii) into a classification model trained with samples of metabolite extracts derived from suitable controls, wherein the classification model produces a disease score and the disease score distinguishes subjects with Lyme disease. Suitable controls are described above. In one example, abundance values are provided for each molecular feature in Table A, Table B, or Table D; the suitable controls comprise a blood sample known to be positive for Lyme disease and a blood sample known to be positive for STARI; and the classification model has an accuracy of at least 80%, at least 85%, at least 90%, or at least 95% for detecting a sample from a subject with Lyme disease and an accuracy of at least 80% or at least 85% for detecting a sample from a subject with STARI. Alternatively, abundance values are provided for each molecular feature in Table A, Table B, or Table D; the suitable controls include a blood sample known to be positive for Lyme disease, a blood sample known to be positive for STARI, and a blood sample known to be negative for both Lyme disease and STARI; and the classification model has an accuracy of at least 80%, at least 85%, or at least 90%, even more preferably at least 95% for detecting a sample from a subject with Lyme disease and an accuracy of at least 80% or at least 85% for detecting a sample from a subject with STARI. In still another alternative, abundance values are provided for each molecular feature in Table C or Table D; the suitable controls include a blood sample known to be positive for Lyme disease, a blood sample known to be positive for STARI, and a blood sample known to be negative for both Lyme disease and STARI; and the classification model has an accuracy of at least 80%, preferably at least 85% for detecting a sample from a subject with Lyme disease; an accuracy of at least 80%, at least 85%, or at least 90% for detecting a sample from a subject with STARI; and an accuracy of at least 80%, at least 85%, at least 90%, or at least 95% for detecting a sample from a healthy subject.

Treatment may comprise one or more standard treatments for Lyme disease. Non-limiting examples of standard pharmacological treatments for Lyme disease include an antibiotic, an antibacterial agent, a vaccine, an immune modulator, an anti-inflammatory agent, or a combination thereof. Suitable antibiotics include, but are not limited to, amoxicillin, doxycycline, cefuroxime axetil, amoxicillin-clavulanic acid, macrolides, ceftriaxone, cefotaxmine, and penicillin G. Antibiotics may be administered orally or parenterally.

Alternatively, treatment may comprise one or more experimental pharmacological treatment (e.g., treatment in a clinical trial). In each of the above examples, treatment may be for the acute or disseminated stage of the disease, or may be a prophylactic treatment. For example, following successful resolution of a primary *Borrelia* infection, the subject may be treated with a vaccine to prevent future infections. In still other examples, treatment may comprise further diagnostic testing. For example, if a subject has early Lyme disease but was negative for Lyme disease by current diagnostic testing (e.g., first-tier testing performed using the C6 EIA and second tier testing using IgM and/or IgG immunoblots following a positive or equivocal first-tier assay), additional testing may be ordered after an amount of time has elapsed (e.g., 3, 5, 7, 10, 14 days or more) to confirm the initial diagnosis.

In another example, the method comprises (a) obtaining a disease score from a test; (b) diagnosing the subject with STARI based on the disease score; and (c) administering a treatment to the subject with STARI, wherein the test comprises measuring the amount of each molecular feature in Table A, Table B, Table C, or Table D; providing abundance values for each molecular feature measured; and inputting the abundance values into a classification model trained with samples derived from suitable controls, wherein the classification model produces a disease score and the disease score distinguishes subjects with STARI from subjects with Lyme disease, including early Lyme disease, and optionally from healthy subjects. In some examples, the test is a method of Section IV. In further examples, the test comprises (i) deproteinizing a blood sample from a subject to produce a metabolite extract; (ii) performing liquid chromatography coupled to mass spectrometry on a sample of the metabolite extract; (iii) providing abundance values for each molecular feature in Table A, Table B, Table C or Table D; and (iv) inputting the abundance values from step (iii) into a classification model trained with samples of metabolite extracts derived from suitable controls, wherein the classification model produces a disease score and the disease score distinguishes subjects with STARI. Suitable controls are described above. In one example, abundance values are provided for each molecular feature in Table A, Table B, or Table D; the suitable controls comprise a blood sample known to be positive for Lyme disease and a blood sample known to be positive for STARI; and the classification model has an accuracy of at least 80%, at least 85%, at least 90%, or at least 95% for detecting a sample from a subject with Lyme disease and an accuracy of at least 80% or at least 85% for detecting a sample from a subject with STARI. Alternatively, abundance values are provided for each molecular feature in Table A, Table B, or Table D; the suitable controls include a blood sample known to be positive for Lyme disease, a blood sample known to be positive for STARI, and a blood sample known to be negative for both Lyme disease and STARI; and the classification model has an accuracy of at least 80%, at least 85%, or at least 90%, even more preferably at least 95% for detecting a sample from a subject with Lyme disease and an accuracy of at least 80% or at least 85% for detecting a sample from a subject with STARI. In still another alternative, abundance values are provided for each molecular feature in Table C or Table D; the suitable controls include a blood sample known to be positive for Lyme disease, a blood sample known to be positive for STARI, and a blood sample known to be negative for both Lyme disease and STARI; and the classification model has an accuracy of at least 80%, preferably at least 85% for detecting a sample from a subject with Lyme disease; an accuracy of at least 80%, at least 85%, or at least 90% for detecting a sample from a subject with STARI; and an accuracy of at least 80%, at least 85%, at least 90%, or at least 95% for detecting a sample from a healthy subject.

Treatment may comprise one or more standard treatments for STARI. There are no therapeutic agents specifically approved for STARI, in part because the causative agent is not known. Nonetheless, non-limiting examples of standard pharmacological treatments for STARI include an antibiotic, an antibacterial agent, a vaccine, an immune modulator, an anti-inflammatory agent, or a combination thereof. Suitable antibiotics include, but are not limited to, amoxicillin, doxycycline, cefuroxime axetil, amoxicillin-clavulanic acid, macrolides, ceftriaxone, cefotaxmine, and penicillin G. Antibiotics may be administered orally or parenterally. Alternatively, treatment may comprise one or more experimental pharmacological treatment (e.g., treatment in a clinical trial). In each of the above examples, treatment may be for acute disease, or may be a prophylactic treatment. For example, following successful treatment of STARI (as defined the by the current clinical standard of the time), the subject may be treated with a vaccine to prevent future infections. In still other another example, treatment may comprise further diagnostic testing. For example, if a subject is diagnosed with STARI, additional testing may be ordered after an amount of time has elapsed (e.g., 3, 5, 7, 10, 14 days or more) to confirm the initial diagnosis. In yet another example, treatment may consist of supportive care only, e.g., non-pharmacological treatments or over-the-counter pharmaceutical agents to alleviate symptoms, such as fever, aches, etc.

In certain examples, obtaining a result from a test of Section IV comprises analyzing a blood sample obtained from the subject as described in Section III and/or classifying the subject as described in Section IV. In certain examples, obtaining a result from a test of Section IV comprises requesting (e.g., placing a medical order or prescription) from a third party a test that analyzes a blood sample obtained from the subject as described in Section III and classifies the subject as described in Section IV, or requesting from a third party a test that analyzes a blood sample obtained from the subject as described in Section III, and then performing the classification as described in Section IV.

In each of the above examples, the method may further comprise obtaining a second result (for a sample obtained from the subject after treatment has begun) from the same test of Section IV as before treatment and adjusting treatment based on the test result.

Accordingly, yet another aspect of the disclosure is a method for monitoring the effectiveness of a therapeutic agent intended to treat a subject with Lyme disease or STARI. The method comprises obtaining a result from a test of Section IV, administering a therapeutic agent to the subject, obtaining a result from the same test of Section IV as before treatment, wherein the treatment is effective if the disease score classifies the subject as more healthy than before. A first sample obtained before treatment began may be used as a baseline. Alternatively, the first sample may be obtained after treatment has begun. Samples may be collected from a subject over time, including 0.5, 1, 2, 3, 4, 5, 6, 7, 8, 9, 10, 11, 12 or more days apart. For example, blood samples may be collected 0.5, 1, 2, 3, or 4 days apart. Alternatively, blood samples may be collected 4, 5, 6, or 7 days apart. Further, blood samples may be collected 7, 8, 9, or 10 days apart. Still further, blood samples may be collected 10, 11, 12 or more days apart.

The following examples are included to demonstrate preferred examples of the invention. It should be appreciated by those of skill in the art that the techniques disclosed in the examples that follow represent techniques discovered by the inventors to function well in the practice of the invention. Those of skill in the art should, however, in light of the present disclosure, appreciate that changes may be made in the specific examples that are disclosed and still obtain a like or similar result without departing from the spirit and scope of the invention. Therefore, all matter set forth or shown in the examples and accompanying drawings is to be interpreted as illustrative and not in a limiting sense.

EXAMPLES

The following examples illustrate various iterations of the invention.

Example 1

Lyme disease is a multisystem bacterial infection that in the United States is primarily caused by infection with *Borrelia burgdorferi* sensu stricto. Over 300,000 cases of Lyme disease are estimated to occur annually in the United States, with over 3.4 million laboratory diagnostic tests performed each year (1, 2). Symptoms associated with this infection include fever, chills, headache, fatigue, muscle and joint aches, and swollen lymph nodes; however, the most prominent clinical manifestation in the early stage is the presence of one or more erythema migrans (EM) skin lesions (3). This annular, expanding erythematous skin lesion occurs at the site of the tick bite in 70 to 80% of infected individuals and is typically 5 cm or more in diameter (4, 5). Although an EM lesion is a hallmark for Lyme disease, other types of skin lesions can be confused with EM (3, 5, 6). These include rashes caused by tick-bite hypersensitivity reactions, certain cutaneous fungal infections, bacterial cellulitis and the rash of southern tick-associated rash illness (STARI) (7, 8).

STARI is associated with a bite from the lone star tick (*Amblyomma americanum*) and, in addition to the development of an EM-like skin lesion, individuals with STARI can present with mild systemic symptoms (including muscle and joint pains, fatigue, fever, chills, and headache) that are similar to those occurring in patients with Lyme disease (7, 9, 10). These characteristics of STARI have led some to postulate that the etiology of this illness is a *Borrelia* species, including *B. burgdorferi* (10, 11) or *B. lonestari* (12-15); however, multiple studies have refuted that STARI is caused by *B. burgdorferi* (7, 16-19) and additional cases associating *B. lonestari* with STARI have not emerged (20, 21). Additionally, STARI patients have been screened serologically for reactivity to rickettsial agents, but no evidence was obtained to demonstrate that *rickettsia* causes this illness (10, 22). Thus, at present no infectious etiology is known for STARI.

STARI cases occur over the geographic region where the lone star tick is present. This includes a region that currently expands from central Texas and Oklahoma upward into the Midwestern states and eastward, including the southern states and along the Atlantic coast into Maine (23). Unlike STARI, Lyme disease is transmitted to humans through the bite of the blacklegged tick (*Ixodes scapularis*) that is present in the northeastern, mid-Atlantic, and north-central United States, and the western blacklegged tick (*I. pacificus*), which is present on the Pacific Coast (24). The geographic distribution of human Lyme disease and the vectors for this disease is expanding (24-26), and there is a similar expansion of areas inhabited by the lone star tick (23). Importantly, a strict geographic segregation of Lyme disease and STARI does not exist, as there are regions where STARI and Lyme disease are co-prevalent (25). Thus, there is a growing need for diagnostic methods to differentiate between Lyme disease and STARI, and that facilitate proper treatment, patient management and disease surveillance.

Clinically, the skin lesions of STARI and early Lyme disease are indistinguishable, and no laboratory tool or method exists for the diagnosis of STARI or differentiation of STARI from Lyme disease. The only biomarkers evaluated for differential diagnosis of early Lyme disease and STARI have been serum antibodies to *B. burgdorferi* (10, 16). However, these tests have poor sensitivity for early stages of Lyme disease, and thus a lack of *B. burgdorferi* antibodies cannot be used as a reliable differential marker for STARI.

The experiments herein describe the development of a metabolomics-driven approach to identify biomarkers that discriminate early Lyme disease from STARI, and provide evidence that these two diseases are biochemically distinct. A retrospective cohort of well-characterized sera from patients with early Lyme disease and STARI was evaluated to identify a differentiating metabolic biosignature. Using statistical modeling, this metabolic biosignature accurately classified test samples that included healthy controls. Additionally, the metabolic biosignature revealed that N-acyl ethanolamine (NAE) and primary fatty acid amide (PFAM) metabolism differed significantly between these two diseases.

Clinical Samples:

A total of 220 well-characterized retrospective serum samples from three different repositories were used to develop and test a metabolic biosignature that accurately classifies early Lyme disease and STARI (Table 2). All samples from Lyme disease patients were culture confirmed and/or PCR positive for *B. burgdorferi*. The median age for early Lyme disease patients was 45 years and 74% were males. STARI patients had an overall median age of 45 years and 55% were males.

To establish a Lyme disease diagnostic baseline, the recommended two-tiered serology testing for Lyme disease was performed on all samples. First-tier testing was performed using the C6 EIA and was positive for 66% of Lyme disease samples. When STARI and healthy controls were tested by the C6 EIA, two STARI samples (2%) and five healthy controls (9%) tested positive or equivocal. Two-tiered testing using IgM and IgG immunoblots as the second-tier test following a positive or equivocal first-tier assay resulted in a sensitivity of 44% for early Lyme disease samples (duration of illness was not considered for IgM immunoblot testing). The sensitivity of two-tiered testing for early Lyme disease samples included in the Discovery/Training-Sets and the Test-Sets was 38% and 53%, respectively. All STARI and healthy control samples were negative by two-tiered testing (Table 2).

Development of a Metabolic Biosignature for Early Lyme Disease and STARI Differentiation:

Metabolic profiling by liquid chromatography-mass spectrometry (LC-MS) of a retrospective cohort of well-characterized sera from patients with early Lyme disease (n=40) and STARI (n=36) (Table 2 and FIG. 1) comprising the Discovery-Set (i.e. Test-Set samples that were not used in molecular feature selection) resulted in a biosignature of 792 molecular features (MFs) that differed significantly (adjusted-p<0.05) with a ≥2 fold change in relative abundance between early Lyme disease and STARI. Down-selection of MFs based on their robustness in replicate analyses of the same sera produced a refined biosignature of 261 MFs (FIG. 1 and Table 3). Of these 261 MFs, 60 and 201 displayed an increased and decreased abundance, respectively, in early Lyme disease as compared to STARI. The large number of MFs that differed significantly between early Lyme disease and STARI patients indicated that these two patient groups had distinguishing biochemical profiles. These variances were applied to define alterations of specific metabolic pathways (FIG. 1) and used to develop diagnostic classification models (FIG. 1).

Figure 2:
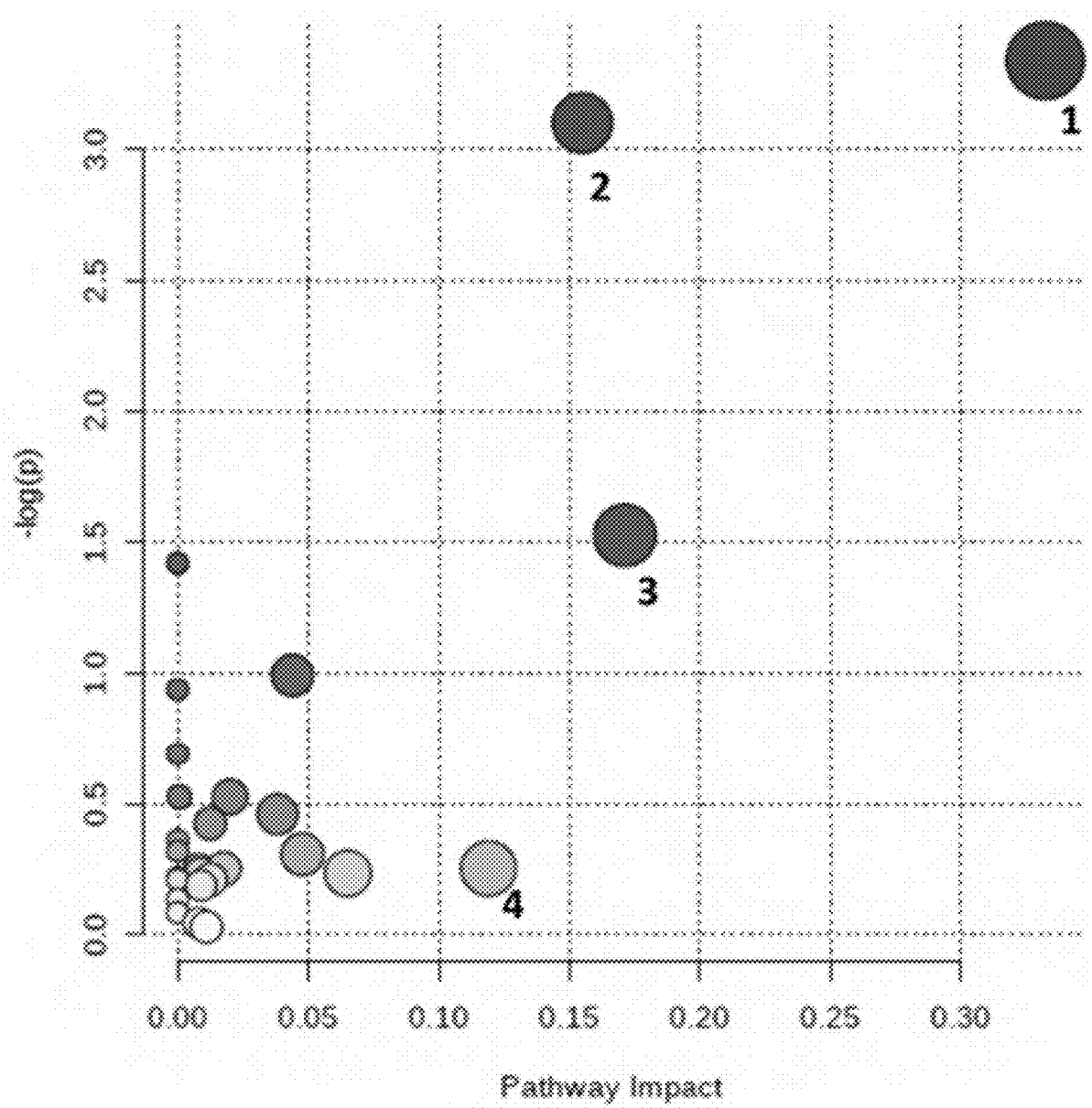
FIG. 2 is a graphical depiction of pathways differentially regulated in patients with early Lyme disease and STARI. The 122 presumptively identified MFs were analyzed using MetaboAnalyst to identify perturbed pathways between early Lyme disease and STARI. The color and size of each circle is based on P values and pathway impact values. Pathways with a >0.1 impact were considered to be perturbed and differentially regulated between patients with early Lyme disease and STARI. There were a total of four pathways affected: 1) glycerophospholipid metabolism; 2) sphingolipid metabolism; 3) valine, leucine and isoleucine biosynthesis; and 4) phenylalanine metabolism.

In Silico Analysis of Metabolic Pathways:

Presumptive chemical identification was applied to the 261 MFs. This yielded predicted chemical formulae for 149 MFs, and 122 MFs were assigned a putative chemical structure based on interrogation of each MF's monoisotopic mass (+ or −15 ppm) against the Metlin database and the Human Metabolome Database (HMDB) (Table 3). An in silico interrogation of potentially altered metabolic pathways was performed using the presumptive identifications for the 122 MFs and MetaboAnalyst (28). Four differentiating pathways were predicted to have the greatest impact, with the most significant being glycerophospholipid metabolism and sphingolipid metabolism (FIG. 2 and Table 4). Specifically, the MetaboAnalyst analysis indicated that differences in phosphatidic acid, phosphatidylethanolamine, phosphatidylcholine and lysophosphotidylcholine were the major contributors to altered glycerophospholipid metabolism between STARI and early Lyme disease (Table 4). Altered sphingolipid metabolism between these two groups was attributable to changes in the relative abundances of sphingosine, dehydrosphinganine and sulfatide (Table 4). Manual interrogation of the predicted structural identifications revealed that 26 and 7 of the 122 MFs assigned a putative structural identification were associated with glycerophospholipid and sphingolipid metabolism, respectively (Table 3).

Figure 3A:
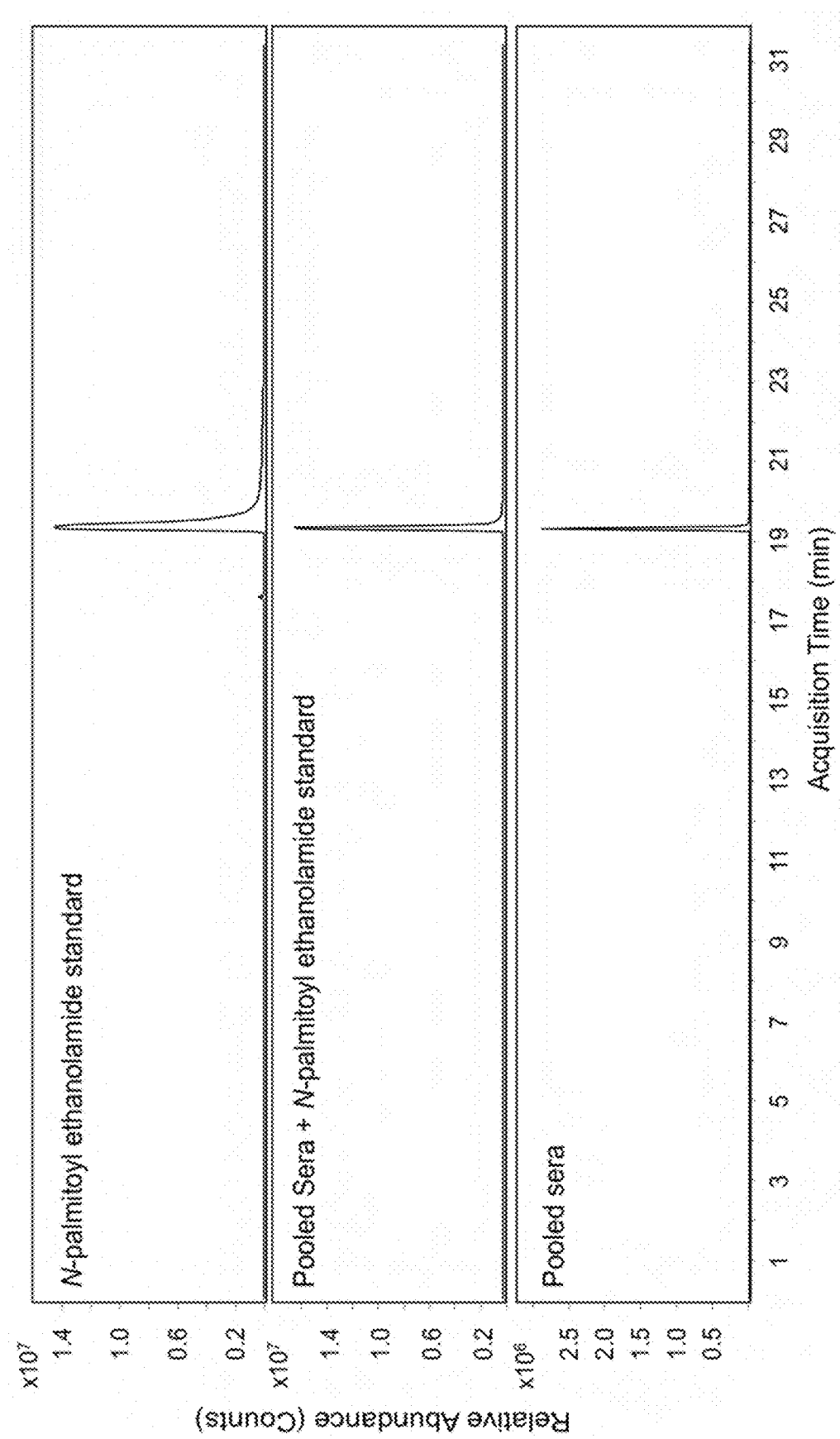
FIGS. 3A-E show metabolite identification and the association with NAE and PFAM metabolism. Structural identification of palmitoyl ethanolamide (FIG. 3A and FIG. 3B) and other NAEs in the 261 MF biosignature indicated alteration of NAE metabolism (FIG. 3C), a pathway that can influence the production of PFAMs. Further MF identification revealed that palmitamide (FIG. 3D and FIG. 3E) and other PFAMs also differed in abundance between STARI and early Lyme disease patients. Structural identification was achieved by retention-time alignment (FIG. 3A and FIG. 3D) of authentic standard (top panel), authentic standard spiked in pooled patient sera (middle panel), and the targeted metabolite in pooled patient sera (bottom panel), and by comparison of MS/MS spectra (FIG. 3B and FIG. 3E) of the authentic standards (top) and the targeted metabolites in patient sera (bottom). Retention-time alignments for palmitoyl ethanolamide (FIG. 3A) and palmitamide (FIG. 3D) were generated with extracted ion chromatograms for m/z 300.2892 and m/z 256.2632, respectively. The relationship of PFAM formation to NAE metabolism is highlighted in pink in FIG. 3C. The * and ** represent steps for the formation of palmitoyl ethanolamide and palmitamide, respectively. PLA, phospholipase A; PLC, phospholipase C; PLD, phospholipase D; ADH, alcohol dehydrogenase; PAM, peptidylglycine α-amidating monooxygenase.
Figure 3B:
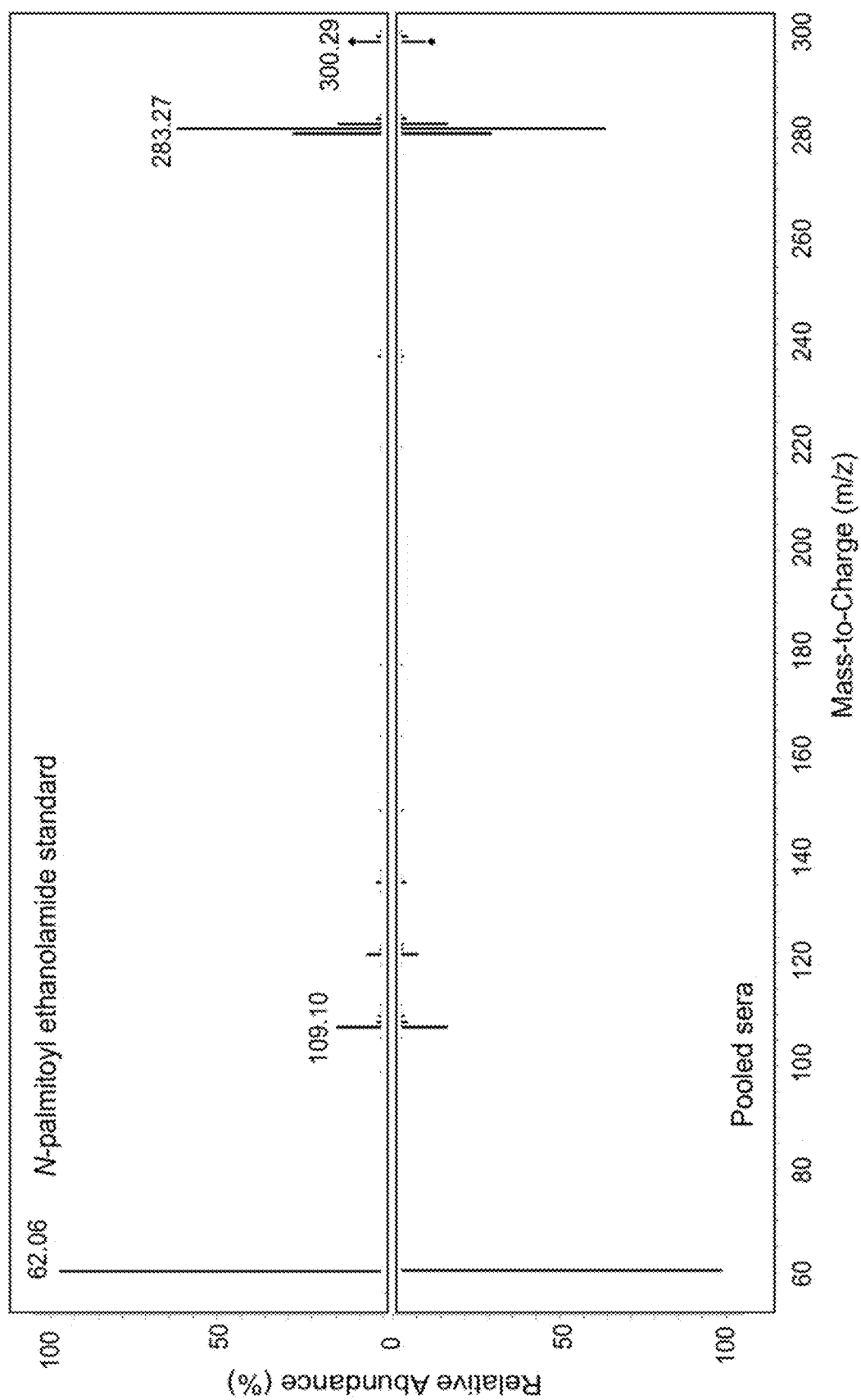
Figure 3C:
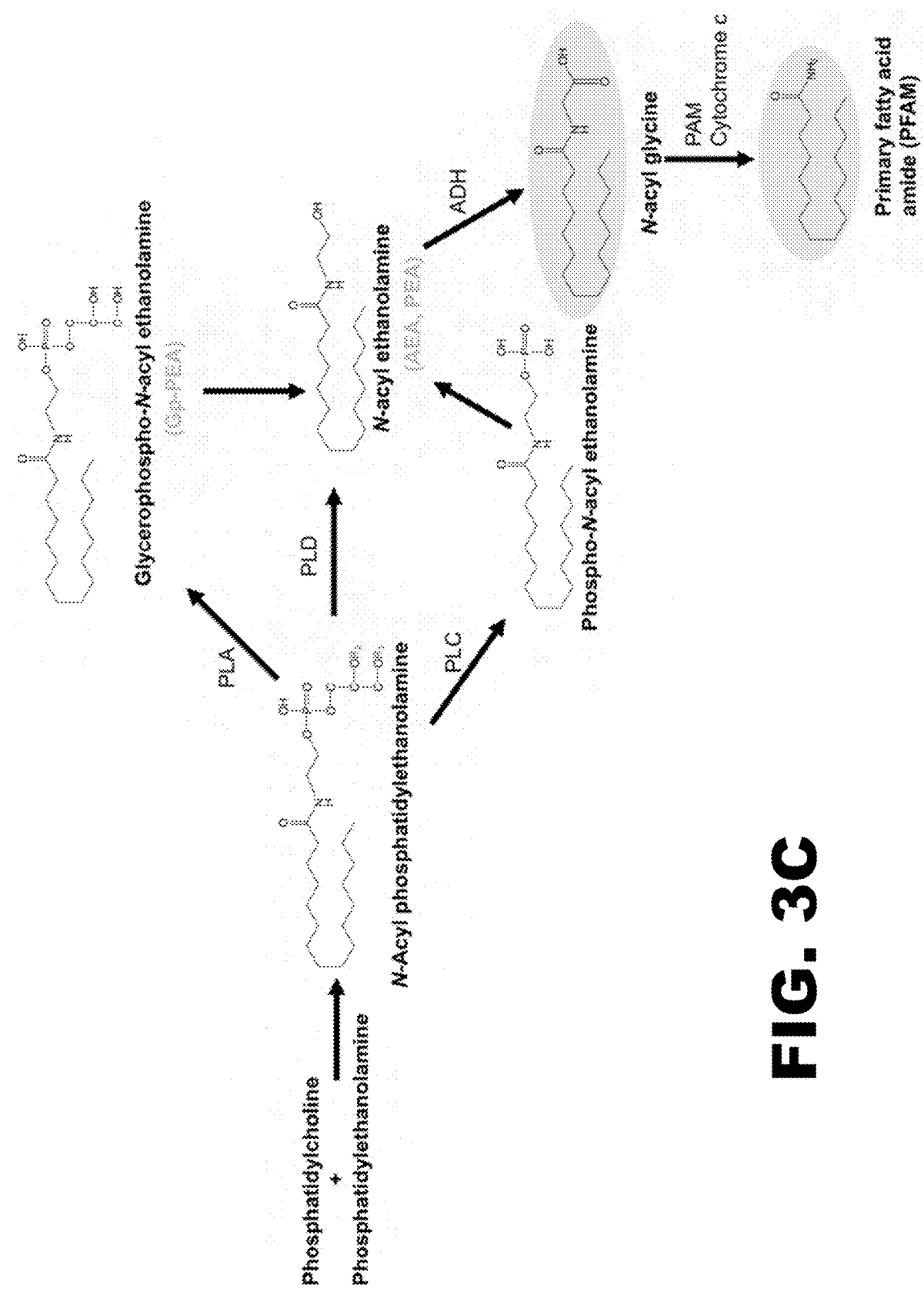
Figure 3D:
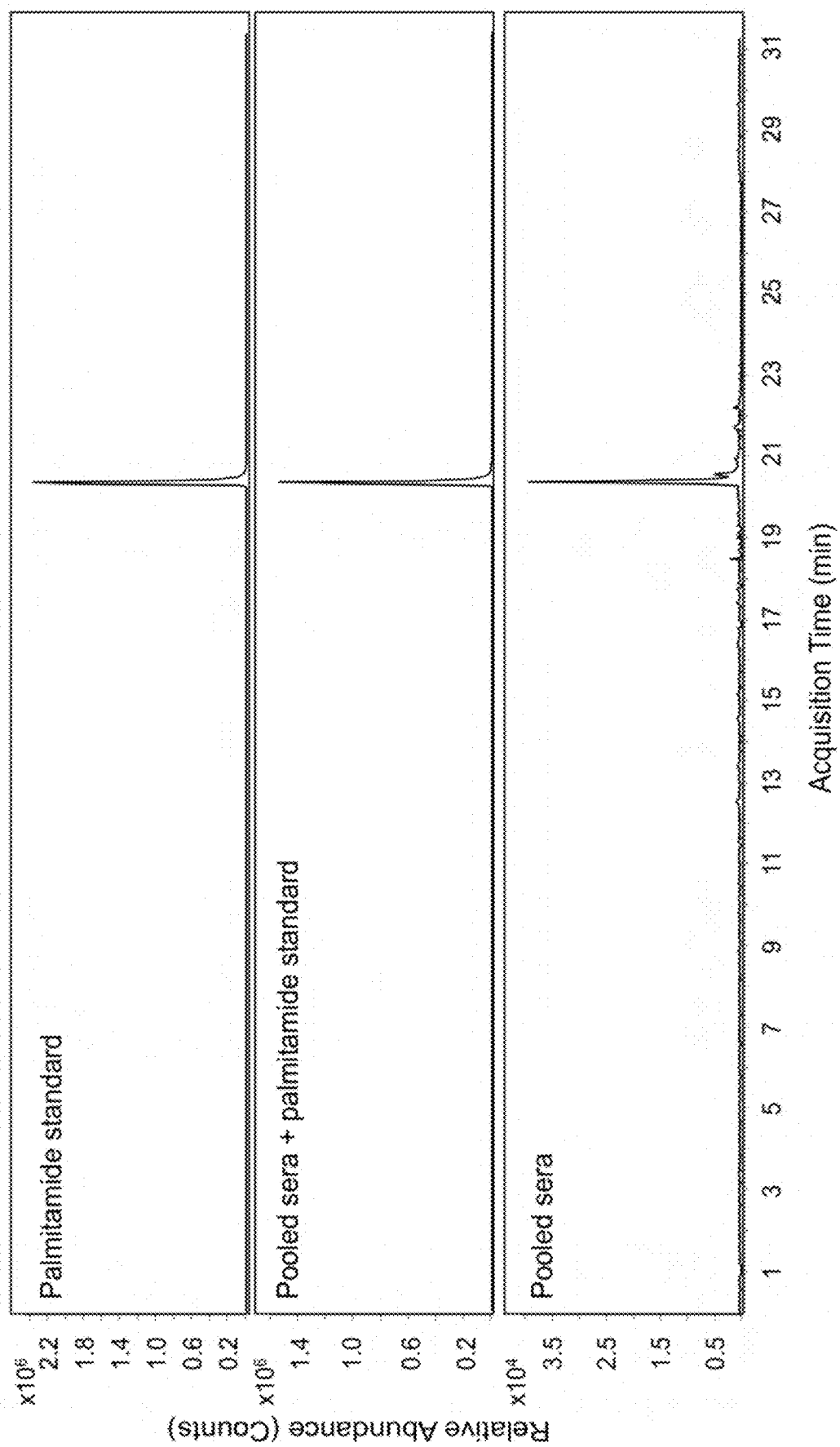
Figure 3E:
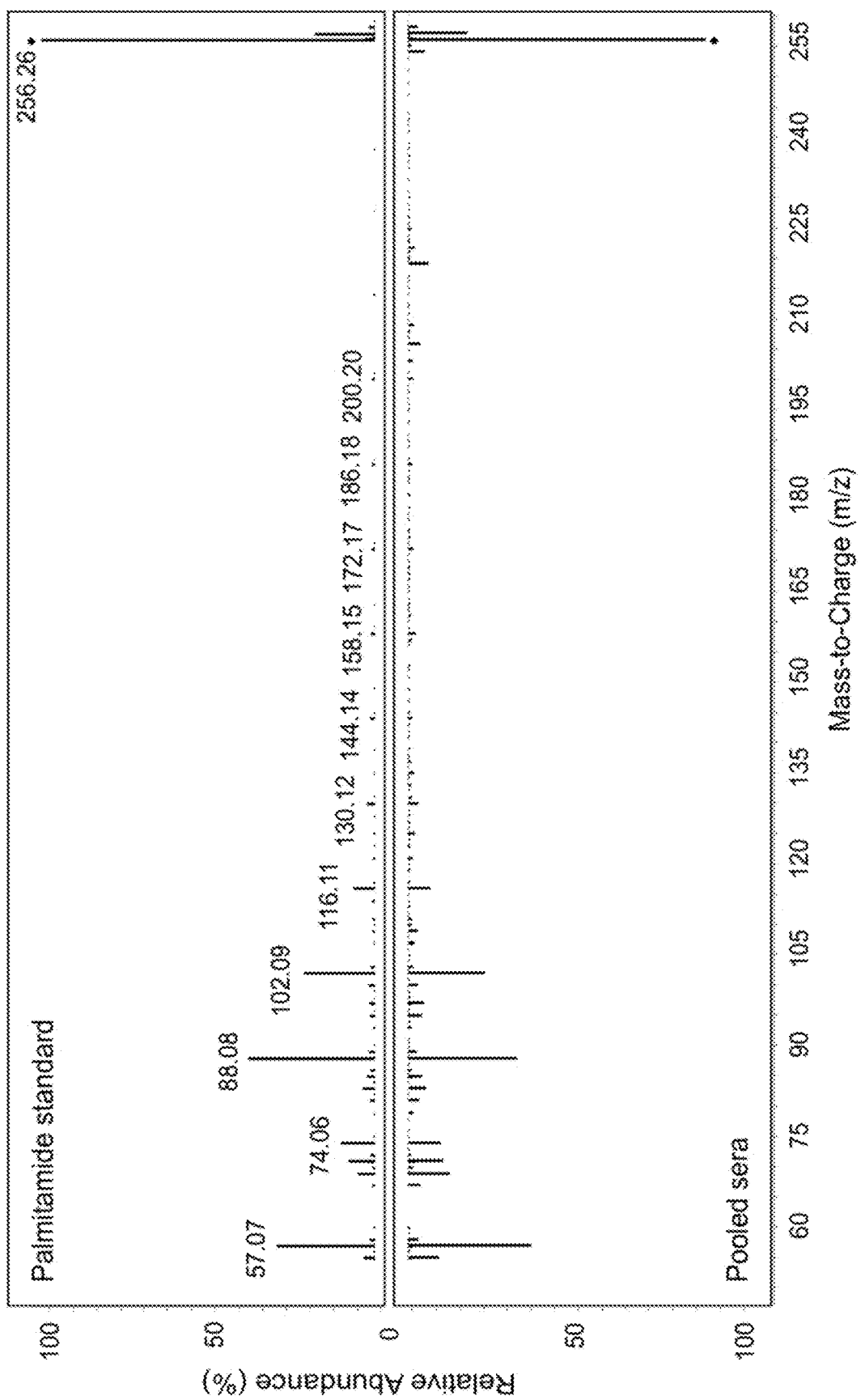
Figure 7A:
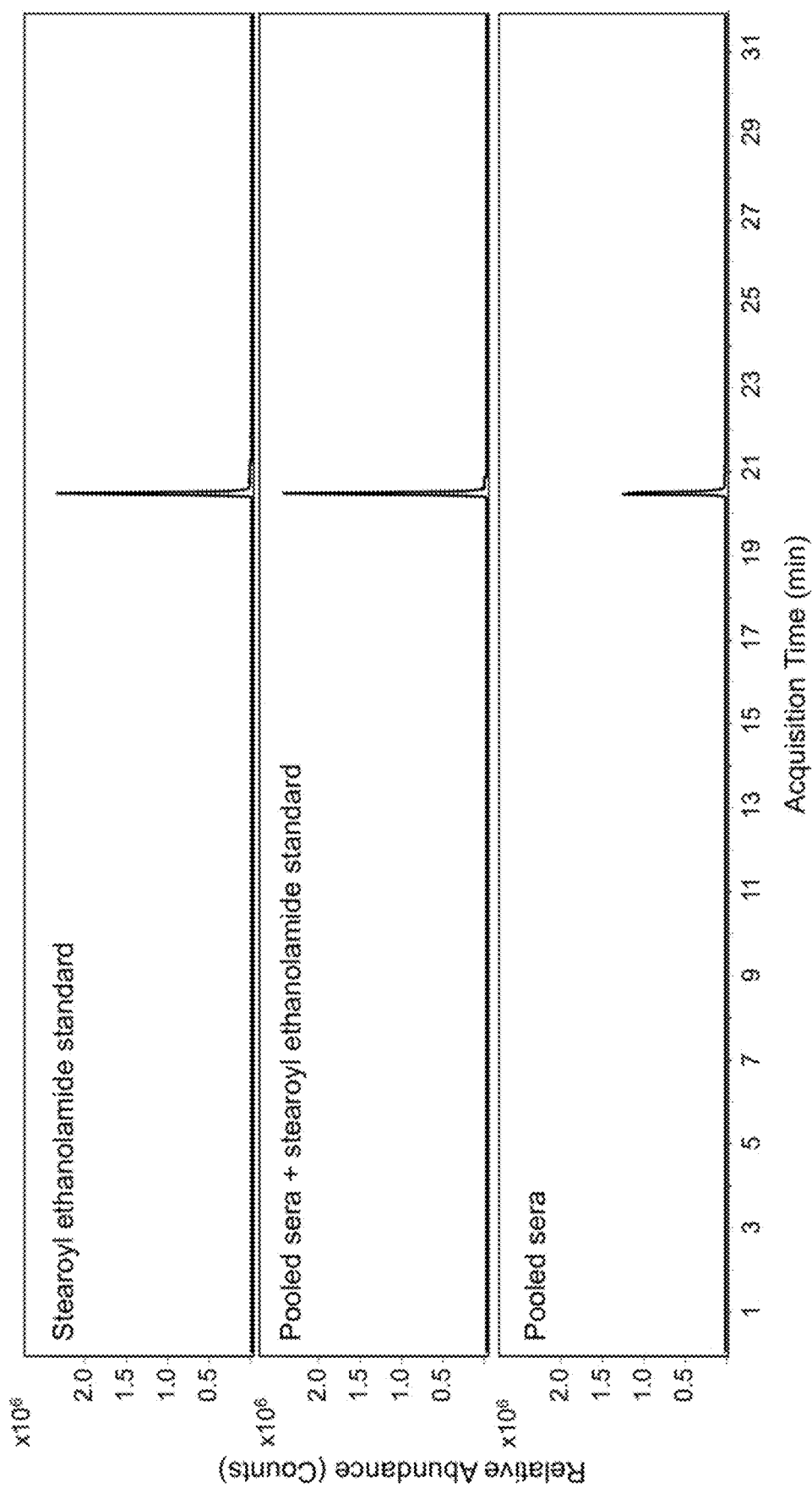
FIGS. 7A-B show data from level 1 identification of stearoyl ethanolamide. Confirmation of the structural identity of stearoyl ethanolamide was achieved by retention-time alignment (FIG. 7A) of authentic standard (top panel), authentic standard spiked in pooled patient sera (middle panel), and the targeted metabolite in pooled patient sera; and by comparison of MS/MS spectra (FIG. 7B) of the authentic standard (top) and the targeted metabolite in pooled patient sera (bottom). Retention-time alignments for stearoyl ethanolamide (FIG. 7A) were generated with extracted ion chromatograms for m/z 328.3204. MS/MS spectra for stearoyl ethanolamide were obtained with a collision energy of 20 eV.
Figure 7B:
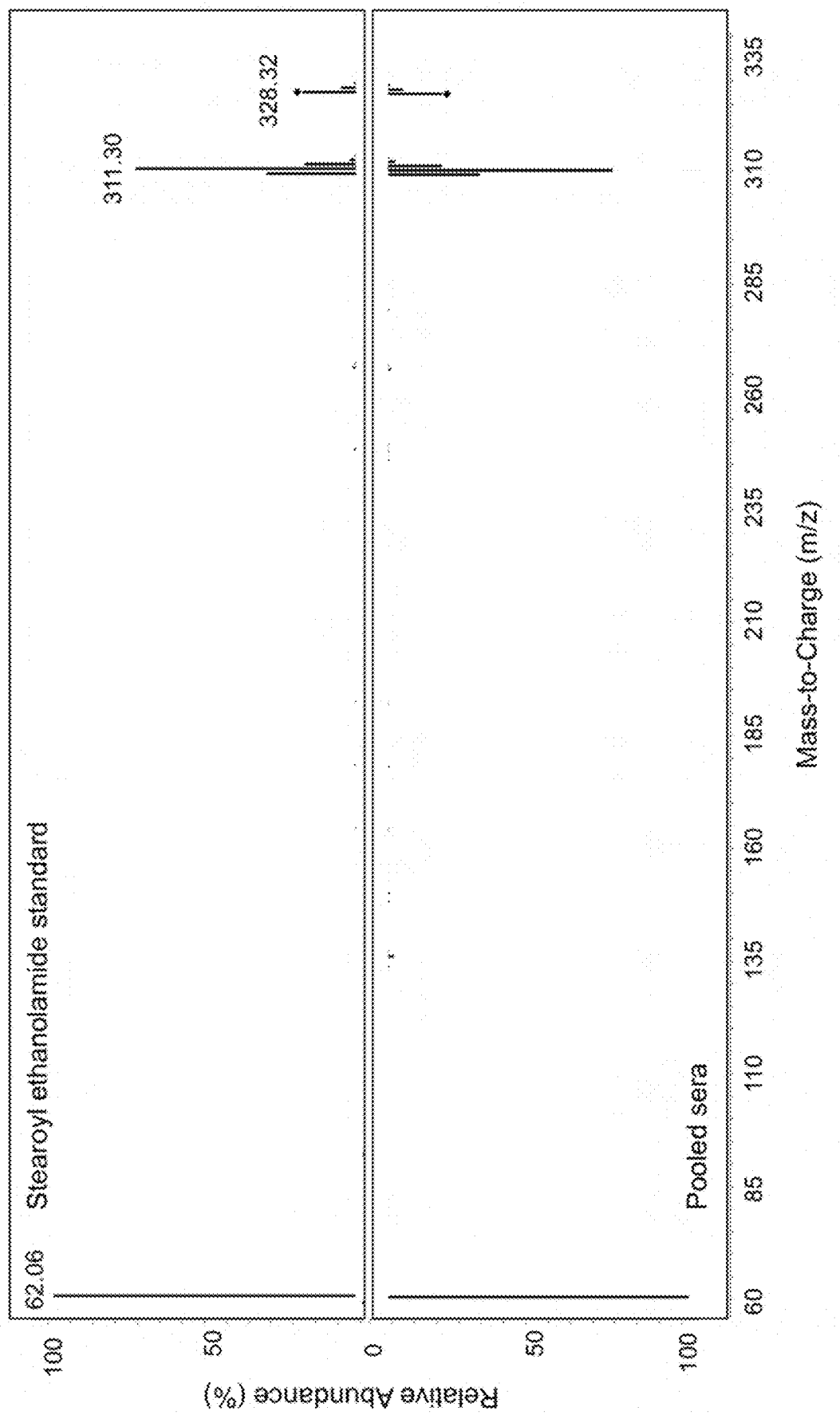
Figure 8A:
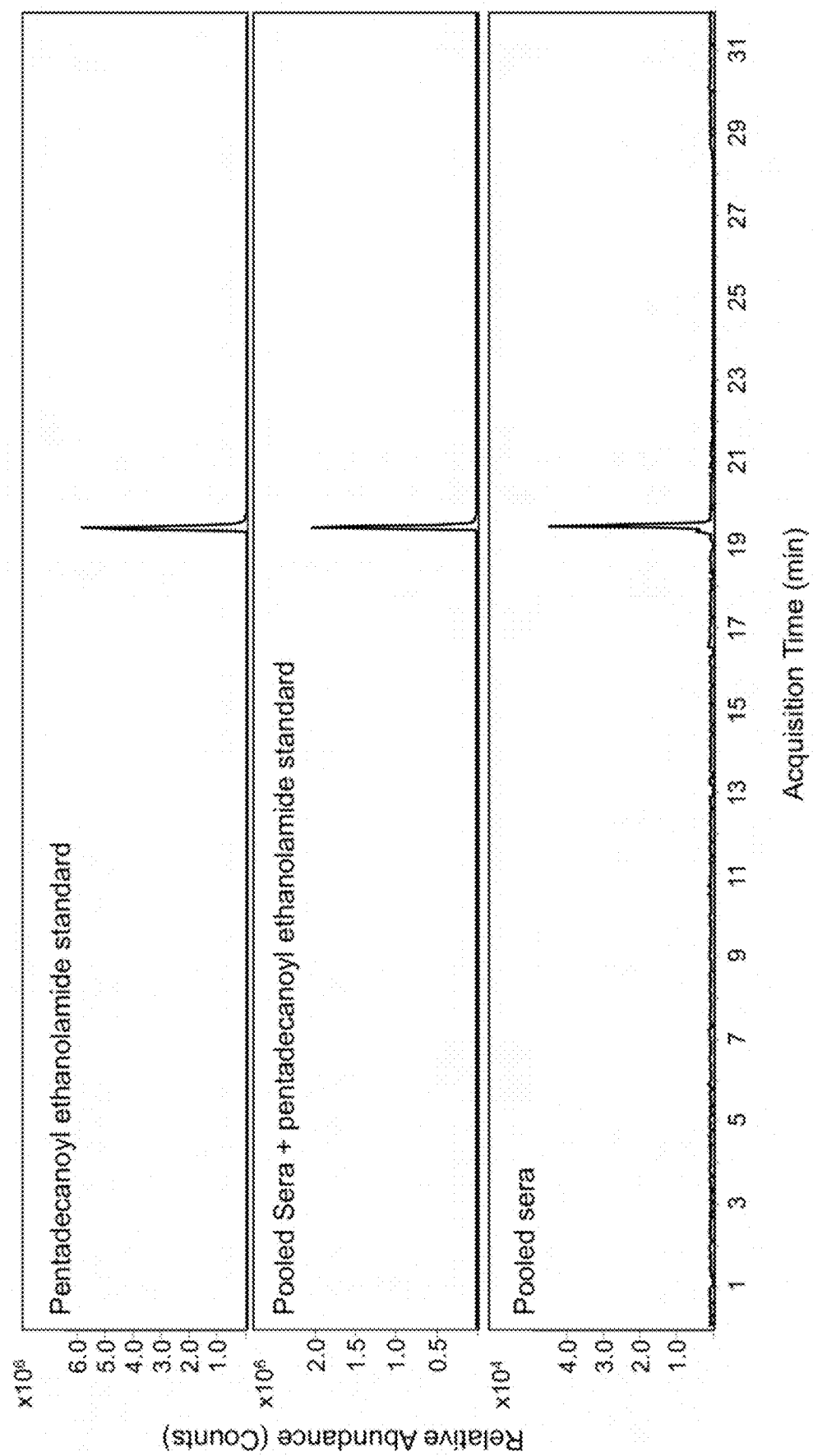
FIGS. 8A-B show data from level 1 identification of pentadecanoyl ethanolamide. Confirmation of the structural identity of pentadecanoyl ethanolamide was achieved by retention-time alignment (FIG. 8A) of authentic standard (top panel), authentic standard spiked in pooled patient sera (middle panel), and the targeted metabolite in pooled patient sera; and by comparison of MS/MS spectra (FIG. 8B) of the authentic standard (top) and the targeted metabolite in pooled patient sera (bottom). Retention-time alignments for pentadecanoyl ethanolamide (FIG. 8A) were generated with extracted ion chromatograms for m/z 286.2737. MS/MS spectra for pentadecanoyl ethanolamide were obtained with a collision energy of 20 eV.
Figure 8B:
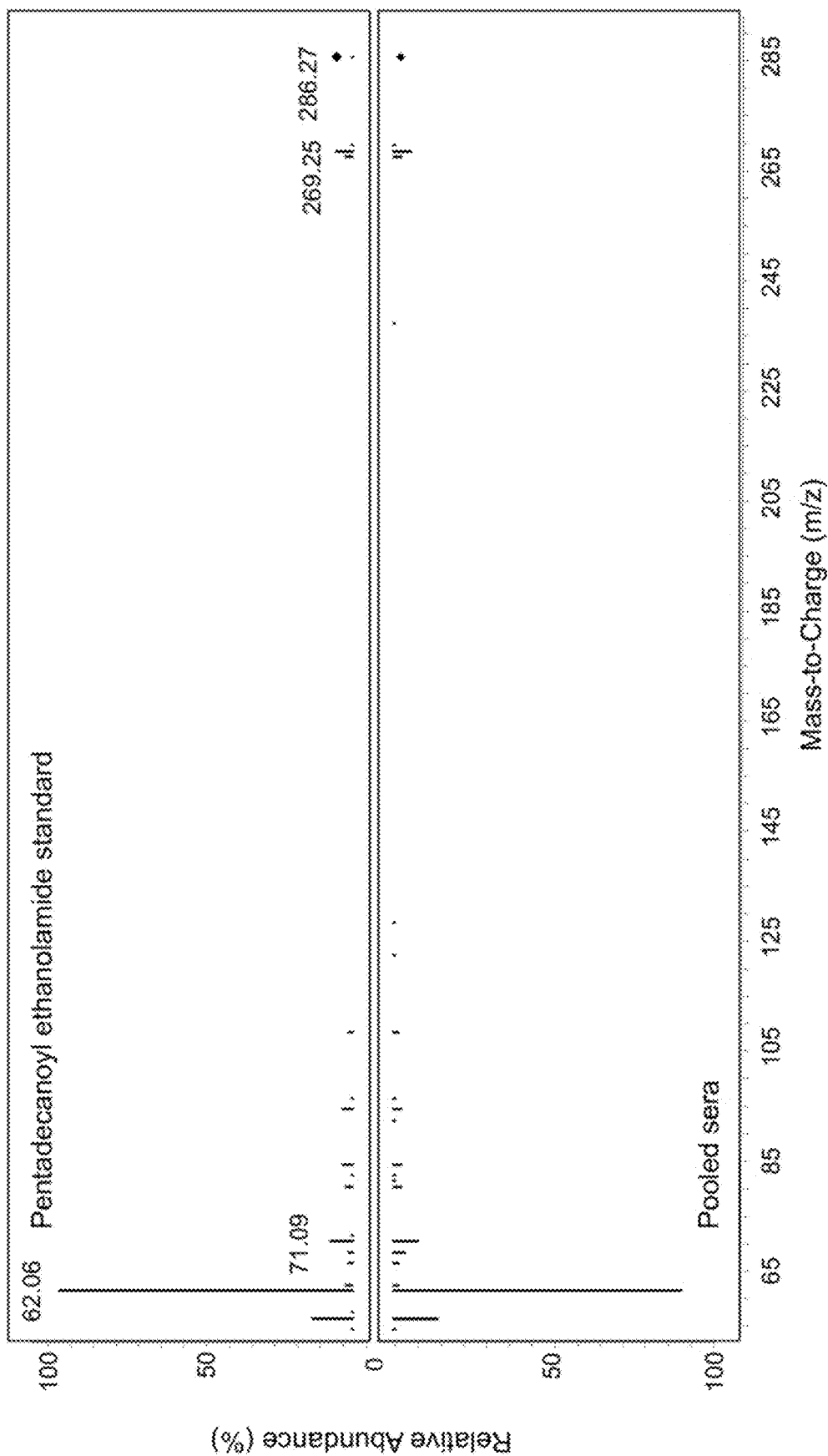
Figure 9A:
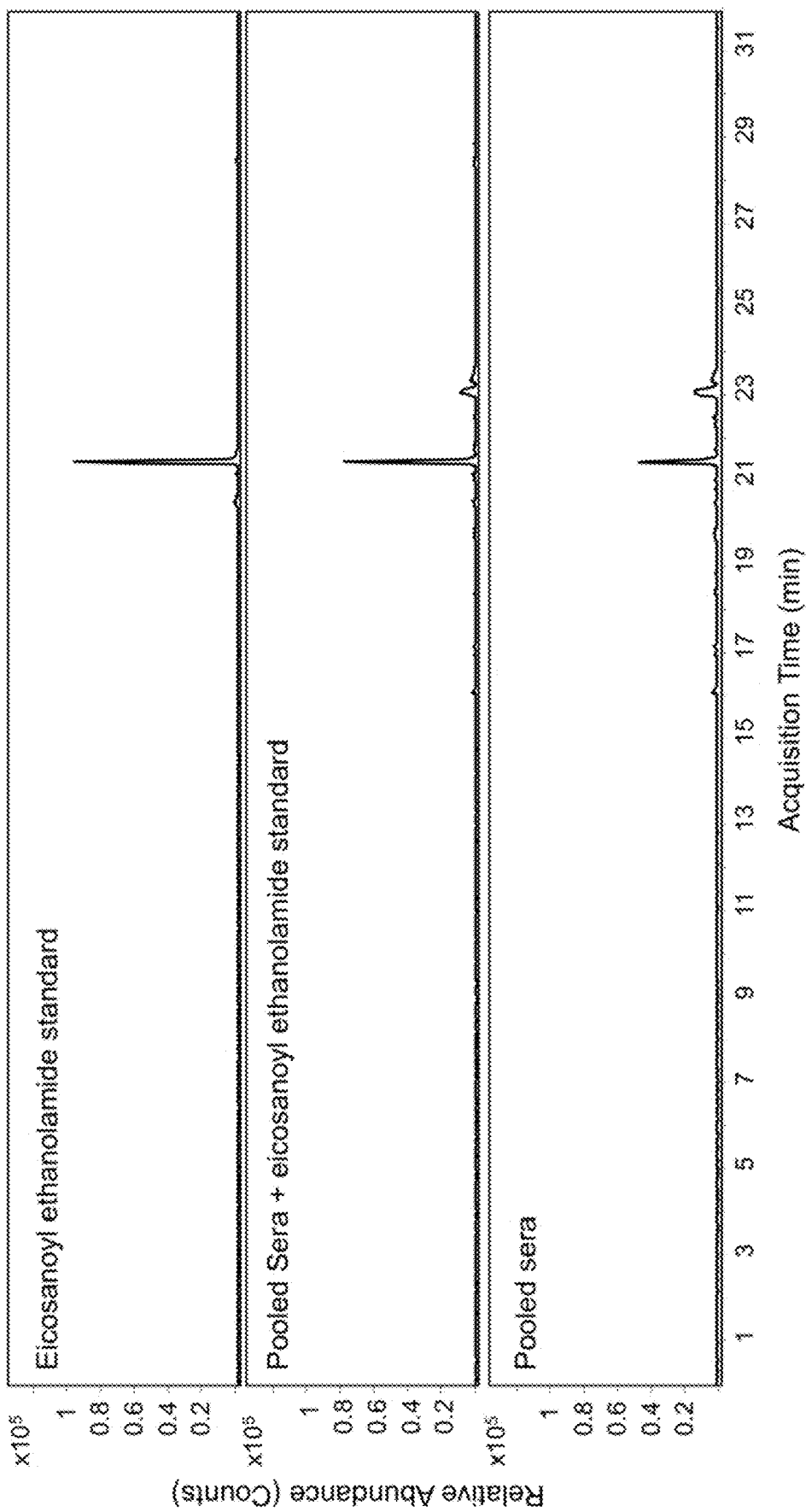
FIGS. 9A-B show data from level 1 identification of eicosanoyl ethanolamide. Confirmation of the structural identity of eicosanoyl ethanolamide was achieved by retention-time alignment (FIG. 9A) of authentic standard (top panel), authentic standard spiked in pooled patient sera (middle panel), and the targeted metabolite in pooled patient sera; and by comparison of MS/MS spectra (FIG. 9B) of the authentic standard (top) and the targeted metabolite in pooled patient sera (bottom). Retention-time alignments for eicosanoyl ethanolamide (FIG. 9A) were generated with extracted ion chromatograms for m/z 356.3517. MS/MS spectra for eicosanoyl ethanolamide were obtained with a collision energy of 20 eV.
Figure 9B:
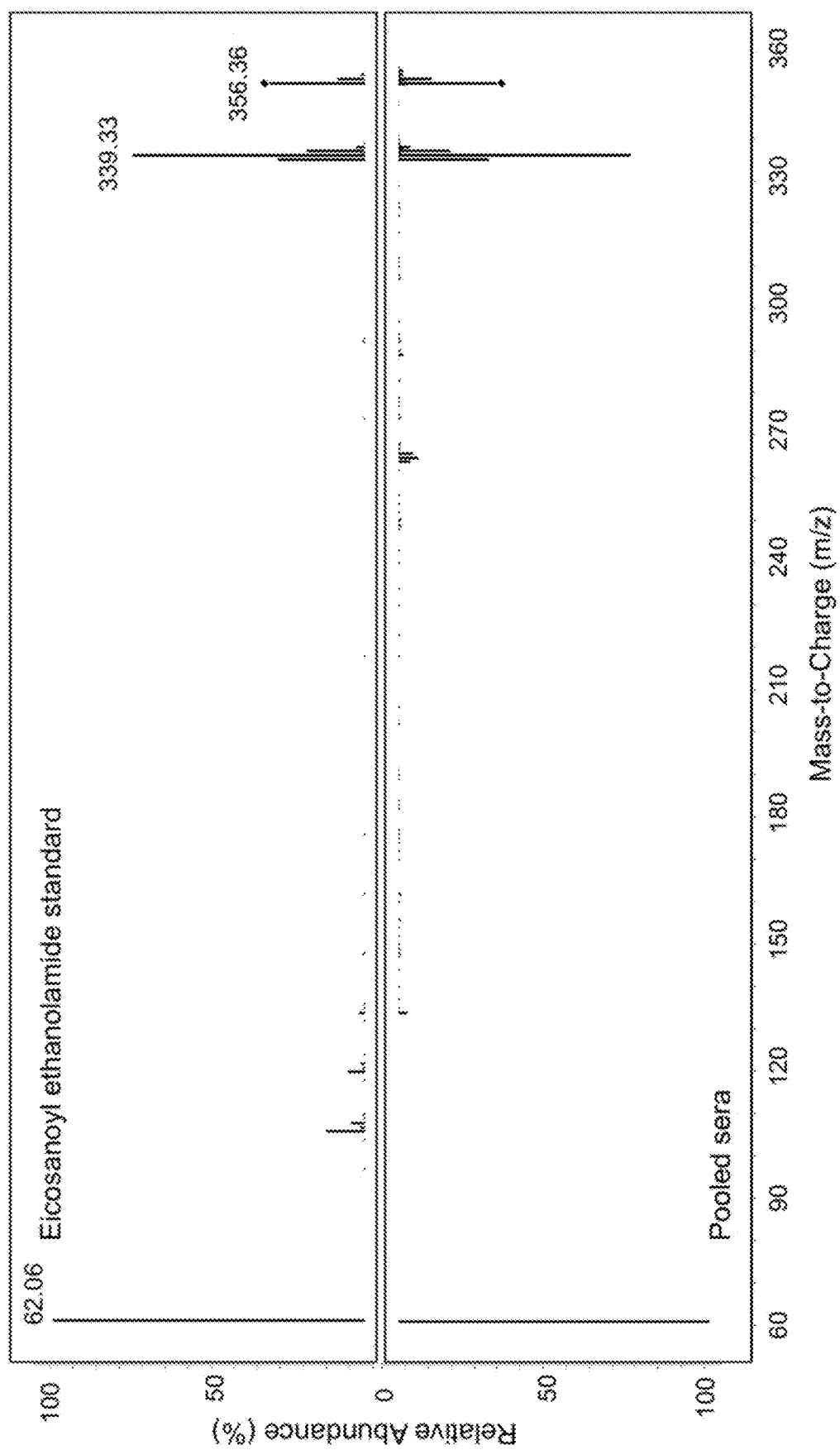
Figure 10A:
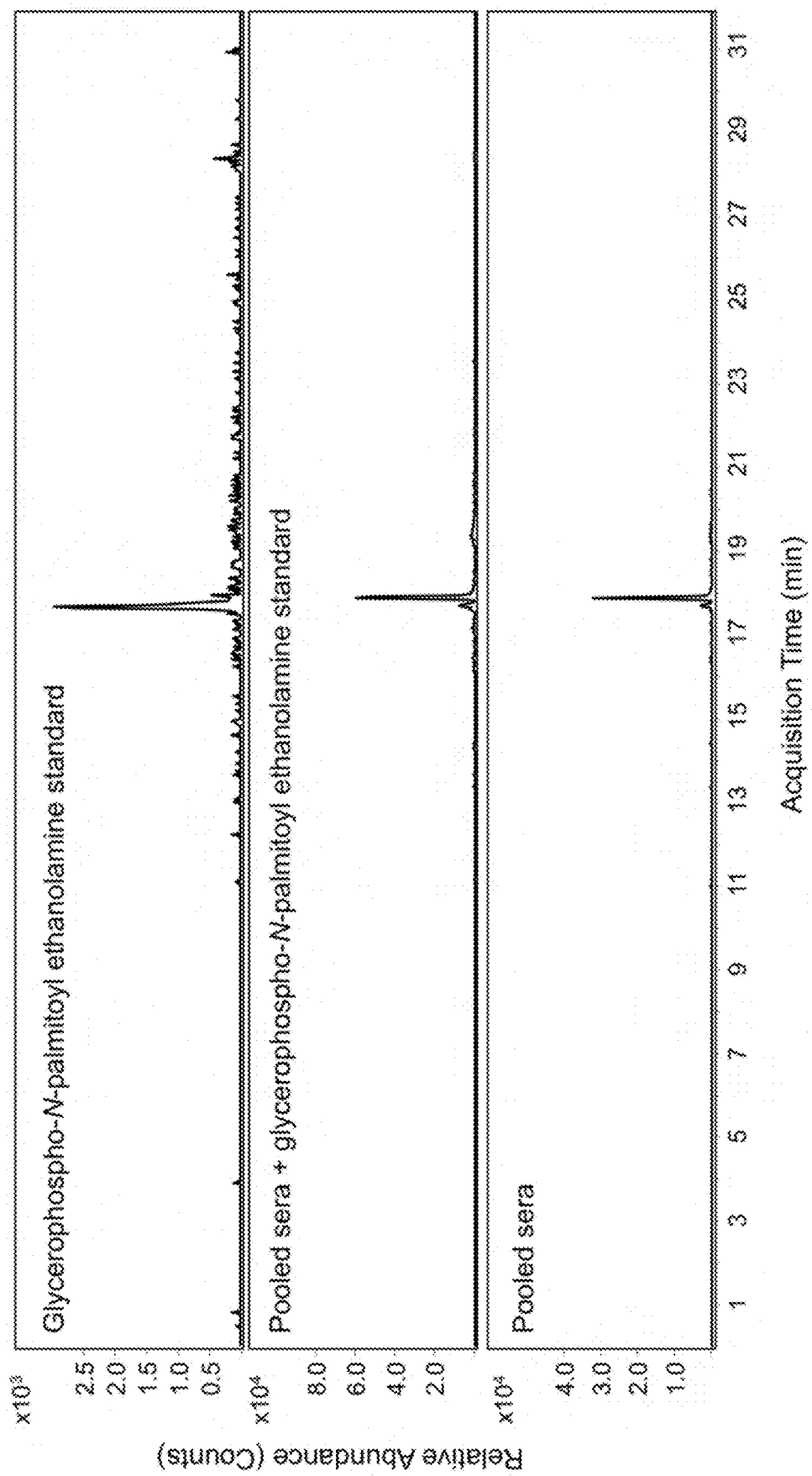
FIGS. 10A-B show data from level 1 identification of glycerophospho-N-palmitoyl ethanolamine. Confirmation of the structural identity of glycerophospho-N-palmitoyl ethanolamine was achieved by retention-time alignment (FIG. 10A) of authentic standard (top panel), authentic standard spiked in pooled patient sera (middle panel), and the targeted metabolite in pooled patient sera; and by comparison of MS/MS spectra (FIG. 10B) of the authentic standard (top) and the targeted metabolite in pooled patient sera (bottom). Retention-time alignments for glycerophospho-N-palmitoyl ethanolamine (FIG. 10A) were generated with extracted ion chromatograms for m/z 454.2923. MS/MS spectra for glycerophospho-N-palmitoyl ethanolamine were obtained with a collision energy of 20 eV.
Figure 10B:
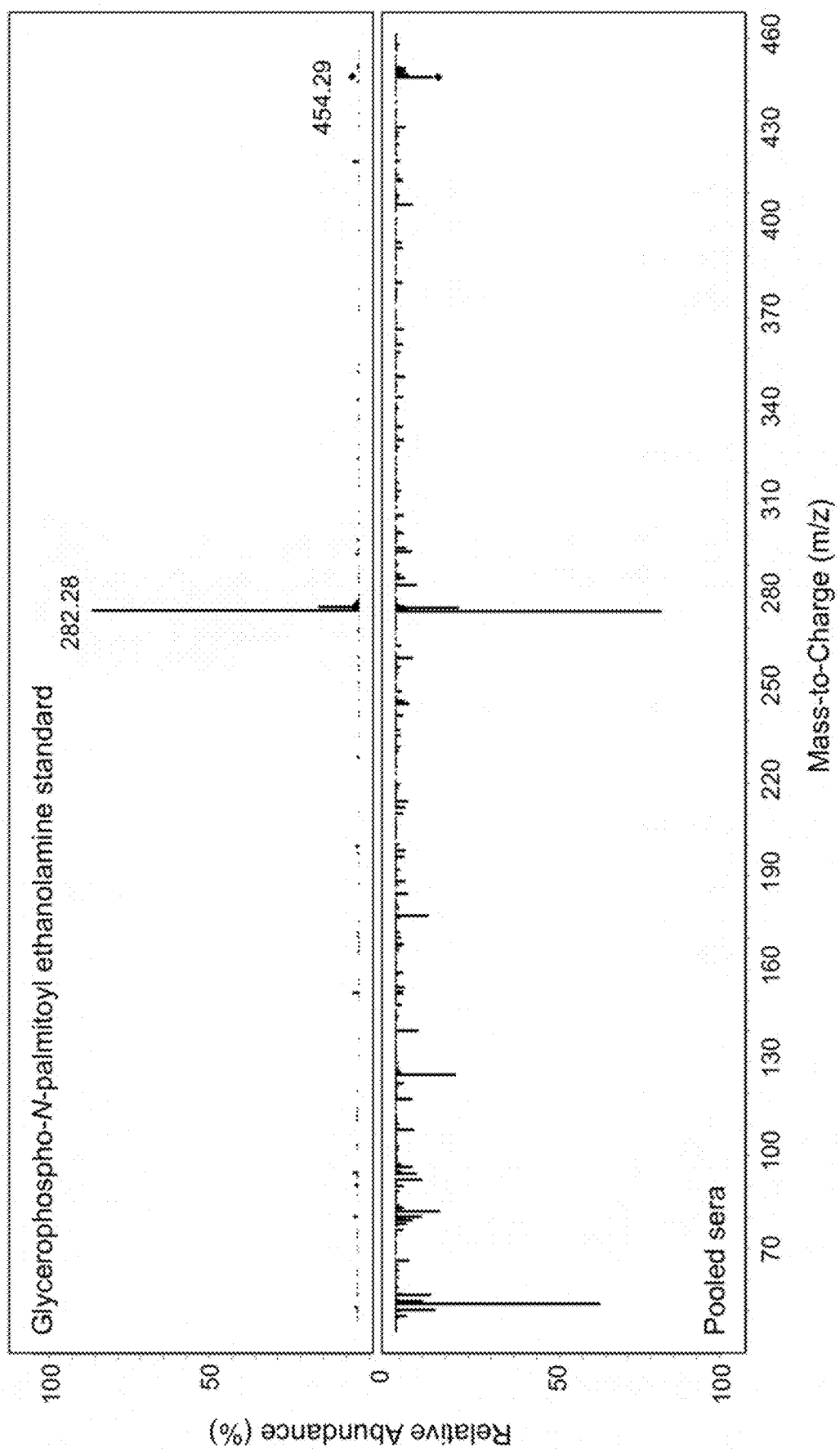
Figure 11A:
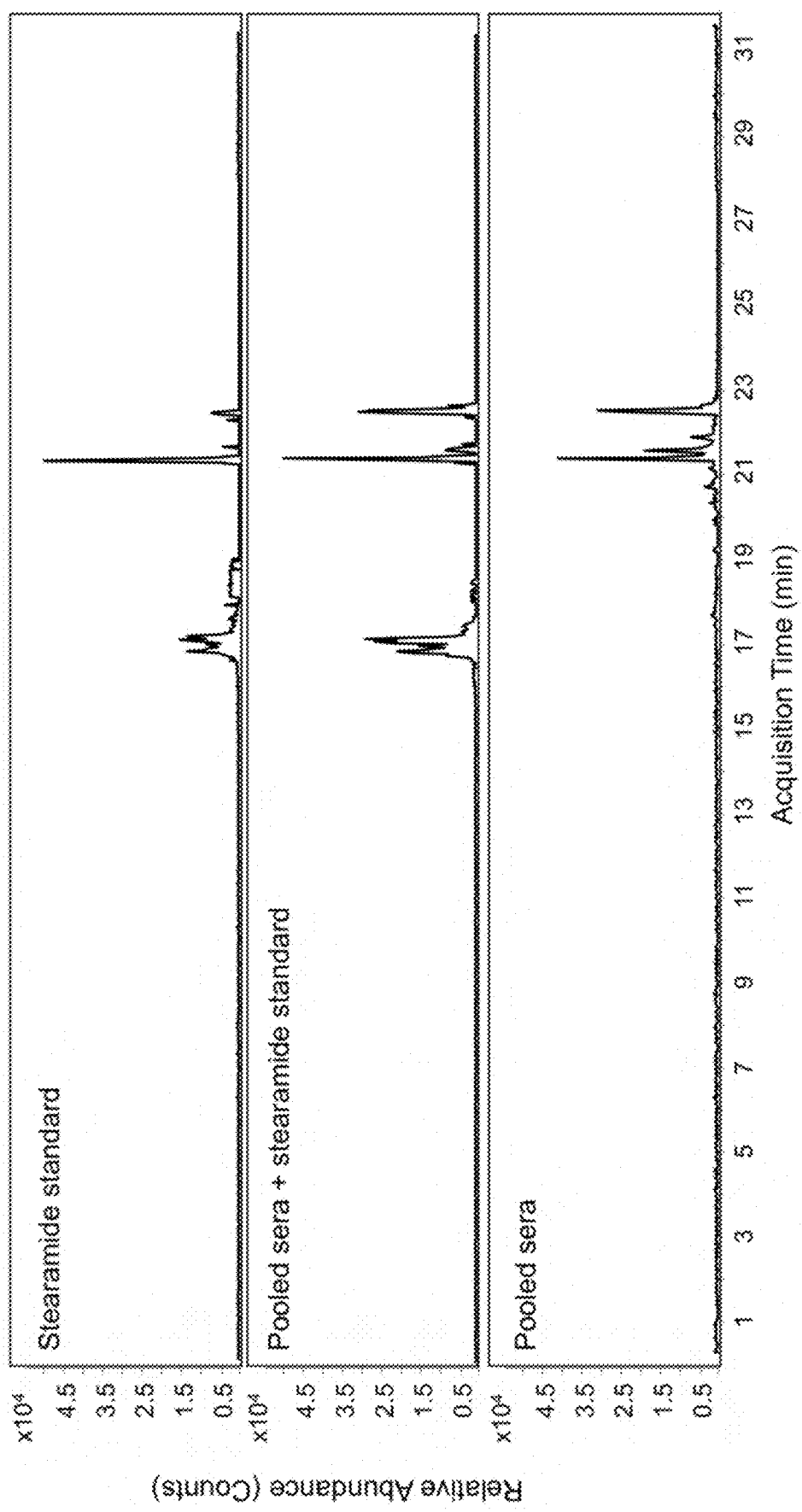
FIGS. 11A-B show data from level 1 identification of stearamide. Confirmation of the structural identity of stearamide was achieved by retention-time alignment (FIG. 11A) of authentic standard (top panel), authentic standard spiked in pooled patient sera (middle panel), and the targeted metabolite in pooled patient sera; and by comparison of MS/MS spectra (FIG. 11B) of the authentic standard (top) and the targeted metabolite in pooled patient sera (bottom). Retention-time alignments for stearamide (FIG. 11A) were generated with extracted ion chromatograms for m/z 284.2943. MS/MS spectra for stearamide were obtained with a collision energy of 20 eV.
Figure 11B:
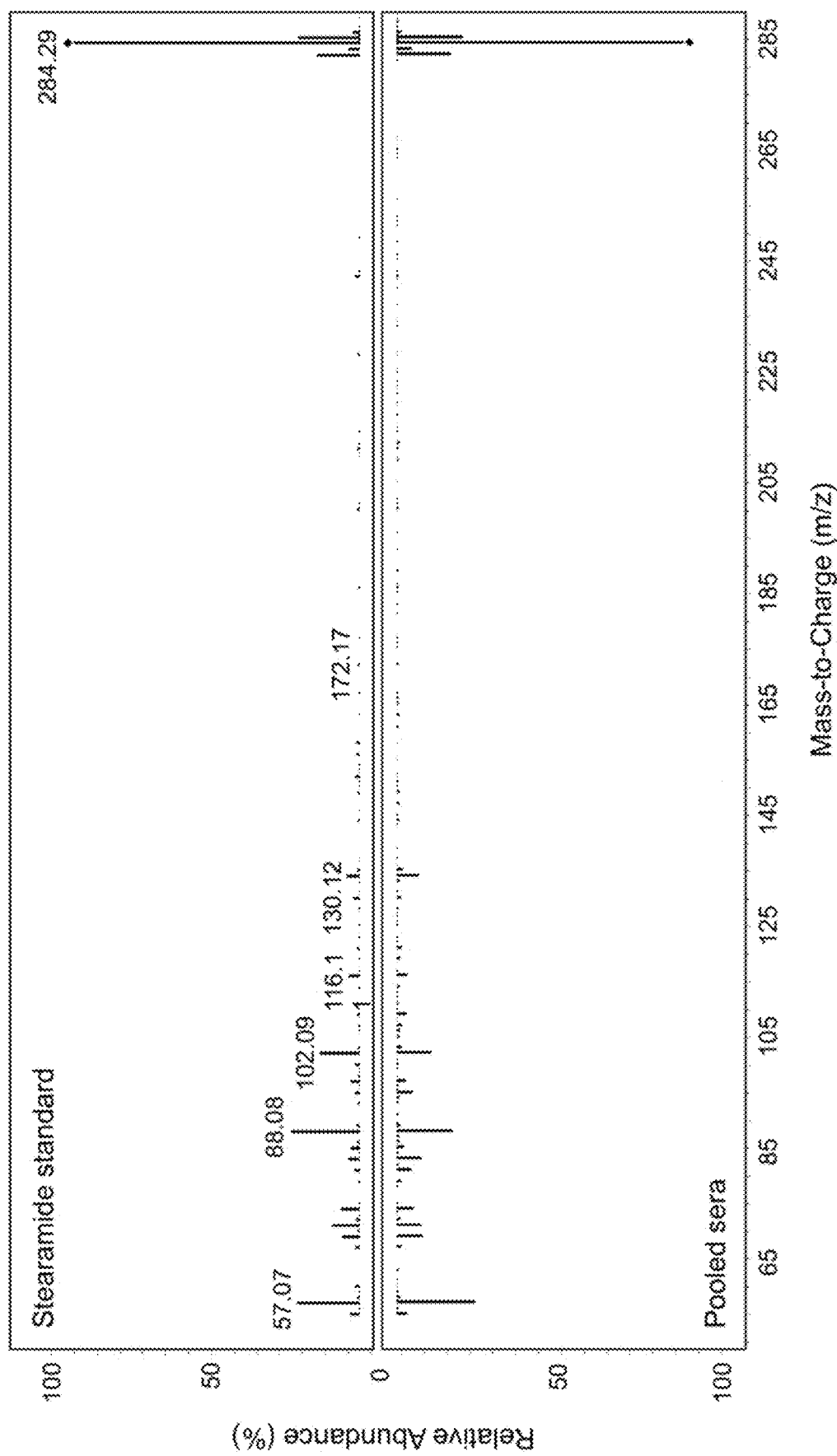
Figure 12A:
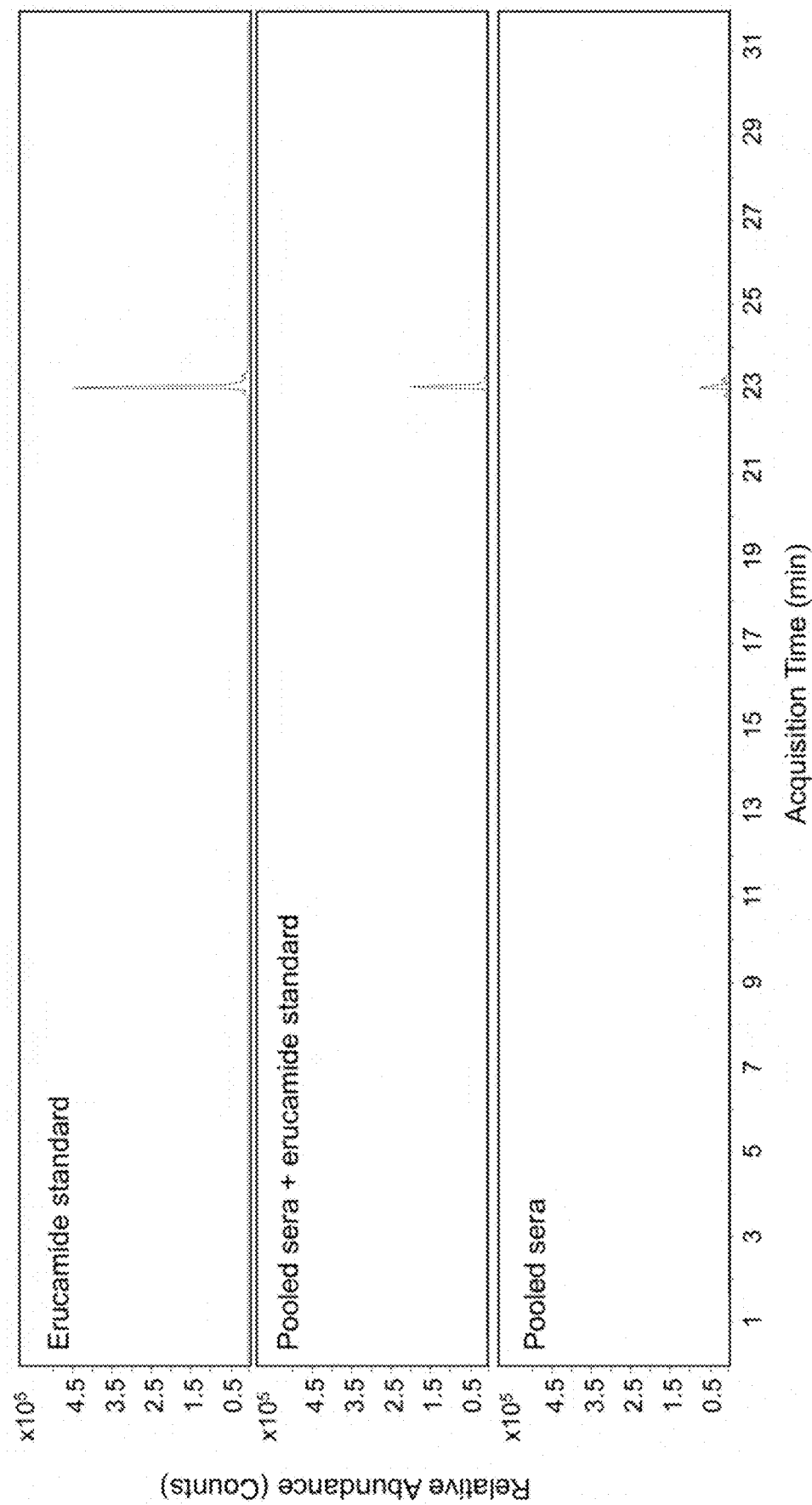
FIGS. 12A-B show data from level 1 identification of erucamide. Confirmation of the structural identity of erucamide was achieved by retention-time alignment (FIG. 12A) of authentic standard (top panel), authentic standard spiked in pooled patient sera (middle panel), and the targeted metabolite in pooled patient sera; and by comparison of MS/MS spectra (FIG. 12B) of the authentic standard (top) and the targeted metabolite in pooled patient sera (bottom). Retention-time alignments for erucamide (FIG. 12A) were generated with extracted ion chromatograms for m/z 338.3430. MS/MS spectra for erucamide were obtained with a collision energy of 20 eV.
Figure 12B:
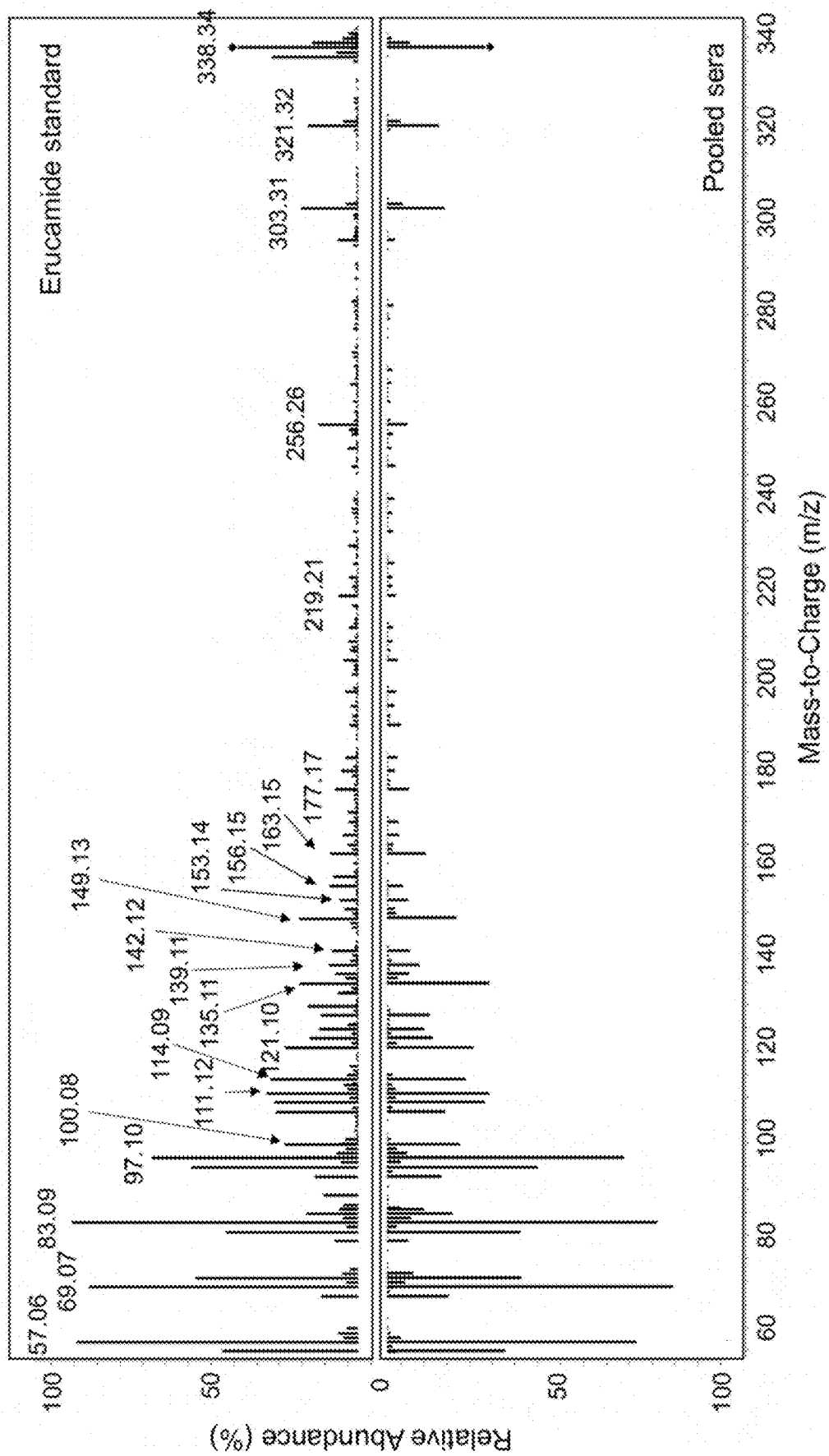

Elucidation of Altered NAE Metabolism:

The prediction of altered metabolic pathways was based on the presumptive structural identification of the early Lyme disease versus STARI differentiating MFs. Thus, to further define the metabolic differences between these two patient groups, structural confirmation of selected MFs was undertaken. Two MFs that displayed relatively large abundance differences (m/z 300.2892, RT 19.66; and m/z 328.3204, RT 20.72) were putatively identified as sphingosine-C18 or 3-ketosphinganine, and sphingosine-C20 or N,N-dimethyl sphingosine, respectively. However, both of these MFs had alternative predicted structures of palmitoyl ethanolamide and stearoyl ethanolamide, respectively. The interrogation of authentic standards against these two serum MFs revealed RTs and MS/MS spectra that identified the m/z 300.2892 and m/z 328.3204 products as palmitoyl ethanolamide (FIGS. 3A and 3B) and stearoyl ethanolamide (FIG. 7), respectively. These two products, as well as other NAEs, are derived from phosphatidylethanolamine and phosphatidylcholine, and represent a class of structures termed endocannabinoids and endocannabinoid-like (29) (FIG. 3C). Further analysis of the 122 MFs identified five additional MFs with a predicted structure that mapped to the NAE pathway. Specifically, MF m/z 286.2737, RT 19.08 was putatively identified as a sphingosine-C17 or pentadecanoyl ethanolamide, and was confirmed to be the latter (FIG. 8). MF m/z 356.3517, RT 21.67 was putatively identified and confirmed to be eicosanoyl ethanolamide (FIG. 9), and MF m/z 454.2923, RT 18.08 was confirmed to be glycerophospho-N-palmitoyl ethanolamine (FIG. 10), which is an intermediate in the formation of palmitoyl ethanolamide. A second group of lipids, the PFAMs that act as signaling molecules and that are potentially associated with the metabolism of NAEs were also identified as having significant relative abundance differences between the early Lyme disease and STARI patient samples. Specifically, MFs m/z 256.2632, RT 20.08; m/z 284.2943, RT 21.15; and m/z 338.3430, RT 22.14 were confirmed to be palmitamide (FIG. 3D and FIG. 3E), stearamide (FIG. 11) and erucamide (FIG. 12), respectively.

Figure 13A:
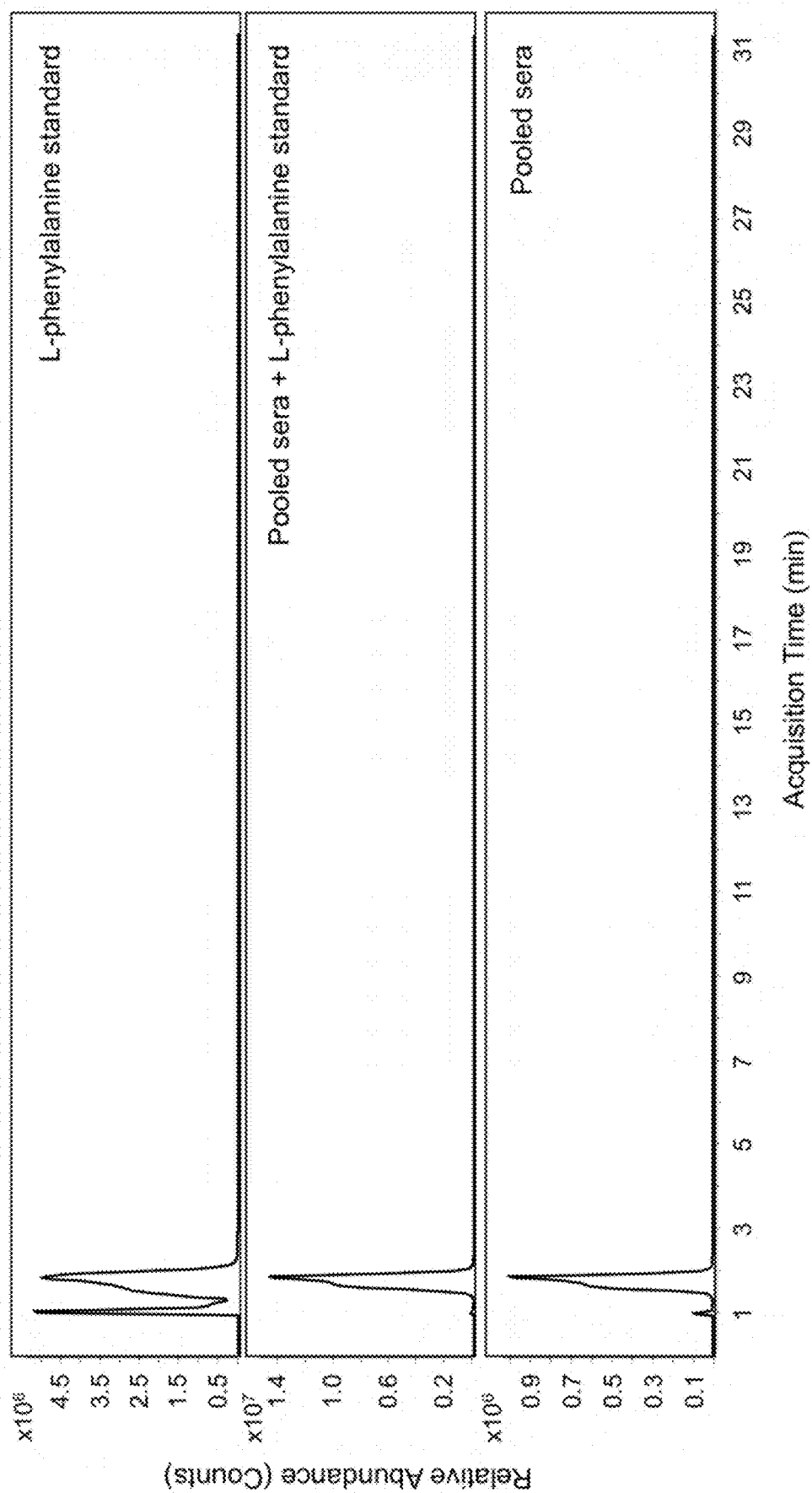
FIGS. 13A-B show data from level 1 identification of L-phenylalanine. Confirmation of the structural identity of L-phenylalanine was achieved by retention-time alignment (FIG. 13A) of authentic standard (top panel), authentic standard spiked in pooled patient sera (middle panel), and the targeted metabolite in pooled patient sera; and by comparison of MS/MS spectra (FIG. 13B) of the authentic standard (top) and the targeted metabolite in pooled patient sera (bottom). Retention-time alignments for L-phenylalanine (FIG. 13A) were generated with extracted ion chromatograms for m/z 166.0852. MS/MS spectra for L-phenylalanine were obtained with a collision energy of 20 eV.
Figure 13B:
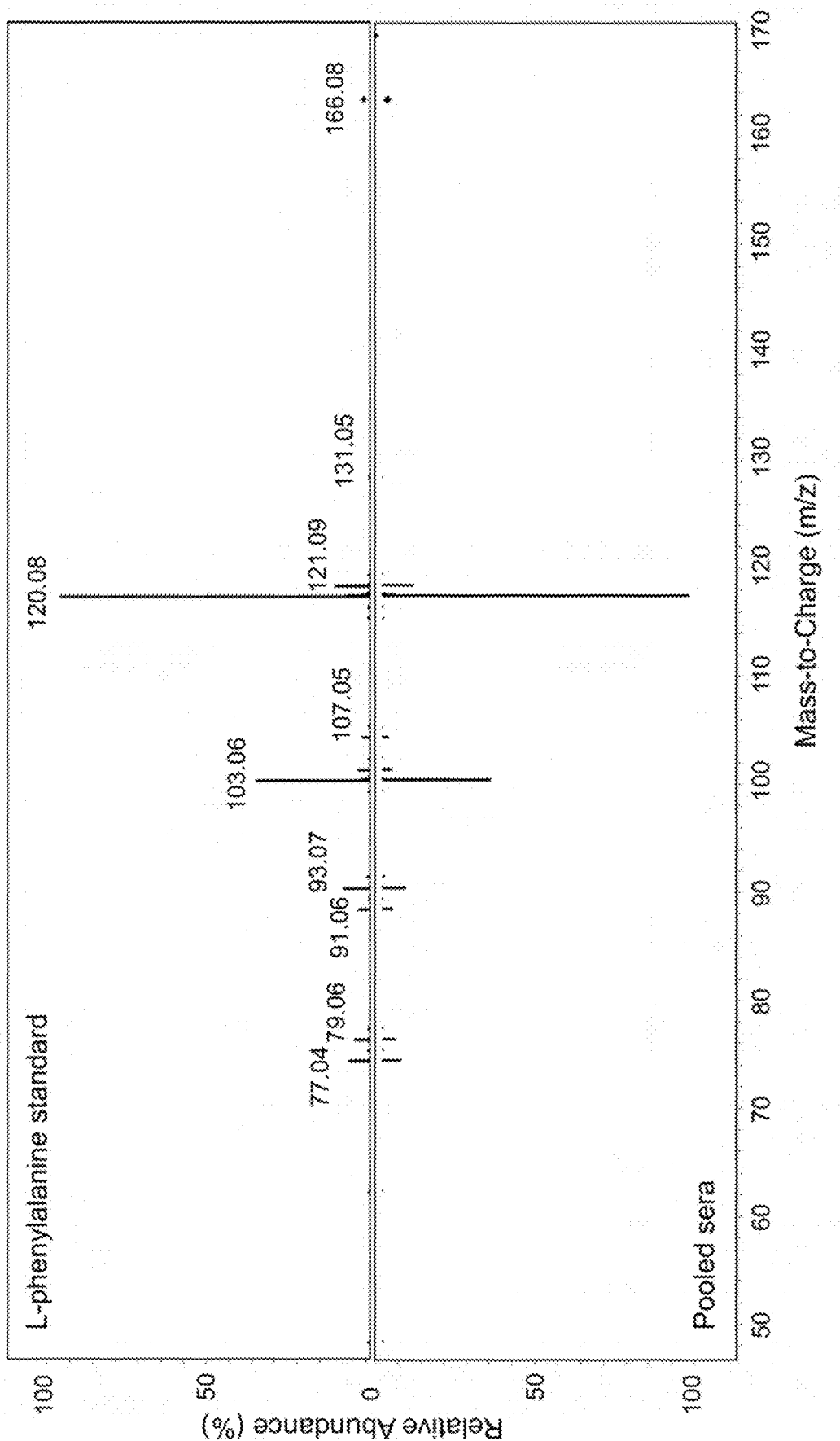
Figure 14A:
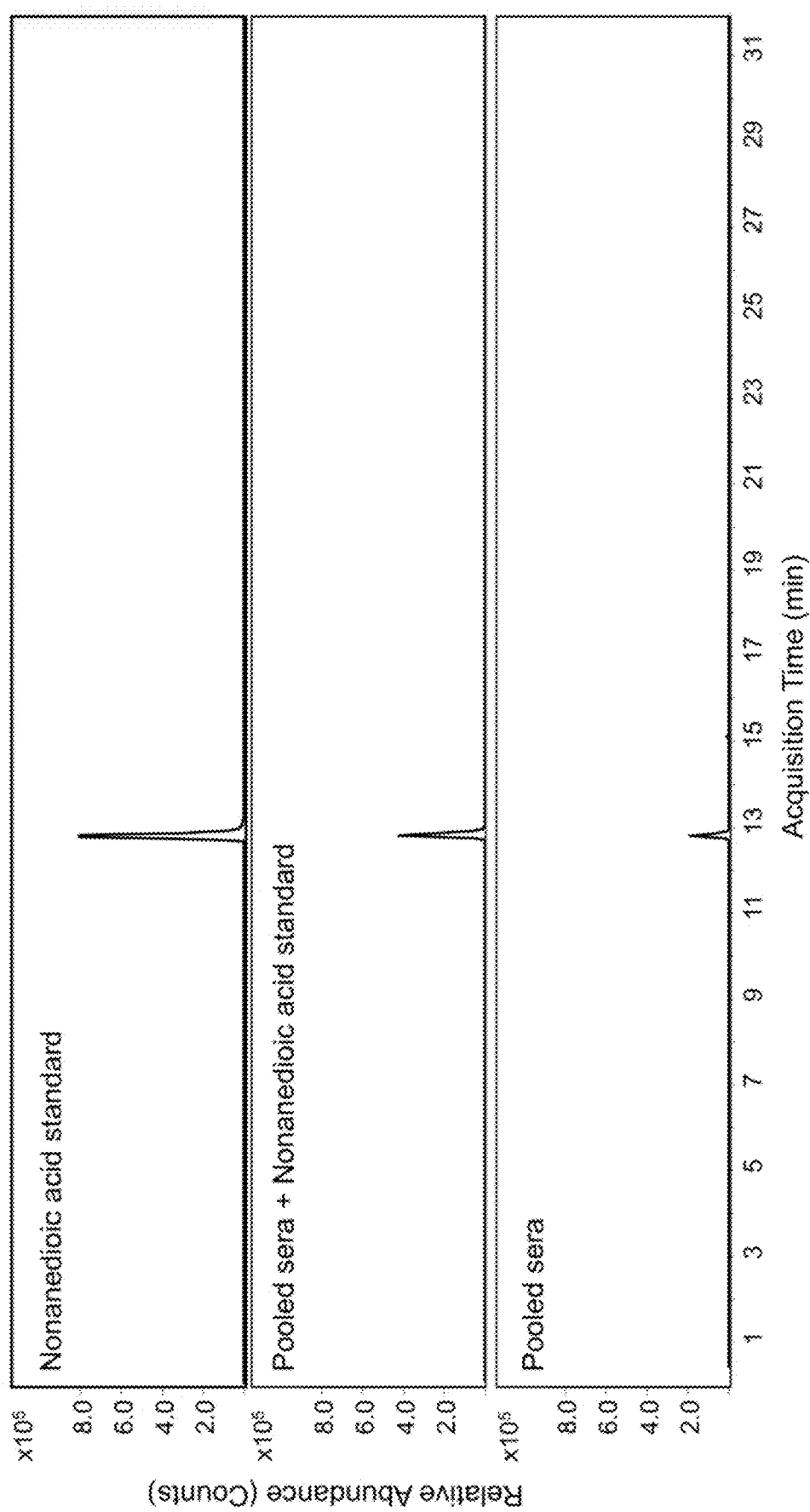
FIGS. 14A-B show data from level 1 identification of nonanedioic acid. Confirmation of the structural identity of nonanedioic acid was achieved by retention-time alignment (FIG. 14A) of authentic standard (top panel), authentic standard spiked in pooled patient sera (middle panel), and the targeted metabolite in pooled patient sera; and by comparison of MS/MS spectra (FIG. 14B) of the authentic standard (top) and the targeted metabolite in pooled patient sera (bottom). Retention-time alignments for nonanedioic acid (FIG. 14A) were generated with extracted ion chromatograms for m/z 189.1122. MS/MS spectra for nonanedioic acid were obtained with a collision energy of 10 eV.
Figure 14B:
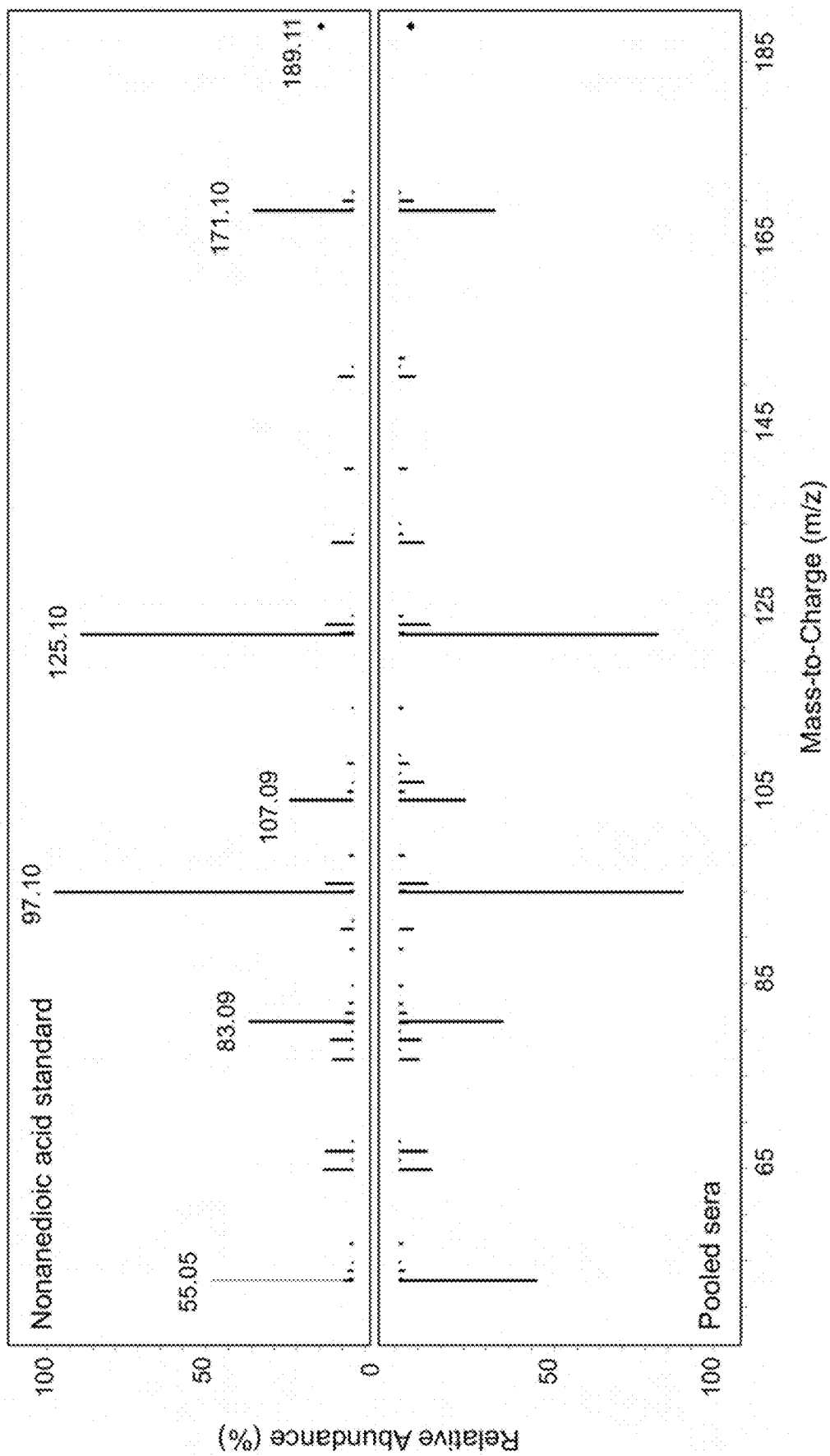
Figure 15A:
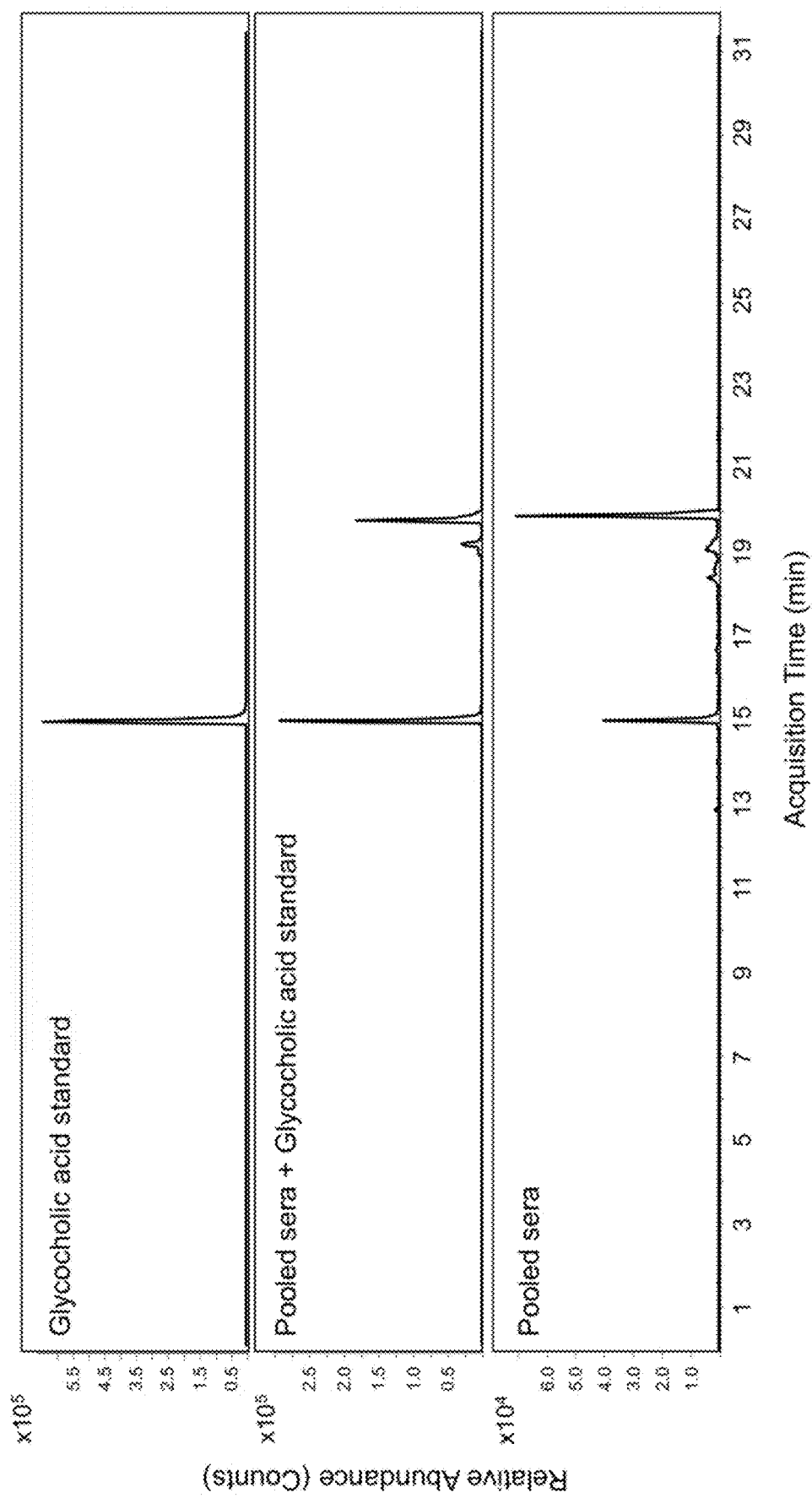
FIGS. 15A-B show data from level 1 identification of glycocholic acid. Confirmation of the structural identity of glycocholic acid was achieved by retention-time alignment (FIG. 15A) of authentic standard (top panel), authentic standard spiked in pooled patient sera (middle panel), and the targeted metabolite in pooled patient sera; and by comparison of MS/MS spectra (FIG. 15B) of the authentic standard (top) and the targeted metabolite in pooled patient sera (bottom). Retention-time alignments for glycocholic acid (FIG. 15A) were generated with extracted ion chromatograms for m/z 466.3152. MS/MS spectra for glycocholic acid were obtained with a collision energy of 20 eV.
Figure 15B:
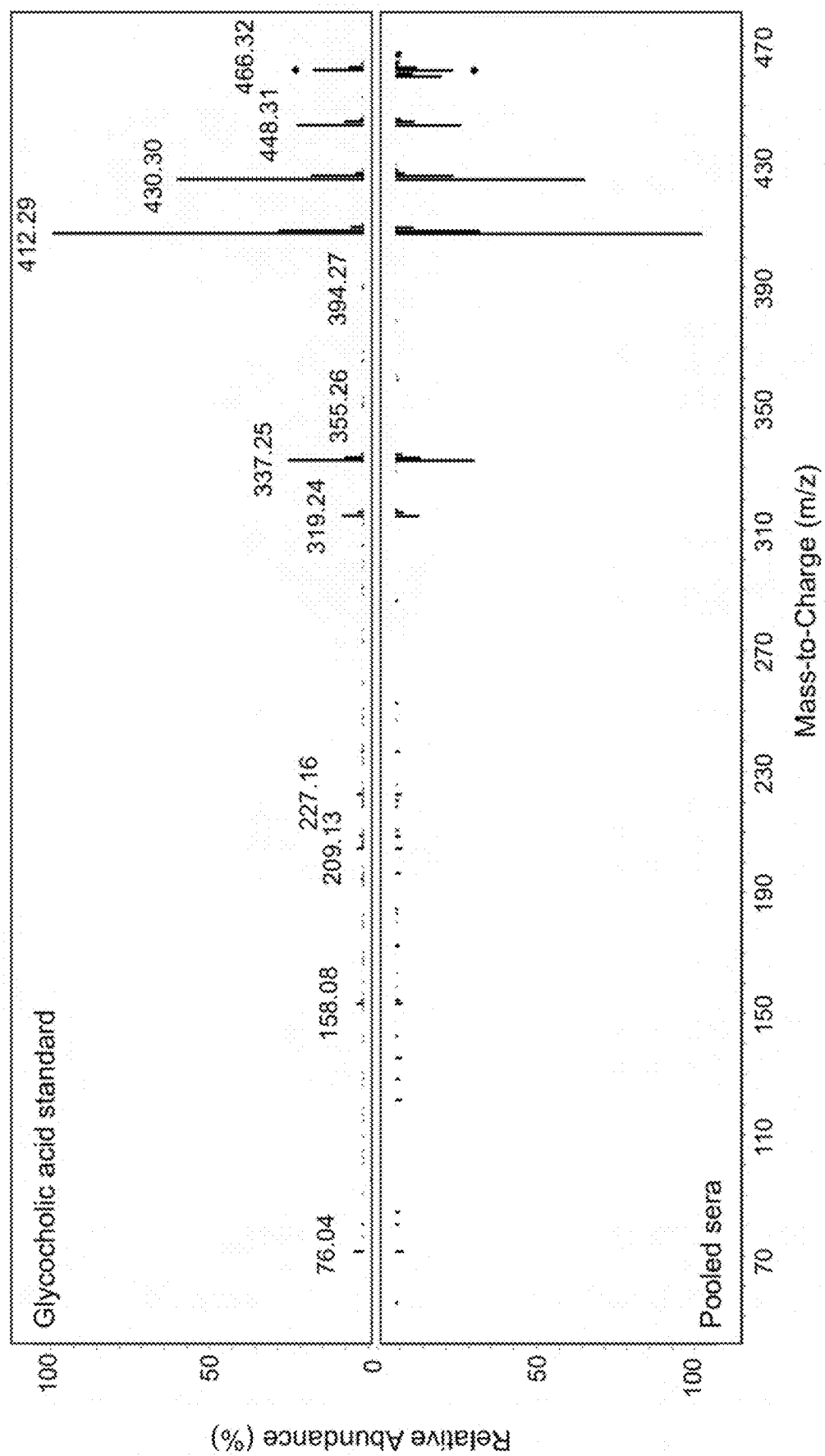
Figure 16A:
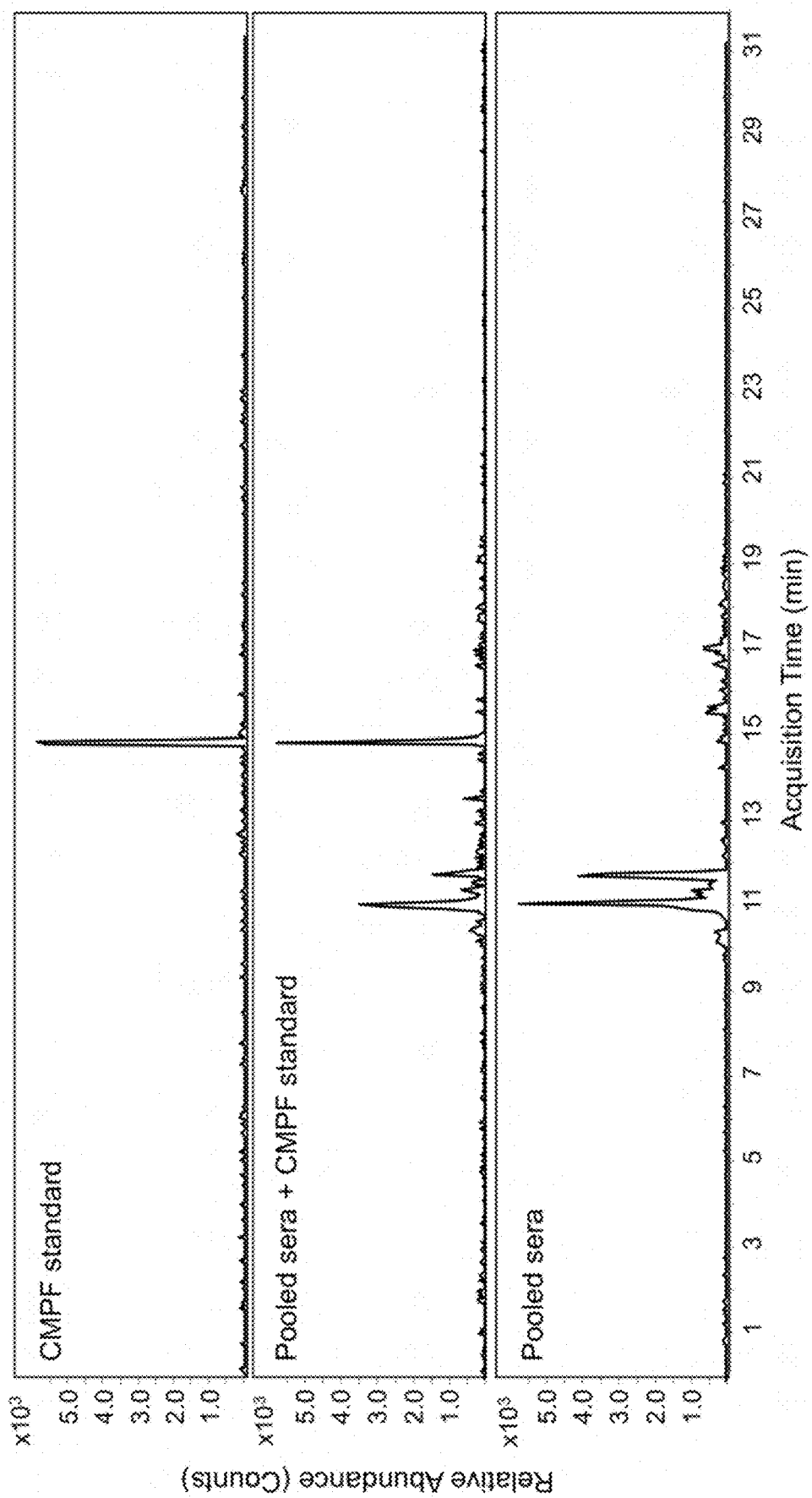
FIGS. 16A-B show data from level 1 identification of 3-carboxy-4-methyl-5-propyl-2-furanpropanoic acid (CMPF). Confirmation of the structural identity of CMPF was achieved by retention-time alignment (FIG. 16A) of authentic standard (top panel), authentic standard spiked in pooled patient sera (middle panel), and the targeted metabolite in pooled patient sera; and by comparison of MS/MS spectra (FIG. 16B) of the authentic standard (top) and the targeted metabolite in pooled patient sera (bottom). Retention-time alignments for CMPF (FIG. 16A) were generated with extracted ion chromatograms for m/z 241.1069. MS/MS spectra for CMPF were obtained with a collision energy of 20 eV.
Figure 16B:
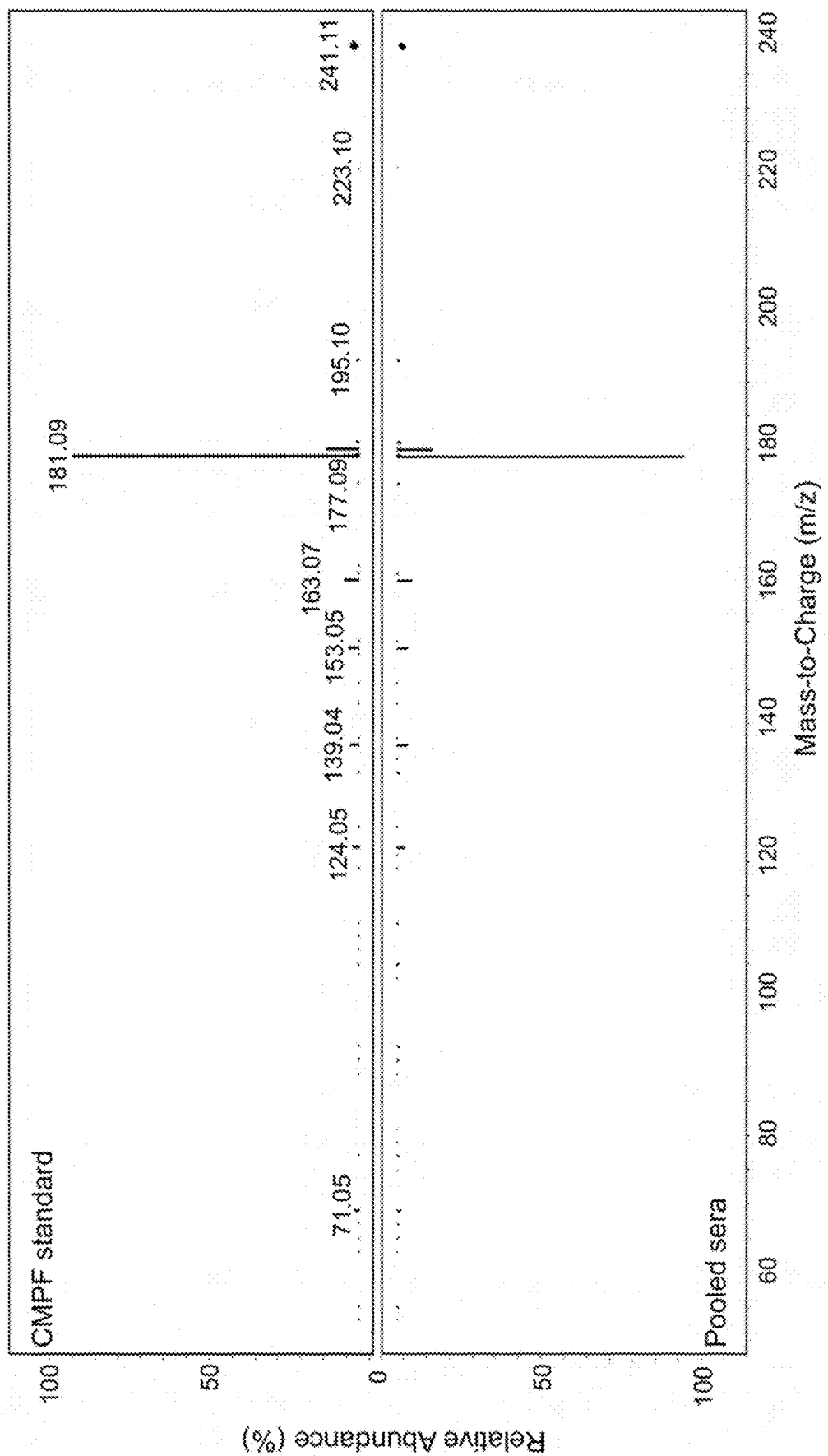
Figure 17:
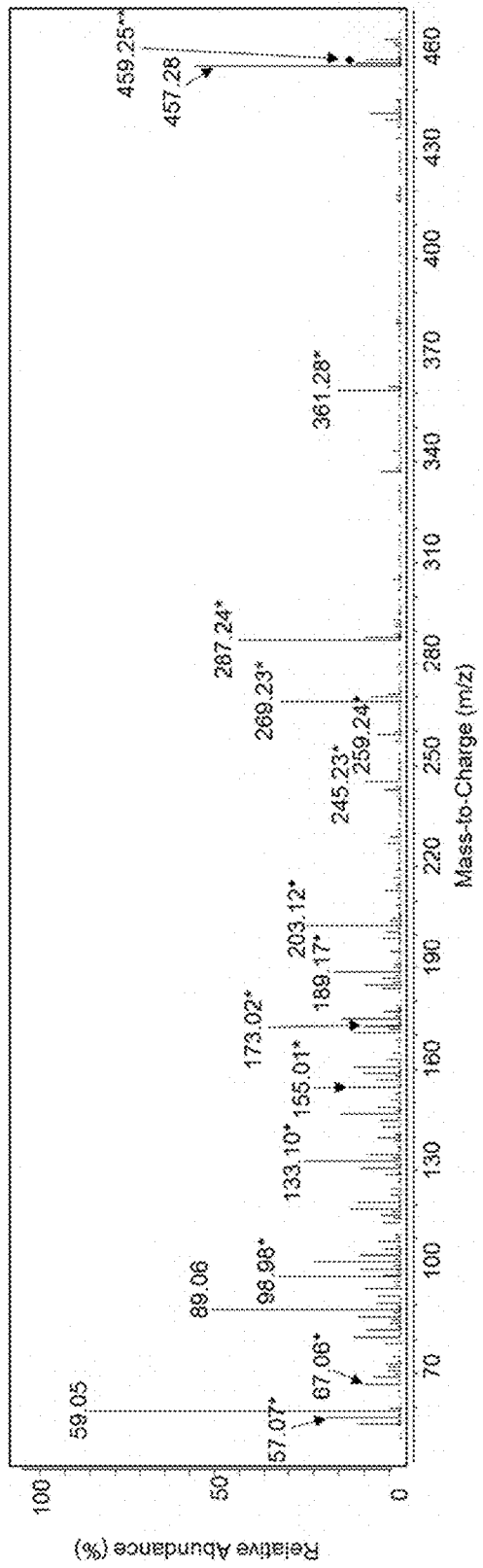
FIG. 17 shows data from level 2 identification of Lyso PA (20:4) by MS/MS spectral matching. The MS/MS fragmentation pattern for m/z 459.2502 (**) in pooled sera at RT 19.02 is shown. A match to the fragmentation of arachidonoyl lysophosphatidic acid (Lyso PA (20:4)) in the Metlin database is indicated by (*). MS/MS spectra for m/z 459.2502 were obtained with a collision energy of 20 eV.
Figure 18:
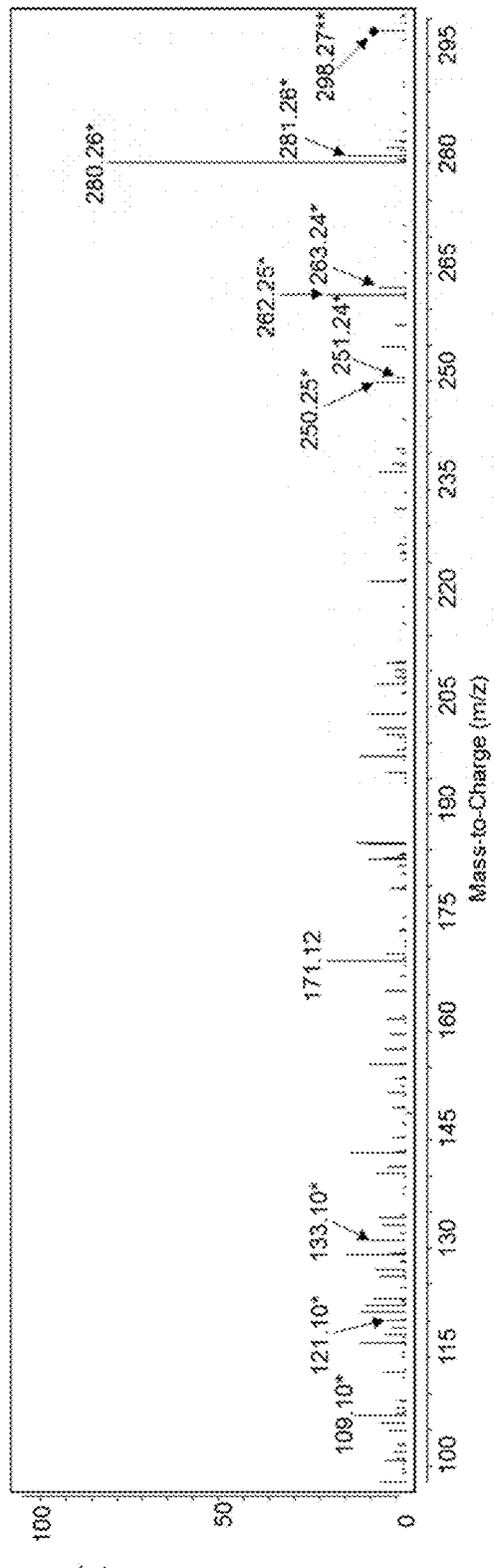
FIG. 18 shows data from level 2 identification of 3-ketosphingosine by MS/MS spectral matching. The MS/MS fragmentation pattern for m/z 298.2740 (**) in pooled sera at RT 16.44 is shown. A match to the fragmentation of 3-ketosphingosine in the Metlin database is indicated by (*). MS/MS spectra for m/z 298.2740 were obtained with a collision energy of 20 eV.

The large number of differentiating MFs associated with NAE metabolism suggested that this is a major biological difference between STARI and early Lyme disease (FIG. 3C and Table 3). Four additional MFs of the 261 MF biosignature, and that fit known host biochemical pathways, were also structurally confirmed. These included L-phenylalanine (FIG. 13), nonanedioic acid (FIG. 14), glycocholic acid (FIG. 15) and 3-carboxy-4-methyl-5-propyl-2-furanpropanoic acid (CMPF) (FIG. 16). Additionally, two MFs that provided strong matches to MS/MS spectra in the Metlin databases were putatively identified as arachidonoyl lysophosphatidic acid [Lyso PA (20:4)] (FIG. 17) and 3-ketosphingosine (FIG. 18).

Figure 4A:
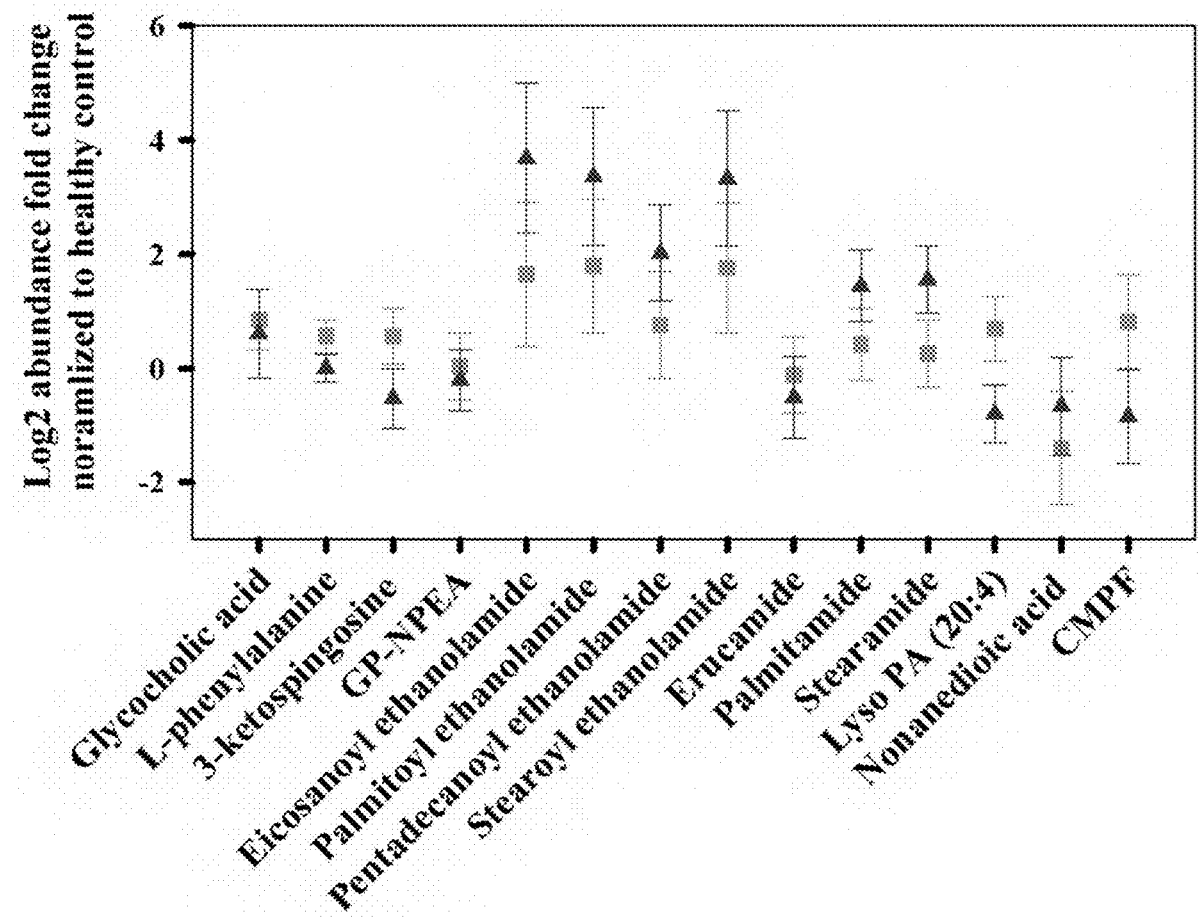
FIGS. 4A-C graphically depict comparisons of MF abundances from the Lyme disease-STARI biosignature against healthy controls.
Figure 4B:
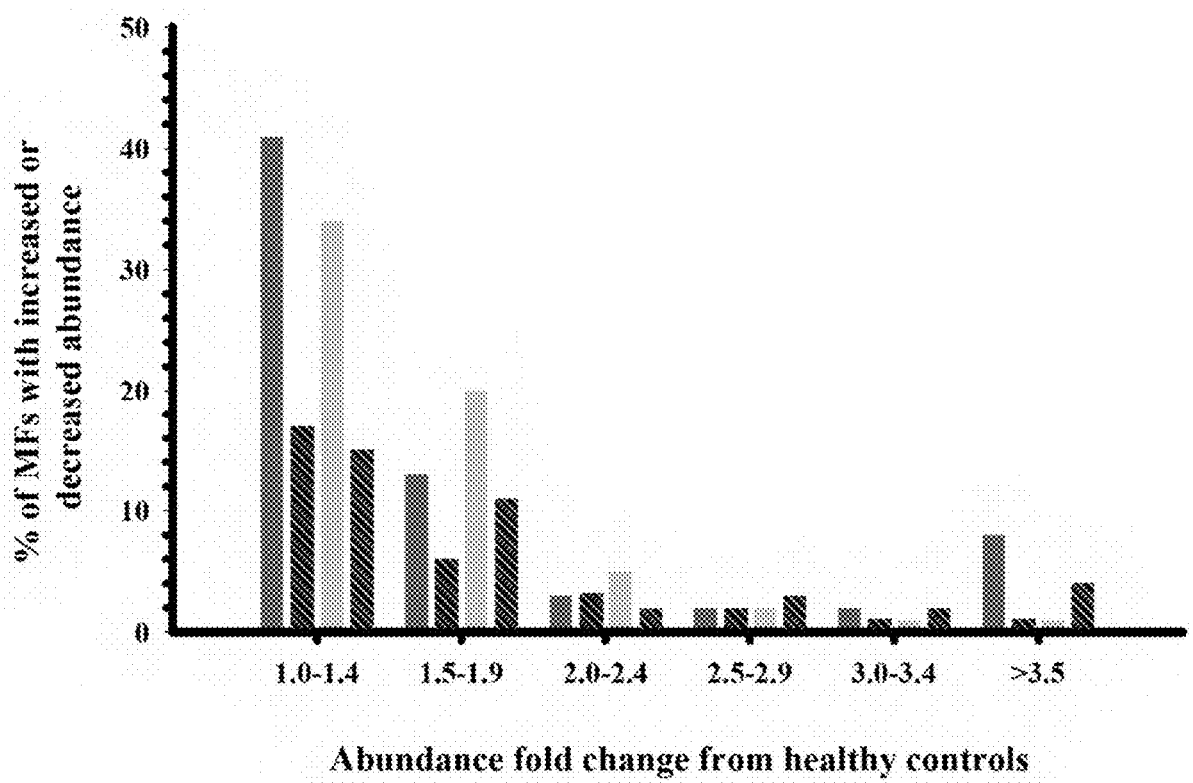
Figure 4C:
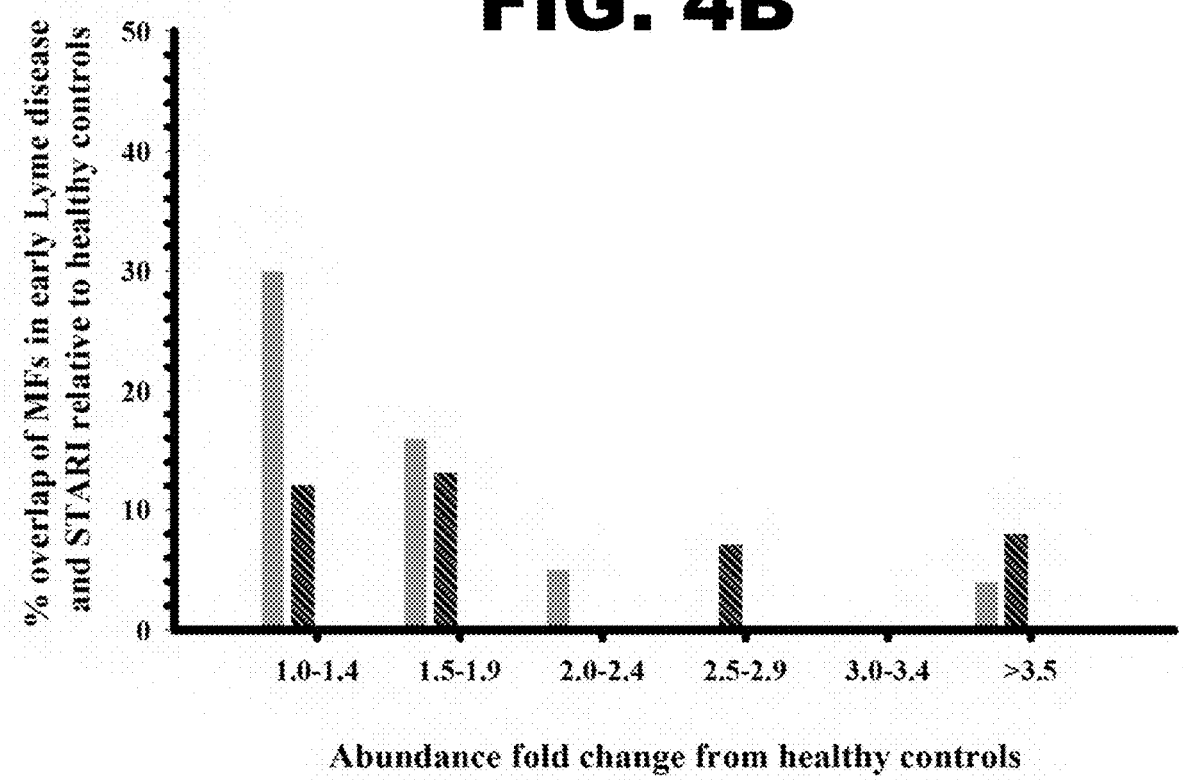

The 261 MF Biosignature List Revealed Metabolic Dissimilarity Between Lyme Disease and STARI:

To test whether early Lyme disease and STARI represent distinct metabolic states that would be reflected in the comparison of MF abundances in these two disease states to those of healthy controls, the abundance fold-change for each structurally confirmed MF in early Lyme disease and STARI sera as compared to healthy controls was determined. This revealed that the majority of these MFs maintained fold change differences with respect to healthy controls that allowed for segregation of early Lyme disease and STARI patient samples (FIG. 4A). For three MFs (3-ketosphingosine, CMPF, and Lyso PA 20:4), the levels in early Lyme disease were increased as compared to the healthy controls while the levels in STARI were decreased. Additionally, all of the NAEs and PFAMs had abundances in early Lyme disease patients that were closer to those of healthy controls, whereas the abundances in STARI were greatly increased. This analysis was expanded to all 261 MFs of the early Lyme disease-STARI biosignature (FIG. 4B). The percent of MFs with increased and decreased abundances relative to healthy controls were similar across the abundance fold changes for both early Lyme disease and STARI. However, when the MFs with increased or decreased abundances were compared between early Lyme disease and STARI for each range of abundance fold change, the concordance was low (0 to 30%) (FIG. 4C). This indicated that the metabolic changes in early Lyme disease and STARI as compared to healthy controls differed.

Figure 5A:
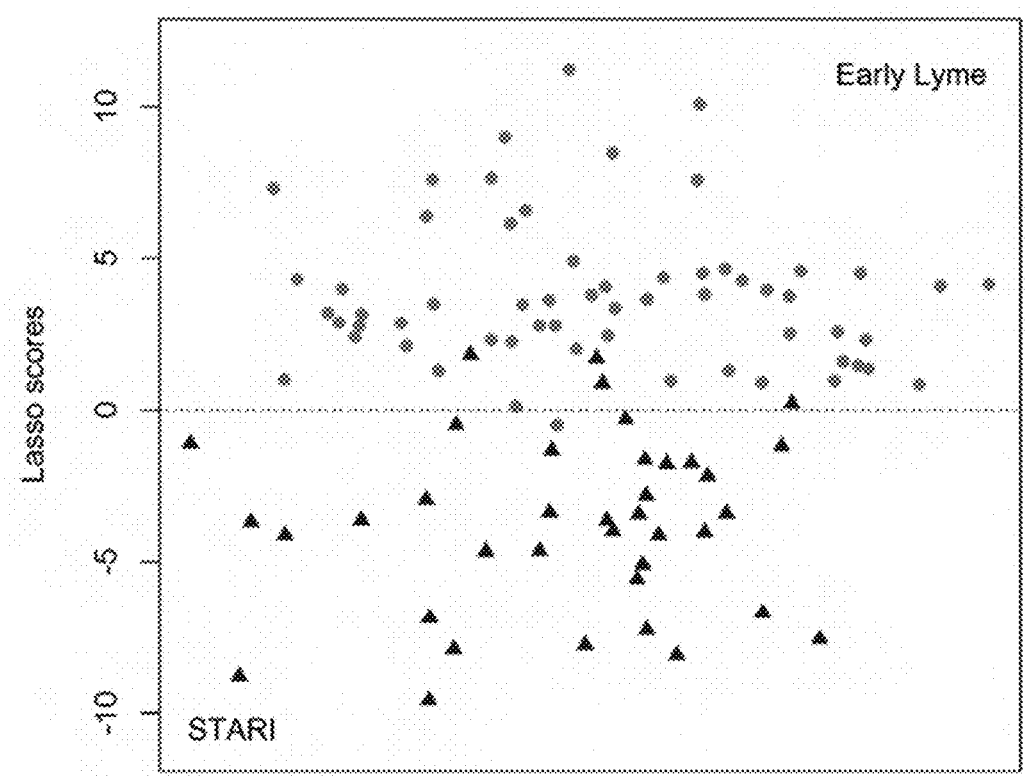
FIGS. 5A-C graphically depict evaluations of the performance of classification models' described in the Example 1.
Figure 5B:
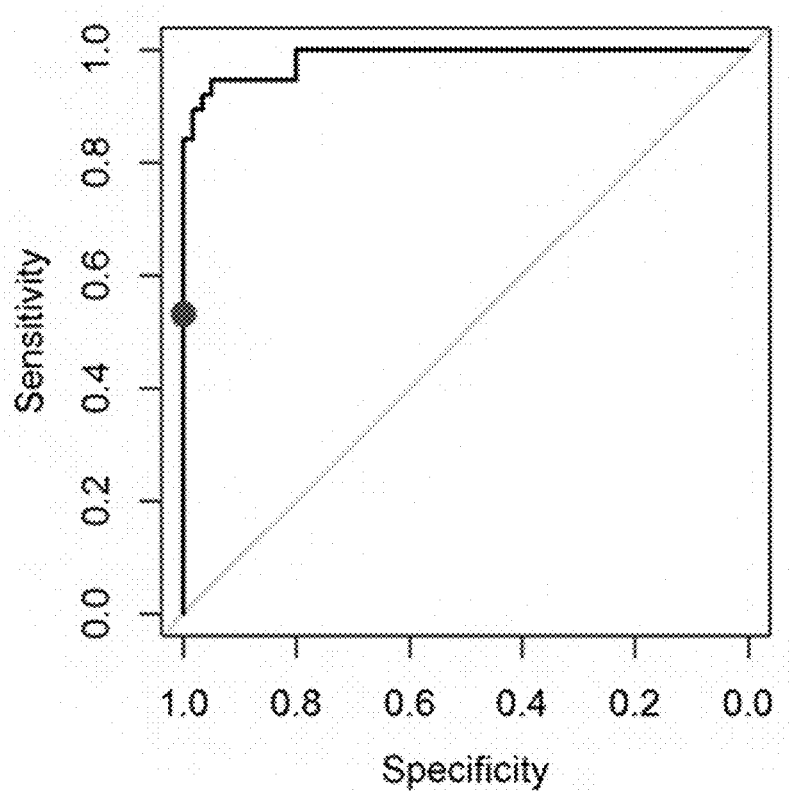

Diagnostic Classification of Early Lyme Disease Vs STARI:

Classification models were used to determine whether the 261 MF biosignature could be applied to discriminate early Lyme disease from STARI (Table 1 and FIG. 1). Specifically, two classification models, least absolute shrinkage and selection operator (LASSO) and random forest (RF) were trained with the 261 MF biosignature using abundance data from the Training-Set samples only (FIG. 1). Test-Set samples were not used for molecular feature selection or to train the classification models. The LASSO model selected 38 MFs, and RF by default does not perform feature selection and thus used all 261 MFs for classification of the STARI and early Lyme disease patient populations (Table 3 and Table 5). When Test-Set samples (FIG. 1) (i.e. those not included in the Discovery/Training-Set) were tested in duplicate, early Lyme disease samples were classified by RF and LASSO with an accuracy of 97% and 98%, respectively. The STARI samples had a classification accuracy of 89% with both models (Table 1 and Table 6). A depiction of the LASSO scores for the Test-Set data showed segregation of the early Lyme disease and STARI patient samples, and demonstrated the discriminating power of the 38 MFs selected by the LASSO model (FIG. 5A). A receiver operating characteristic (ROC) curve was plotted to demonstrate the performance of the LASSO model for differentiating early Lyme disease from STARI patients. The area under the curve (AUC) was calculated to be 0.986 (FIG. 5B). The 38 MFs of the LASSO model encompassed four of the 14 structurally confirmed metabolites: CMPF, L-phenylalanine, palmitoyl ethanolamide, and arachidonoyl lysophosphatidic acid (Table 3).

Figure 5C:
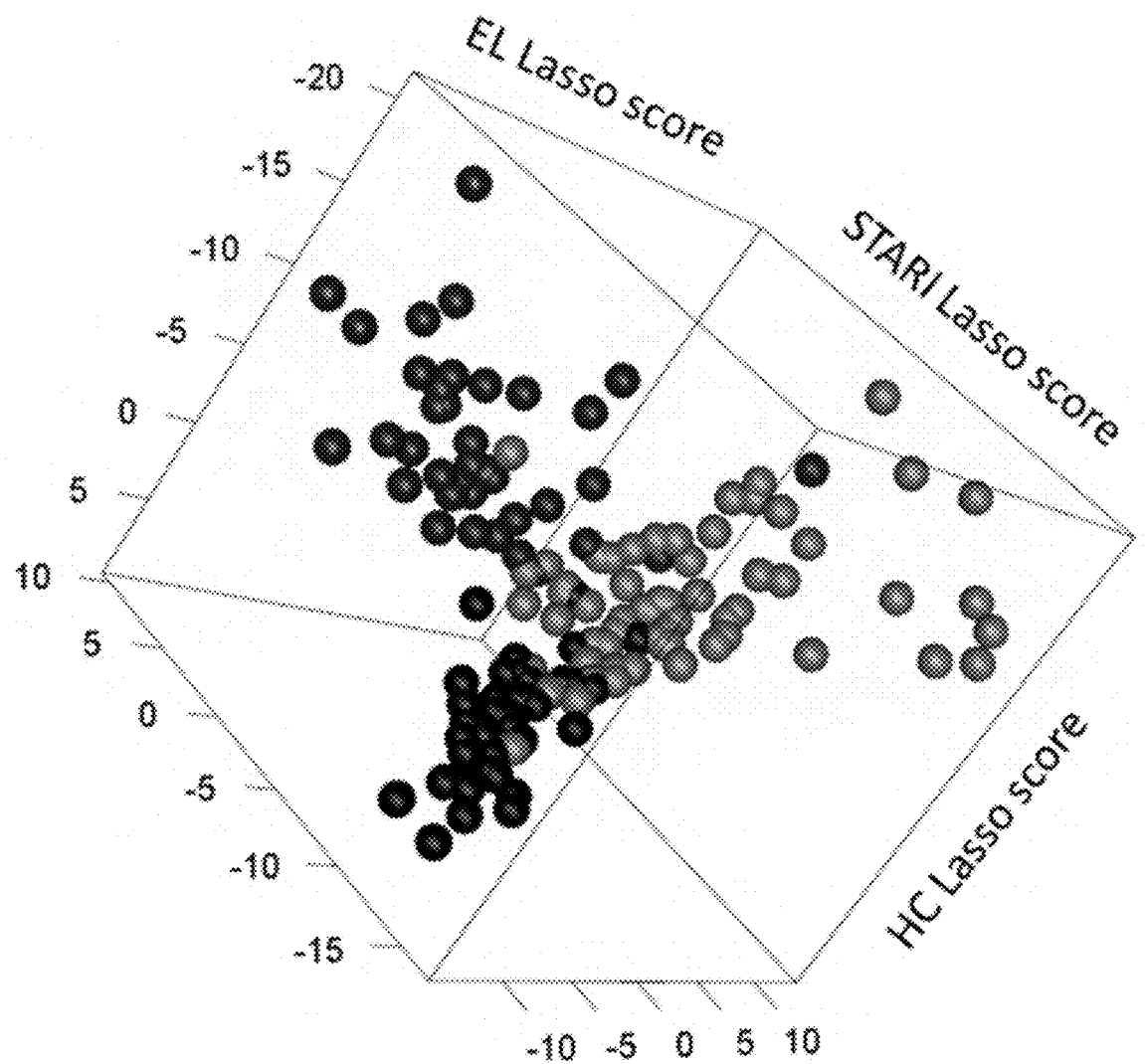

Diagnostic Classification of Early Lyme Disease Vs STARI Vs Healthy Controls:

Separate three-way classification models using LASSO and RF were developed by including LC-MS data collected for healthy controls in the Training-Set samples (FIG. 1). For model training LASSO selected 82 MFs (Table 3). The regression coefficients for the 82 MFs selected by LASSO are provided in Table 7. Evaluation of the RF and LASSO three-way classification models with Test-Set samples (those not used in the Discovery/Training-Sets) revealed classification accuracies of 85% and 92% for early Lyme disease and STARI, respectively. Surprisingly, healthy controls were classified with accuracies of 95% and 93% with the RF and LASSO models, respectively (Table 1 and Table 8). Plotting of LASSO scores calculated for Test-Set data revealed three groupings that corresponded with early Lyme disease, STARI and healthy controls (FIG. 5C). Of the early Lyme disease samples that were misclassified with the RF model (n=9), all were predicted to be healthy controls; and those misclassified by the LASSO model (n=9), three were classified as STARI and six as healthy controls. Of the STARI samples that were misclassified by the RF and LASSO models (n=3 for both models), all samples were misclassified as early Lyme disease. When healthy controls were misclassified using the RF model (n=2) and LASSO model (n=3), all were misclassified as early Lyme disease.

Of the 38 MFs selected by LASSO for the two-way classification model, 33 were included in the 82 MFs of the LASSO three-way classification model (Table 3). The 82 MFs of the LASSO three-way classification included seven of the 14 structurally confirmed metabolites: 3-ketosphingosine, glycocholic acid and pentadecanoyl ethanolamide, as well as the four included in the LASSO two-way classification model (Table 3).

Figure 6A:
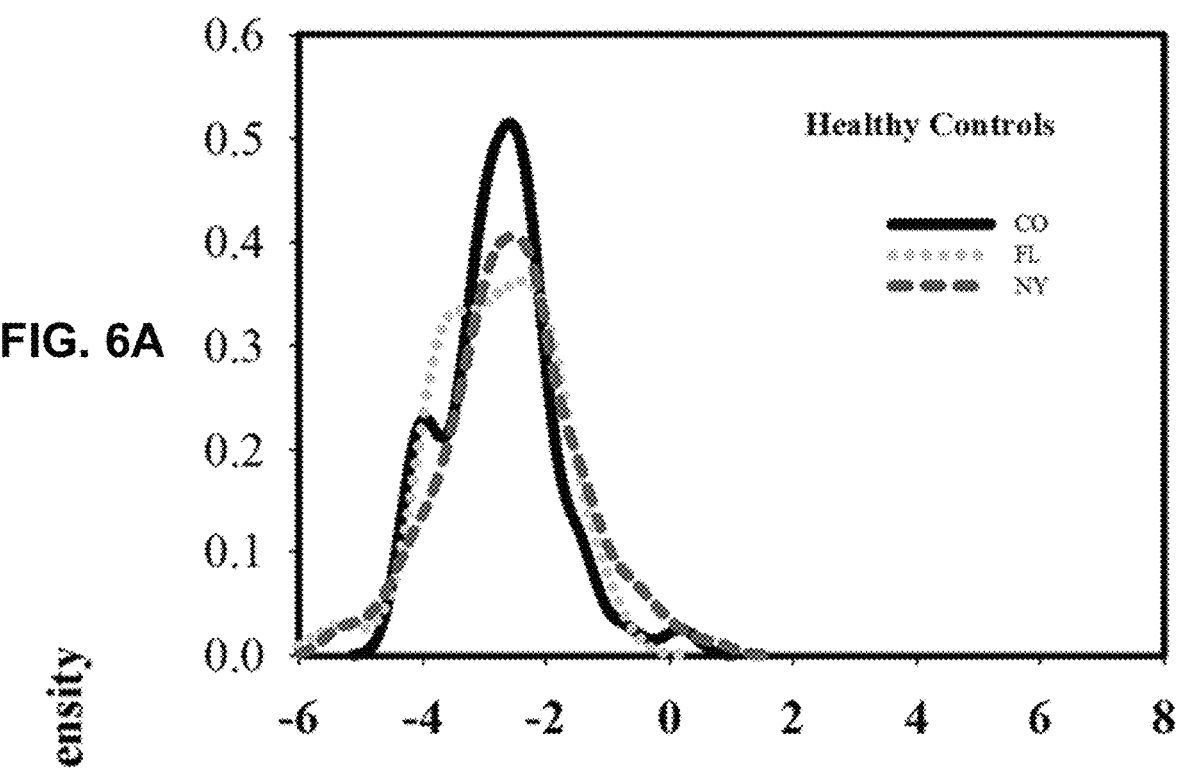
FIGS. 6A-B graphically depict evaluations of intra- and inter-group variability in healthy controls (FIG. 6A) and STARI subjects (FIG. 6B). Linear discriminant analysis was performed using the 82 MFs picked by LASSO in the three-way classification model to assess the intra-group variability based on the geographical region or laboratory from which healthy control (CO-black, solid; FL-light gray, dotted; and NY-dark gray, dashed) and STARI (MO-dark blue, solid; NC-light blue, dotted; and Other-black, dashed) sera were obtained. Only slight intra-group variation was observed. This analysis also compared and showed clear differentiation of all healthy control from STARI samples regardless of geographical region or laboratory origin. Healthy controls from FL were included in this analysis to demonstrate that healthy controls from an area with low incidence of Lyme disease and where STARI cases occur do not differ from the healthy controls obtained from other regions and used in the classification modeling.
Figure 6B:
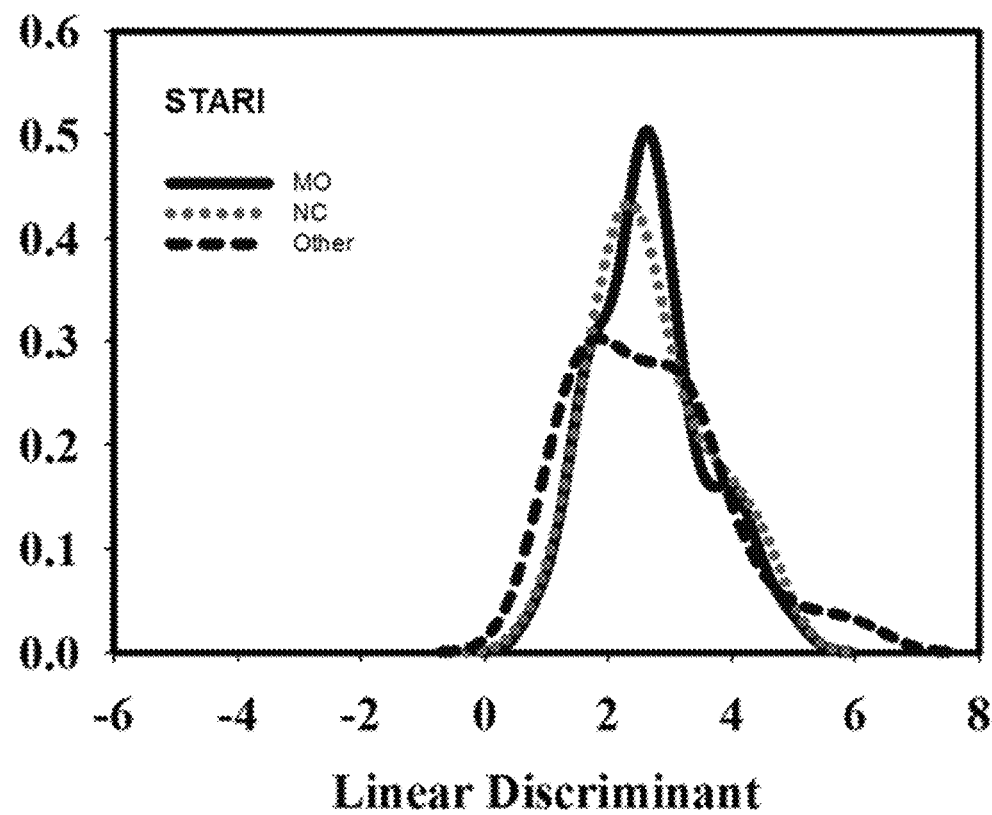

Biosignature was not Influenced by Geographic Variability:

Since retrospective samples collected by multiple laboratories were used in these studies, analyses were performed to assess whether a geographic bias was introduced. To address this, three healthy control groups and three STARI groups (all early Lyme disease samples came from one geographic region) were evaluated by linear discriminant analysis using the 82 MFs of the LASSO three-way classification model (FIG. 6). For healthy controls, those samples used in the modeling (collected in New York and Colorado) were evaluated. Additionally, healthy controls from Florida, a region with low prevalence for Lyme disease and reported to have STARI cases, were included to evaluate whether samples collected in the southern United States would differ from those collected in New York or Colorado. For STARI, three patient samples groups collected in Missouri, NC and other states (included VA, GA, KY, TN, AL, IA and NE) were compared. The linear discriminant analysis demonstrated that although slight variation exists between the three healthy control groups (NY, CO and FL), there is greater variability between all healthy controls and all STARI samples than within healthy controls or STARI samples based on geographic location of collection (FIG. 6).

Discussion:

The inability to detect *B. burgdorferi* by PCR or culture and the lack of a serological response to *B. burgdorferi* antigens in STARI patients is widely accepted as evidence that the etiologies of STARI and Lyme disease differ (7, 16). This is further supported by the different tick species associated with these two diseases (8, 25). Nevertheless, the strong overlap in clinical symptoms, including the development of an EM-like skin lesion, creates confusion and controversy for the clinical differentiation of STARI and Lyme disease (30). The data reported here demonstrated marked differences between the metabolic profiles of early Lyme disease and STARI patients, and thus provide compelling positive data to support the concept that these two illnesses are distinct entities. Interestingly, metabolic pathway analyses and the structural identification of several MFs with significant abundance differences between early Lyme disease and STARI identified multiple NAEs. These endogenous lipid mediators are derived from phosphatidylcholine and phosphatidylethanolamine via the endocannabinoid system (FIG. 3C) (29). Arachidonoylethanolamide (AEA) is the most widely studied endocannabinoid, as it is an endogenous agonist of the cannabinoid receptors; however, it is a minor component of animal tissues. In contrast, congeners of AEA, such as the NAEs identified in the early Lyme disease-STARI biosignature, are significant products of animal tissues, including the skin (29, 31). The serum levels of NAEs possessing long-chain saturated fatty acids were significantly increased in the serum of STARI patients. These NAEs are produced in response to inflammation, and act in an anti-inflammatory manner as agonists of PPAR-α or by enhancing AEA activity (32, 33). The NAEs are generally degraded via fatty acid amide hydrolase; however, it was recently demonstrated that NAEs can be converted to N-acylglycine structures via an alcohol dehydrogenase, and further degraded to PFAMs (34). Interestingly, the data generated from these studies not only demonstrated a STARI-associated increase in NAEs with saturated fatty acids, but also an increase in the corresponding PFAMs. Although the mechanism for the increased abundance of NAEs and PFAMs in STARI patients is unknown, decrease in fatty acid amide hydrolase activity which releases free fatty acids from both NAEs and PFAMs would result in the observed increase in abundance of these metabolites (35). The anti-inflammatory activity of the NAEs also raises the possibility that these metabolites are partially responsible for the milder symptoms associated with STARI (9). As the enzymes involved with the genesis and degradation of NAEs and PFAMs are known (29, 36), studies can be constructed to further elucidate the mechanism(s) by which NAEs and PFAMs accumulate in the sera of STARI patients.

This current work expands demonstrates the ability to distinguish early Lyme disease from an illness with nearly identical symptoms or what would be considered a Lyme disease-like illness (37). The existing diagnostic algorithm for Lyme disease is a two-tiered serologic approach that utilizes an EIA or IFA as a first-tier test followed by IgM and IgG immunoblotting as the second-tier test (38). For early Lyme disease, the sensitivity of this diagnostic is 29-40% and the specificity is 95-100% (39). The current antibody-based approaches do not distinguish between active and previous infections, an important limitation. In the current study all of the STARI samples were negative by two-tiered testing, and only 2% were positive by the first-tier EIA. Early Lyme disease samples were 44% positive (38% positivity for the early Lyme disease samples used in the Discovery and Training Sets and 53% positivity for early Lyme disease samples used in the Test Sets) by two-tiered testing. In contrast, when classification modeling was applied to the 261 MFs of the early Lyme disease-STARI biosignature, diagnostic accuracy for early Lyme disease was dramatically increased (85 to 98% accuracy depending on the model) as compared to serology. Classification by RF or LASSO was overall highly accurate for early Lyme disease and STARI, in particular when using the two-way classification models. Interestingly, when healthy controls were introduced and used to develop a three-way classification model there was a slight increase in the accuracy for STARI and decrease in the accuracy for early Lyme disease, but healthy controls were classified with a 93-95% accuracy. This was surprising as healthy controls were not used to create the initial 261 MF biosignature, and furthers supported that STARI and early Lyme disease are metabolically distinct from healthy controls, but in different ways.

To date the development of a diagnostic tool for STARI or for differentiation of early Lyme disease and STARI has received little attention. As the geographic distribution of Lyme disease continues to expand (25, 26), so will the geographic range where there is overlap of Lyme disease and STARI. Thus, a diagnostic tool that accurately differentiates these two diseases could have a major impact on patient management. Lyme disease is treated with antibiotics, and although there is no defined infectious etiology for STARI, this illness is also commonly treated in a similar manner (7, 20, 40). Establishment of a robust diagnostic tool would not only facilitate antibiotic stewardship, it would also allow for proper studies to assess the true impact of therapies for STARI. Lyme disease is also a reportable disease and in order to maintain accurate disease surveillance in low incidence areas, it is essential that diseases such as STARI be excluded (30). Additionally, vaccines are currently being developed for Lyme disease (41-44) and as these are tested, it will be important to identify STARI patients in order to properly assess vaccine efficacy.

To apply the discoveries of this work towards the development of an assay that can be used for the clinical differentiation of early Lyme disease and STARI, it should first be determined whether an emphasis should be placed on the diagnosis of Lyme disease or STARI. As there is no defined etiology of STARI, and Lyme disease is not necessarily self-limiting without antibiotics and can have subsequent complications if untreated, we envision that the final assay would focus on being highly sensitive for early Lyme disease and be primarily applied in regions where Lyme disease and STARI overlap. Although existing laboratory tests for Lyme disease emphasize specificity, this strategy needs to be reconsidered for a differential diagnostic test of STARI and early Lyme disease, since any illness presenting with an EM in a region with a known incidence of Lyme disease would likely be treated with antibiotics (7, 20, 40). As with all diagnostic tests, use of a metabolic biosignature for differentiation of early Lyme disease and STARI would need to be performed in conjunction with clinical evaluation of the patient, and consideration of their medical history and epidemiologic risk for these two diseases.

The approach outlined in this study applies semi-quantitative mass spectrometry and the use of biochemical signatures for the classification of patients. Clinical application of such an approach would likely occur in a specialized clinical diagnostic laboratory. However, it should be noted that the second-tier immunoblot assays for the serological diagnosis of Lyme disease are already performed in specialized laboratories (1, 45, 46). Mass spectrometry assays are currently used in clinical laboratories for the analyses of small molecule metabolites. The majority of these tests are under Clinical Laboratory Improvement Amendments (CLIA) guidelines, but an FDA cleared mass spectrometry-based test for inborn metabolic errors is in use (47). The most accurate quantification of metabolites by mass spectrometry is achieved by Multiple Reaction Monitoring (MRM) assays (48). Such assays are developed with the knowledge of a MF's chemical structure. To this end, the chemical structure of 14 MFs have been identified. The chemical structure of the remainder of the MFs can be identified by the methods described herein. It should be noted that the NAEs and PFAMs that were revealed via our pathway analyses are amenable to MRM assays (49). These metabolites are now being investigated for their ability to accurately classify STARI and early Lyme disease.

The data reported here were generated from the analysis of retrospectively collected serum samples from various repositories that have been archived for different lengths of time. To reduce the impact of the potential variability associated with these samples, stringent criteria were applied to the data analysis. In addition to the requirement of a significant fold change, those MFs selected for the final early Lyme disease-STARI biosignature were required to be present in at least 80% of samples within a sample group and maintain the median fold-change difference in at least 50% of samples within a group. While the STARI and healthy control sera were collected by multiple laboratories and from multiple geographic locations, the early Lyme disease sera were obtained from a single laboratory. This is a potential limitation of the study. However, linear discriminate analysis was applied to assess the variability within the healthy control and STARI samples collected by different laboratories. This analysis demonstrated little to no variability among the STARI or healthy control samples indicating that the criteria used for MF selection effectively reduced non-biological variability. As noted, data were collected by non-absolute semi-quantitative mass spectrometry. Nevertheless, this is a common practice applied in the development of differentiating biosignatures for infectious diseases (27, 50-53), and the workflow ensured that the most robust MFs were selected and used for classification modeling.

Without knowledge of a known etiologic agent, it is recognized that STARI simply encompasses a clinical syndrome. The STARI samples used in this current work included those collected in studies used to define this illness (9), as well as samples collected outside those original studies. Additional samples collected prospectively will be useful to assess the applicability of our current metabolic biosignature in a real world scenario. Future sample collection will also target patient populations with non-Lyme EM-like lesions, including tick-bite hypersensitivity reactions, certain cutaneous fungal infections and bacterial cellulitis. Additionally, other factors such as confections with other vector-borne pathogens will need to be addressed with prospective studies. In the Southeastern United States, there is evidence for enzootic transmission of *B. burgdorferi*;

however, it is debatable whether Lyme disease occurs in this region (11, 30, 54, 55). The current study was not designed to provide evidence for or against the presence of Lyme disease in the southern United States. Nevertheless, metabolic profiling offers a novel approach that is orthogonal to the methods currently employed to address this issue.

Example 2

STARI is an illness that has received little attention over the years, but is a confounding factor in diagnosing early Lyme disease in areas where both illnesses overlap and contributes to the debate surrounding the presence of Lyme disease in the southern United States. No diagnostic tool exists for STARI or for differentiating early Lyme disease from STARI. Based on documented differences between early Lyme disease and STARI (9, 16, 56), we metabolically profiled serum to develop a biochemical biosignature that when applied could accurately classify early Lyme disease and STARI patients (See Example 1). This example describes the design of the study described in Example 1.

An unbiased-metabolomics study was designed to directly compare the metabolic host responses between these two illnesses, and subsequently evaluate how this metabolic biosignature distinguishes these two illnesses. The use of unbiased metabolomics for biosignature discovery does not lend itself to power calculations to determine sample size. Thus, sample sizes were selected based on our previous studies (27, 50, 51). To obtain a sufficient number of well-characterized STARI sera, retrospectively collected samples from two separate studies were used. Specifically, the first set of STARI serum samples (n=33) was obtained from the CDC repository. These samples were collected through a prospective study performed between 2007 and 2009 (57). Patients were enrolled through CDC outreach efforts (n=17) or by contract with the University of North Carolina at Chapel Hill (n=16). The states where patients were recruited included NC, 18; VA, 4; TN, 3; KY, 2; GA, 2; IA, 2; AL, 1; and NE, 1. All samples were collected pre-treatment with the exception of one patient who was treated with doxycycline 1-2 days before the serum sample was obtained. The second set of STARI samples (n=22) was obtained from the New York Medical College serum repository (20). These samples were collected between 2001 and 2004 from patients living in Missouri.

Sufficient numbers of well-characterized early Lyme disease serum samples were acquired from New York, an area of high incidence for Lyme disease and low incidence of STARI (9). Specifically, all early Lyme disease samples (n=70) were culture and/or PCR positive for *B. burgdorferi* and were collected pre-treatment. To ensure appropriate representation of both non-disseminated and disseminated forms of early EM Lyme disease, samples from patients with a single EM that were skin culture and/or PCR positive for *B. burgdorferi* and blood culture negative (n=35), and patients with multiple EMs or a single EM that were blood culture positive (n=35) were used. Early Lyme disease samples were collected between 1992 and 2007, and 1 to 33 days post-onset of symptoms. To understand the relationship of our findings to a healthy control population serum samples from healthy donors were also included in the study. These were procured from repositories at New York Medical College, the CDC and the University of Central Florida. A detailed description of inclusion and exclusion criteria for each patient and donor population is provided in Table 2. All participating institutions obtained institutional review board (IRB) approval for this study. IRB review and approval for this study ensured that the retrospective samples used had been collected under informed consent.

All samples were analyzed in duplicate and were randomized prior to processing for LC-MS analyses. Healthy control sera were used as quality control samples for each LC-MS experiment. The serum samples and respective LC-MS data files of each patient group and healthy controls were randomly separated into a Discovery-Set/Training-Sets 1 and 2, and Test-Sets 1 and 2. Specifically, 40 of the 70 early Lyme disease and 36 of the 55 STARI samples were randomly selected as the Discovery-Set samples. This sample set was used for molecular feature selection. To train the classification models, two training-sets were used. The first, Training-Set 1, was identical to the Discovery-Set (i.e. contained the same early Lyme disease and STARI samples) and the second, Training-Set 2, had the same samples as Training-Set 1 with the addition of 38 of the 58 healthy control samples. Lastly, Test-Sets 1 and 2 were created. Test-Set 1 was comprised of 30 early Lyme disease and 19 STARI samples that were not included in the Discovery/Training samples sets. Test-Set 2 had the same samples as those used in Test-Set 1 with the addition of 20 healthy control samples that were not included in the Training-Set 2 samples. Test-Sets 1 and 2 were exclusively used for blinded testing of the classification models.

Randomization into Discovery/Training-Sets or Test-Sets was done in a manner that ensured bias was not introduced based on the repository from which STARI samples were obtained or on whether the early Lyme disease samples were from a non-disseminated or disseminated case. Biosignature development was performed by screening MFs based on stringent criteria outlined in FIG. 1 and detailed in the Biosignature development section (below).

Example 3

This example describes methods used for Lyme disease serologic testing of all serum samples used in the examples above. Standard two-tiered testing was performed on all samples (38). The C6 *B. burgdorferi* (Lyme) ELISA (Immunetics, Boston, Mass.) was used as a first-tier test, and any positive or equivocal samples were reflexed to Marblot IgM and IgG immunoblots (MarDx Diagnostics, Inc., Carlsbad, Calif.) as the second-tier test. Serologic assays were performed according to the manufacturer's instructions, and the data were interpreted according to established CDC guidelines (38). Duration of illness, however, was not considered for test interpretation.

Example 4

This example describes liquid chromatography-mass spectrometry (LC-MS) methods used in the examples above. Serum samples were randomized prior to extraction of small molecule metabolites and LC-MS analyses. Small molecule metabolites were extracted from sera as previously reported (27). An aliquot (10 µl) of the serum metabolite extract was applied to a Poroshell 120, EC-C8, 2.1×100 mm, 2.7 µm LC Column (Agilent Technologies, Palo Alto, Calif.). The metabolites were eluted with a 2-98% nonlinear gradient of acetonitrile in 0.1% formic acid at a flow rate of 250 µl/min with an Agilent 1200 series LC system. The eluent was introduced directly into an Agilent 6520 quadrupole time of flight mass (Q-TOF) spectrometer and MS was performed as previously described (27, 50). LC-MS and LC-MS/MS data were collected under the following parameters: gas temperature, 310° C.; drying gas at 10 liters per min; nebulizer at 45 lb per in², capillary voltage, 4,000 V; fragmentation energy, 120 V; skimmer, 65 V; and octapole RF setting, 750 V. The positive-ion MS data for the mass range of 75 to 1,700 Da were acquired at a rate of 2 scans per sec. Data were collected in both centroid and profile modes in 4-GHz high-resolution mode. Positive-ion reference masses of 121.050873 m/z and 922.009798 m/z were introduced to ensure mass accuracy. To monitor instrument performance, quality control samples having a metabolite extract of healthy control serum (BioreclamationIVT, Westbury, N.Y.) was analyzed in duplicate at the beginning of each analysis day and every 20 samples during the analysis day.

Example 5

This example describes the methods used for biosignature development as described in the examples above. LC-MS data from an initial Discovery-Set of samples comprised of randomly selected early Lyme disease (n=40) and randomly selected STARI patients (n=36) that were exclusively used for molecular feature selection and classification model training were processed with the Molecular Feature Extractor algorithm tool of the Agilent MassHunter Qualitative Analysis software version B.05.00 (Agilent Technologies, Santa Clara, Calif.). The MFs were aligned between data files with a 0.25 min retention time window and 15 ppm mass tolerance. Comparative analyses of differentiating MFs between patient groups were performed using the workflow presented in FIG. 1A. Specifically, the Discovery-Set data was analyzed using Mass Profiler Pro (MPP) software version B.12.05 (Agilent Technologies). Using MPP a univariate, unpaired t-test was performed on each metabolite to test for a difference in mean (standardized) abundance between early Lyme disease and STARI groups. Multiple testing was accounted for by computing false-discovery rate (FDR)-adjusted p-values (Benjamin and Hochberg, 1995). To prevent selection of MFs biased by uncontrolled variables (diet, other undisclosed illnesses, etc.), only MFs present in 50% or more of samples in at least one group and that differed between the groups with a significance of adjusted-p<0.05 were selected. Quantitative Analysis software version B.05.01 (Agilent Technologies) was used to extract area abundance values for all differentially selected MFs from the MS data files. Duplicate MFs were removed by assessing adduct ions, as well as mass, retention time and abundance similarities; this resulted in the Discovery MF List. A duplicate LC-MS analysis of the Discovery-Set samples was performed and the area abundance for MFs of the discovery MF List were extracted using the Quantitative Analysis software. These data with those from the first LC-MS analysis formed the Targeted-Discovery-Set.

Abundance data from the Targeted-Discovery-Set data files were normalized using a two-step method. First, abundances (area under the peak for the monoisotopic mass) of each Discovery MF were normalized by the median intensity of the stable MFs detected in each individual sample (58). Stable MFs were those identified in the original extraction of LC-MS data files with the Agilent MassHunter Qualitative Analysis software and present in at least 50% of all sample data files. Secondly, median fold changes of stable MFs between the initial quality control sample (applied at the beginning of the LC-MS analysis) and each of the subsequent quality control samples (applied every 20 clinical samples throughout the LC-MS analysis) were calculated. The median fold change calculated for the quality control sample that directly followed each series of 20 clinical samples was multiplied against the normalized Discovery-MF abundances in the clinical samples of that series. This second normalization step was performed to correct for instrument variability. To apply stringency to the development of a final early Lyme disease-STARI biosignature, MFs were filtered based on consistency in the duplicate LC-MS data sets by requiring the same directional abundance change between the patient groups. Specifically, MFs with at least a ≥2-fold abundance difference and a 1.5-fold abundance difference between the medians of the two groups (early Lyme disease and STARI) for LC-MS analysis-1 and LC-MS analysis-2, respectively, were selected. Further criteria applied to ensure that the most robust MFs were being selected included: removing MFs with >20% missing values in both groups, and selecting only MFs where at least 50% of the samples within a patient group produced a fold change of ≥2 in comparison to the mean of the other patient group. This selection process resulted in the MFs included in the early Lyme disease-STARI biosignature.

Example 6

This example describes the methods used for prediction and verification of MF chemical structure. Confirmation of the chemical structures of selected MFs was performed by LC-MS-MS to provide level-1 or level-2 identifications (59). Commercial standards palmitoyl ethanolamide, stearoyl ethanolamide, eicosanoyl ethanolamide, glycero-phospho-N-palmitoyl ethanolamine, pentadecanoyl ethanolamide, and erucamide were obtained from Cayman Chemical (Ann Arbor, Mich., USA). Commercial standards piperine and nonanedioic acid were obtained from Sigma Aldrich (Saint Louis, Mo., USA). Commercial standards methyl oleate, stearamide, palmitamide, CMPF, and glycocholic acid were obtained from Santa Cruz Biotechnology, Inc. (Santa Cruz, Calif., USA). The LC conditions used were the same as those used for the LC-MS analyses of serum metabolites. MS/MS spectra of the targeted MFs and commercial standards were obtained with an Agilent 6520 Q-TOF mass spectrometer. Electrospray ionization was performed in the positive ion mode as described for MS analyses, except the mass spectrometer was operated in the 2 GHz extended dynamic range mode. The positive ion MS/MS data (50 to 1,700 Da) were acquired at a rate of 1 scan per sec. Precursor ions were selected by the quadrupole and fragmented via collision-induced dissociation (CID) with nitrogen at collision energies of 10, 20, or 40 eV. To provide a level-1 identification, the MS/MS spectra of the targeted metabolites were compared to spectra of commercial standards. Additionally, LC retention time comparisons between the targeted MF and the respective standard were made. A retention time window of ±5 sec was applied as a cutoff for identification. The MS/MS spectra of selected serum metabolites were compared to spectra in the Metlin database for a level-2 identification.

Example 7

Metabolic pathway analysis in the examples above was performed by MetaboAnalyst. The experimentally obtained monoisotopic masses corresponding to the MFs of the 261 biosignature list were searched against HMDB using a 15 ppm window. The resulting list of potential metabolite structures were applied to the MetaboAnalyst pathway analysis tool (28) Settings for pathway analysis included applying *Homo sapiens* pathway library; the Hypergeometric Test for the over-representation analysis and Relative-betweenness centrality to estimate node importance in the pathway topology.

Example 8

Methods for statistical analyses and classification modeling are described in this example. Methods to filter the list of MFs and to normalize abundances are described in the section on biosignature development. Prior to analysis, the normalized abundances were log 2 transformed and each MF was scaled to have a mean of zero and standard deviation of 1. Statistical analyses were performed using R software (60).

For classification modeling, Training- and Test-Set samples were used as previously described (27, 50) and as shown in FIG. 1. Separate classification analyses were performed for comparison of two groups (early Lyme disease and STARI) and three groups (early Lyme disease, STARI and healthy controls). For each scenario, two classification approaches were applied: random forest (RF) using the Random Forest package (61), with 16 features randomly selected for each clade and a total of 500 trees; and LASSO logistic (two-way) and multinomial (three-way) regression analysis using the glmnet package (62), with the tuning parameter chosen for minimum misclassification error over a 10-fold cross-validation. The ROC curve and AUC were generated for predicted responses on the Test-Set samples only using the pROC package (63). For the purpose of visualization, LASSO scores for individual patient samples were calculated by multiplying the respective regression coefficients (Table 5 and Table 7) resulting from LASSO analysis by the transformed abundance of each MF in the biosignature (38 MFs in the case of two-way classification and 82 MFs in the case of three-way classification) and summing for each sample. The rgl package was used to generate the 3-dimensional scatterplot of LASSO scores (64).

A linear discriminant analysis was performed with the 82 MFs selected by the three-way LASSO model using linear discriminant analysis function in R. MF abundance data included in the linear discriminant analysis were from healthy controls from Colorado, Florida, and New York, and from STARI patients from North Carolina, Missouri, and other states. Before linear discriminant analysis data were transformed by taking the log 2 value and standardizing to the mean 0 and variance 1 within each MF. Samples were differentiated by healthy and STARI.

REFERENCES

1. A. F. Hinckley, N. P. Connally, J. I. Meek, B. J. Johnson, M. M. Kemperman, K. A. Feldman, J. L. White, P. S. Mead, Lyme disease testing by large commercial laboratories in the United States. *Clin. Infect. Dis.* 59, 676-681 (2014).
2. C. A. Nelson, S. Saha, K. J. Kugeler, M. J. Delorey, M. B. Shankar, A. F. Hinckley, P. S. Mead, Incidence of Clinician-Diagnosed Lyme Disease, United States, 2005-2010. *Emerg. Infect. Dis.* 21, 1625-1631 (2015).
3. G. Stanek, G. P. Wormser, J. Gray, F. Strle, Lyme borreliosis. *Lancet* 379, 461-473 (2012).
4. A. C. Steere, S. E. Malawista, J. A. Hardin, S. Ruddy, W. Askenase, W. A. Andiman, Erythema chronicum migrans and Lyme arthritis. The enlarging clinical spectrum. *Ann. Intern. Med.* 86, 685-698 (1977).
5. G. P. Wormser, Clinical practice. Early Lyme disease. *N. Engl. J. Med.* 354, 2794-2801 (2006).
6. R. B. Nadelman, Erythema migrans. *Infect. Dis. Clin. North Am.* 29, 211-239 (2015).
7. E. J. Masters, H. D. Donnell, Epidemiologic and diagnostic studies of patients with suspected early Lyme disease Missouri, 1990-1993. *J. Infect. Dis.* 173, 1527-1528 (1996).
8. E. Masters, S. Granter, P. Duray, P. Cordes, Physician-diagnosed erythema migrans and erythema migrans-like rashes following Lone Star tick bites. *Arch. Dermatol.* 134, 955-960 (1998).
9. G. P. Wormser, E. Masters, J. Nowakowski, D. McKenna, D. Holmgren, K. Ma, L. Ihde, L. F. Cavaliere, R. B. Nadelman, Prospective clinical evaluation of patients from Missouri and New York with erythema migrans-like skin lesions. *Clin. Infect. Dis.* 41, 958-965 (2005).
10. G. L. Campbell, W. S. Paul, M. E. Schriefer, R. B. Craven, K. E. Robbins, D. T. Dennis, Epidemiologic and diagnostic studies of patients with suspected early Lyme disease, Missouri, 1990-1993. *J. Infect. Dis.* 172, 470-480 (1995).
11. K. L. Clark, B. Leydet, S. Hartman, Lyme borreliosis in human patients in Florida and Georgia, USA. *Int. J. Med. Sci.* 10, 915-931 (2013).
12. R. M. Bacon, R. D. Gilmore, Jr., M. Quintana, J. Piesman, B. J. Johnson, DNA evidence of *Borrelia lonestari* in *Amblyomma americanum* (Acari: Ixodidae) in southeast Missouri. *J. Med. Entomol.* 40, 590-592 (2003).
13. A. S. Varela, M. P. Luttrell, E. W. Howerth, V. A. Moore, W. R. Davidson, D. E. Stallknecht, S. E. Little, First culture isolation of *Borrelia lonestari*, putative agent of southern tick-associated rash illness. *J. Clin. Microbiol.* 42, 1163-1169 (2004).
14. A. M. James, D. Liveris, G. P. Wormser, I. Schwartz, M. A. Montecalvo, B. J. Johnson, *Borrelia lonestari* infection after a bite by an *Amblyomma americanum* tick. *J. Infect. Dis.* 183, 1810-1814 (2001).
15. C. N. Grigery, P. Moyer, S. E. Little, E. J. Masters, Bacteriocidal activity of lizard and mouse serum for *Borrelia lonestari*, putative agent of a Lyme-like illness (AKA STARI or Masters disease) in Missouri. *Mo. Med.* 102, 442-446 (2005).
16. M. T. Philipp, E. Masters, G. P. Wormser, W. Hogrefe, D. Martin, Serologic evaluation of patients from Missouri with erythema migrans-like skin lesions with the C6 Lyme test. *Clin. Vaccine Immunol.* 13, 1170-1171 (2006).
17. M. W. Felz, F. W. Chandler, Jr., J. H. Oliver, Jr., D. W. Rahn, M. E. Schriefer, Solitary erythema migrans in Georgia and South Carolina. *Arch. Dermatol.* 135, 1317-1326 (1999).
18. K. B. Kirkland, T. B. Klimko, R. A. Meriwether, M. Schriefer, M. Levin, J. Levine, W. R. Mac Kenzie, D. T. Dennis, Erythema migrans-like rash illness at a camp in North Carolina: a new tick-borne disease? *Arch. Intern. Med.* 157, 2635-2641 (1997).
19. S. M. Rich, P. M. Armstrong, R. D. Smith, S. R. Telford, 3rd, Lone star tick-infecting borreliae are most closely related to the agent of bovine borreliosis. *J. Clin. Microbiol.* 39, 494-497 (2001).
20. G. P. Wormser, E. Masters, D. Liveris, J. Nowakowski, R. B. Nadelman, D. Holmgren, S. Bittker, D. Cooper, G. Wang, I. Schwartz, Microbiologic evaluation of patients from Missouri with erythema migrans. *Clin. Infect. Dis.* 40, 423-428 (2005).
21. E. J. Masters, H. D. Donnell, Lyme and/or Lyme-like disease in Missouri. *Mo. Med.* 92, 346-353 (1995).

22. W. L. Nicholson, E. Masters, G. P. Wormser, Preliminary serologic investigation of 'Rickettsia amblyommii' in the aetiology of Southern tick associated rash illness (STARI). *Clin. Microbiol. Infect.* 15 Suppl 2, 235-236 (2009).
23. Y. P. Springer, C. S. Jarnevich, D. T. Barnett, A. J. Monaghan, R. J. Eisen, Modeling the Present and Future Geographic Distribution of the Lone Star Tick, *Amblyomma americanum* (Ixodida: Ixodidae), in the Continental United States. *Am. J. Trop. Med. Hyg.* 93, 875-890 (2015).
24. M. B. Hahn, C. S. Jarnevich, A. J. Monaghan, R. J. Eisen, Modeling the Geographic Distribution of *Ixodes scapularis* and *Ixodes pacificus* (Acari: Ixodidae) in the Contiguous United States. *J. Med. Entomol.* Epub ahead of print. (2016).
25. K. J. Kugeler, G. M. Farley, J. D. Forrester, P. S. Mead, Geographic Distribution and Expansion of Human Lyme Disease, United States. *Emerg. Infect. Dis.* 21, 1455-1457 (2015).
26. P. M. Lantos, L. E. Nigrovic, P. G. Auwaerter, V. G. Fowler, Jr., F. Ruffin, R. J. Brinkerhoff, J. Reber, C. Williams, J. Broyhill, W. K. Pan, D. N. Gaines, Geographic Expansion of Lyme Disease in the Southeastern United States, 2000-2014. *Open Forum Infect. Dis.* 2, ofv143 (2015).
27. C. R. Molins, L. V. Ashton, G. P. Wormser, A. M. Hess, M. J. Delorey, S. Mahapatra, M. E. Schriefer, J. T. Belisle, Development of a metabolic biosignature for detection of early Lyme disease. *Clin. Infect. Dis.* 60, 1767-1775 (2015).
28. J. Xia, I. V. Sinelnikov, B. Han, D. S. Wishart, MetaboAnalyst 3.0—making metabolomics more meaningful. *Nucleic Acids Res.* 43, W251-257 (2015).
29. F. A. Iannotti, V. Di Marzo, S. Petrosino, Endocannabinoids and endocannabinoid-related mediators: Targets, metabolism and role in neurological disorders. *Prog. Lipid Res.* 62, 107-128 (2016).
30. J. D. Forrester, M. Brett, J. Matthias, D. Stanek, C. B. Springs, N. Marsden-Haug, H. Oltean, J. S. Baker, K. J. Kugeler, P. S. Mead, A. Hinckley, Epidemiology of Lyme disease in low-incidence states. *Ticks Tick Borne Dis.* 6, 721-723 (2015).
31. M. Dalle Carbonare, E. Del Giudice, A. Stecca, D. Colavito, M. Fabris, A. D'Arrigo, D. Bernardini, M. Dam, A. Leon, A saturated N-acylethanolamine other than N-palmitoyl ethanolamine with anti-inflammatory properties: a neglected story. *J. Neuroendocrinol* 20 Suppl 1, 26-34 (2008).
32. V. Di Marzo, D. Melck, P. Orlando, T. Bisogno, O. Zagoory, M. Bifulco, Z. Vogel, L. De Petrocellis, Palmitoylethanolamide inhibits the expression of fatty acid amide hydrolase and enhances the anti-proliferative effect of anandamide in human breast cancer cells. *Biochem. J.* 358, 249-255 (2001).
33. J. Lo Verme, J. Fu, G. Astarita, G. La Rana, R. Russo, A. Calignano, D. Piomelli, The nuclear receptor peroxisome proliferator-activated receptor-alpha mediates the anti-inflammatory actions of palmitoylethanolamide. *Mol. Pharmacol.* 67, 15-19 (2005).
34. H. B. Bradshaw, N. Rimmerman, S. S. Hu, V. M. Benton, J. M. Stuart, K. Masuda, B. F. Cravatt, D. K. O'Dell, J. M. Walker, The endocannabinoid anandamide is a precursor for the signaling lipid N-arachidonoyl glycine by two distinct pathways. *BMC Biochem.* 10, 14 (2009).
35. B. F. Cravatt, D. K. Giang, S. P. Mayfield, D. L. Boger, R. A. Lerner, N. B. Gilula, Molecular characterization of an enzyme that degrades neuromodulatory fatty-acid amides. *Nature* 384, 83-87 (1996).
36. E. B. Divito, M. Cascio, Metabolism, physiology, and analyses of primary fatty acid amides. *Chem. Rev.* 113, 7343-7353 (2013).
37. E. J. Masters, C. N. Grigery, R. W. Masters, STARI, or Masters disease: Lone Star tick-vectored Lyme-like illness. *Infect. Dis. Clin. North Am.* 22, 361-376, (2008).
38. C. f. D. C. a. Prevention, Recommendations for test performance and interpretation from the Second National Conference on Serologic Diagnosis of Lyme Disease. *Morb. Mortal. Wkly. Rep.* 44, 590-591 (1995).
39. M. E. Aguero-Rosenfeld, G. Wang, I. Schwartz, G. P. Wormser, Diagnosis of lyme borreliosis. *Clin. Microbiol. Rev.* 18, 484-509 (2005).
40. E. J. Masters, Lyme-like illness currently deserves Lyme-like treatment. *Clin. Infect. Dis.* 42, 580-581; author reply 581-582 (2006).
41. P. Comstedt, M. Hanner, W. Schuler, A. Meinke, R. Schlegl, U. Lundberg, Characterization and optimization of a novel vaccine for protection against Lyme borreliosis. *Vaccine* 33, 5982-5988 (2015).
42. N. Wressnigg, P. N. Barrett, E. M. Pollabauer, M. O'Rourke, D. Portsmouth, M. G. Schwendinger, B. A. Crowe, I. Livey, T. Dvorak, B. Schmitt, M. Zeitlinger, H. Kollaritsch, M. Esen, P. G. Kremsner, T. Jelinek, R. Aschoff, R. Weisser, I. F. Naudts, G. Aichinger, A Novel multivalent OspA vaccine against Lyme borreliosis is safe and immunogenic in an adult population previously infected with *Borrelia burgdorferi* sensu lato. *Clin. Vaccine Immunol.* 21, 1490-1499 (2014).
43. M. Gomes-Solecki, Blocking pathogen transmission at the source: reservoir targeted OspA-based vaccines against *Borrelia burgdorferi*. *Front Cell Infect. Microbiol.* 4, 136 (2014).
44. L. M. Richer, D. Brisson, R. Melo, R. S. Ostfeld, N. Zeidner, M. Gomes-Solecki, Reservoir targeted vaccine against *Borrelia burgdorferi*: a new strategy to prevent Lyme disease transmission. *J. Infect. Dis.* 209, 1972-1980 (2014).
45. B. J. B. Johnson, in *Lyme Disease: An Evidence-based Approach*. (CAB International, Wallingford, Oxfordshire, UK; Cambridge, Mass. 2011), chap. 4, pp. 73-87.
46. G. P. Wormser, A. Levin, S. Soman, O. Adenikinju, M. V. Longo, J. A. Branda, Comparative cost-effectiveness of two-tiered testing strategies for serodiagnosis of lyme disease with noncutaneous manifestations. *J. Clin. Microbiol.* 51, 4045-4049 (2013).
47. F. G. Strathmann, A. N. Hoofnagle, Current and future applications of mass spectrometry to the clinical laboratory. *Am. J. Clin. Pathol.* 136, 609-616 (2011).
48. N. R. Kitteringham, R. E. Jenkins, C. S. Lane, V. L. Elliott, B. K. Park, Multiple reaction monitoring for quantitative biomarker analysis in proteomics and metabolomics. *J. Chromatogr. B Analyt. Technol. Biomed. Life Sci.* 877, 1229-1239 (2009).
49. D. S. Dumlao, M. W. Buczynski, P. C. Norris, R. Harkewicz, E. A. Dennis, High-throughput lipidomic analysis of fatty acid derived eicosanoids and N-acylethanolamines. *Biochim. Biophys. Acta* 1811, 724-736 (2011).
50. S. Mahapatra, A. M. Hess, J. L. Johnson, K. D. Eisenach, M. A. DeGroote, P. Gitta, M. L. Joloba, G. Kaplan, G. Walzl, W. H. Boom, J. T. Belisle, A metabolic biosignature of early response to anti-tuberculosis treatment. *BMC Infect. Dis.* 14, 53 (2014).

51. N. V. Voge, R. Perera, S. Mahapatra, L. Gresh, A. Balmaseda, M. A. Lorono-Pino, A. S. Hopf-Jannasch, J. T. Belisle, E. Harris, C. D. Blair, B. J. Beaty, Metabolomics-Based Discovery of Small Molecule Biomarkers in Serum Associated with Dengue Virus Infections and Disease Outcomes. *PLoS Negl. Trop. Dis.* 10, e0004449 (2016).
52. L. Tritten, J. Keiser, M. Godejohann, J. Utzinger, M. Vargas, O. Beckonert, E. Holmes, J. Saric, Metabolic profiling framework for discovery of candidate diagnostic markers of malaria. *Sci. Rep.* 3, 2769 (2013).
53. N. Vinayavekhin, G. Mahipant, A. S. Vangnai, P. Sangvanich, Untargeted metabolomics analysis revealed changes in the composition of glycerolipids and phospholipids in *Bacillus subtilis* under 1-butanol stress. *Appl. Microbiol. Biotechnol.* 99, 5971-5983 (2015).
54. K. L. Clark, B. F. Leydet, C. Threlkeld, Geographical and genospecies distribution of *Borrelia burgdorferi* sensu lato DNA detected in humans in the USA. *J. Med. Microbiol.* 63, 674-684 (2014).
55. J. H. Oliver, Jr., T. Lin, L. Gao, K. L. Clark, C. W. Banks, L. A. Durden, A. M. James, F. W. Chandler, Jr., An enzootic transmission cycle of Lyme borreliosis spirochetes in the southeastern United States. *Proc. Natl. Acad. Sci. USA.* 100, 11642-11645 (2003).
56. H. M. Feder, Jr., D. M. Floss, L. Zemel, S. R. Telford, 3rd, F. Dias, G. P. Wormser, Southern Tick-Associated Rash Illness (STARI) in the North: STARI following a tick bite in Long Island, N.Y. *Clin. Infect. Dis.* 53, e142-146 (2011).
57. M. F. Vaughn, P. D. Sloane, K. Knierim, D. Varkey, M. A. Pilgard, B. J. Johnson, Practice-Based Research Network Partnership with CDC to acquire clinical specimens to study the etiology of southern tick-associated rash illness (STARI). *J. Am. Board Fam. Med.* 23, 720-727 (2010).
58. W. Wang, H. Zhou, H. Lin, S. Roy, T. A. Shaler, L. R. Hill, S. Norton, P. Kumar, M. Anderle, C. H. Becker, Quantification of proteins and metabolites by mass spectrometry without isotopic labeling or spiked standards. *Anal. Chem.* 75, 4818-4826 (2003).
59. R. M. Salek, C. Steinbeck, M. R. Viant, R. Goodacre, W. B. Dunn, The role of reporting standards for metabolite annotation and identification in metabolomic studies. *Gigascience* 2, 13 (2013).
60. R. C. Team. (R Foundation for Statistical Computing, Vienna, Austria, 2016).
61. A. L. a. M. Wiener, Classification and Regression by random Forest. *R News* 3, 18-22 (2002).
62. J. Friedman, T. Hastie, R. Tibshirani, Regularization Paths for Generalized Linear Models via Coordinate Descent. *J. Stat. Softw.* 33, 1-22 (2010).
63. X. Robin, N. Turck, A. Hainard, N. Tiberti, F. Lisacek, J. C. Sanchez, M. Muller, pROC: an open-source package for R and S+ to analyze and compare ROC curves. *BMC Bioinformatics* 12, 77 (2011).
64. D. M. D. Adler, rgl: 3D Visualization Using OpenGL. R package version 0.96.0. (2016).

TABLE 1

Classification modeling using the 261 molecular feature biosignature list.

| | | | RF (261 MFs) | | LASSO (38/82 MFs$^\pm$) | |
|---|---|---|---|---|---|---|
| Classification Model | Test-Set Sample Group | Number of Data Files* | Number Correctly Predicted | % Classification Accuracy | Number Correctly Predicted | % Classification Accuracy |
| 1: Two-Way Model | Early Lyme Disease | 60 | 58 | 97 | 59 | 98 |
| | STARI | 38 | 34 | 89 | 34 | 89 |
| 2: Three-Way Model | Early Lyme Disease | 60 | 51 | 85 | 51 | 85 |
| | STARI | 38 | 35 | 92 | 35 | 92 |
| | Healthy Controls | 40 | 38 | 95 | 37 | 93 |

RF, random forest; LASSO, least absolute shrinkage and selection operator; MF, molecular feature.
*Samples were analyzed in duplicate by LC-MS.
$^\pm$A total of 38 MFs were selected by the LASSO model for two-way modeling and 82 MFs were selected by the LASSO for three-way modeling.

TABLE 2

Serum samples used in the study

| Description of Samples | Sample Nos. | Sample Criteria for Inclusion | Sample Purpose | State Collected | Sample Provider* | Ref. |
|---|---|---|---|---|---|---|
| Early Lyme Disease (n = 70) | | | | | | |
| Age: 16-81 Male (52) Female (18) | 70 | At least one EM present on initial visit to the clinic. Samples were collected at initial visit to the clinic and pre-treatment. Positive culture and/or PCR test for *B. burgdorferi*. Patients lived in an endemic area for LD. | Discovery Training and Test | NY | NYMC | (27) |
| STARI (n = 55) | | | | | | |
| STARI Group 1 Age: 4-82 | 33 | All patients had a physician-diagnosed erythema migrans- | Discovery Training and | NC, VA, GA, KY, | CDC, Fort Collins, | (57) |

TABLE 2-continued

Serum samples used in the study

| Description of Samples | Sample Nos. | Sample Criteria for Inclusion | Sample Purpose | State Collected | Sample Provider* | Ref. |
|---|---|---|---|---|---|---|
| Male (17) Female (16) STARI Group 2 Age: 8-80 Male (13) Female (9) | 22 | like rash ≥ 5 cm and a recent history of possible or verified exposure to *Amblyomma americanum* (lone star) ticks before the onset of symptoms. Patients lived in a non-endemic area for LD with the exception of three patients.± Samples were standard two-tiered negative for LD. | Test | TN, AL, IA and NE MO | CO NYMC | (20) |
| Healthy Donors (n = 95) | | | | | | |
| Healthy Group 1 Age: 18-unknown Male (8) Female (20) | 28 | No history of tick-borne disease within the last 12 months and lived in a non-endemic area for LD. Samples were standard two-tiered negative for LD. | Discovery Training and Test | CO | CDC, Fort Collins, CO | — |
| Healthy Group 2†# Age: 18-74§ | 30 | No history of Lyme disease and lived in an endemic area for LD. Samples were standard two-tiered negative for LD. | | NY | NYMC | — |
| Healthy Group 3† Age: 18-60 | 37 | No previous diagnosis with and/or treated for LD; and could not have lived within the past 10 years in a state with a high incidence of LD (CT, DE, ME, MD, MA, MN, NH, NJ, NY, PA, VT, VA and WI). Samples were standard two-tiered negative for LD. | Verification¥ | FL | UCF (65) | (65) |

NYMC, New York Medical College;
CDC, Centers for Disease Control and Prevention;
UCF, University of Central Florida;
LD, Lime disease
*Sample handling varied among laboratories that provided samples.
±Two patients were from southwest Iowa and one was from southeast Virginia; both areas are considered to have low risk for Lyme disease and a higher prevalence of *A. americanum* as compared to *I. scapularis*.
†The gender of these donors was approximately 50% females and 50% males.
The samples were obtained from the same geographic location as the early Lyme disease samples.
§Age ranged from 18-74 for all donors (n = 100). Only a subset of 30 donors were used for this study.
¥Healthy controls from Florida were used to verify that the dysregulation of MFs between EL and STARI were not due to regional differences.

TABLE 3

261 MF biosignature list The experimentally obtained mass of each MF was used to search against the Metlin database and the Human Metabolome Database (HMDB). The predicted chemical structures had to match to the MF mass within 15 ppm. MFs could have matches to multiple chemical structures of within the same classes of chemicals or to structures of a different chemical class. The putative chemical structure data obtained by interrogation against the HMDB were used to evaluate possible metabolic pathways that differed between early Lyme disease and STARI patients (see Table 4).

| MF # | m/z Mass Retention Time | Compound Predicted Formula Predicted Chemical Structure (based on accurate mass) | Metabolite Class or Pathway | Level of Iden. | # of Alternate Chemical Structures ± 15 ppm | RF Model | 2 Way LASSO Model | 3 Way LASSO Model |
|---|---|---|---|---|---|---|---|---|
| CSU/CDC-001 | 166.0852 165.078 1.86 | $C_9H_{11}NO_2$ Phenylalanine | Phenylalanine metabolism | 1 | >5 | x | x | x |
| CSU/CDC-002 | 239.0919 238.0844 11.66 | $C_{12}H_{14}O_5$ Trans-2,3,4-trimethoxycinnamate | Phenylpropanoid and polyketide metabolism | 4 | 5 | x | x | |
| CSU/CDC-003 | 886.4296 1770.8438 12.18 | — | — | 4 | 0 | x | | x |
| CSU/CDC-004 | 181.0859 180.0788 14.7 | $C_{10}H_{12}O_3$ 5'-(3'-Methoxy-4'-hydroxyphenyl)-gamma-valerolactone | Endogenous metabolite associated with microbiome | 4 | >5 | x | | x |

TABLE 3-continued

261 MF biosignature list The experimentally obtained mass of each MF was used to search against the Metlin database and the Human Metabolome Database (HMDB). The predicted chemical structures had to match to the MF mass within 15 ppm. MFs could have matches to multiple chemical structures of within the same classes of chemicals or to structures of a different chemical class. The putative chemical structure data obtained by interrogation against the HMDB were used to evaluate possible metabolic pathways that differed between early Lyme disease and STARI patients (see Table 4).

| MF # | m/z Mass Retention Time | Compound Predicted Formula Predicted Chemical Structure (based on accurate mass) | Metabolite Class or Pathway | Level of Iden. | # of Alternate Chemical Structures ± 15 ppm | RF Model | 2 Way LASSO Model | 3 Way LASSO Model |
|---|---|---|---|---|---|---|---|---|
| CSU/CDC-005 | 223.0968 222.0895 14.69 | $C_{12}H_{14}O_4$ — | — | 4 | >5 | x | | |
| CSU/CDC-006 | 286.1444 285.1371 16.08 | $C_{17}H_{19}NO_3$ Piperine | Alkaloid metabolism | 1 | >5 | x | | x |
| CSU/CDC-007 | 286.1437 285.1364 16.06 | $C_{17}H_{19}NO_3$ — | — | 4 | >5 | x | | |
| CSU/CDC-008 | 463.2339 462.2248 16.36 | $C_{25}H_{34}O_8$ Ala Lys Met Asn | Peptide | 4 | >5 | x | | x |
| CSU/CDC-009 | 242.2844 241.2772 17.1 | $C_{16}H_{35}N$ — | — | 4 | 1 | x | | x |
| CSU/CDC-010 | 1112.6727 1111.6663 17.86 | — — | — | 4 | 0 | x | | |
| CSU/CDC-011 | 454.2923 453.2867 18.08 | $C_{21}H_{44}NO_7P$ Glycerophospho-N-Palmitoyl Ethanolamine | N-acyl ethanolamine metabolism | 3 | >5 | x | | |
| CSU/CDC-012 | 270.3156 269.3076 18.02 | $C_{18}H_{39}N$ — | — | 4 | 1 | x | x | x |
| CSU/CDC-013 | 284.3314 283.3236 18.13 | $C_{19}H_{41}N$ — | — | 4 | 1 | x | x | x |
| CSU/CDC-014 | 300.6407 599.268 18.27 | $C_{33}H_{37}N_5O_6$ Asp Phe Arg Tyr | Peptide | 4 | >5 | x | x | x |
| CSU/CDC-015 | 522.3580 521.3483 18.5 | $C_{26}H_{52}NO_7P$ PC(18:1) | Glycerophospholipid metabolism | 3 | >5 | x | | |
| CSU/CDC-016 | 363.2192 362.2132 18.58 | $C_{21}H_{30}O_5$ 4,5α-dihydrocortisone | Sterol metabolism | 4 | >5 | x | | |
| CSU/CDC-017 | 590.4237 589.4194 19.24 | — — | — | 4 | 0 | x | | x |
| CSU/CDC-018 | 388.3939 387.3868 19.53 | — — | — | 4 | 0 | x | | |
| CSU/CDC-019 | 300.2892 299.2821 19.66 | $C_{18}H_{37}NO_2$ Palmitoyl ethanolamide | N-acyl ethanolamine metabolism | 1 | >5 | x | x | x |
| CSU/CDC-020 | 256.2632 255.2561 20.08 | $C_{16}H_{33}NO$ Palmitic amide | Primary Fatty Acid Amide Metabolism | 1 | 1 | x | | |
| CSU/CDC-021 | 394.3515 376.3171 20.09 | — — | — | 4 | 0 | x | | |
| CSU/CDC-022 | 228.1955 227.1885 20.99 | — — | — | 4 | 0 | x | | |
| CSU/CDC-023 | 284.2943 283.2872 21.15 | $C_{18}H_{37}NO$ Stearamide | Primary Fatty Acid Amide Metabolism | 1 | 1 | x | | |
| CSU/CDC-024 | 338.3430 337.3344 22.14 | $C_{22}H_{43}NO$ 13Z-Docosenamide (Erucamide) | Primary Fatty Acid Amide Metabolism | 1 | 3 | x | | |
| CSU/CDC-025 | 689.5604 688.5504 22.52 | $C_{38}H_{77}N_2O_6P$ SM(d18:1-15:0)/ SM (d18:1/14:1-OH) | Sphingolipid metabolism | 3 | >5 | x | | |

TABLE 3-continued

261 MF biosignature list The experimentally obtained mass of each MF was used to search against the Metlin database and the Human Metabolome Database (HMDB). The predicted chemical structures had to match to the MF mass within 15 ppm. MFs could have matches to multiple chemical structures of within the same classes of chemicals or to structures of a different chemical class. The putative chemical structure data obtained by interrogation against the HMDB were used to evaluate possible metabolic pathways that differed between early Lyme disease and STARI patients (see Table 4).

| MF # | m/z Mass Retention Time | Compound Predicted Formula Predicted Chemical Structure (based on accurate mass) | Metabolite Class or Pathway | Level of Iden. | # of Alternate Chemical Structures ± 15 ppm | RF Model | 2 Way LASSO Model | 3 Way LASSO Model |
|---|---|---|---|---|---|---|---|---|
| CSU/CDC-026 | 553.3904 552.3819 23.38 | $C_{35}H_{52}O_5$ Furohyperforin | Endogenous metabolite - derived from food | 4 | 3 | x | | x |
| CSU/CDC-027 | 432.2803 431.2727 10.8 | $C_{25}H_{37}NO_5$ Ala Ile Lys Thr | Peptide | 4 | >5 | x | | |
| CSU/CDC-028 | 389.2174 388.2094 15.47 | $C_{19}H_{32}O_8$ Methyl 10,12,13,15-bisepidioxy-16-hydroperoxy-8E-octadecenoate | Fatty acid metabolism | 4 | >5 | x | x | |
| CSU/CDC-029 | 385.2211 384.2147 15.84 | $C_{16}H_{28}N_6O_5$ Lys His Thr | Peptides | 4 | >5 | x | | |
| CSU/CDC-030 | 399.2364 398.2313 16.23 | — | — | 4 | 0 | x | | x |
| CSU/CDC-031 | 449.3261 879.6122 17.07 | $C_{46}H_{89}NO_{12}S$ C22-OH Sulfatide | Sphingolipid metabolism | 4 | 2 | x | | |
| CSU/CDC-032 | 467.3821 444.2717 17.1 | $C_{24}H_{40}O_8$ 2-glyceryl-6-keto-PGF1α | Prostaglandin metabolism | 4 | >5 | x | | |
| CSU/CDC-033 | 836.5936 835.5845 17.15 | $C_{44}H_{85}NO_{11}S$ C20 Sulfatide | Sphingolipid metabolism | 4 | 1 | x | | |
| CSU/CDC-034 | 792.5646 791.5581 17.17 | $C_{42}H_{82}NO_{10}P$ PS(36:0) | Glycerophospholipid metabolism | 4 | >5 | x | | |
| CSU/CDC-035 | 356.2802 355.2722 17.35 | — | — | 4 | 0 | x | | |
| CSU/CDC-036 | 806.5798 805.5746 17.71 | $C_{43}H_{84}NO_{10}P$ PS(37:0) | Glycerophospholipid metabolism | 4 | >5 | x | | |
| CSU/CDC-037 | 762.5582 761.5482 17.79 | $C_{41}H_{80}NO_9P$ PS-O(35:1) | Glycerophospholipid metabolism | 4 | >5 | x | | |
| CSU/CDC-038 | 718.5308 700.4946 17.88 | $C_{39}H_{73}O_8P$ PA(36:2) | Glycerophospholipid metabolism | 4 | >5 | x | | |
| CSU/CDC-039 | 734.5079 1449.9753 17.81 | — | — | 4 | 0 | x | x | x |
| CSU/CDC-040 | 690.4825 1361.924 17.95 | — | — | 4 | 0 | x | | |
| CSU/CDC-041 | 426.1798 425.1725 18.03 | — | — | 4 | 0 | x | | |
| CSU/CDC-042 | 580.4144 1158.8173 18.26 | — | — | 4 | 0 | x | | x |
| CSU/CDC-043 | 741.5154 1481.0142 18.24 | $C_{83}H_{150}O_{17}P_2$ CL(74:6) | Glycerophospholipid metabolism | 4 | 2 | x | | |
| CSU/CDC-044 | 864.6245 863.6166 18.17 | $C_{46}H_{89}NO_{11}S$ C22 Sulfatide | Sphingolipid metabolism | 4 | 2 | x | | |
| CSU/CDC-045 | 558.4017 1080.7347 18.28 | — | — | 4 | 0 | x | | |
| CSU/CDC-046 | 719.5012 1402.9377 18.26 | — | — | 4 | 0 | x | | |

TABLE 3-continued

261 MF biosignature list The experimentally obtained mass of each MF was used to search against the Metlin database and the Human Metabolome Database (HMDB). The predicted chemical structures had to match to the MF mass within 15 ppm. MFs could have matches to multiple chemical structures of within the same classes of chemicals or to structures of a different chemical class. The putative chemical structure data obtained by interrogation against the HMDB were used to evaluate possible metabolic pathways that differed between early Lyme disease and STARI patients (see Table 4).

| MF # | m/z Mass Retention Time | Compound Predicted Formula Predicted Chemical Structure (based on accurate mass) | Metabolite Class or Pathway | Level of Iden. | # of Alternate Chemical Structures ± 15 ppm | RF Model | 2 Way LASSO Model | 3 Way LASSO Model |
|---|---|---|---|---|---|---|---|---|
| CSU/CDC-047 | 536.3897 1053.7382 18.36 | — | — | 4 | 0 | x | | |
| CSU/CDC-048 | 538.8674 1058.696 18.4 | — | — | 4 | 0 | x | | |
| CSU/CDC-049 | 653.4619 1270.8593 18.43 | — | — | 4 | 0 | x | | |
| CSU/CDC-050 | 732.5450 714.5092 18.47 | $C_{40}H_{75}O_8P$ PA(37:2) | Glycerophospholipid metabolism | 4 | >5 | x | | |
| CSU/CDC-051 | 748.5232 1478.0059 18.58 | — | — | 4 | 0 | x | | |
| CSU/CDC-052 | 704.4985 1372.925 18.7 | — | — | 4 | 0 | x | | x |
| CSU/CDC-053 | 682.4841 1328.9008 18.77 | — | — | 4 | 0 | x | | |
| CSU/CDC-054 | 360.3615 359.3555 18.89 | — | — | 4 | 0 | x | | |
| CSU/CDC-055 | 441.2412 440.2325 19.09 | $C_{20}H_{32}N_4O_7$ Pro Asp Pro Leu | Peptide | 4 | >5 | x | | |
| CSU/CDC-056 | 638.4554 1240.847 18.92 | — | — | 4 | 0 | x | | |
| CSU/CDC-057 | 755.5311 1474.9941 18.94 | $C_{83}H_{144}O_{17}P_2$ CL(74:9) | Glycero-phospholipid metabolism | 4 | 2 | x | | |
| CSU/CDC-058 | 711.5023 1386.9417 19.09 | — | — | 4 | 0 | x | | |
| CSU/CDC-059 | 784.5530 1567.0908 19.27 | — | — | 4 | 0 | x | | |
| CSU/CDC-060 | 645.4660 1271.8896 19.36 | — | — | 4 | 0 | x | | |
| CSU/CDC-061 | 623.4521 1210.8362 19.55 | — | — | 4 | 0 | x | | x |
| CSU/CDC-062 | 370.1837 369.1757 19.7 | $C_{19}H_{23}N_5O_3$ — | — | 4 | 1 | x | x | x |
| CSU/CDC-063 | 300.2886 282.2569 19.84 | $C_{18}H_{34}O_2$ 13Z-octadecenoic acid | Fatty acid metabolism | 4 | >5 | x | | |
| CSU/CDC-064 | 309.0981 308.0913 2.06 | $C_{15}H_{16}O_7$ — | — | 4 | 3 | x | | |
| CSU/CDC-065 | 561.2965 1120.5778 11.7 | $C_{54}H_{88}O_{24}$ Camellioside D | Endogenous metabolite - derived from food | 4 | 5 | x | | |
| CSU/CDC-066 | 811.1942 810.1869 12.07 | $C_{42}H_{30}N_6O_{12}$ — | — | 4 | 1 | x | x | x |
| CSU/CDC-067 | 947.7976 946.7936 14.55 | $C_{62}H_{106}O_6$ TAG(59:7) | Triacylglycerol metabolism | 4 | >5 | x | x | x |
| CSU/CDC-068 | 1106.2625 2209.5193 14.53 | — | — | 4 | 0 | x | | |

TABLE 3-continued

261 MF biosignature list The experimentally obtained mass of each MF was used to search against the Metlin database and the Human Metabolome Database (HMDB). The predicted chemical structures had to match to the MF mass within 15 ppm. MFs could have matches to multiple chemical structures of within the same classes of chemicals or to structures of a different chemical class. The putative chemical structure data obtained by interrogation against the HMDB were used to evaluate possible metabolic pathways that differed between early Lyme disease and STARI patients (see Table 4).

| MF # | m/z Mass Retention Time | Compound Predicted Formula Predicted Chemical Structure (based on accurate mass) | Metabolite Class or Pathway | Level of Iden. | # of Alternate Chemical Structures ± 15 ppm | RF Model | 2 Way LASSO Model | 3 Way LASSO Model |
|---|---|---|---|---|---|---|---|---|
| CSU/CDC-069 | 371.2070 370.1997 15.52 | $C_{15}H_{26}N_6O_7$ His Ser Lys | Peptide | 4 | >5 | x | | |
| CSU/CDC-070 | 389.2178 388.2099 15.52 | $C_{19}H_{32}O_8$ | — | 4 | >5 | x | | x |
| CSU/CDC-071 | 443.2649 442.256 15.52 | $C_{19}H_{34}N_6O_6$ Pro Gln Ala Lys | Peptide | 3 | >5 | x | | |
| CSU/CDC-072 | 410.2033 409.196 17.18 | — | — | 4 | 3 | x | x | x |
| CSU/CDC-073 | 850.6093 849.6009 17.63 | $C_{48}H_{84}NO_9P$ PS-O(42:6) | Glycero-phospholipid metabolism | 4 | 1 | x | | |
| CSU/CDC-074 | 1111.6690 1110.6656 17.89 | — | — | 4 | 0 | x | | x |
| CSU/CDC-075 | 1487.0005 1485.9987 18.17 | — | — | 4 | 0 | x | x | x |
| CSU/CDC-076 | 697.4896 1358.909 18.32 | — | — | 4 | 0 | x | | |
| CSU/CDC-077 | 439.8234 877.6325 18.71 | — | — | 4 | 0 | x | | |
| CSU/CDC-078 | 567.8897 566.8818 18.73 | — | — | 4 | 0 | x | | |
| CSU/CDC-079 | 435.2506 434.243 19 | $C_{21}H_{39}O_7P$ Lyso-PA(18:2) | Glycero-phospholipid metabolism | 4 | >5 | x | | |
| CSU/CDC-080 | 834.6136 833.6057 18.83 | $C_{45}H_{88}NO_{10}P$ PS(39:0) | Glycero-phospholipid metabolism | 4 | >5 | x | | |
| CSU/CDC-081 | 534.8834 533.8771 18.82 | — | — | 4 | 0 | x | | |
| CSU/CDC-082 | 468.8441 467.8373 19.13 | — | — | 4 | 0 | x | | |
| CSU/CDC-083 | 482.4040 481.3976 19.99 | — | — | 4 | 0 | x | | x |
| CSU/CDC-084 | 533.1929 532.1854 20.84 | $C_{23}H_{28}N_6O_9$ Asp His Phe Asp | Peptide | 4 | >5 | x | | x |
| CSU/CDC-085 | 312.3259 311.319 22.05 | — | — | 4 | 0 | x | | |
| CSU/CDC-086 | 137.0463 136.0378 1.37 | $C_4H_8O_5$ Threonate | Sugar metabolite | 4 | >5 | x | x | x |
| CSU/CDC-087 | 466.3152 465.3085 14.73 | $C_{26}H_{43}NO_6$ Glycocholic acid | Bile acid metabolism | 1 | 3 | x | | x |
| CSU/CDC-088 | 228.1955 227.1884 15.22 | — | — | 4 | 0 | x | | |
| CSU/CDC-089 | 385.2211 384.2143 15.83 | $C_{20}H_{32}O_7$ Lys His Thr | Peptide | 4 | >5 | x | | |
| CSU/CDC-090 | 403.2338 402.2253 15.84 | $C_{16}H_{30}N_6O_6$ Lys Gln Gln | Peptide | 3 | >5 | x | | |

TABLE 3-continued

261 MF biosignature list The experimentally obtained mass of each MF was used to search against the Metlin database and the Human Metabolome Database (HMDB). The predicted chemical structures had to match to the MF mass within 15 ppm. MFs could have matches to multiple chemical structures of within the same classes of chemicals or to structures of a different chemical class. The putative chemical structure data obtained by interrogation against the HMDB were used to evaluate possible metabolic pathways that differed between early Lyme disease and STARI patients (see Table 4).

| MF # | m/z Mass Retention Time | Compound Predicted Formula Predicted Chemical Structure (based on accurate mass) | Metabolite Class or Pathway | Level of Iden. | # of Alternate Chemical Structures ± 15 ppm | RF Model | 2 Way LASSO Model | 3 Way LASSO Model |
|---|---|---|---|---|---|---|---|---|
| CSU/CDC-091 | 683.4728 1347.9062 17.56 | — | — | 4 | 0 | x | | x |
| CSU/CDC-092 | 675.4753 1348.9377 18.37 | — | — | 4 | 0 | x | | |
| CSU/CDC-093 | 682.4841 1345.9257 18.76 | — | — | 4 | 0 | x | | |
| CSU/CDC-094 | 762.5401 1506.0367 19.36 | — | — | 4 | 0 | x | | |
| CSU/CDC-095 | 227.0897 204.1002 9.68 | $C_9H_{16}O_5$ — | — | 4 | 2 | x | | x |
| CSU/CDC-177 | 189.1122 188.1049 12.27 | $C_9H_{14}O_4$ Nonanedioic Acid | Fatty acid metabolism | 1 | >5 | x | | |
| CSU/CDC-097 | 169.0860 168.0786 9.94 | $C_9H_{12}O_3$ 2,6-Dimethoxy-4-methylphenol | Endogenous metabolite - derived from food | 4 | >5 | x | | |
| CSU/CDC-098 | 183.1016 182.0943 10.89 | $C_{10}H_{14}O_3$ — | — | 4 | >5 | x | | x |
| CSU/CDC-099 | 476.3055 475.2993 11.09 | $C_{26}H_{41}N_3O_5$ — | — | 4 | 5 | x | | x |
| CSU/CDC-100 | 276.1263 275.1196 11.16 | $C_{15}H_{17}NO_4$ — | — | 4 | 3 | x | | |
| CSU/CDC-101 | 314.0672 313.06 11.56 | $C_{10}H_{12}N_5O_5P$ — | — | 4 | 1 | x | | |
| CSU/CDC-102 | 201.1122 200.1047 11.56 | $C_{10}H_{16}O_4$ — | Fatty acid metabolism | 3 | >5 | x | | |
| CSU/CDC-103 | 115.0391 114.0318 11.57 | $C_5H_6O_3$ — | Phenylalanine metabolism | 4 | >5 | x | | |
| CSU/CDC-104 | 491.1569 490.1504 11.56 | $C_{24}H_{26}O_{11}$ — | — | 4 | >5 | x | | |
| CSU/CDC-105 | 241.1054 218.1157 11.57 | $C_{10}H_{18}O_5$ 3-Hydroxy-sebacic acid | Fatty acid metabolism | 4 | 3 | x | | |
| CSU/CDC-106 | 105.0914 104.0841 11.57 | — | — | 4 | 0 | x | | |
| CSU/CDC-107 | 811.7965 810.7882 12.07 | — | — | 4 | 0 | x | x | x |
| CSU/CDC-108 | 311.1472 328.1391 12.22 | $C_{18}H_{20}N_2O_4$ Phe Tyr | Peptide | 3 | >5 | x | | |
| CSU/CDC-109 | 271.1543 270.1464 12.24 | — | — | 4 | 0 | x | | |
| CSU/CDC-110 | 169.0860 168.0787 12.24 | $C_9H_{12}O_3$ 2,6-Dimethoxy-4-methylphenol | Endogenous metabolite - derived from food | 4 | >5 | x | | |
| CSU/CDC-111 | 187.0967 186.0889 12.24 | $C_9H_{14}O_4$ — | — | 4 | 4 | x | | |

TABLE 3-continued

261 MF biosignature list The experimentally obtained mass of each MF was used to search against the Metlin database and the Human Metabolome Database (HMDB). The predicted chemical structures had to match to the MF mass within 15 ppm. MFs could have matches to multiple chemical structures of within the same classes of chemicals or to structures of a different chemical class. The putative chemical structure data obtained by interrogation against the HMDB were used to evaluate possible metabolic pathways that differed between early Lyme disease and STARI patients (see Table 4).

| MF # | m/z Mass Retention Time | Compound Predicted Formula Predicted Chemical Structure (based on accurate mass) | Metabolite Class or Pathway | Level of Iden. | # of Alternate Chemical Structures ± 15 ppm | RF Model | 2 Way LASSO Model | 3 Way LASSO Model |
|---|---|---|---|---|---|---|---|---|
| CSU/CDC-112 | 215.1283 214.1209 12.32 | $C_{11}H_{18}O_4$ alpha-Carboxy-delta-decalactone | Endogenous metabolite - derived from food | 4 | 4 | x | | x |
| CSU/CDC-113 | 475.1635 474.1547 12.25 | $C_{25}H_{22}N_4O_6$ His Cys Asp Thr | Peptide | 4 | >5 | x | | |
| CSU/CDC-114 | 129.0547 128.0474 12.33 | $C_6H_8O_3$ (4E)-2-Oxohexenoic acid | Fatty acid metabolism | 4 | >5 | x | | |
| CSU/CDC-115 | 519.1881 518.1813 12.33 | $C_{20}H_{30}N_4O_{12}$ Poly-g-D-glutamate | Poly D-glutamate metabolism | 4 | >5 | x | | x |
| CSU/CDC-116 | 125.0599 124.0527 13.12 | $C_7H_8O_2$ 4-Methylcatechol | Catechol metabolism | 3 | >5 | x | | |
| CSU/CDC-117 | 247.1550 246.1469 13.13 | $C_{12}H_{22}O_5$ 3-Hydroxy-dodecanedioic acid | Fatty acid metabolism | 4 | 4 | x | | |
| CSU/CDC-118 | 517.2614 516.2544 13.13 | $C_{21}H_{36}N_6O_9$ Gln Glu Gln Ile | Peptide | 4 | >5 | x | | |
| CSU/CDC-119 | 301.0739 300.0658 13.14 | $C_{16}H_{12}O_6$ Chrysoeriol | Endogenous metabolite - derived from food | 4 | >5 | x | | |
| CSU/CDC-120 | 327.1773 304.1885 14.17 | $C_{16}H_{24}N_4O_2$ — | — | 4 | 1 | x | | |
| CSU/CDC-121 | 387.2023 386.1935 14.51 | $C_{19}H_{30}O_8$ Citroside A | Endogenous metabolite - derived from food | 4 | >5 | x | | |
| CSU/CDC-122 | 875.8451 1749.684 14.55 | — | — | 4 | 0 | x | | |
| CSU/CDC-123 | 737.5118 736.5056 14.52 | $C_{42}H_{73}O_8P$ PA(39:5) | Glycero-phospholipid metabolism | 4 | >5 | x | | |
| CSU/CDC-124 | 1274.3497 1273.3481 14.96 | — | — | 4 | 0 | x | | |
| CSU/CDC-125 | 1274.2092 1273.2 14.96 | — | — | 4 | 0 | x | | |
| CSU/CDC-126 | 1486.5728 2971.1328 14.95 | — | — | 4 | 0 | x | | |
| CSU/CDC-127 | 965.3818 964.3727 15.37 | — | — | 4 | 0 | x | | |
| CSU/CDC-128 | 1086.1800 2170.3435 15.38 | — | — | 4 | 0 | x | | x |
| CSU/CDC-129 | 1086.0562 2170.0908 15.38 | $C_{97}H_{167}N_5O_{48}$ NeuAcalpha2-3Galbeta1-3GalNAcbeta1-4(9-OAc-NeuAcalpha2-8NeuAcalpha2-3)Galbeta1-4Glcbeta-Cer(d18:1/18:0) | Sphingolipid metabolism | 4 | 1 | x | | |

TABLE 3-continued

261 MF biosignature list The experimentally obtained mass of each MF was used to search against the Metlin database and the Human Metabolome Database (HMDB). The predicted chemical structures had to match to the MF mass within 15 ppm. MFs could have matches to multiple chemical structures of within the same classes of chemicals or to structures of a different chemical class. The putative chemical structure data obtained by interrogation against the HMDB were used to evaluate possible metabolic pathways that differed between early Lyme disease and STARI patients (see Table 4).

| MF # | m/z Mass Retention Time | Compound Predicted Formula Predicted Chemical Structure (based on accurate mass) | Metabolite Class or Pathway | Level of Iden. | # of Alternate Chemical Structures ± 15 ppm | RF Model | 2 Way LASSO Model | 3 Way LASSO Model |
|---|---|---|---|---|---|---|---|---|
| CSU/CDC-130 | 1086.4344 2169.8474 15.39 | — | | 4 | 0 | x | | |
| CSU/CDC-131 | 1240.7800 1239.7712 15.38 | — | — | 4 | 0 | x | | |
| CSU/CDC-132 | 616.1776 615.1699 15.43 | — | — | 4 | 0 | x | x | x |
| CSU/CDC-133 | 285.2061 284.1993 15.99 | $C_{16}H_{28}O_4$ — | — | 4 | 1 | x | | x |
| CSU/CDC-134 | 357.1363 356.1284 15.98 | $C_{20}H_{20}O_6$ Xanthoxylol | Endogenous metabolite - derived from food | 4 | >5 | x | | x |
| CSU/CDC-135 | 317.1956 316.1885 16.24 | $C_{12}H_{24}N_6O_4$ Arg Ala Ala | Peptide | 4 | >5 | x | | |
| CSU/CDC-136 | 299.1853 298.1781 16.24 | $C_{16}H_{26}O_5$ Tetranor-PGE1 | Prostaglandin metabolism | 4 | >5 | x | | x |
| CSU/CDC-137 | 334.2580 333.2514 16.36 | — | — | 4 | 0 | x | | x |
| CSU/CDC-138 | 317.2317 316.2254 16.63 | — | — | 4 | 0 | x | | x |
| CSU/CDC-139 | 299.2219 298.2148 16.64 | $C_{17}H_{30}O_4$ 8E-Heptadecenedioic acid | Fatty acid metabolism | 4 | 2 | x | | |
| CSU/CDC-140 | 748.5408 747.5317 17.23 | $C_{40}H_{78}NO_9P$ PS-O(34:1) | Glycerophospholipid metabolism | 4 | >5 | x | | |
| CSU/CDC-141 | 331.2471 330.2403 17.26 | $C_{18}H_{34}O_5$ 11,12,13-trihydroxy-9-octadecenoic acid | Fatty acid metabolism | 4 | >5 | x | | x |
| CSU/CDC-142 | 712.4935 1422.9749 17.82 | $C_{79}H_{140}O_{17}P_2$ CL(70:7) | Glycerophospholipid metabolism | 4 | 1 | x | | |
| CSU/CDC-143 | 674.5013 673.4957 17.99 | $C_{37}H_{72}NO_7P$ PE-P(32:1) | Glycerophospholipid metabolism | 4 | >5 | x | | |
| CSU/CDC-144 | 583.3480 582.3379 18.04 | $C_{27}H_{46}N_6O_8$ Leu Lys Glu Pro Pro | Peptide | 4 | 1 | x | | x |
| CSU/CDC-145 | 677.9537 676.9478 18.36 | — | — | 4 | 0 | x | | |
| CSU/CDC-146 | 531.3522 530.3457 18.4 | $C_{35}H_{46}O_4$ — | — | 4 | 2 | x | | |
| CSU/CDC-147 | 585.2733 584.2649 18.39 | $C_{33}H_{36}N_4O_6$ 15,16-Dihydrobiliverdin | Bilirubin breakdown products - Porphyrin metabolism | 4 | >5 | x | | |
| CSU/CDC-148 | 513.3431 512.3352 18.4 | — | — | 4 | 0 | x | | |
| CSU/CDC-149 | 611.9156 610.9073 18.59 | — | — | 4 | 0 | x | | |

TABLE 3-continued

261 MF biosignature list The experimentally obtained mass of each MF was used to search against the Metlin database and the Human Metabolome Database (HMDB). The predicted chemical structures had to match to the MF mass within 15 ppm. MFs could have matches to multiple chemical structures of within the same classes of chemicals or to structures of a different chemical class. The putative chemical structure data obtained by interrogation against the HMDB were used to evaluate possible metabolic pathways that differed between early Lyme disease and STARI patients (see Table 4).

| MF # | m/z Mass Retention Time | Compound Predicted Formula Predicted Chemical Structure (based on accurate mass) | Metabolite Class or Pathway | Level of Iden. | # of Alternate Chemical Structures ± 15 ppm | RF Model | 2 Way LASSO Model | 3 Way LASSO Model |
|---|---|---|---|---|---|---|---|---|
| CSU/CDC-150 | 549.0538 531.0181 18.38 | — | — | 4 | 0 | x | | |
| CSU/CDC-151 | 755.5311 1509.0457 18.93 | — | — | 4 | 0 | x | | |
| CSU/CDC-152 | 713.4492 712.4391 19.35 | $C_{38}H_{65}O_{10}P$ PG(32:5) | Glycerophospholipid metabolism | 4 | 4 | x | x | x |
| CSU/CDC-153 | 599.4146 598.4079 19.59 | $C_{40}H_{54}O_4$ Isomytiloxanthin | Isoflavinoid | 4 | >5 | x | | |
| CSU/CDC-154 | 762.5029 761.4919 19.66 | $C_{43}H_{72}NO_8P$ PE(38:7) | Glycero-phospholipid metabolism | 4 | >5 | x | | |
| CSU/CDC-155 | 502.3376 484.3039 19.87 | $C_{27}H_{40}N_4O_4$ Gln Leu Pro Lys | Peptide | 4 | >5 | x | x | x |
| CSU/CDC-156 | 741.4805 740.4698 19.96 | $C_{40}H_{69}O_{10}P$ PG(34:5) | Glycero-phospholipid metabolism | 4 | >5 | x | | |
| CSU/CDC-157 | 648.4672 647.4609 19.98 | $C_{34}H_{66}NO_8P$ PE(29:1) | Glycero-phospholipid metabolism | 4 | >5 | x | | x |
| CSU/CDC-158 | 415.3045 414.2978 20.19 | — | — | 4 | 0 | x | x | x |
| CSU/CDC-159 | 516.3532 498.3199 20.27 | $C_{23}H_{42}N_6O_6$ Ala Leu Ala Pro Lys | Peptide | 4 | 1 | x | | |
| CSU/CDC-160 | 769.5099 768.5018 20.53 | $C_{42}H_{73}O_{10}P$ PG(36:5) | Glycero-phospholipid metabolism | 4 | >5 | x | | |
| CSU/CDC-161 | 862.5881 861.5818 20.86 | — | — | 4 | 0 | x | | |
| CSU/CDC-162 | 837.5358 836.5274 21.11 | $C_{53}H_{72}O_8$ Amitenone | Endogenous metabolite - derived from food | 4 | 2 | x | | |
| CSU/CDC-163 | 558.3995 540.367 21.44 | $C_{26}H_{48}N_6O_6$ Leu Ala Pro Lys Ile | Peptide | 4 | 2 | x | | |
| CSU/CDC-164 | 366.3729 365.3655 22.79 | — | — | 4 | 0 | x | x | x |
| CSU/CDC-165 | 445.2880 854.5087 12.48 | $C_{45}H_{74}O_{15}$ (3b,21b)-12-Oleanene-3,21,28-triol 28-[arabinosyl-(1->3)-arabinosyl-(1->3)-arabinoside] | Endogenous metabolite - derived from food | 4 | 1 | x | | x |
| CSU/CDC-166 | 333.1446 332.1373 12.89 | $C_{12}H_{20}N_4O_7$ Glu Gln Gly | Peptide | 4 | >5 | x | x | x |
| CSU/CDC-167 | 1105.9305 2209.8462 14.53 | — | — | 4 | 0 | x | | |
| CSU/CDC-168 | 329.1049 328.0976 14.61 | $C_{18}H_{16}O_6$ 2-Oxo-3-phenylpropanoic acid | Phenylalanine metabolism | 4 | >5 | x | | |
| CSU/CDC-169 | 1241.2053 1240.2 15.38 | — | — | 4 | 0 | x | | |

TABLE 3-continued

261 MF biosignature list The experimentally obtained mass of each MF was used to search against the Metlin database and the Human Metabolome Database (HMDB). The predicted chemical structures had to match to the MF mass within 15 ppm. MFs could have matches to multiple chemical structures of within the same classes of chemicals or to structures of a different chemical class. The putative chemical structure data obtained by interrogation against the HMDB were used to evaluate possible metabolic pathways that differed between early Lyme disease and STARI patients (see Table 4).

| MF # | m/z Mass Retention Time | Compound Predicted Formula Predicted Chemical Structure (based on accurate mass) | Metabolite Class or Pathway | Level of Iden. | # of Alternate Chemical Structures ± 15 ppm | RF Model | 2 Way LASSO Model | 3 Way LASSO Model |
|---|---|---|---|---|---|---|---|---|
| CSU/CDC-170 | 1088.6731 1087.6676 17.85 | — | — | 4 | 0 | x | | |
| CSU/CDC-171 | 667.4391 666.4323 20.35 | $C_{37}H_{63}O_8P$ PA(24:5) | Glycerophospholipid metabolism | 4 | >5 | x | | |
| CSU/CDC-172 | 133.0497 132.0423 11.57 | $C_5H_8O_4$ 2-Acetolactic acid | Pantothenate and CoA Biosynthesis Pathway | 4 | >5 | x | | |
| CSU/CDC-173 | 259.1540 258.1469 11.75 | — | — | 4 | 0 | x | | |
| CSU/CDC-174 | 311.1472 288.1574 12.23 | $C_{10}H_{20}N_6O_4$ Asn Arg | Dipeptide | 4 | >5 | x | | |
| CSU/CDC-175 | 147.0652 146.0579 12.33 | $C_6H_{10}O_4$ α-Ketopantoic acid | Pantothenate and CoA Biosynthesis Pathway | 4 | >5 | x | | |
| CSU/CDC-176 | 169.0860 168.0788 12.29 | $C_9H_{12}O_3$ Epoxyoxophorone | Endogenous metabolite - derived from food | 4 | >5 | x | | |
| CSU/CDC-096 | 187.0965 186.0894 9.93 | $C_9H_{14}O_4$ 5-Butyltetrahydro-2-oxo-3-furancarboxylic acid | Endogenous metabolite - derived from food | 4 | >5 | x | | |
| CSU/CDC-178 | 139.1116 138.1044 12.95 | $C_9H_{14}O_4$ 3,6-Nonadienal | Endogenous metabolite - derived from food | 4 | >5 | x | | |
| CSU/CDC-179 | 515.2811 514.2745 13.14 | $C_{26}H_{42}O_{10}$ Cofaryloside | Endogenous metabolite - derived from food | 4 | >5 | x | | |
| CSU/CDC-180 | 283.1522 282.1444 13.93 | $C_{25}H_{42}N_2O_7S$ Epidihydrophaseic acid | Endogenous metabolite - derived from food | 4 | >5 | x | | |
| CSU/CDC-181 | 1486.7386 2971.4668 14.97 | — | — | 4 | 0 | x | | x |
| CSU/CDC-182 | 285.2065 284.1991 16.02 | $C_{16}H_{28}O_4$ — | — | 4 | 1 | x | x | |
| CSU/CDC-183 | 668.4686 1317.8969 18.04 | $C_{16}H_{28}O_4$ Omphalotin A | Endogenous metabolite - derived from food | 4 | 1 | x | | x |
| CSU/CDC-184 | 454.2924 436.2587 18.1 | $C_{21}H_{41}O_7P$ Lyso-PA(18:1) | Glycerophospholipid metabolism | 4 | >5 | x | | x |
| CSU/CDC-185 | 706.9750 705.9684 18.7 | — | — | 4 | 0 | x | | |
| CSU/CDC-186 | 607.9324 606.9246 19.01 | — | — | 4 | 0 | x | | x |
| CSU/CDC-187 | 834.5575 833.5502 20.32 | — | — | 4 | 0 | x | | |
| CSU/CDC-188 | 521.4202 503.3858 21.06 | — | — | 4 | 0 | x | | x |

TABLE 3-continued

261 MF biosignature list The experimentally obtained mass of each MF was used to search against the Metlin database and the Human Metabolome Database (HMDB). The predicted chemical structures had to match to the MF mass within 15 ppm. MFs could have matches to multiple chemical structures of within the same classes of chemicals or to structures of a different chemical class. The putative chemical structure data obtained by interrogation against the HMDB were used to evaluate possible metabolic pathways that differed between early Lyme disease and STARI patients (see Table 4).

| MF # | m/z Mass Retention Time | Compound Predicted Formula Predicted Chemical Structure (based on accurate mass) | Metabolite Class or Pathway | Level of Iden. | # of Alternate Chemical Structures ± 15 ppm | RF Model | 2 Way LASSO Model | 3 Way LASSO Model |
|---|---|---|---|---|---|---|---|---|
| CSU/CDC-189 | 683.4727 1364.9294 17.54 | — | — | 4 | 0 | x | | |
| CSU/CDC-190 | 728.9890 1455.9633 18.63 | — | — | 4 | 1 | x | | |
| CSU/CDC-191 | 726.5104 1451.0035 18.64 | $C_{81}H_{144}O_{17}P_2$ CL(72:7) | Glycero-phospholipid metabolism | 4 | 2 | x | | |
| CSU/CDC-192 | 633.9280 632.9206 18.47 | — | — | 4 | 0 | x | | |
| CSU/CDC-193 | 176.0746 175.0667 2.31 | — | — | 4 | 0 | x | | x |
| CSU/CDC-194 | 596.9082 1191.8033 19.1 | — | — | 4 | 0 | x | | x |
| CSU/CDC-195 | 209.0784 208.0713 9.92 | $C_{17}H_{24}O_3$ Benzylsuccinate | Phenyl-propanoic acid metabolism | 4 | >5 | x | | |
| CSU/CDC-196 | 792.5483 1566.055 18.46 | — | — | 4 | 0 | x | | |
| CSU/CDC-197 | 618.9221 1218.8083 19.02 | — | — | 4 | 0 | x | | |
| CSU/CDC-198 | 549.0543 531.0189 18.37 | — | — | 4 | 0 | x | | |
| CSU/CDC-199 | 553.7262 552.7188 18.74 | — | — | 4 | 0 | x | | |
| CSU/CDC-200 | 756.0320 755.0266 18.95 | — | — | 4 | 0 | x | | |
| CSU/CDC-201 | 639.6307 638.6205 19.58 | — | — | 4 | 0 | x | | |
| CSU/CDC-202 | 753.4414 730.4513 19.37 | $C_{42}H_{67}O_8P$ PA(39:8) | Glycerophospholipid metabolism | 4 | 2 | x | | |
| CSU/CDC-203 | 532.5606 531.5555 18.38 | — | — | 4 | 0 | x | | x |
| CSU/CDC-204 | 279.1693 278.1629 11.05 | $C_{15}H_{22}N_2O_3$ Phe Leu | Dipeptide | 4 | >5 | x | x | |
| CSU/CDC-205 | 241.1069 240.0996 14.7 | $C_{12}H_{16}O_5$ 3-Carboxy-4-methyl-5-propyl-2-furanpropanoic acid (CMPF) | Fatty acid metabolism | 1 | >5 | x | x | x |
| CSU/CDC-206 | 337.1667 336.1599 20.67 | $C_{12}H_{24}N_4O_7$ | — | 4 | 2 | x | | x |
| CSU/CDC-207 | 328.3204 327.3148 20.72 | $C_{20}H_{41}NO_2$ Stearoyl ethanolamide | N-acyl ethanolamine metabolism | 1 | 5 | x | | |
| CSU/CDC-208 | 514.3718 1009.7122 18.42 | $C_{56}H_{99}NO_{14}$ 3-O-acetyl-sphingosine-2,3,4,6-tetra-O-acetyl-GalCer(d18:1/h22:0) | Sphingolipid metabolism | 4 | 1 | x | | |

TABLE 3-continued

261 MF biosignature list The experimentally obtained mass of each MF was used to search against the Metlin database and the Human Metabolome Database (HMDB). The predicted chemical structures had to match to the MF mass within 15 ppm. MFs could have matches to multiple chemical structures of within the same classes of chemicals or to structures of a different chemical class. The putative chemical structure data obtained by interrogation against the HMDB were used to evaluate possible metabolic pathways that differed between early Lyme disease and STARI patients (see Table 4).

| MF # | m/z Mass Retention Time | Compound Predicted Formula Predicted Chemical Structure (based on accurate mass) | Metabolite Class or Pathway | Level of Iden. | # of Alternate Chemical Structures ± 15 ppm | RF Model | 2 Way LASSO Model | 3 Way LASSO Model |
|---|---|---|---|---|---|---|---|---|
| CSU/CDC-209 | 630.4594 1241.8737 19.95 | — | — | 4 | 0 | x | | |
| CSU/CDC-210 | 415.1634 207.0784 12.2 | $C_8H_9N_5O_2$ 6-Amino-9H-purine-9-propanoic acid | Endogenous metabolite - derived from food | 4 | 2 | x | | x |
| CSU/CDC-211 | 464.1916 463.1849 13.05 | $C_{16}H_{29}N_7O_7S$ Arg Asp Cys Ala | Peptide | 4 | >5 | x | x | x |
| CSU/CDC-212 | 1249.2045 1248.1993 15.31 | — | — | 4 | 0 | x | x | x |
| CSU/CDC-213 | 1248.9178 1247.9141 15.3 | — | — | 4 | 0 | x | x | x |
| CSU/CDC-214 | 244.2270 243.22 17.17 | $C_{14}H_{29}NO_2$ Lauroyl ethanolamide | N-acyl ethanolamine metabolism | 4 | 3 | x | | |
| CSU/CDC-215 | 463.3426 924.6699 18.08 | — | — | 4 | 0 | x | | |
| CSU/CDC-216 | 468.3892 450.3553 19.17 | $C_{31}H_{46}O_2$ — | — | 4 | 1 | x | | |
| CSU/CDC-217 | 438.3787 420.3453 420.3453 | — | — | 4 | 0 | x | | |
| CSU/CDC-218 | 364.3407 346.3068 20.72 | — | — | 4 | 0 | x | | x |
| CSU/CDC-219 | 158.1539 157.1466 15.36 | — | — | 4 | 0 | x | x | x |
| CSU/CDC-220 | 792.0006 790.995 12.04 | — | — | 4 | 0 | x | | |
| CSU/CDC-221 | 792.2025 791.1947 12.04 | — | — | 4 | 0 | x | | |
| CSU/CDC-222 | 989.5004 1976.9858 12.03 | — | — | 4 | 0 | x | | x |
| CSU/CDC-223 | 791.6016 790.594 12.04 | — | — | 4 | 0 | x | | |
| CSU/CDC-224 | 819.6064 1635.8239 12.06 | — | — | 4 | 0 | x | | x |
| CSU/CDC-225 | 1115.5593 2228.1028 14.95 | — | — | 4 | 0 | x | | |
| CSU/CDC-226 | 1486.9176 2970.7976 14.96 | — | — | 4 | 0 | x | | |
| CSU/CDC-227 | 529.3381 528.3296 16.89 | $C_{24}H_{44}N_6O_7$ Gln Val Leu Leu Gly | Peptide | 4 | 5 | x | x | x |
| CSU/CDC-228 | 430.3161 412.2845 20.23 | $C_{23}H_{40}O_6$ — | — | 4 | 1 | x | | |
| CSU/CDC-229 | 282.2776 264.2456 20.56 | $C_{18}H_{32}O$ — | — | 4 | >5 | x | x | x |
| CSU/CDC-230 | 297.2793 296.2734 20.66 | $C_{19}H_{36}O_2$ Methyl oleate | Oleic acid ester | 1 | >5 | x | | |

TABLE 3-continued

261 MF biosignature list The experimentally obtained mass of each MF was used to search against the Metlin database and the Human Metabolome Database (HMDB). The predicted chemical structures had to match to the MF mass within 15 ppm. MFs could have matches to multiple chemical structures of within the same classes of chemicals or to structures of a different chemical class. The putative chemical structure data obtained by interrogation against the HMDB were used to evaluate possible metabolic pathways that differed between early Lyme disease and STARI patients (see Table 4).

| MF # | m/z Mass Retention Time | Compound Predicted Formula Predicted Chemical Structure (based on accurate mass) | Metabolite Class or Pathway | Level of Iden. | # of Alternate Chemical Structures ± 15 ppm | RF Model | 2 Way LASSO Model | 3 Way LASSO Model |
|---|---|---|---|---|---|---|---|---|
| CSU/CDC-231 | 714.3655 1426.718 11.73 | — | — | 4 | 0 | x | | |
| CSU/CDC-232 | 714.5306 1427.0479 11.76 | — | — | 4 | 0 | x | | |
| CSU/CDC-233 | 989.7499 1977.4865 12.03 | — | — | 4 | 0 | x | | |
| CSU/CDC-234 | 221.0744 220.0672 13.7 | $C_7H_{12}N_2O_6$ L-beta-aspartyl-L-serine | Peptide | 4 | >5 | x | | |
| CSU/CDC-235 | 190.1260 189.1187 14.12 | $C_9H_{19}NOS$ 8-Methylthiooctanal doxime | 2-oxocarboxylic acid metabolism | 4 | 2 | x | x | x |
| CSU/CDC-236 | 313.2734 312.2663 18.91 | $C_{19}H_{36}O_3$ 2-oxo-nonadecanoic acid | Fatty acid metabolism | 4 | 5 | x | | |
| CSU/CDC-237 | 286.2737 285.2666 19.08 | $C_{17}H_{35}NO_2$ Pentadecanoyl ethanolamide | N-acyl ethanolamine metabolism | 1 | 4 | x | | x |
| CSU/CDC-238 | 382.3675 381.3603 20.23 | $C_{24}H_{47}NO_2$ Erucicoyl ethanolamide | N-acyl ethanolamine metabolism | 4 | 1 | x | x | x |
| CSU/CDC-239 | 337.2712 314.282 20.66 | $C_{19}H_{38}O_3$ 2-Hydroxy-nonadecanoic acid | Fatty acid metabolism | 4 | 2 | x | | |
| CSU/CDC-240 | 441.3687 440.3614 21.26 | $C_{30}H_{48}O_2$ 4,4-Dimethyl-14a-formyl-5a-cholesta-8,24-dien-3b-ol | Sterol metabolism | 4 | >5 | x | | |
| CSU/CDC-241 | 425.3735 424.3666 21.5 | $C_{30}H_{48}O$ Butyrospermone | Sterol metabolism | 4 | >5 | x | | |
| CSU/CDC-242 | 356.3517 355.3448 21.67 | $C_{22}H_{45}NO_2$ Eicosanoyl ethanolamide | N-acyl ethanolamine metabolism | 1 | 2 | x | | |
| CSU/CDC-243 | 393.2970 370.3082 22.46 | $C_{22}H_{42}O_4$ — | — | 4 | 3 | x | | |
| CSU/CDC-244 | 477.2968 476.2898 22.79 | $C_{31}H_{40}O_4$ Lys Lys Thr Thr | Peptide | 4 | >5 | x | x | x |
| CSU/CDC-245 | 614.4833 613.4772 19.78 | — | — | 4 | 0 | x | | x |
| CSU/CDC-246 | 167.9935 166.9861 13.2 | $C_7H_5NS_2$ — | — | 4 | 1 | x | | |
| CSU/CDC-247 | 714.6967 1427.3824 11.76 | — | — | 4 | 0 | x | x | |
| CSU/CDC-248 | 459.3968 458.3904 19.08 | — | — | 4 | 0 | x | x | x |
| CSU/CDC-249 | 677.6170 676.6095 20.71 | $C_{47}H_{80}O_2$ Cholesterol ester (20:2) | Sterol metabolism | 4 | >5 | x | | |
| CSU/CDC-250 | 298.2740 297.2668 16.44 | $C_{18}H_{35}NO_2$ 3-Ketospingosine | Sphingolipid metabolism | 2 | >5 | x | | x |

TABLE 3-continued

261 MF biosignature list The experimentally obtained mass of each MF was used to search against the Metlin database and the Human Metabolome Database (HMDB). The predicted chemical structures had to match to the MF mass within 15 ppm. MFs could have matches to multiple chemical structures of within the same classes of chemicals or to structures of a different chemical class. The putative chemical structure data obtained by interrogation against the HMDB were used to evaluate possible metabolic pathways that differed between early Lyme disease and STARI patients (see Table 4).

| MF # | m/z Mass Retention Time | Compound Predicted Formula Predicted Chemical Structure (based on accurate mass) | Metabolite Class or Pathway | Level of Iden. | # of Alternate Chemical Structures ± 15 ppm | RF Model | 2 Way LASSO Model | 3 Way LASSO Model |
|---|---|---|---|---|---|---|---|---|
| CSU/CDC-251 | 460.2695 459.2627 16.87 | $C_{26}H_{37}NO_6$ — | — | 4 | >5 | x | | |
| CSU/CDC-252 | 1003.7020 1002.696 18.46 | — | — | 4 | 0 | x | | x |
| CSU/CDC-253 | 342.2635 341.2565 15.62 | $C_{19}H_{35}NO_4$ — | — | 4 | 2 | x | x | x |
| CSU/CDC-254 | 529.3827 1022.6938 17.86 | — | — | 4 | 0 | x | x | x |
| CSU/CDC-255 | 630.4765 612.4417 18.11 | — | — | 4 | 0 | x | | |
| CSU/CDC-256 | 514.3734 1026.7281 18.41 | — | — | 4 | 0 | x | | |
| CSU/CDC-257 | 667.4754 1315.916 19.28 | — | — | 4 | 0 | x | | |
| CSU/CDC-258 | 459.2502 458.2429 19.02 | $C_{23}H_{39}O_7P$ Lyso PA(20:4) | Glycero-phospholipid metabolism | 2 | >5 | x | x | x |
| CSU/CDC-259 | 516.8549 1031.6945 18.43 | — | — | 4 | 0 | x | | |
| CSU/CDC-260 | 740.5242 1479.0334 | $C_{83}H_{148}O_{17}P_2$ CL(74:7) | Glycero-phospholipid metabolism | 4 | 2 | x | | |
| CSU/CDC-261 | 1104.0614 2206.1096 15.2 | — | — | 4 | 0 | x | | |

TABLE 4

MetaboAnalyst results

| Pathway Hit | Total | Expected | Hits | Raw p | -log(p) | Holm adjust | FDR | Impact |
|---|---|---|---|---|---|---|---|---|
| Glycerophospholipid metabolism | 39 | 1.2638 | 4† | 0.035545 | 3.337 | 1 | 1 | 0.33235 |
| Sphingolipid metabolism | 25 | 0.81014 | 3± | 0.045107 | 3.0987 | 1 | 1 | 0.15499 |
| Valine, leucine and isoleucine biosynthesis | 27 | 0.87495 | 2 | 0.21724 | 1.5268 | 1 | 1 | 0.17117 |
| Phenylalanine metabolism | 45 | 1.4582 | 1 | 0.77605 | 0.25353 | 1 | 1 | 0.11906 |
| alpha-Linolenic acid metabolism | 29 | 0.93976 | 2 | 0.24148 | 1.421 | 1 | 1 | 0 |
| Glycosylphosphatidylinositol(GP1)-anchor biosynthesis | 14 | 0.45368 | 1 | 0.37027 | 0.99353 | 1 | 1 | 0.0439 |
| Linoleic acid metabolism | 15 | 0.48608 | 1 | 0.39079 | 0.93957 | 1 | 1 | 0 |
| Riboflavin metabolism | 21 | 0.68052 | 1 | 0.50079 | 0.69157 | 1 | 1 | 0 |
| Phenylalanine, tyrosine and tryptophan biosynthesis | 27 | 0.87495 | 1 | 0.59113 | 0.52572 | 1 | 1 | 0.00062 |
| Pantothenate and CoA biosynthesis | 27 | 0.87495 | 1 | 0.59113 | 0.52572 | 1 | 1 | 0.02002 |
| Steroid hormone biosynthesis | 99 | 3.2081 | 3 | 0.63116 | 0.4602 | 1 | 1 | 0.0382 |

TABLE 4-continued

MetaboAnalyst results

| Pathway Hit | Total | Expected | Hits | Raw p | -log(p) | Holm adjust | FDR | Impact |
|---|---|---|---|---|---|---|---|---|
| Glycerolipid metabolism | 32 | 1.037 | 1 | 0.65393 | 0.42476 | 1 | 1 | 0.01247 |
| Ubiquinone and other terpenoid-quinone bios+A14:129ynthesis | 36 | 1.1666 | 1 | 0.69723 | 0.36064 | 1 | 1 | 0 |
| Nitrogen metabolism | 39 | 1.2638 | 1 | 0.72615 | 0.32 | 1 | 1 | 0 |
| Butanoate metabolism | 40 | 1.2962 | 1 | 0.73517 | 0.30766 | 1 | 1 | 0.04772 |
| Ascorbate and aldarate metabolism | 45 | 1.4582 | 1 | 0.77605 | 0.25353 | 1 | 1 | 0.00802 |
| Drug metabolism - cytochrome P450 | 86 | 2.7869 | 2 | 0.77721 | 0.25205 | 1 | 1 | 0.0176 |
| Primary bile acid biosynthesis | 47 | 1.5231 | 1 | 0.7906 | 0.23496 | 1 | 1 | 0.00846 |
| Lysine degradation | 47 | 1.5231 | 1 | 0.7906 | 0.23496 | 1 | 1 | 0.06505 |
| Fatty acid biosynthesis | 49 | 1.5879 | 1 | 0.80422 | 0.21788 | 1 | 1 | 0 |
| Fatty acid metabolism | 50 | 1.6203 | 1 | 0.81069 | 0.20986 | 1 | 1 | 0 |
| Starch and sucrose metabolism | 50 | 1.6203 | 1 | 0.81069 | 0.20986 | 1 | 1 | 0.01265 |
| Pentose and glucuronate interconversions | 53 | 1.7175 | 1 | 0.82888 | 0.18768 | 1 | 1 | 0.009 |
| Arachidonic acid metabolism | 62 | 2.0091 | 1 | 0.87371 | 0.135 | 1 | 1 | 0 |
| Aminoacyl-tRNA biosynthesis | 75 | 2.4304 | 1 | 0.91874 | 0.084752 | 1 | 1 | 0 |
| Purine metabolism | 92 | 2.9813 | 1 | 0.95452 | 0.046547 | 1 | 1 | 0.00791 |
| Porphyrin and chlorophyll metabolism | 104 | 3.3702 | 1 | 0.96989 | 0.030577 | 1 | 1 | 0.01101 |

Total, the total number of compounds in the pathway;
Hits, the actual number of compounds in the pathway matched from the 261 MF biosignature list;
Raw p, the original p value calculated from the enrichment analysis;
Holm adjust, the adjusted p value by the Holm-Bonferroni method;
FDR, the p value adjusted using False Discovery Rate;
Impact, the pathway impact value calculated from pathway topology analysis.
The MetaboAnalyst results were used to target specific MFs in the early Lyme disease-STARI biosignature for structural identification.
†The 4 hits in the glycerophospholipid metabolism pathway were phosphatidic acid, phosphatidylethanolamine, phosphatidylcholine and lysophosphotidylcholine.
‡The 3 hits in the sphingolipid metabolism pathway were in sphingosine, dehydrosphinganine and sulfatide.

TABLE 5

Regression coefficients (β) of the LASSO two-way statistical model

| MF Id | Coefficient | MF Id | Coefficient | MF Id | Coefficient | MF Id | Coefficient |
|---|---|---|---|---|---|---|---|
| Intercept | −0.5089 | CSU/CDC-166 | −0.2033 | CSU/CDC-075 | 0.10409 | CSU/CDC-238 | 0.7812 |
| CSU/CDC-001 | −0.3032 | CSU/CDC-182 | −0.1077 | CSU/CDC-086 | 0.71497 | CSU/CDC-244 | −0.7325 |
| CSU/CDC-002 | −0.0359 | CSU/CDC-204 | −0.163 | CSU/CDC-107 | −0.2586 | CSU/CDC-247 | 0.00621 |
| CSU/CDC-012 | −0.31 | CSU/CDC-205 | −0.8688 | CSU/CDC-132 | 0.88577 | CSU/CDC-248 | 0.38858 |
| CSU/CDC-013 | −0.2256 | CSU/CDC-211 | 0.43327 | CSU/CDC-152 | −0.6125 | CSU/CDC-253 | 0.10575 |
| CSU/CDC-014 | 0.05737 | CSU/CDC-212 | −0.3513 | CSU/CDC-155 | −0.0083 | CSU/CDC-254 | 0.27792 |
| CSU/CDC-028 | 0.21447 | CSU/CDC-213 | −0.422 | CSU/CDC-158 | −0.027 | CSU/CDC-258 | −0.5593 |
| CSU/CDC-039 | 0.29641 | CSU/CDC-219 | 1.01872 | CSU/CDC-164 | 0.22005 | | |
| CSU/CDC-062 | 0.0152 | CSU/CDC-227 | 0.43588 | | | | |
| CSU/CDC-066 | −0.0559 | CSU/CDC-229 | 0.11674 | | | | |
| CSU/CDC-067 | 0.63951 | CSU/CDC-235 | 0.3664 | | | | |
| CSU/CDC-072 | −0.1451 | CSU/CDC-019 | 0.52461 | | | | |

The regression coefficient for each of the 38 MFs (CSU/CDC-#) used in the LASSO two-way classification model are provided. The regression coefficients were generated with data from the Training-Set samples, and applied in the classification of the Test-Set samples as shown in Table 6.

TABLE 6

LASSO and RF two-way model classification probability scores
The LASSO and RF probability scores are provided for each patient sample tested in duplicate. These are probability scores for the Test-Set samples. A probability score of ≥0.5 classified the samples as early Lyme disease (EL), and a probability score of <0.5 resulted in the sample being classified as STARI.

| Coded Sample ID | LASSO Probability Score | LASSO Classification | RF Probability Score | RF Classification | Sample ID | Patient Type |
|---|---|---|---|---|---|---|
| Valb1618 | 0.9979 | EL | 0.8980 | EL | EDL134-022315 | EL |
| Valb1591 | 0.9995 | EL | 0.8980 | EL | EDL134-120214 | EL |
| Valb1454 | 0.9900 | EL | 0.6320 | EL | EDL135-022315 | EL |

TABLE 6-continued

LASSO and RF two-way model classification probability scores
The LASSO and RF probability scores are provided for each patient sample tested in duplicate. These are probability scores for the Test-Set samples. A probability score of ≥0.5 classified the samples as early Lyme disease (EL), and a probability score of <0.5 resulted in the sample being classified as STARI.

| Coded Sample ID | LASSO Probability Score | LASSO Classification | RF Probability Score | RF Classification | Sample ID | Patient Type |
|---|---|---|---|---|---|---|
| Valb0820 | 0.5264 | EL | 0.8660 | EL | EDL135-120214 | EL |
| Valb0989 | 0.9820 | EL | 0.8620 | EL | EDL136-022315 | EL |
| Valb0546 | 0.8814 | EL | 0.8960 | EL | EDL136-120214 | EL |
| Valb1573 | 0.9875 | EL | 0.5840 | EL | EDL137-022315 | EL |
| Valb1299 | 0.7198 | EL | 0.4380 | STARI | EDL137-120214 | EL |
| Valb0477 | 0.9247 | EL | 0.7780 | EL | EDL138-022315 | EL |
| Valb0160 | 0.9868 | EL | 0.9160 | EL | EDL138-120214 | EL |
| Valb0813 | 0.7300 | EL | 0.4880 | STARI | EDL139-022315 | EL |
| Valb0443 | 0.8307 | EL | 0.7680 | EL | EDL139-120214 | EL |
| Valb1412 | 0.9287 | EL | 0.7200 | EL | EDL140-022315 | EL |
| Valb0886 | 0.9045 | EL | 0.8140 | EL | EDL140-120214 | EL |
| Valb0827 | 0.9846 | EL | 0.9040 | EL | EDL71-022315 | EL |
| Valb0186 | 0.9609 | EL | 0.9180 | EL | EDL71-120214 | EL |
| Valb1337 | 0.9417 | EL | 0.8200 | EL | EDL73-022315 | EL |
| Valb0714 | 0.9836 | EL | 0.9000 | EL | EDL73-120214 | EL |
| Valb1510 | 0.9773 | EL | 0.7720 | EL | EDL74-022315 | EL |
| Valb0642 | 0.9986 | EL | 0.8520 | EL | EDL74-120214 | EL |
| Valb1586 | 0.9995 | EL | 0.9020 | EL | EDL75-022315 | EL |
| Valb1402 | 1.0000 | EL | 0.9160 | EL | EDL75-120214 | EL |
| Valb0593 | 0.9595 | EL | 0.8020 | EL | EDL76-022315 | EL |
| Valb0608 | 0.6940 | EL | 0.7980 | EL | EDL76-120214 | EL |
| Valb0808 | 0.9205 | EL | 0.8720 | EL | EDL77-022315 | EL |
| Valb0750 | 0.9998 | EL | 0.7240 | EL | EDL77-120214 | EL |
| Valb0907 | 0.9459 | EL | 0.6720 | EL | EDL78-022315 | EL |
| Valb0585 | 0.9891 | EL | 0.9180 | EL | EDL78-120214 | EL |
| Valb1638 | 0.9832 | EL | 0.6000 | EL | EDL79-022315 | EL |
| Valb1640 | 0.9906 | EL | 0.8500 | EL | EDL79-120214 | EL |
| Valb1430 | 0.9812 | EL | 0.7580 | EL | ELL06-022315 | EL |
| Valb1155 | 0.9995 | EL | 0.8080 | EL | ELL06-120214 | EL |
| Valb1553 | 0.9783 | EL | 0.7780 | EL | ELL07-022315 | EL |
| Valb1562 | 0.9999 | EL | 0.7920 | EL | ELL07-120214 | EL |
| Valb1445 | 0.8085 | EL | 0.7160 | EL | ELL08-022315 | EL |
| Valb1188 | 0.9983 | EL | 0.7860 | EL | ELL08-120214 | EL |
| Valb1613 | 0.9993 | EL | 0.8640 | EL | ELL09-022315 | EL |
| Valb1514 | 1.0000 | EL | 0.8820 | EL | ELL09-120214 | EL |
| Valb1479 | 0.3775 | STARI | 0.6320 | EL | ELL10-022315 | EL |
| Valb0933 | 0.9095 | EL | 0.8380 | EL | ELL10-120214 | EL |
| Valb0923 | 0.7083 | EL | 0.8120 | EL | ELL16-022315 | EL |
| Valb0338 | 0.7215 | EL | 0.8320 | EL | ELL16-120214 | EL |
| Valb0783 | 0.7849 | EL | 0.8880 | EL | ELL17-022315 | EL |
| Valb0261 | 0.9862 | EL | 0.9120 | EL | ELL17-120214 | EL |
| Valb1264 | 0.9418 | EL | 0.8240 | EL | ELL18-022315 | EL |
| Valb0545 | 0.9738 | EL | 0.8480 | EL | ELL18-120214 | EL |
| Valb1427 | 0.9704 | EL | 0.8480 | EL | ELL61-022315 | EL |
| Valb1071 | 0.9664 | EL | 0.7620 | EL | ELL61-120214 | EL |
| Valb1211 | 0.7950 | EL | 0.7360 | EL | ELL62-022315 | EL |
| Valb1217 | 0.7831 | EL | 0.8360 | EL | ELL62-120214 | EL |
| Valb1414 | 0.9892 | EL | 0.9100 | EL | ELL63-022315 | EL |
| Valb1104 | 0.9699 | EL | 0.8600 | EL | ELL63-120214 | EL |
| Valb0736 | 0.9469 | EL | 0.9300 | EL | ELL64-022315 | EL |
| Valb0384 | 0.9780 | EL | 0.9040 | EL | ELL64-120214 | EL |
| Valb0672 | 0.9415 | EL | 0.7680 | EL | ELL65-022315 | EL |
| Valb0300 | 0.9927 | EL | 0.8920 | EL | ELL65-120214 | EL |
| Valb1018 | 0.9093 | EL | 0.8320 | EL | ELL66-022315 | EL |
| Valb0458 | 0.8905 | EL | 0.8480 | EL | ELL66-120214 | EL |
| Valb1356 | 0.9174 | EL | 0.8100 | EL | ELL67-022315 | EL |
| Valb0492 | 0.9747 | EL | 0.7260 | EL | ELL67-120214 | EL |
| Valb1561 | 0.0313 | STARI | 0.4860 | STARI | M06A-022315 | STARI |
| Valb1328 | 0.8608 | EL | 0.6060 | EL | M06A-120214 | STARI |
| Valb0329 | 0.1613 | STARI | 0.2680 | STARI | M09A-022315 | STARI |
| Valb0070 | 0.2476 | STARI | 0.4080 | STARI | M09A-120214 | STARI |
| Valb1052 | 0.0242 | STARI | 0.4060 | STARI | M13A-022315 | STARI |
| Valb0809 | 0.8461 | EL | 0.8340 | EL | M13A-120214B | STARI |
| Valb1256 | 0.0157 | STARI | 0.2900 | STARI | M16A-022315 | STARI |
| Valb1100 | 0.3798 | STARI | 0.4120 | STARI | M16A-120214 | STARI |
| Valb1236 | 0.2314 | STARI | 0.6800 | EL | M19A-022315 | STARI |
| Valb0580 | 0.5508 | EL | 0.6140 | EL | M19A-120214 | STARI |
| Valb1525 | 0.7045 | EL | 0.4720 | STARI | M22A-022315 | STARI |
| Valb0534 | 0.0496 | STARI | 0.4580 | STARI | M22A-120214 | STARI |
| Valb0556 | 0.1448 | STARI | 0.3400 | STARI | M26A-022315 | STARI |
| Valb0116 | 0.4234 | STARI | 0.2860 | STARI | M26A-120214 | STARI |

TABLE 6-continued

LASSO and RF two-way model classification probability scores
The LASSO and RF probability scores are provided for each patient sample tested in duplicate. These are
probability scores for the Test-Set samples. A probability score of ≥0.5 classified the samples as early Lyme
disease (EL), and a probability score of <0.5 resulted in the sample being classified as STARI.

| Coded Sample ID | LASSO Probability Score | LASSO Classification | RF Probability Score | RF Classification | Sample ID | Patient Type |
|---|---|---|---|---|---|---|
| Valb0461 | 0.0037 | STARI | 0.2360 | STARI | M27A-022315 | STARI |
| Valb0266 | 0.1015 | STARI | 0.2080 | STARI | M27A-120214 | STARI |
| Valb0447 | 0.0316 | STARI | 0.1220 | STARI | S03-022315 | STARI |
| Valb0026 | 0.0060 | STARI | 0.1420 | STARI | S03-120214 | STARI |
| Valb1114 | 0.0010 | STARI | 0.1760 | STARI | S09-022315 | STARI |
| Valb0464 | 0.0254 | STARI | 0.2120 | STARI | S09-120214 | STARI |
| Valb1292 | 0.0004 | STARI | 0.1280 | STARI | S17-022315 | STARI |
| Valb0754 | 0.0005 | STARI | 0.1020 | STARI | S17-120214 | STARI |
| Valb0434 | 0.0257 | STARI | 0.2520 | STARI | S21-022315 | STARI |
| Valb0044 | 0.0559 | STARI | 0.4300 | STARI | S21-120214 | STARI |
| Valb0873 | 0.0173 | STARI | 0.1840 | STARI | S33-022315 | STARI |
| Valb0352 | 0.0012 | STARI | 0.2200 | STARI | S33-120214 | STARI |
| Valb1141 | 0.0001 | STARI | 0.1120 | STARI | S39-022315 | STARI |
| Valb0480 | 0.0002 | STARI | 0.1160 | STARI | S39-120214 | STARI |
| Valb0618 | 0.0158 | STARI | 0.3220 | STARI | S43-022315 | STARI |
| Valb0660 | 0.1493 | STARI | 0.3020 | STARI | S43-120214 | STARI |
| Valb0223 | 0.0007 | STARI | 0.0960 | STARI | S47-022315 | STARI |
| Valb0054 | 0.0095 | STARI | 0.0940 | STARI | S47-120214 | STARI |
| Valb0335 | 0.0093 | STARI | 0.0660 | STARI | S53-022315 | STARI |
| Valb0197 | 0.0183 | STARI | 0.0360 | STARI | S53-120214 | STARI |
| Valb0409 | 0.2080 | STARI | 0.2080 | STARI | S55-022315 | STARI |
| Valb0060 | 0.0332 | STARI | 0.1280 | STARI | S55-120214 | STARI |
| Valb0437 | 0.0004 | STARI | 0.0980 | STARI | S65-022315 | STARI |
| Valb0093 | 0.0003 | STARI | 0.1500 | STARI | S65-120214 | STARI |

TABLE 7

Regression coefficients (β) of the LASSO three-way statistical model.

| MF Id | Early Lyme Disease | Healthy Controls | STARI |
|---|---|---|---|
| Intercept | 0.5755 | −0.4927 | −0.0828 |
| CSU/CDC-001 | 0.37556 | 0 | 0 |
| CSU/CDC-003 | 0 | 0.4377 | 0 |
| CSU/CDC-004 | 0 | 0.00298 | 0 |
| CSU/CDC-006 | 0.0704 | 0 | 0 |
| CSU/CDC-008 | −0.1193 | 0 | 0 |
| CSU/CDC-009 | 0.22921 | 0 | 0 |
| CSU/CDC-012 | 0.15307 | 0 | −0.2457 |
| CSU/CDC-013 | 0 | 0 | −0.1007 |
| CSU/CDC-014 | 0 | 0 | 0.72128 |
| CSU/CDC-017 | 0.11117 | 0 | 0 |
| CSU/CDC-026 | 0 | −0.0633 | 0.05925 |
| CSU/CDC-030 | 0 | 0.05795 | 0 |
| CSU/CDC-039 | 0 | −0.6065 | 0.06517 |
| CSU/CDC-042 | −0.4151 | 0.02856 | 0 |
| CSU/CDC-052 | 0 | 0.05484 | 0 |
| CSU/CDC-061 | 0 | 0.08714 | 0 |
| CSU/CDC-062 | 0 | 0 | 0.60672 |
| CSU/CDC-066 | 0 | 0 | −0.3676 |
| CSU/CDC-067 | −1.1528 | 0 | 0 |
| CSU/CDC-070 | −0.5929 | 0.5531 | 0 |
| CSU/CDC-072 | 0 | 0 | −0.0857 |
| CSU/CDC-074 | 0.01711 | 0 | 0 |
| CSU/CDC-075 | 0 | 0 | 0.18553 |
| CSU/CDC-083 | 0 | −0.0872 | 0 |
| CSU/CDC-084 | 0 | −0.2013 | 0.21541 |
| CSU/CDC-086 | −1.1622 | 0 | 0.06776 |
| CSU/CDC-087 | 0 | 0.03553 | 0 |
| CSU/CDC-091 | 0 | −0.6683 | 0 |
| CSU/CDC-095 | 0 | 0 | −0.0694 |
| CSU/CDC-098 | 0 | 0.05396 | 0 |
| CSU/CDC-099 | 0 | −0.0398 | 0 |
| CSU/CDC-107 | 0.36836 | 0 | −0.1847 |
| CSU/CDC-112 | 0 | 1.11724 | 0 |
| CSU/CDC-115 | 0 | 0.12435 | 0 |
| CSU/CDC-128 | 0 | 0.4206 | −0.1927 |
| CSU/CDC-132 | 0 | 0 | 1.0998 |
| CSU/CDC-133 | 0.35613 | −0.1349 | 0 |
| CSU/CDC-134 | 0 | −0.1009 | 0 |
| CSU/CDC-136 | 0 | −1.2108 | 0 |
| CSU/CDC-137 | 0 | −0.2512 | 0 |
| CSU/CDC-138 | −0.0183 | 0 | 0 |
| CSU/CDC-141 | 0 | 0 | 0.2233 |
| CSU/CDC-144 | 0 | −0.1318 | 0 |
| CSU/CDC-152 | 0.70277 | 0 | 0 |
| CSU/CDC-155 | 0.27512 | 0 | 0 |
| CSU/CDC-157 | 0 | 0 | 0.0505 |
| CSU/CDC-158 | 0 | 1.89865 | 0 |
| CSU/CDC-164 | −0.2964 | 0 | 0 |
| CSU/CDC-165 | 0 | −0.4008 | 0 |
| CSU/CDC-166 | 0.14382 | 0 | 0 |
| CSU/CDC-181 | 0 | 1.3044 | 0 |
| CSU/CDC-183 | 0 | −0.7613 | 0.01014 |
| CSU/CDC-184 | 0.35021 | 0 | 0 |
| CSU/CDC-186 | 0 | 0.40861 | 0 |
| CSU/CDC-188 | 0 | 0.5533 | 0 |
| CSU/CDC-193 | 0 | −1.2355 | 0 |
| CSU/CDC-194 | 0 | 0.57412 | 0 |
| CSU/CDC-203 | −0.0308 | 0 | 0 |
| CSU/CDC-205 | 0.50193 | 0 | −0.3139 |
| CSU/CDC-206 | 0 | −0.0668 | 0 |
| CSU/CDC-210 | 0 | 0 | −0.218 |
| CSU/CDC-211 | −0.7208 | 0 | 0.20891 |
| CSU/CDC-212 | 0 | 0 | −0.0139 |
| CSU/CDC-213 | 0 | 0 | −0.2463 |
| CSU/CDC-218 | 0 | 0.00722 | 0 |
| CSU/CDC-219 | −1.0252 | 0 | 0 |
| CSU/CDC-222 | 0 | −0.4632 | 0 |
| CSU/CDC-224 | 0 | −0.516 | 0 |
| CSU/CDC-227 | −0.4157 | 0 | 0.59261 |
| CSU/CDC-229 | 0 | 0 | 0.86651 |
| CSU/CDC-235 | −0.9905 | 0 | 0 |
| CSU/CDC-019 | 0 | −0.0326 | 0.52245 |
| CSU/CDC-237 | 0 | 0.62355 | 0 |

TABLE 7-continued

Regression coefficients (β) of the LASSO three-way statistical model.

| MF Id | Early Lyme Disease | Healthy Controls | STARI |
|---|---|---|---|
| CSU/CDC-238 | 0 | 0 | 0.96539 |
| CSU/CDC-244 | 1.5845 | 0 | 0 |
| CSU/CDC-245 | 0 | −1.3521 | 0 |
| CSU/CDC-248 | −0.0904 | 0 | 0.06017 |
| CSU/CDC-250 | 0 | 0 | −0.0882 |
| CSU/CDC-252 | 0 | −0.0646 | 0 |
| CSU/CDC-253 | 0 | 0 | 0.16563 |
| CSU/CDC-254 | −0.1985 | 0 | 0 |
| CSU/CDC-258 | 0 | 0 | −0.7011 |

The regression coefficient for each of the 82 MFs (CSU/CDC-#) used in the LASSO three-way classification model are provided. The regression coefficients were generated with data from the Training-Set samples, and applied in the classification of the Test-Set samples as shown in Table 8.

TABLE 8

LASSO and RF three-way model classification probability scores.
The LASSO and RF probability scores are provided for each patient sample tested in duplicate. These are probability scores for the Test-Set samples. Both the LASSO and RF classifiers provided a probability score for a sample being early Lyme disease patient (EL), healthy control (HC) and STARI. The sample was classified based on the highest probability score for membership in one of the three groups (EL, HC, or STARI).

| Coded Sample ID | LASSO Probability Score for EL, HC, and STARI | LASSO Classification | RF Probability Score for EL, HC, and STARI | RF Classification | Sample ID | Patient Type |
|---|---|---|---|---|---|---|
| Valb1618 | 0.9998<br>0.0000<br>0.0002 | EL | 0.8420<br>0.0560<br>0.1020 | EL | EDL134-022315 | EL |
| Valb1591 | 1.0000<br>0.0000<br>0.0000 | EL | 0.8600<br>0.0320<br>0.1080 | EL | EDL134-120214 | EL |
| Valb1454 | 0.9978<br>0.0003<br>0.0019 | EL | 0.5140<br>0.0840<br>0.4020 | EL | EDL135-022315 | EL |
| Valb0820 | 0.9798<br>0.0010<br>0.0192 | EL | 0.6560<br>0.1140<br>0.2300 | EL | EDL135-120214 | EL |
| Valb0989 | 0.9765<br>0.0190<br>0.0045 | EL | 0.3620<br>0.5660<br>0.0720 | HC | EDL136-022315 | EL |
| Valb0546 | 0.9184<br>0.0198<br>0.0618 | EL | 0.5760<br>0.3360<br>0.0880 | EL | EDL136-120214 | EL |
| Valb1573 | 0.6006<br>0.3980<br>0.0015 | EL | 0.4640<br>0.1620<br>0.3740 | EL | EDL137-022315 | EL |
| Valb1299 | 0.0350<br>0.0012<br>0.9639 | STARI | 0.4640<br>0.1380<br>0.3980 | EL | EDL137-120214 | EL |
| Valb0477 | 0.9823<br>0.0001<br>0.0175 | EL | 0.5760<br>0.2480<br>0.1760 | EL | EDL138-022315 | EL |
| Valb0160 | 0.9570<br>0.0284<br>0.0146 | EL | 0.5800<br>0.3560<br>0.0640 | EL | EDL138-120214 | EL |
| Valb0813 | 0.7815<br>0.1288<br>0.0897 | EL | 0.3380<br>0.3340<br>0.3280 | EL | EDL139-022315 | EL |
| Valb0443 | 0.1403<br>0.8550<br>0.0047 | HC | 0.5140<br>0.3480<br>0.1380 | EL | EDL139-120214 | EL |
| Valb1412 | 0.9258<br>0.0010<br>0.0732 | EL | 0.5260<br>0.1860<br>0.2880 | EL | EDL140-022315 | EL |
| Valb0886 | 0.6301<br>0.1495<br>0.2204 | EL | 0.4060<br>0.4380<br>0.1560 | HC | EDL140-120214 | EL |
| Valb0827 | 0.9395<br>0.0600<br>0.0005 | EL | 0.5600<br>0.3240<br>0.1160 | EL | EDL71-022315 | EL |
| Valb0186 | 0.9623<br>0.0341<br>0.0036 | EL | 0.5460<br>0.3980<br>0.0560 | EL | EDL71-120214 | EL |
| Valb1337 | 0.9873<br>0.0000<br>0.0127 | EL | 0.6840<br>0.0480<br>0.2680 | EL | EDL73-022315 | EL |
| Valb0714 | 0.9991<br>0.0000<br>0.0009 | EL | 0.7480<br>0.0740<br>0.1780 | EL | EDL73-120214 | EL |

TABLE 8-continued

LASSO and RF three-way model classification probability scores.
The LASSO and RF probability scores are provided for each patient sample tested in duplicate. These are probability scores for the Test-Set samples. Both the LASSO and RF classifiers provided a probability score for a sample being early Lyme disease patient (EL), healthy control (HC) and STARI. The sample was classified based on the highest probability score for membership in one of the three groups (EL, HC, or STARI).

| Coded Sample ID | LASSO Probability Score for EL, HC, and STARI | LASSO Classification | RF Probability Score for EL, HC, and STARI | RF Classification | Sample ID | Patient Type |
| --- | --- | --- | --- | --- | --- | --- |
| Valb1510 | 0.9795<br>0.0000<br>0.0205 | EL | 0.6700<br>0.1140<br>0.2160 | EL | EDL74-022315 | EL |
| Valb0642 | 0.9990<br>0.0000<br>0.0000 | EL | 0.7280<br>0.1080<br>0.1640 | EL | EDL74-120214 | EL |
| Valb1586 | 1.0000<br>0.0000<br>0.0000 | EL | 0.8180<br>0.0920<br>0.0900 | EL | EDL75-022315 | EL |
| Valb1402 | 1.0000<br>0.0000<br>0.0000 | EL | 0.8460<br>0.0640<br>0.0900 | EL | EDL75-120214 | EL |
| Valb0593 | 0.9699<br>0.0155<br>0.0146 | EL | 0.5380<br>0.3180<br>0.1440 | EL | EDL76-022315 | EL |
| Valb0608 | 0.2554<br>0.4250<br>0.3197 | HC | 0.4000<br>0.4320<br>0.1680 | HC | EDL76-120214 | EL |
| Valb0808 | 0.9747<br>0.0135<br>0.0118 | EL | 0.5080<br>0.3480<br>0.1440 | EL | EDL77-022315 | EL |
| Valb0750 | 1.0000<br>0.0000<br>0.0000 | EL | 0.5600<br>0.2140<br>0.2260 | EL | EDL77-120214 | EL |
| Valb0907 | 0.9570<br>0.0006<br>0.0424 | EL | 0.5640<br>0.1900<br>0.2460 | EL | EDL78-022315 | EL |
| Valb0585 | 0.8967<br>0.0837<br>0.0196 | EL | 0.5760<br>0.3440<br>0.0800 | EL | EDL78-120214 | EL |
| Valb1638 | 0.9978<br>0.0000<br>0.0022 | EL | 0.5880<br>0.0940<br>0.3180 | EL | EDL79-022315 | EL |
| Valb1640 | 0.9891<br>0.0000<br>0.0109 | EL | 0.8180<br>0.0700<br>0.1120 | EL | EDL79-120214 | EL |
| Valb1430 | 0.9960<br>0.0000<br>0.0040 | EL | 0.6740<br>0.0980<br>0.2280 | EL | ELL06-022315 | EL |
| Valb1155 | 0.9921<br>0.0073<br>0.0006 | EL | 0.7140<br>0.1020<br>0.1840 | EL | ELL06-120214 | EL |
| Valb1553 | 0.9522<br>0.0308<br>0.0170 | EL | 0.4940<br>0.3240<br>0.1820 | EL | ELL07-022315 | EL |
| Valb1562 | 0.9989<br>0.0011<br>0.0000 | EL | 0.6360<br>0.1900<br>0.1740 | EL | ELL07-120214 | EL |
| Valb1445 | 0.8847<br>0.0032<br>0.1122 | EL | 0.6300<br>0.1880<br>0.1820 | EL | ELL08-022315 | EL |
| Valb1188 | 0.9871<br>0.0124<br>0.0005 | EL | 0.6260<br>0.1600<br>0.2140 | EL | ELL08-120214 | EL |
| Valb1613 | 1.0000<br>0.0000<br>0.0000 | EL | 0.8320<br>0.0740<br>0.0940 | EL | ELL09-022315 | EL |
| Valb1514 | 1.0000<br>0.0000<br>0.0000 | EL | 0.7780<br>0.1120<br>0.1100 | EL | ELL09-120214 | EL |
| Valb1479 | 0.2786<br>0.1610<br>0.5604 | STARI | 0.5340<br>0.2020<br>0.2640 | EL | ELL10-022315 | EL |
| Valb0933 | 0.5295<br>0.3586<br>0.1119 | EL | 0.6060<br>0.2880<br>0.1060 | EL | ELL10-120214 | EL |
| Valb0923 | 0.6352<br>0.1147<br>0.2501 | EL | 0.5600<br>0.2900<br>0.1500 | EL | ELL16-022315 | EL |

TABLE 8-continued

LASSO and RF three-way model classification probability scores.
The LASSO and RF probability scores are provided for each patient sample tested in duplicate. These are
probability scores for the Test-Set samples. Both the LASSO and RF classifiers provided a probability score for a
sample being early Lyme disease patient (EL), healthy control (HC) and STARI. The sample was classified based
on the highest probability score for membership in one of the three groups (EL, HC, or STARI).

| Coded Sample ID | LASSO Probability Score for EL, HC, and STARI | LASSO Classification | RF Probability Score for EL, HC, and STARI | RF Classification | Sample ID | Patient Type |
|---|---|---|---|---|---|---|
| Valb0338 | 0.4277 | STARI | 0.4760 | EL | ELL16-120214 | EL |
|  | 0.0788 |  | 0.4300 |  |  |  |
|  | 0.4935 |  | 0.0940 |  |  |  |
| Valb0783 | 0.8276 | EL | 0.5720 | EL | ELL17-022315 | EL |
|  | 0.0090 |  | 0.3660 |  |  |  |
|  | 0.1634 |  | 0.0620 |  |  |  |
| Valb0261 | 0.9899 | EL | 0.6060 | EL | ELL17-120214 | EL |
|  | 0.0038 |  | 0.3060 |  |  |  |
|  | 0.0064 |  | 0.0880 |  |  |  |
| Valb1264 | 0.7738 | EL | 0.5880 | EL | ELL18-022315 | EL |
|  | 0.0116 |  | 0.2880 |  |  |  |
|  | 0.2146 |  | 0.1240 |  |  |  |
| Valb0545 | 0.1309 | HC | 0.5000 | EL | ELL18-120214 | EL |
|  | 0.8465 |  | 0.3480 |  |  |  |
|  | 0.0225 |  | 0.1520 |  |  |  |
| Valb1427 | 0.9965 | EL | 0.5460 | EL | ELL61-022315 | EL |
|  | 0.0022 |  | 0.3180 |  |  |  |
|  | 0.0012 |  | 0.1360 |  |  |  |
| Valb1071 | 0.9949 | EL | 0.5240 | EL | ELL61-120214 | EL |
|  | 0.0040 |  | 0.3060 |  |  |  |
|  | 0.0011 |  | 0.1700 |  |  |  |
| Valb1211 | 0.6844 | EL | 0.4780 | EL | ELL62-022315 | EL |
|  | 0.3003 |  | 0.3280 |  |  |  |
|  | 0.0153 |  | 0.1940 |  |  |  |
| Valb1217 | 0.0136 | HC | 0.4560 | EL | ELL62-120214 | EL |
|  | 0.9855 |  | 0.4140 |  |  |  |
|  | 0.0009 |  | 0.1300 |  |  |  |
| Valb1414 | 0.9456 | EL | 0.6260 | EL | ELL63-022315 | EL |
|  | 0.0523 |  | 0.2680 |  |  |  |
|  | 0.0020 |  | 0.1060 |  |  |  |
| Valb1104 | 0.4263 | HC | 0.4460 | HC | ELL63-120214 | EL |
|  | 0.5711 |  | 0.4700 |  |  |  |
|  | 0.0026 |  | 0.0840 |  |  |  |
| Valb0736 | 0.8514 | EL | 0.4700 | HC | ELL64-022315 | EL |
|  | 0.1341 |  | 0.4880 |  |  |  |
|  | 0.0145 |  | 0.0420 |  |  |  |
| Valb0384 | 0.7501 | EL | 0.4000 | HC | ELL64-120214 | EL |
|  | 0.2400 |  | 0.5680 |  |  |  |
|  | 0.0100 |  | 0.0320 |  |  |  |
| Valb0672 | 0.9502 | EL | 0.4200 | HC | ELL65-022315 | EL |
|  | 0.0479 |  | 0.4660 |  |  |  |
|  | 0.0019 |  | 0.1140 |  |  |  |
| Valb0300 | 0.9441 | EL | 0.5220 | EL | ELL65-120214 | EL |
|  |  |  | 0.4020 |  |  |  |
|  |  |  | 0.0760 |  |  |  |
| Valb1018 | 0.2340 | HC | 0.3360 | HC | ELL66-022315 | EL |
|  | 0.7645 |  | 0.6140 |  |  |  |
|  | 0.0015 |  | 0.0500 |  |  |  |
| Valb0458 | 0.5250 | EL | 0.2980 | HC | ELL66-120214 | EL |
|  | 0.4676 |  | 0.6620 |  |  |  |
|  | 0.0074 |  | 0.0400 |  |  |  |
| Valb1356 | 0.6663 | EL | 0.6480 | EL | ELL67-022315 | EL |
|  | 0.3313 |  | 0.1860 |  |  |  |
|  | 0.0024 |  | 0.1660 |  |  |  |
| Valb0492 | 0.7816 | EL | 0.5200 | EL | ELL67-120214 | EL |
|  | 0.2169 |  | 0.3160 |  |  |  |
|  | 0.0015 |  | 0.1640 |  |  |  |
| Valb0408 | 0.0012 | HC | 0.0840 | HC | HCN07-022315 | HC |
|  | 0.9984 |  | 0.8860 |  |  |  |
|  | 0.0004 |  | 0.0300 |  |  |  |
| Valb0311 | 0.0039 | HC | 0.0720 | HC | HCN07-120214 | HC |
|  | 0.9653 |  | 0.8880 |  |  |  |
|  | 0.0308 |  | 0.0400 |  |  |  |
| Valb0440 | 0.0006 | HC | 0.1480 | HC | HCN08-022315 | HC |
|  | 0.9993 |  | 0.8140 |  |  |  |
|  | 0.0001 |  | 0.0380 |  |  |  |
| Valb0123 | 0.0189 | HC | 0.1960 | HC | HCN08-120214 | HC |
|  | 0.9758 |  | 0.7700 |  |  |  |
|  | 0.0053 |  | 0.0340 |  |  |  |

TABLE 8-continued

LASSO and RF three-way model classification probability scores.
The LASSO and RF probability scores are provided for each patient sample tested in duplicate. These are
probability scores for the Test-Set samples. Both the LASSO and RF classifiers provided a probability score for a
sample being early Lyme disease patient (EL), healthy control (HC) and STARI. The sample was classified based
on the highest probability score for membership in one of the three groups (EL, HC, or STARI).

| Coded Sample ID | LASSO Probability Score for EL, HC, and STARI | LASSO Classification | RF Probability Score for EL, HC, and STARI | RF Classification | Sample ID | Patient Type |
|---|---|---|---|---|---|---|
| Valb0327 | 0.0029<br>0.9970<br>0.0001 | HC | 0.1180<br>0.8600<br>0.0220 | HC | HCN09-022315 | HC |
| Valb0112 | 0.0000<br>0.9995<br>0.0005 | HC | 0.0540<br>0.9260<br>0.0200 | HC | HCN09-120214 | HC |
| Valb1108 | 0.0042<br>0.9957<br>0.0001 | HC | 0.3780<br>0.5120<br>0.1100 | HC | HCN16-022315 | HC |
| Valb0269 | 0.0724<br>0.9238<br>0.0039 | HC | 0.0700<br>0.9120<br>0.0180 | HC | HCN16-120214 | HC |
| Valb0411 | 0.0243<br>0.9710<br>0.0047 | HC | 0.2760<br>0.6700<br>0.0540 | HC | HCN17-022315 | HC |
| Valb0029 | 0.0491<br>0.9435<br>0.0074 | HC | 0.0620<br>0.9220<br>0.0160 | HC | HCN17-120214 | HC |
| Valb0860 | 0.1211<br>0.8540<br>0.0250 | HC | 0.3560<br>0.4300<br>0.2140 | HC | HCN18-022315 | HC |
| Valb0302 | 0.0198<br>0.9792<br>0.0010 | HC | 0.0240<br>0.9720<br>0.0040 | HC | HCN18-120214 | HC |
| Valb0709 | 0.0060<br>0.9930<br>0.0010 | HC | 0.2980<br>0.5740<br>0.1280 | HC | HCN19-022315 | HC |
| Valb0178 | 0.0024<br>0.9940<br>0.0036 | HC | 0.0480<br>0.9260<br>0.0260 | HC | HCN19-120214 | HC |
| Valb0962 | 0.0978<br>0.8543<br>0.0479 | HC | 0.3700<br>0.4420<br>0.1880 | HC | HCN25-022315 | HC |
| Valb0418 | 0.6988<br>0.1304<br>0.1708 | EL | 0.2500<br>0.5540<br>0.1960 | HC | HCN25-120214 | HC |
| Valb0632 | 0.0014<br>0.9982<br>0.0005 | HC | 0.1080<br>0.8440<br>0.0480 | HC | HCN28-022315 | HC |
| Valb0124 | 0.0226<br>0.9655<br>0.0119 | HC | 0.0800<br>0.8780<br>0.0420 | HC | HCN28-120214 | HC |
| Valb0690 | 0.9013<br>0.0929<br>0.0058 | EL | 0.5920<br>0.3340<br>0.0740 | EL | HCN29-022315 | HC |
| Valb0066 | 0.0876<br>0.8866<br>0.0257 | HC | 0.1260<br>0.8560<br>0.0180 | HC | HCN29-120214 | HC |
| Valb1466 | 0.0038<br>0.9957<br>0.0005 | HC | 0.1860<br>0.7800<br>0.0340 | HC | HCW13-022315 | HC |
| Valb0777 | 0.2406<br>0.7540<br>0.0054 | HC | 0.1320<br>0.8560<br>0.0120 | HC | HCW13-120214 | HC |
| Valb1405 | 0.0021<br>0.9959<br>0.0019 | HC | 0.2540<br>0.5900<br>0.1560 | HC | HCW21-022315 | HC |
| Valb0802 | 0.2993<br>0.6973<br>0.0034 | HC | 0.1660<br>0.8180<br>0.0160 | HC | HCW21-120214 | HC |
| Valb1254 | 0.5258<br>0.4539<br>0.0203 | EL | 0.4020<br>0.3720<br>0.2260 | EL | HCW25-022315 | HC |
| Valb0697 | 0.0064<br>0.9906<br>0.0031 | HC | 0.4060<br>0.4180<br>0.1760 | HC | HCW25-120214 | HC |
| Valb1138 | 0.0005<br>0.9988<br>0.0007 | HC | 0.1720<br>0.7260<br>0.1020 | HC | HCW26-022315 | HC |

TABLE 8-continued

LASSO and RF three-way model classification probability scores.
The LASSO and RF probability scores are provided for each patient sample tested in duplicate. These are probability scores for the Test-Set samples. Both the LASSO and RF classifiers provided a probability score for a sample being early Lyme disease patient (EL), healthy control (HC) and STARI. The sample was classified based on the highest probability score for membership in one of the three groups (EL, HC, or STARI).

| Coded Sample ID | LASSO Probability Score for EL, HC, and STARI | LASSO Classification | RF Probability Score for EL, HC, and STARI | RF Classification | Sample ID | Patient Type |
|---|---|---|---|---|---|---|
| Valb0520 | 0.0041 | HC | 0.1580 | HC | HCW26- | HC |
|  | 0.9956 |  | 0.7940 |  | 120214 |  |
|  | 0.0004 |  | 0.0480 |  |  |  |
| Valb1119 | 0.0001 | HC | 0.2120 | HC | HCW28- | HC |
|  | 0.9998 |  | 0.7240 |  | 022315 |  |
|  | 0.0001 |  | 0.0640 |  |  |  |
| Valb0572 | 0.1165 | HC | 0.1180 | HC | HCW28- | HC |
|  | 0.8831 |  | 0.8600 |  | 120214 |  |
|  | 0.0004 |  | 0.0220 |  |  |  |
| Valb0943 | 0.0616 | HC | 0.2260 | HC | HCW29- | HC |
|  | 0.9320 |  | 0.5440 |  | 022315 |  |
|  | 0.0064 |  | 0.2300 |  |  |  |
| Valb0419 | 0.3990 | HC | 0.2480 | HC | HCW29- | HC |
|  | 0.5992 |  | 0.6840 |  | 120214 |  |
|  | 0.0018 |  | 0.0680 |  |  |  |
| Valb1282 | 0.0191 | HC | 0.2980 | HC | HCW34- | HC |
|  | 0.6025 |  | 0.4380 |  | 022315 |  |
|  | 0.3783 |  | 0.2640 |  |  |  |
| Valb0719 | 0.0209 | HC | 0.0980 | HC | HCW34- | HC |
|  | 0.9768 |  | 0.8980 |  | 120214 |  |
|  | 0.0024 |  | 0.0040 |  |  |  |
| Valb1535 | 0.0056 | HC | 0.2160 | HC | HCW37- | HC |
|  | 0.9885 |  | 0.5380 |  | 022315 |  |
|  | 0.0059 |  | 0.2460 |  |  |  |
| Valb1091 | 0.0163 | HC | 0.2120 | HC | HCW37- | HC |
|  | 0.9766 |  | 0.7280 |  | 120214 |  |
|  | 0.0071 |  | 0.0600 |  |  |  |
| Valb1509 | 0.1004 | HC | 0.3080 | HC | HCW44- | HC |
|  | 0.8845 |  | 0.5860 |  | 022315 |  |
|  | 0.0151 |  | 0.1060 |  |  |  |
| Valb0944 | 0.0532 | HC | 0.2300 | HC | HCW44- | HC |
|  | 0.9143 |  | 0.7280 |  | 120214 |  |
|  | 0.0325 |  | 0.0420 |  |  |  |
| Valb1349 | 0.0037 | HC | 0.3080 | HC | HCW46- | HC |
|  | 0.9898 |  | 0.6100 |  | 022315 |  |
|  | 0.0066 |  | 0.0820 |  |  |  |
| Valb0801 | 0.0039 | HC | 0.2640 | HC | HCW46- | HC |
|  | 0.9822 |  | 0.6500 |  | 120214 |  |
|  | 0.0139 |  | 0.0860 |  |  |  |
| Valb1561 | 0.0005 | STARI | 0.0044 | STARI | M06A- | STARI |
|  | 0.0000 |  | 0.1788 |  | 022315 |  |
|  | 0.9995 |  | 0.8168 |  |  |  |
| Valb1328 | 0.6469 | EL | 0.5180 | EL | M06A- | STARI |
|  | 0.0097 |  | 0.0960 |  | 120214 |  |
|  | 0.3434 |  | 0.3860 |  |  |  |
| Valb0329 | 0.2186 | STARI | 0.2140 | STARI | M09A- | STARI |
|  | 0.0048 |  | 0.0740 |  | 022315 |  |
|  | 0.7767 |  | 0.7120 |  |  |  |
| Valb0070 | 0.0212 | STARI | 0.2480 | STARI | M09A- | STARI |
|  | 0.0066 |  | 0.0980 |  | 120214 |  |
|  | 0.9722 |  | 0.6540 |  |  |  |
| Valb1052 | 0.0298 | STARI | 0.3840 | STARI | M13A- | STARI |
|  | 0.0061 |  | 0.1920 |  | 022315 |  |
|  | 0.9640 |  | 0.4240 |  |  |  |
| Valb0809 | 0.0020 | EL | 0.1560 | EL | M13A- | STARI |
|  | 0.9494 |  | 0.6200 |  | 120214 |  |
|  | 0.0486 |  | 0.2240 |  | B |  |
| Valb1256 | 0.0016 | STARI | 0.2340 | STARI | M16A- | STARI |
|  | 0.0002 |  | 0.1440 |  | 022315 |  |
|  | 0.9982 |  | 0.6220 |  |  |  |
| Valb1100 | 0.0232 | STARI | 0.2400 | STARI | M16A- | STARI |
|  | 0.0055 |  | 0.0820 |  | 120214 |  |
|  | 0.9713 |  | 0.6780 |  |  |  |
| Valb1236 | 0.1166 | STARI | 0.4740 | EL | M19A- | STARI |
|  | 0.0227 |  | 0.2340 |  | 022315 |  |
|  | 0.8607 |  | 0.2920 |  |  |  |
| Valb0580 | 0.1942 | STARI | 0.4080 | STARI | M19A- | STARI |
|  | 0.1003 |  | 0.1800 |  | 120214 |  |
|  | 0.7055 |  | 0.4120 |  |  |  |

TABLE 8-continued

LASSO and RF three-way model classification probability scores.
The LASSO and RF probability scores are provided for each patient sample tested in duplicate. These are probability scores for the Test-Set samples. Both the LASSO and RF classifiers provided a probability score for a sample being early Lyme disease patient (EL), healthy control (HC) and STARI. The sample was classified based on the highest probability score for membership in one of the three groups (EL, HC, or STARI).

| Coded Sample ID | LASSO Probability Score for EL, HC, and STARI | LASSO Classification | RF Probability Score for EL, HC, and STARI | RF Classification | Sample ID | Patient Type |
|---|---|---|---|---|---|---|
| Valb1525 | 0.9962<br>0.0000<br>0.0038 | EL | 0.3660<br>0.1700<br>0.4640 | STARI | M22A-022315 | STARI |
| Valb0534 | 0.1791<br>0.0000<br>0.8208 | STARI | 0.3520<br>0.1880<br>0.4600 | STARI | M22A-120214 | STARI |
| Valb0556 | 0.3684<br>0.1161<br>0.5155 | STARI | 0.3120<br>0.0300<br>0.6580 | STARI | M26A-022315 | STARI |
| Valb0116 | 0.4121<br>0.0005<br>0.5874 | STARI | 0.1900<br>0.0560<br>0.7540 | STARI | M26A-120214 | STARI |
| Valb0461 | 0.0048<br>0.0293<br>0.9659 | STARI | 0.2000<br>0.0860<br>0.7140 | STARI | M27A-022315 | STARI |
| Valb0266 | 0.0169<br>0.0001<br>0.9830 | STARI | 0.1300<br>0.0560<br>0.8140 | STARI | M27A-120214 | STARI |
| Valb0447 | 0.0016<br>0.1106<br>0.8877 | STARI | 0.1280<br>0.0780<br>0.7940 | STARI | S03-022315 | STARI |
| Valb0026 | 0.0005<br>0.0004<br>0.9992 | STARI | 0.1320<br>0.0640<br>0.8040 | STARI | S03-120214 | STARI |
| Valb1114 | 0.0013<br>0.0004<br>0.9982 | STARI | 0.1800<br>0.2660<br>0.5540 | STARI | S09-022315 | STARI |
| Valb0464 | 0.1404<br>0.0000<br>0.8596 | STARI | 0.1320<br>0.2000<br>0.6680 | STARI | S09-120214 | STARI |
| Valb1292 | 0.0002<br>0.0000<br>0.9997 | STARI | 0.1360<br>0.1980<br>0.6660 | STARI | S17-022315 | STARI |
| Valb0754 | 0.0001<br>0.0000<br>0.9999 | STARI | 0.0980<br>0.1480<br>0.7540 | STARI | S17-120214 | STARI |
| Valb0434 | 0.0209<br>0.0896<br>0.8896 | STARI | 0.1780<br>0.2000<br>0.6220 | STARI | S21-022315 | STARI |
| Valb0044 | 0.0148<br>0.0203<br>0.9649 | STARI | 0.2560<br>0.1920<br>0.5520 | STARI | S21-120214 | STARI |
| Valb0873 | 0.0079<br>0.0169<br>0.9753 | STARI | 0.1340<br>0.2480<br>0.6180 | STARI | S33-022315 | STARI |
| Valb0352 | 0.0003<br>0.0087<br>0.9910 | STARI | 0.1280<br>0.2180<br>0.6540 | STARI | S33-120214 | STARI |
| Valb1141 | 0.0000<br>0.0169<br>0.9831 | STARI | 0.1060<br>0.1100<br>0.7840 | STARI | S39-022315 | STARI |
| Valb0480 | 0.0000<br>0.0002<br>0.9998 | STARI | 0.0540<br>0.0500<br>0.8960 | STARI | S39-120214 | STARI |
| Valb0618 | 0.0015<br>0.0010<br>0.9975 | STARI | 0.2640<br>0.2060<br>0.5300 | STARI | S43-022315 | STARI |
| Valb0660 | 0.0018<br>0.0008<br>0.9973 | STARI | 0.2700<br>0.1400<br>0.5900 | STARI | S43-120214 | STARI |
| Valb0223 | 0.0002<br>0.0340<br>0.9658 | STARI | 0.1080<br>0.3080<br>0.5840 | STARI | S47-022315 | STARI |
| Valb0054 | 0.0023<br>0.0168<br>0.9808 | STARI | 0.0640<br>0.0740<br>0.8620 | STARI | S47-120214 | STARI |
| Valb0335 | 0.0085<br>0.0023<br>0.9893 | STARI | 0.0660<br>0.0440<br>0.8900 | STARI | S53-022315 | STARI |

TABLE 8-continued

LASSO and RF three-way model classification probability scores.
The LASSO and RF probability scores are provided for each patient sample tested in duplicate. These are probability scores for the Test-Set samples. Both the LASSO and RF classifiers provided a probability score for a sample being early Lyme disease patient (EL), healthy control (HC) and STARI. The sample was classified based on the highest probability score for membership in one of the three groups (EL, HC, or STARI).

| Coded Sample ID | LASSO Probability Score for EL, HC, and STARI | LASSO Classification | RF Probability Score for EL, HC, and STARI | RF Classification | Sample ID | Patient Type |
|---|---|---|---|---|---|---|
| Valb0197 | 0.0050 | STARI | 0.0320 | STARI | S53-120214 | STARI |
|  | 0.0001 |  | 0.0320 |  |  |  |
|  | 0.9949 |  | 0.9360 |  |  |  |
| Valb0409 | 0.0714 | STARI | 0.1680 | STARI | S55-022315 | STARI |
|  | 0.0715 |  | 0.1420 |  |  |  |
|  | 0.8571 |  | 0.6900 |  |  |  |
| Valb0060 | 0.0119 | STARI | 0.1020 | STARI | S55-120214 | STARI |
|  | 0.0059 |  | 0.1180 |  |  |  |
|  | 0.9821 |  | 0.7800 |  |  |  |
| Valb0437 | 0.0001 | STARI | 0.0800 | STARI | S65-022315 | STARI |
|  | 0.0078 |  | 0.1060 |  |  |  |
|  | 0.9921 |  | 0.8140 |  |  |  |
| Valb0093 | 0.0000 | STARI | 0.1060 | STARI | S65-120214 | STARI |
|  | 0.0001 |  | 0.0720 |  |  |  |
|  | 0.9999 |  | 0.8220 |  |  |  |

What is claimed is:

1. A method for treating a subject with Lyme disease, the method comprising:
   (a) obtaining a disease score from a mass spectrometry based test;
   (b) diagnosing the subject with Lyme disease based on the disease score; and
   (c) administering a treatment to the subject diagnosed with Lyme disease based on the disease score, wherein the treatment is a pharmacological treatment for Lyme disease selected from an antibiotic, an antibacterial agent, an immune modulator, an anti-inflammatory agent, or a combination thereof;
wherein the mass spectrometry based test comprises:
   (i) deproteinizing a blood sample from a subject to produce a metabolite extract;
   (ii) performing liquid chromatography coupled to mass spectrometry on a sample of the metabolite extract;
   (iii) providing abundance values for each molecular feature in Table A, Table C, or Table D:

TABLE A

| MF # | Name | m/z (positive ion) | Mass | Retention Time (see examples) |
|---|---|---|---|---|
| 1 | CSU/CDC-001 | 166.0852 | 165.078 | 1.86 |
| 2 | CSU/CDC-012 | 270.3156 | 269.3076 | 18.02 |
| 3 | CSU/CDC-013 | 284.3314 | 283.3236 | 18.13 |
| 4 | CSU/CDC-014 | 300.6407 | 599.268 | 18.27 |
| 5 | CSU/CDC-019 | 300.2892 | 299.2821 | 19.66 |
| 6 | CSU/CDC-039 | 734.5079 | 1449.9753 | 17.81 |
| 7 | CSU/CDC-062 | 370.1837 | 369.1757 | 19.7 |
| 8 | CSU/CDC-066 | 811.1942 | 810.1869 | 12.07 |
| 9 | CSU/CDC-067 | 947.7976 | 946.7936 | 14.55 |
| 10 | CSU/CDC-072 | 410.2033 | 409.196 | 17.18 |
| 11 | CSU/CDC-075 | 1487.0005 | 1485.9987 | 18.17 |
| 12 | CSU/CDC-086 | 137.0463 | 136.0378 | 1.37 |
| 13 | CSU/CDC-107 | 811.7965 | 810.7882 | 12.07 |
| 14 | CSU/CDC-132 | 616.1776 | 615.1699 | 15.43 |
| 15 | CSU/CDC-152 | 713.4492 | 712.4391 | 19.35 |
| 16 | CSU/CDC-155 | 502.3376 | 484.3039 | 19.87 |
| 17 | CSU/CDC-158 | 415.3045 | 414.2978 | 20.19 |
| 18 | CSU/CDC-164 | 366.3729 | 365.3655 | 22.79 |
| 19 | CSU/CDC-166 | 333.1446 | 332.1373 | 12.89 |
| 20 | CSU/CDC-205 | 241.1069 | 240.0996 | 14.7 |
| 21 | CSU/CDC-211 | 464.1916 | 463.1849 | 13.05 |
| 22 | CSU/CDC-212 | 1249.2045 | 1248.1993 | 15.31 |
| 23 | CSU/CDC-213 | 1248.9178 | 1247.9141 | 15.3 |
| 24 | CSU/CDC-219 | 158.1539 | 157.1466 | 15.36 |
| 25 | CSU/CDC-227 | 529.3381 | 528.3296 | 16.89 |
| 26 | CSU/CDC-229 | 282.2776 | 264.2456 | 20.56 |
| 27 | CSU/CDC-235 | 190.1260 | 189.1187 | 14.12 |
| 28 | CSU/CDC-238 | 382.3675 | 381.3603 | 20.23 |
| 29 | CSU/CDC-244 | 477.2968 | 476.2898 | 22.79 |
| 30 | CSU/CDC-248 | 459.3968 | 458.3904 | 19.08 |
| 31 | CSU/CDC-253 | 342.2635 | 341.2565 | 15.62 |
| 32 | CSU/CDC-254 | 529.3827 | 1022.6938 | 17.86 |
| 33 | CSU/CDC-258 | 459.2502 | 458.2429 | 19.02 |
| 34 | CSU/CDC-002 | 239.0919 | 238.0844 | 11.66 |
| 35 | CSU/CDC-028 | 389.2174 | 388.2094 | 15.47 |
| 36 | CSU/CDC-182 | 285.2065 | 284.1991 | 16.02 |
| 37 | CSU/CDC-204 | 279.1693 | 278.1629 | 11.05 |
| 38 | CSU/CDC-247 | 714.6967 | 1427.3824 | 11.76 |

| MF # | Name | Compound Predicted Formula | Predicted Chemical Structure (based on accurate mass) | Metabolite Class or Pathway |
|---|---|---|---|---|
| 1 | CSU/CDC-001 | $C_9H_{11}NO_2$ | Phenylalanine | Phenylalanine metabolism |

TABLE A-continued

| | | | | |
|---|---|---|---|---|
| 2 | CSU/CDC-012 | $C_{18}H_{39}N$ | — | — |
| 3 | CSU/CDC-013 | $C_{19}H_{41}N$ | — | — |
| 4 | CSU/CDC-014 | $C_{33}H_{37}N_5O_6$ | Asp Phe Arg Tyr (SEQ ID NO: 1) | Peptide |
| 5 | CSU/CDC-019 | $C_{18}H_{37}NO_2$ | Palmitoyl ethanolamide | N-acyl ethanolamine metabolism |
| 6 | CSU/CDC-039 | — | — | — |
| 7 | CSU/CDC-062 | $C_{19}H_{23}N_5O_3$ | — | — |
| 8 | CSU/CDC-066 | $C_{42}H_{30}N_6O_{12}$ | — | — |
| 9 | CSU/CDC-067 | $C_{62}H_{106}O_6$ | TAG (59:7) | Triacylglycerol metabolism |
| 10 | CSU/CDC-072 | — | — | — |
| 11 | CSU/CDC-075 | — | — | — |
| 12 | CSU/CDC-086 | $C_4H_8O_5$ | Threonate | Sugar metabolite |
| 13 | CSU/CDC-107 | — | — | — |
| 14 | CSU/CDC-132 | — | — | — |
| 15 | CSU/CDC-152 | $C_{38}H_{65}O_{10}P$ | PG(32:5) | Glycerophospholipid metabolism |
| 16 | CSU/CDC-155 | $C_{27}H_{40}N_4O_4$ | Gln Leu Pro Lys (SEQ ID NO: 2) | Peptide |
| 17 | CSU/CDC-158 | — | — | — |
| 18 | CSU/CDC-164 | — | — | — |
| 19 | CSU/CDC-166 | $C_{12}H_{20}N_4O_7$ | Glu Gln Gly | Peptide |
| 20 | CSU/CDC-205 | $C_{12}H_{16}O_5$ | 3-Carboxy-4-methyl-5-propyl-2-furanpropanoic acid (CMPF) | Fatty acid metabolism |
| 21 | CSU/CDC-211 | $C_{16}H_{29}N_7O_7S$ | Arg Asp Cys Ala (SEQ ID NO: 3) | Peptide |
| 22 | CSU/CDC-212 | — | — | — |
| 23 | CSU/CDC-213 | — | — | — |
| 24 | CSU/CDC-219 | — | — | — |
| 25 | CSU/CDC-227 | $C_{24}H_{44}N_6O_7$ | Gln Val Leu Leu Gly (SEQ ID NO: 4) | Peptide |
| 26 | CSU/CDC-229 | $C_{18}H_{32}O$ | — | — |
| 27 | CSU/CDC-235 | $C_9H_{19}NOS$ | 8-Methylthiooctanal doxime | 2-oxocarboxylic acid metabolism |
| 28 | CSU/CDC-238 | $C_{24}H_{47}NO_2$ | Erucicoyl ethanolamide | N-acyl ethanolamine metabolism |
| 29 | CSU/CDC-244 | $C_{31}H_{40}O_4$ | Lys Lys Thr Thr (SEQ ID NO: 5) | Peptide |
| 30 | CSU/CDC-248 | — | — | — |
| 31 | CSU/CDC-253 | $C_{19}H_{35}NO_4$ | — | — |
| 32 | CSU/CDC-254 | — | — | — |
| 33 | CSU/CDC-258 | $C_{23}H_{39}O_7P$ | Lyso PA(20:4) | Glycerophospholipid metabolism |
| 34 | CSU/CDC-002 | $C_{12}H_{14}O_5$ | Trans-2,3,4-trimethoxycinnamate | Phenylpropanoid and polyketide metabolism |

TABLE A-continued

| | | | | |
|---|---|---|---|---|
| 35 | CSU/CDC-028 | $C_{19}H_{32}O_8$ | Methyl 10,12,13,15-bisepidioxy-16-hydroperoxy-8E-octadecenoate | Fatty acid metabolism |
| 36 | CSU/CDC-182 | $C_{16}H_{28}O_4$ | — | — |
| 37 | CSU/CDC-204 | $C_{15}H_{22}N_2O_3$ | Phe Leu | Dipeptide |
| 38 | CSU/CDC-247 | — | — | — |

TABLE C

| MF # | Name | m/z (positive ion) | Mass | Retention Time (see examples) |
|---|---|---|---|---|
| 1 | CSU/CDC-001 | 166.0852 | 165.078 | 1.86 |
| 2 | CSU/CDC-012 | 270.3156 | 269.3076 | 18.02 |
| 3 | CSU/CDC-013 | 284.3314 | 283.3236 | 18.13 |
| 4 | CSU/CDC-014 | 300.6407 | 599.268 | 18.27 |
| 5 | CSU/CDC-019 | 300.2892 | 299.2821 | 19.66 |
| 6 | CSU/CDC-039 | 734.5079 | 1449.9753 | 17.81 |
| 7 | CSU/CDC-062 | 370.1837 | 369.1757 | 19.7 |
| 8 | CSU/CDC-066 | 811.1942 | 810.1869 | 12.07 |
| 9 | CSU/CDC-067 | 947.7976 | 946.7936 | 14.55 |
| 10 | CSU/CDC-072 | 410.2033 | 409.196 | 17.18 |
| 11 | CSU/CDC-075 | 1487.0005 | 1485.9987 | 18.17 |
| 12 | CSU/CDC-086 | 137.0463 | 136.0378 | 1.37 |
| 13 | CSU/CDC-107 | 811.7965 | 810.7882 | 12.07 |
| 14 | CSU/CDC-132 | 616.1776 | 615.1699 | 15.43 |
| 15 | CSU/CDC-152 | 713.4492 | 712.4391 | 19.35 |
| 16 | CSU/CDC-155 | 502.3376 | 484.3039 | 19.87 |
| 17 | CSU/CDC-158 | 415.3045 | 414.2978 | 20.19 |
| 18 | CSU/CDC-164 | 366.3729 | 365.3655 | 22.79 |
| 19 | CSU/CDC-166 | 333.1446 | 332.1373 | 12.89 |
| 20 | CSU/CDC-205 | 241.1069 | 240.0996 | 14.7 |
| 21 | CSU/CDC-211 | 464.1916 | 463.1849 | 13.05 |
| 22 | CSU/CDC-212 | 1249.2045 | 1248.1993 | 15.31 |
| 23 | CSU/CDC-213 | 1248.9178 | 1247.9141 | 15.3 |
| 24 | CSU/CDC-219 | 158.1539 | 157.1466 | 15.36 |
| 25 | CSU/CDC-227 | 529.3381 | 528.3296 | 16.89 |
| 26 | CSU/CDC-229 | 282.2776 | 264.2456 | 20.56 |
| 27 | CSU/CDC-235 | 190.1260 | 189.1187 | 14.12 |
| 28 | CSU/CDC-238 | 382.3675 | 381.3603 | 20.23 |
| 29 | CSU/CDC-244 | 477.2968 | 476.2898 | 22.79 |
| 30 | CSU/CDC-248 | 459.3968 | 458.3904 | 19.08 |
| 31 | CSU/CDC-253 | 342.2635 | 341.2565 | 15.62 |
| 32 | CSU/CDC-254 | 529.3827 | 1022.6938 | 17.86 |
| 33 | CSU/CDC-258 | 459.2502 | 458.2429 | 19.02 |
| 34 | CSU/CDC-003 | 886.4296 | 1770.8438 | 12.18 |
| 35 | CSU/CDC-004 | 181.0859 | 180.0788 | 14.7 |
| 36 | CSU/CDC-006 | 286.1444 | 285.1371 | 16.08 |
| 37 | CSU/CDC-008 | 463.2339 | 462.2248 | 16.36 |
| 38 | CSU/CDC-009 | 242.2844 | 241.2772 | 17.1 |
| 39 | CSU/CDC-017 | 590.4237 | 589.4194 | 19.24 |
| 40 | CSU/CDC-026 | 553.3904 | 552.3819 | 23.38 |
| 41 | CSU/CDC-030 | 399.2364 | 398.2313 | 16.23 |
| 42 | CSU/CDC-042 | 580.4144 | 1158.8173 | 18.26 |
| 43 | CSU/CDC-052 | 704.4985 | 1372.925 | 18.7 |
| 44 | CSU/CDC-061 | 623.4521 | 1210.8362 | 19.55 |
| 45 | CSU/CDC-070 | 389.2178 | 388.2099 | 15.52 |
| 46 | CSU/CDC-074 | 1111.6690 | 1110.6656 | 17.89 |
| 47 | CSU/CDC-083 | 482.4040 | 481.3976 | 19.99 |
| 48 | CSU/CDC-084 | 533.1929 | 532.1854 | 20.84 |
| 49 | CSU/CDC-087 | 466.3152 | 465.3085 | 14.73 |
| 50 | CSU/CDC-091 | 683.4728 | 1347.9062 | 17.56 |
| 51 | CSU/CDC-095 | 227.0897 | 204.1002 | 9.68 |
| 52 | CSU/CDC-098 | 183.1016 | 182.0943 | 10.89 |
| 53 | CSU/CDC-099 | 476.3055 | 475.2993 | 11.09 |
| 54 | CSU/CDC-112 | 215.1283 | 214.1209 | 12.32 |
| 55 | CSU/CDC-115 | 519.1881 | 518.1813 | 12.33 |
| 56 | CSU/CDC-128 | 1086.1800 | 2170.3435 | 15.38 |
| 57 | CSU/CDC-133 | 285.2061 | 284.1993 | 15.99 |
| 58 | CSU/CDC-134 | 357.1363 | 356.1284 | 15.98 |
| 59 | CSU/CDC-136 | 299.1853 | 298.1781 | 16.24 |
| 60 | CSU/CDC-137 | 334.2580 | 333.2514 | 16.36 |
| 61 | CSU/CDC-138 | 317.2317 | 316.2254 | 16.63 |
| 62 | CSU/CDC-141 | 331.2471 | 330.2403 | 17.26 |
| 63 | CSU/CDC-144 | 583.3480 | 582.3379 | 18.04 |
| 64 | CSU/CDC-157 | 648.4672 | 647.4609 | 19.98 |
| 65 | CSU/CDC-165 | 445.2880 | 854.5087 | 12.48 |
| 66 | CSU/CDC-181 | 1486.7386 | 2971.4668 | 14.97 |
| 67 | CSU/CDC-183 | 668.4686 | 1317.8969 | 18.04 |
| 68 | CSU/CDC-184 | 454.2924 | 436.2587 | 18.1 |
| 69 | CSU/CDC-186 | 607.9324 | 606.9246 | 19.01 |
| 70 | CSU/CDC-188 | 521.4202 | 503.3858 | 21.06 |
| 71 | CSU/CDC-193 | 176.0746 | 175.0667 | 2.31 |
| 72 | CSU/CDC-194 | 596.9082 | 1191.8033 | 19.1 |
| 73 | CSU/CDC-203 | 532.5606 | 531.5555 | 18.38 |
| 74 | CSU/CDC-206 | 337.1667 | 336.1599 | 20.67 |
| 75 | CSU/CDC-210 | 415.1634 | 207.0784 | 12.2 |
| 76 | CSU/CDC-218 | 364.3407 | 346.3068 | 20.72 |
| 77 | CSU/CDC-222 | 989.5004 | 1976.9858 | 12.03 |
| 78 | CSU/CDC-224 | 819.6064 | 1635.8239 | 12.06 |
| 79 | CSU/CDC-237 | 286.2737 | 285.2666 | 19.08 |
| 80 | CSU/CDC-245 | 614.4833 | 613.4772 | 19.78 |
| 81 | CSU/CDC-250 | 298.2740 | 297.2668 | 16.44 |
| 82 | CSU/CDC-252 | 1003.7020 | 1002.696 | 18.46 |

| MF # | Name | Compound Predicted Formula | Predicted Chemical Structure (based on accurate mass) | Metabolite Class or Pathway |
|---|---|---|---|---|
| 1 | CSU/CDC-001 | $C_9H_{11}NO_2$ | Phenylalanine | Phenylalanine metabolism |
| 2 | CSU/CDC-012 | $C_{18}H_{39}N$ | — | — |
| 3 | CSU/CDC-013 | $C_{19}H_{41}N$ | — | — |
| 4 | CSU/CDC-014 | $C_{33}H_{37}N_5O_6$ | Asp Phe Arg Tyr (SEQ ID NO: 1) | Peptide |
| 5 | CSU/CDC-019 | $C_{18}H_{37}NO_2$ | Palmitoyl ethanolamide | N-acyl ethanolamine metabolism |
| 6 | CSU/CDC-039 | — | — | — |
| 7 | CSU/CDC-062 | $C_{19}H_{23}N_5O_3$ | — | — |
| 8 | CSU/CDC-066 | $C_{42}H_{30}N_6O_{12}$ | — | — |
| 9 | CSU/CDC-067 | $C_{62}H_{106}O_6$ | TAG(59:7) | Triacylglycerol metabolism |
| 10 | CSU/CDC-072 | — | — | — |
| 11 | CSU/CDC-075 | — | — | — |
| 12 | CSU/CDC-086 | $C_4H_8O_5$ | Threonate | Sugar metabolite |
| 13 | CSU/CDC-107 | — | — | — |
| 14 | CSU/CDC-132 | — | — | — |
| 15 | CSU/CDC-152 | $C_{38}H_{65}O_{10}P$ | PG(32:5) | Glycerophospholipid metabolism |
| 16 | CSU/CDC-155 | $C_{27}H_{40}N_4O_4$ | Gln Leu Pro Lys (SEQ ID NO: 2) | Peptide |
| 17 | CSU/CDC-158 | — | — | — |
| 18 | CSU/CDC-164 | — | — | — |
| 19 | CSU/CDC-166 | $C_{12}H_{20}N_4O_7$ | Glu Gln Gly | Peptide |
| 20 | CSU/CDC-205 | $C_{12}H_{16}O_5$ | 3-Carboxy-4-methyl-5-propyl-2-furanpropanoic acid (CMPF) | Fatty acid metabolism |
| 21 | CSU/CDC-211 | $C_{16}H_{29}N_7O_7S$ | Arg Asp Cys Ala (SEQ ID NO: 3) | Peptide |
| 22 | CSU/CDC-212 | — | — | — |
| 23 | CSU/CDC-213 | — | — | — |
| 24 | CSU/CDC-219 | — | — | — |
| 25 | CSU/CDC-227 | $C_{24}H_{44}N_6O_7$ | Gln Val Leu Leu Gly (SEQ ID NO: 4) | Peptide |
| 26 | CSU/CDC-229 | $C_{18}H_{32}O$ | | |

TABLE C-continued

| | | | | |
|---|---|---|---|---|
| 27 | CSU/CDC-235 | $C_9H_{19}NOS$ | 8-Methyl-thiooctanal doxime | 2-oxocarboxylic acid metabolism |
| 28 | CSU/CDC-238 | $C_{24}H_{47}NO_2$ | Erucicoyl ethanolamide | N-acyl ethanolamine metabolism |
| 29 | CSU/CDC-244 | $C_{31}H_{40}O_4$ | Lys Lys Thr Thr (SEQ ID NO: 5) | Peptide |
| 30 | CSU/CDC-248 | — | — | — |
| 31 | CSU/CDC-253 | $C_{19}H_{35}NO_4$ | — | — |
| 32 | CSU/CDC-254 | — | — | — |
| 33 | CSU/CDC-258 | $C_{23}H_{39}O_7P$ | Lyso PA(20:4) | Glycerophospholipid metabolism |
| 34 | CSU/CDC-003 | — | — | — |
| 35 | CSU/CDC-004 | $C_{10}H_{12}O_3$ | 5'-(3'-Methoxy-4'-hydroxy-phenyl)-gamma-valerolactone | Endogenous metabolite associated with microbiome |
| 36 | CSU/CDC-006 | $C_{17}H_{19}NO_3$ | Piperine | Alkaloid metabolism |
| 37 | CSU/CDC-008 | $C_{25}H_{34}O_8$ | Ala Lys Met Asn (SEQ ID NO: 6) | Peptide |
| 38 | CSU/CDC-009 | $C_{16}H_{35}N$ | — | — |
| 39 | CSU/CDC-017 | — | — | — |
| 40 | CSU/CDC-026 | $C_{35}H_{52}O_5$ | Furohyperforin | Endogenous metabolite - derived from food |
| 41 | CSU/CDC-030 | — | — | — |
| 42 | CSU/CDC-042 | — | — | — |
| 43 | CSU/CDC-052 | — | — | — |
| 44 | CSU/CDC-061 | — | — | — |
| 45 | CSU/CDC-070 | $C_{19}H_{32}O_8$ | — | — |
| 46 | CSU/CDC-074 | — | — | — |
| 47 | CSU/CDC-083 | — | — | — |
| 48 | CSU/CDC-084 | $C_{23}H_{28}N_6O_9$ | Asp His Phe Asp (SEQ ID NO: 7) | Peptide |
| 49 | CSU/CDC-087 | $C_{26}H_{43}NO_6$ | Glycocholic acid | Bile acid metabolism |
| 50 | CSU/CDC-091 | — | — | — |
| 51 | CSU/CDC-095 | $C_9H_{16}O_5$ | — | — |
| 52 | CSU/CDC-098 | $C_{10}H_{14}O_3$ | — | — |
| 53 | CSU/CDC-099 | $C_{26}H_{41}N_3O_5$ | — | — |
| 54 | CSU/CDC-112 | $C_{11}H_{18}O_4$ | alpha-Carboxy-delta-decalactone | Endogenous metabolite - derived from food |
| 55 | CSU/CDC-115 | $C_{20}H_{30}N_4O_{12}$ | Poly-g-D-glutamate | Poly D-glutamate metabolism |
| 56 | CSU/CDC-128 | — | — | — |
| 57 | CSU/CDC-133 | $C_{16}H_{28}O_4$ | — | — |
| 58 | CSU/CDC-134 | $C_{20}H_{20}O_6$ | Xanthoxylol | Endogenous metabolite - derived from food |
| 59 | CSU/CDC-136 | $C_{16}H_{26}O_5$ | Tetranor-PGE1 | Prostaglandin metabolism |
| 60 | CSU/CDC-137 | — | — | — |
| 61 | CSU/CDC-138 | — | — | — |
| 62 | CSU/CDC-141 | $C_{18}H_{34}O_5$ | 11,12,13-trihydroxy-9-octadecenoic acid | Fatty acid metabolism |
| 63 | CSU/CDC-144 | $C_{27}H_{46}N_6O_8$ | Leu Lys Glu Pro Pro (SEQ ID NO: 8) | Peptide |
| 64 | CSU/CDC-157 | $C_{34}H_{66}NO_8P$ | PE(29:1) | Glycerophospholipid metabolism |
| 65 | CSU/CDC-165 | $C_{45}H_{74}O_{15}$ | (3b,21b)-12-Oleanene-3,21,28-triol 28-[arabinosyl-(1->3)-arabinosyl-(1->3)-arabinoside] | Endogenous metabolite - derived from food |
| 66 | CSU/CDC-181 | — | — | — |
| 67 | CSU/CDC-183 | $C_{16}H_{28}O_4$ | Omphalotin A | Endogenous metabolite - derived from food |
| 68 | CSU/CDC-184 | $C_{21}H_{41}O_7P$ | Lyso-PA(18:1) | Glycerophospholipid metabolism |
| 69 | CSU/CDC-186 | — | — | — |
| 70 | CSU/CDC-188 | — | — | — |
| 71 | CSU/CDC-193 | — | — | — |
| 72 | CSU/CDC-194 | — | — | — |
| 73 | CSU/CDC-203 | — | — | — |
| 74 | CSU/CDC-206 | $C_{12}H_{24}N_4O_7$ | — | — |
| 75 | CSU/CDC-210 | $C_8H_9N_5O_2$ | 6-Amino-9H-purine-9-propanoic acid | Endogenous metabolite - derived from food |
| 76 | CSU/CDC-218 | — | — | — |
| 77 | CSU/CDC-222 | — | — | — |
| 78 | CSU/CDC-224 | — | — | — |
| 79 | CSU/CDC-237 | $C_{17}H_{35}NO_2$ | Pentadecanoyl ethanolamide | N-acyl ethanolamine metabolism |
| 80 | CSU/CDC-245 | — | — | — |
| 81 | CSU/CDC-250 | $C_{18}H_{35}NO_2$ | 3-Ketosphingosine | Sphingolipid metabolism |
| 82 | CSU/CDC-252 | — | — | — |

TABLE D

| MF # | Name | m/z (positive ion) | Mass | Retention Time (see examples) |
|---|---|---|---|---|
| 1 | CSU/CDC-001 | 166.0852 | 165.078 | 1.86 |
| 2 | CSU/CDC-012 | 270.3156 | 269.3076 | 18.02 |
| 3 | CSU/CDC-013 | 284.3314 | 283.3236 | 18.13 |
| 4 | CSU/CDC-014 | 300.6407 | 599.268 | 18.27 |
| 5 | CSU/CDC-019 | 300.2892 | 299.2821 | 19.66 |
| 6 | CSU/CDC-039 | 734.5079 | 1449.9753 | 17.81 |
| 7 | CSU/CDC-062 | 370.1837 | 369.1757 | 19.7 |
| 8 | CSU/CDC-066 | 811.1942 | 810.1869 | 12.07 |
| 9 | CSU/CDC-067 | 947.7976 | 946.7936 | 14.55 |
| 10 | CSU/CDC-072 | 410.2033 | 409.196 | 17.18 |
| 11 | CSU/CDC-075 | 1487.0005 | 1485.9987 | 18.17 |
| 12 | CSU/CDC-086 | 137.0463 | 136.0378 | 1.37 |
| 13 | CSU/CDC-107 | 811.7965 | 810.7882 | 12.07 |
| 14 | CSU/CDC-132 | 616.1776 | 615.1699 | 15.43 |
| 15 | CSU/CDC-152 | 713.4492 | 712.4391 | 19.35 |
| 16 | CSU/CDC-155 | 502.3376 | 484.3039 | 19.87 |
| 17 | CSU/CDC-158 | 415.3045 | 414.2978 | 20.19 |
| 18 | CSU/CDC-164 | 366.3729 | 365.3655 | 22.79 |
| 19 | CSU/CDC-166 | 333.1446 | 332.1373 | 12.89 |
| 20 | CSU/CDC-205 | 241.1069 | 240.0996 | 14.7 |
| 21 | CSU/CDC-211 | 464.1916 | 463.1849 | 13.05 |
| 22 | CSU/CDC-212 | 1249.2045 | 1248.1993 | 15.31 |
| 23 | CSU/CDC-213 | 1248.9178 | 1247.9141 | 15.3 |
| 24 | CSU/CDC-219 | 158.1539 | 157.1466 | 15.36 |
| 25 | CSU/CDC-227 | 529.3381 | 528.3296 | 16.89 |
| 26 | CSU/CDC-229 | 282.2776 | 264.2456 | 20.56 |
| 27 | CSU/CDC-235 | 190.1260 | 189.1187 | 14.12 |
| 28 | CSU/CDC-238 | 382.3675 | 381.3603 | 20.23 |
| 29 | CSU/CDC-244 | 477.2968 | 476.2898 | 22.79 |
| 30 | CSU/CDC-248 | 459.3968 | 458.3904 | 19.08 |
| 31 | CSU/CDC-253 | 342.2635 | 341.2565 | 15.62 |
| 32 | CSU/CDC-254 | 529.3827 | 1022.6938 | 17.86 |
| 33 | CSU/CDC-258 | 459.2502 | 458.2429 | 19.02 |

TABLE D-continued

| | | | | |
|---|---|---|---|---|
| 34 | CSU/CDC-002 | 239.0919 | 238.0844 | 11.66 |
| 35 | CSU/CDC-028 | 389.2174 | 388.2094 | 15.47 |
| 36 | CSU/CDC-182 | 285.2065 | 284.1991 | 16.02 |
| 37 | CSU/CDC-204 | 279.1693 | 278.1629 | 11.05 |
| 38 | CSU/CDC-247 | 714.6967 | 1427.3824 | 11.76 |
| 39 | CSU/CDC-003 | 886.4296 | 1770.8438 | 12.18 |
| 40 | CSU/CDC-004 | 181.0859 | 180.0788 | 14.7 |
| 41 | CSU/CDC-006 | 286.1444 | 285.1371 | 16.08 |
| 42 | CSU/CDC-008 | 463.2339 | 462.2248 | 16.36 |
| 43 | CSU/CDC-009 | 242.2844 | 241.2772 | 17.1 |
| 44 | CSU/CDC-017 | 590.4237 | 589.4194 | 19.24 |
| 45 | CSU/CDC-026 | 553.3904 | 552.3819 | 23.38 |
| 46 | CSU/CDC-030 | 399.2364 | 398.2313 | 16.23 |
| 47 | CSU/CDC-042 | 580.4144 | 1158.8173 | 18.26 |
| 48 | CSU/CDC-052 | 704.4985 | 1372.925 | 18.7 |
| 49 | CSU/CDC-061 | 623.4521 | 1210.8362 | 19.55 |
| 50 | CSU/CDC-070 | 389.2178 | 388.2099 | 15.52 |
| 51 | CSU/CDC-074 | 1111.6690 | 1110.6656 | 17.89 |
| 52 | CSU/CDC-083 | 482.4040 | 481.3976 | 19.99 |
| 53 | CSU/CDC-084 | 533.1929 | 532.1854 | 20.84 |
| 54 | CSU/CDC-087 | 466.3152 | 465.3085 | 14.73 |
| 55 | CSU/CDC-091 | 683.4728 | 1347.9062 | 17.56 |
| 56 | CSU/CDC-095 | 227.0897 | 204.1002 | 9.68 |
| 57 | CSU/CDC-098 | 183.1016 | 182.0943 | 10.89 |
| 58 | CSU/CDC-099 | 476.3055 | 475.2993 | 11.09 |
| 59 | CSU/CDC-112 | 215.1283 | 214.1209 | 12.32 |
| 60 | CSU/CDC-115 | 519.1881 | 518.1813 | 12.33 |
| 61 | CSU/CDC-128 | 1086.1800 | 2170.3435 | 15.38 |
| 62 | CSU/CDC-133 | 285.2061 | 284.1993 | 15.99 |
| 63 | CSU/CDC-134 | 357.1363 | 356.1284 | 15.98 |
| 64 | CSU/CDC-136 | 299.1853 | 298.1781 | 16.24 |
| 65 | CSU/CDC-137 | 334.2580 | 333.2514 | 16.36 |
| 66 | CSU/CDC-138 | 317.2317 | 316.2254 | 16.63 |
| 67 | CSU/CDC-141 | 331.2471 | 330.2403 | 17.26 |
| 68 | CSU/CDC-144 | 583.3480 | 582.3379 | 18.04 |
| 69 | CSU/CDC-157 | 648.4672 | 647.4609 | 19.98 |
| 70 | CSU/CDC-165 | 445.2880 | 854.5087 | 12.48 |
| 71 | CSU/CDC-181 | 1486.7386 | 2971.4668 | 14.97 |
| 72 | CSU/CDC-183 | 668.4686 | 1317.8969 | 18.04 |
| 73 | CSU/CDC-184 | 454.2924 | 436.2587 | 18.1 |
| 74 | CSU/CDC-186 | 607.9324 | 606.9246 | 19.01 |
| 75 | CSU/CDC-193 | 521.4202 | 503.3858 | 21.06 |
| 76 | CSU/CDC-193 | 176.0746 | 175.0667 | 2.31 |
| 77 | CSU/CDC-194 | 596.9082 | 1191.8033 | 19.1 |
| 78 | CSU/CDC-203 | 532.5606 | 531.5555 | 18.38 |
| 79 | CSU/CDC-206 | 337.1667 | 336.1599 | 20.67 |
| 80 | CSU/CDC-210 | 415.1634 | 207.0784 | 12.2 |
| 81 | CSU/CDC-218 | 364.3407 | 346.3068 | 20.72 |
| 82 | CSU/CDC-222 | 989.5004 | 1976.9858 | 12.03 |
| 83 | CSU/CDC-224 | 819.6064 | 1635.8239 | 12.06 |
| 84 | CSU/CDC-237 | 286.2737 | 285.2666 | 19.08 |
| 85 | CSU/CDC-245 | 614.4833 | 613.4772 | 19.78 |
| 86 | CSU/CDC-250 | 298.2740 | 297.2668 | 16.44 |
| 87 | CSU/CDC-252 | 1003.7020 | 1002.696 | 18.46 |
| 88 | CSU/CDC-005 | 223.0968 | 222.0895 | 14.69 |
| 89 | CSU/CDC-007 | 286.1437 | 285.1364 | 16.06 |
| 90 | CSU/CDC-010 | 1112.6727 | 1111.6663 | 17.86 |
| 91 | CSU/CDC-011 | 454.2923 | 453.2867 | 18.08 |
| 92 | CSU/CDC-015 | 522.3580 | 521.3483 | 18.5 |
| 93 | CSU/CDC-016 | 363.2192 | 362.2132 | 18.58 |
| 94 | CSU/CDC-018 | 388.3939 | 387.3868 | 19.53 |
| 95 | CSU/CDC-020 | 256.2632 | 255.2561 | 20.08 |
| 96 | CSU/CDC-021 | 394.3515 | 376.3171 | 20.09 |
| 97 | CSU/CDC-022 | 228.1955 | 227.1885 | 20.99 |
| 98 | CSU/CDC-023 | 284.2943 | 283.2872 | 21.15 |
| 99 | CSU/CDC-024 | 338.3430 | 337.3344 | 22.14 |
| 100 | CSU/CDC-025 | 689.5604 | 688.5504 | 22.52 |
| 101 | CSU/CDC-027 | 432.2803 | 431.2727 | 10.8 |
| 102 | CSU/CDC-029 | 385.2211 | 384.2147 | 15.84 |
| 103 | CSU/CDC-031 | 449.3261 | 879.6122 | 17.07 |
| 104 | CSU/CDC-032 | 467.3821 | 444.2717 | 17.1 |
| 105 | CSU/CDC-033 | 836.5936 | 835.5845 | 17.15 |
| 106 | CSU/CDC-034 | 792.5646 | 791.5581 | 17.17 |
| 107 | CSU/CDC-035 | 356.2802 | 355.2722 | 17.35 |
| 108 | CSU/CDC-036 | 806.5798 | 805.5746 | 17.71 |
| 109 | CSU/CDC-037 | 762.5582 | 761.5482 | 17.79 |
| 110 | CSU/CDC-038 | 718.5308 | 700.4946 | 17.88 |
| 111 | CSU/CDC-040 | 690.4825 | 1361.924 | 17.95 |
| 112 | CSU/CDC-041 | 426.1798 | 425.1725 | 18.03 |
| 113 | CSU/CDC-043 | 741.5154 | 1481.0142 | 18.24 |
| 114 | CSU/CDC-044 | 864.6245 | 863.6166 | 18.17 |
| 115 | CSU/CDC-045 | 558.4017 | 1080.7347 | 18.28 |
| 116 | CSU/CDC-046 | 719.5012 | 1402.9377 | 18.26 |
| 117 | CSU/CDC-047 | 536.3897 | 1053.7382 | 18.36 |
| 118 | CSU/CDC-048 | 538.8674 | 1058.696 | 18.4 |
| 119 | CSU/CDC-049 | 653.4619 | 1270.8593 | 18.43 |
| 120 | CSU/CDC-050 | 732.5450 | 714.5092 | 18.47 |
| 121 | CSU/CDC-051 | 748.5232 | 1478.0059 | 18.58 |
| 122 | CSU/CDC-053 | 682.4841 | 1328.9008 | 18.77 |
| 123 | CSU/CDC-054 | 360.3615 | 359.3555 | 18.89 |
| 124 | CSU/CDC-055 | 441.2412 | 440.2325 | 19.09 |
| 125 | CSU/CDC-056 | 638.4554 | 1240.847 | 18.92 |
| 126 | CSU/CDC-057 | 755.5311 | 1474.9941 | 18.94 |
| 127 | CSU/CDC-058 | 711.5023 | 1386.9417 | 19.09 |
| 128 | CSU/CDC-059 | 784.5530 | 1567.0908 | 19.27 |
| 129 | CSU/CDC-060 | 645.4660 | 1271.8896 | 19.36 |
| 130 | CSU/CDC-063 | 300.2886 | 282.2569 | 19.84 |
| 131 | CSU/CDC-064 | 309.0981 | 308.0913 | 2.06 |
| 132 | CSU/CDC-065 | 561.2965 | 1120.5778 | 11.7 |
| 133 | CSU/CDC-068 | 1106.2625 | 2209.5193 | 14.53 |
| 134 | CSU/CDC-069 | 371.2070 | 370.1997 | 15.52 |
| 135 | CSU/CDC-071 | 443.2649 | 442.256 | 15.52 |
| 136 | CSU/CDC-073 | 850.6093 | 849.6009 | 17.63 |
| 137 | CSU/CDC-076 | 697.4896 | 1358.909 | 18.32 |
| 138 | CSU/CDC-077 | 439.8234 | 877.6325 | 18.71 |
| 139 | CSU/CDC-078 | 567.8897 | 566.6818 | 18.73 |
| 140 | CSU/CDC-079 | 435.2506 | 434.243 | 19 |
| 141 | CSU/CDC-080 | 834.6136 | 833.6057 | 18.83 |
| 142 | CSU/CDC-081 | 534.8834 | 533.8771 | 18.82 |
| 143 | CSU/CDC-082 | 468.8441 | 467.8373 | 19.13 |
| 144 | CSU/CDC-085 | 312.3259 | 311.319 | 22.05 |
| 145 | CSU/CDC-088 | 228.1955 | 227.1884 | 15.22 |
| 146 | CSU/CDC-089 | 385.2211 | 384.2143 | 15.83 |
| 147 | CSU/CDC-090 | 403.2338 | 402.2253 | 15.84 |
| 148 | CSU/CDC-092 | 675.4753 | 1348.9377 | 18.37 |
| 149 | CSU/CDC-093 | 682.4841 | 1345.9257 | 18.76 |
| 150 | CSU/CDC-094 | 762.5401 | 1506.0367 | 19.36 |
| 151 | CSU/CDC-177 | 189.1122 | 188.1049 | 12.27 |
| 152 | CSU/CDC-097 | 169.0860 | 168.0786 | 9.94 |
| 153 | CSU/CDC-100 | 276.1263 | 275.1196 | 11.16 |
| 154 | CSU/CDC-101 | 314.0672 | 313.06 | 11.56 |
| 155 | CSU/CDC-102 | 201.1122 | 200.1047 | 11.56 |
| 156 | CSU/CDC-103 | 115.0391 | 114.0318 | 11.57 |
| 157 | CSU/CDC-104 | 491.1569 | 490.1504 | 11.56 |
| 158 | CSU/CDC-105 | 241.1054 | 218.1157 | 11.57 |
| 159 | CSU/CDC-106 | 105.0914 | 104.0841 | 11.57 |
| 160 | CSU/CDC-108 | 311.1472 | 328.1391 | 12.22 |
| 161 | CSU/CDC-109 | 271.1543 | 270.1464 | 12.24 |
| 162 | CSU/CDC-110 | 169.0860 | 168.0787 | 12.24 |
| 163 | CSU/CDC-111 | 187.0967 | 186.0889 | 12.24 |
| 164 | CSU/CDC-113 | 475.1635 | 474.1547 | 12.25 |
| 165 | CSU/CDC-114 | 129.0547 | 128.0474 | 12.33 |
| 166 | CSU/CDC-116 | 125.0599 | 124.0527 | 13.12 |
| 167 | CSU/CDC-117 | 247.1550 | 246.1469 | 13.13 |
| 168 | CSU/CDC-118 | 517.2614 | 516.2544 | 13.13 |
| 169 | CSU/CDC-119 | 301.0739 | 300.0658 | 13.14 |
| 170 | CSU/CDC-120 | 327.1773 | 304.1885 | 14.17 |
| 171 | CSU/CDC-121 | 387.2023 | 386.1935 | 14.51 |
| 172 | CSU/CDC-122 | 875.8451 | 1749.684 | 14.55 |
| 173 | CSU/CDC-123 | 737.5118 | 736.5056 | 14.52 |
| 174 | CSU/CDC-124 | 1274.3497 | 1273.3481 | 14.96 |
| 175 | CSU/CDC-125 | 1274.2092 | 1273.2 | 14.96 |
| 176 | CSU/CDC-126 | 1486.5728 | 2971.1328 | 14.95 |
| 177 | CSU/CDC-127 | 965.3818 | 964.3727 | 15.37 |
| 178 | CSU/CDC-129 | 1086.0562 | 2170.0908 | 15.38 |
| 179 | CSU/CDC-130 | 1086.4344 | 2169.8474 | 15.39 |
| 180 | CSU/CDC-131 | 1240.7800 | 1239.7712 | 15.38 |
| 181 | CSU/CDC-135 | 317.1956 | 316.1885 | 16.24 |
| 182 | CSU/CDC-139 | 299.2219 | 298.2148 | 16.64 |
| 183 | CSU/CDC-140 | 748.5408 | 747.5317 | 17.23 |
| 184 | CSU/CDC-142 | 712.4935 | 1422.9749 | 17.82 |
| 185 | CSU/CDC-143 | 674.5013 | 673.4957 | 17.99 |
| 186 | CSU/CDC-145 | 677.9537 | 676.9478 | 18.36 |
| 187 | CSU/CDC-146 | 531.3522 | 530.3457 | 18.4 |
| 188 | CSU/CDC-147 | 585.2733 | 584.2649 | 18.39 |
| 189 | CSU/CDC-148 | 513.3431 | 512.3352 | 18.4 |
| 190 | CSU/CDC-149 | 611.9156 | 610.9073 | 18.59 |
| 191 | CSU/CDC-150 | 549.0538 | 531.0181 | 18.38 |
| 192 | CSU/CDC-151 | 755.5311 | 1509.0457 | 18.93 |
| 193 | CSU/CDC-153 | 599.4146 | 598.4079 | 19.59 |

TABLE D-continued

| | | | | |
|---|---|---|---|---|
| 194 | CSU/CDC-154 | 762.5029 | 761.4919 | 19.66 |
| 195 | CSU/CDC-156 | 741.4805 | 740.4698 | 19.96 |
| 196 | CSU/CDC-159 | 516.3532 | 498.3199 | 20.27 |
| 197 | CSU/CDC-160 | 769.5099 | 768.5018 | 20.53 |
| 198 | CSU/CDC-161 | 862.5881 | 861.5818 | 20.86 |
| 199 | CSU/CDC-162 | 837.5358 | 836.5274 | 21.11 |
| 200 | CSU/CDC-163 | 558.3995 | 540.367 | 21.44 |
| 201 | CSU/CDC-167 | 1105.9305 | 2209.8462 | 14.53 |
| 202 | CSU/CDC-168 | 329.1049 | 328.0976 | 14.61 |
| 203 | CSU/CDC-169 | 1241.2053 | 1240.2 | 15.38 |
| 204 | CSU/CDC-170 | 1088.6731 | 1087.6676 | 17.85 |
| 205 | CSU/CDC-171 | 667.4391 | 666.4323 | 20.35 |
| 206 | CSU/CDC-172 | 133.0497 | 132.0423 | 11.57 |
| 207 | CSU/CDC-173 | 259.1540 | 258.1469 | 11.75 |
| 208 | CSU/CDC-174 | 311.1472 | 288.1574 | 12.23 |
| 209 | CSU/CDC-175 | 147.0652 | 146.0579 | 12.33 |
| 210 | CSU/CDC-176 | 169.0860 | 168.0788 | 12.29 |
| 211 | CSU/CDC-096 | 187.0965 | 186.0894 | 9.93 |
| 212 | CSU/CDC-178 | 139.1116 | 138.1044 | 12.95 |
| 213 | CSU/CDC-179 | 515.2811 | 514.2745 | 13.14 |
| 214 | CSU/CDC-180 | 283.1522 | 282.1444 | 13.93 |
| 215 | CSU/CDC-185 | 706.9750 | 705.9684 | 18.7 |
| 216 | CSU/CDC-187 | 834.5575 | 833.5502 | 20.32 |
| 217 | CSU/CDC-189 | 683.4727 | 1364.9294 | 17.54 |
| 218 | CSU/CDC-190 | 728.9890 | 1455.9633 | 18.63 |
| 219 | CSU/CDC-191 | 726.5104 | 1451.0035 | 18.64 |
| 220 | CSU/CDC-192 | 633.9280 | 632.9206 | 18.47 |
| 221 | CSU/CDC-195 | 209.0784 | 208.0713 | 9.92 |
| 222 | CSU/CDC-196 | 792.5483 | 1566.055 | 18.46 |
| 223 | CSU/CDC-197 | 618.9221 | 1218.8083 | 19.02 |
| 224 | CSU/CDC-198 | 549.0543 | 531.0189 | 18.37 |
| 225 | CSU/CDC-199 | 553.7262 | 552.7188 | 18.74 |
| 226 | CSU/CDC-200 | 756.0320 | 755.0266 | 18.95 |
| 227 | CSU/CDC-201 | 639.6307 | 638.6205 | 19.58 |
| 228 | CSU/CDC-202 | 753.4414 | 730.4513 | 19.37 |
| 229 | CSU/CDC-207 | 328.3204 | 327.3148 | 20.72 |
| 230 | CSU/CDC-208 | 514.3718 | 1009.7122 | 18.42 |
| 231 | CSU/CDC-209 | 630.4594 | 1241.8737 | 19.95 |
| 232 | CSU/CDC-214 | 244.2270 | 243.22 | 17.17 |
| 233 | CSU/CDC-215 | 463.3426 | 924.6699 | 18.08 |
| 234 | CSU/CDC-216 | 468.3892 | 450.3553 | 19.17 |
| 235 | CSU/CDC-217 | 438.3787 | 420.3453 | 19.93 |
| 236 | CSU/CDC-220 | 792.0006 | 790.995 | 12.04 |
| 237 | CSU/CDC-221 | 792.2025 | 791.1947 | 12.04 |
| 238 | CSU/CDC-223 | 791.6016 | 790.594 | 12.04 |
| 239 | CSU/CDC-225 | 1115.5593 | 2228.1068 | 14.95 |
| 240 | CSU/CDC-226 | 1486.9176 | 2970.7976 | 14.96 |
| 241 | CSU/CDC-228 | 430.3161 | 412.2845 | 20.23 |
| 242 | CSU/CDC-230 | 297.2793 | 296.2734 | 20.66 |
| 243 | CSU/CDC-231 | 714.3655 | 1426.718 | 11.73 |
| 244 | CSU/CDC-232 | 714.5306 | 1427.0479 | 11.76 |
| 245 | CSU/CDC-233 | 989.7499 | 1977.4865 | 12.03 |
| 246 | CSU/CDC-234 | 221.0744 | 220.0672 | 13.7 |
| 247 | CSU/CDC-236 | 313.2734 | 312.2663 | 18.91 |
| 248 | CSU/CDC-239 | 337.2712 | 314.282 | 20.66 |
| 249 | CSU/CDC-240 | 441.3687 | 440.3614 | 21.26 |
| 250 | CSU/CDC-241 | 425.3735 | 424.3666 | 21.5 |
| 251 | CSU/CDC-242 | 356.3517 | 355.3448 | 21.67 |
| 252 | CSU/CDC-243 | 393.2970 | 370.3082 | 22.46 |
| 253 | CSU/CDC-246 | 167.9935 | 166.9861 | 13.2 |
| 254 | CSU/CDC-249 | 677.6170 | 676.6095 | 20.71 |
| 255 | CSU/CDC-251 | 460.2695 | 459.2627 | 16.87 |
| 256 | CSU/CDC-255 | 630.4765 | 612.4417 | 18.11 |
| 257 | CSU/CDC-256 | 514.3734 | 1026.7281 | 18.41 |
| 258 | CSU/CDC-257 | 667.4754 | 1315.916 | 19.28 |
| 259 | CSU/CDC-259 | 516.8549 | 1031.6945 | 18.43 |
| 260 | CSU/CDC-260 | 740.5242 | 1479.0334 | 19.4 |
| 261 | CSU/CDC-261 | 1104.0614 | 2206.1096 | 15.2 |

| MF # | Name | Compound Predicted Formula | Predicted Chemical Structure (based on accurate mass) | Metabolite Class or Pathway |
|---|---|---|---|---|
| 1 | CSU/CDC-001 | $C_9H_{11}NO_2$ | Phenylalanine | Phenylalanine metabolism |
| 2 | CSU/CDC-012 | $C_{18}H_{39}N$ | — | — |
| 3 | CSU/CDC-013 | $C_{19}H_{41}N$ | — | — |
| 4 | CSU/CDC-014 | $C_{33}H_{37}N_5O_6$ | Asp Phe Arg Tyr (SEQ ID NO: 1) | Peptide |
| 5 | CSU/CDC-019 | $C_{18}H_{37}NO_2$ | Palmitoyl ethanolamide | N-acyl ethanolamine metabolism |
| 6 | CSU/CDC-039 | — | — | — |
| 7 | CSU/CDC-062 | $C_{19}H_{23}N_5O_3$ | — | — |
| 8 | CSU/CDC-066 | $C_{42}H_{30}N_6O_{12}$ | — | — |
| 9 | CSU/CDC-067 | $C_{62}H_{106}O_6$ | TAG(59:7) | Triacylglycerol metabolism |
| 10 | CSU/CDC-072 | — | — | — |
| 11 | CSU/CDC-075 | — | — | — |
| 12 | CSU/CDC-086 | $C_4H_8O_5$ | Threonate | Sugar metabolite |
| 13 | CSU/CDC-107 | — | — | — |
| 14 | CSU/CDC-132 | — | — | — |
| 15 | CSU/CDC-152 | $C_{38}H_{65}O_{10}P$ | PG(32:5) | Glycerophospholipid metabolism |
| 16 | CSU/CDC-155 | $C_{27}H_{40}N_4O_4$ | Gln Leu Pro Lys (SEQ ID NO: 2) | Peptide |
| 17 | CSU/CDC-158 | — | — | — |
| 18 | CSU/CDC-164 | — | — | — |
| 19 | CSU/CDC-166 | $C_{12}H_{20}N_4O_7$ | Glu Gln Gly | Peptide |
| 20 | CSU/CDC-205 | $C_{12}H_{16}O_5$ | 3-Carboxy-4-methyl-5-propyl-2-furanpropanoic acid (CMPF) | Fatty acid metabolism |
| 21 | CSU/CDC-211 | $C_{16}H_{29}N_7O_7S$ | Arg Asp Cys Ala (SEQ ID NO: 3) | Peptide |
| 22 | CSU/CDC-212 | — | — | — |
| 23 | CSU/CDC-213 | — | — | — |
| 24 | CSU/CDC-219 | — | — | — |
| 25 | CSU/CDC-227 | $C_{24}H_{44}N_6O_7$ | Gln Val Leu Leu Gly (SEQ ID NO: 4) | Peptide |
| 26 | CSU/CDC-229 | $C_{18}H_{32}O$ | — | — |
| 27 | CSU/CDC-235 | $C_9H_{19}NOS$ | 8-Methylthiooctanal doxime | 2-oxocarboxylic acid metabolism |
| 28 | CSU/CDC-238 | $C_{24}H_{47}NO_2$ | Erucicoyl ethanolamide | N-acyl ethanolamine metabolism |
| 29 | CSU/CDC-244 | $C_{31}H_{40}O_4$ | Lys Lys Thr Thr (SEQ ID NO: 5) | Peptide |
| 30 | CSU/CDC-248 | — | — | — |
| 31 | CSU/CDC-253 | $C_{19}H_{35}NO_4$ | — | — |
| 32 | CSU/CDC-254 | — | — | — |
| 33 | CSU/CDC-258 | $C_{23}H_{39}O_7P$ | Lyso PA(20:4) | Glycerohosphospholipid metabolism |
| 34 | CSU/CDC-002 | $C_{12}H_{14}O_5$ | Trans-2,3,4-trimethoxy-cinnamate | Phenylpropanoid and polyketide metabolism |
| 35 | CSU/CDC-028 | $C_{19}H_{32}O_8$ | Methyl 10,12,13,15-bisepidioxy-16-hydroperoxy-8E-octadecenoate | Fatty acid metabolism |
| 36 | CSU/CDC-182 | $C_{16}H_{28}O_4$ | — | — |
| 37 | CSU/CDC-204 | $C_{15}H_{22}N_2O_3$ | — | — |
| 38 | CSU/CDC-247 | — | — | — |
| 39 | CSU/CDC-003 | — | — | — |
| 40 | CSU/CDC-004 | $C_{10}H_{12}O_3$ | 5'-(3'-Methoxy-4'-hydroxyphenyl)-gamma-valerolactone | Endogenous metabolite associated with microbiome |

TABLE D-continued

| # | ID | Formula | Name | Category |
|---|---|---|---|---|
| 41 | CSU/CDC-006 | $C_{17}H_{19}NO_3$ | Piperine | Alkaloid metabolism |
| 42 | CSU/CDC-008 | $C_{25}H_{34}O_8$ | Ala Lys Met Asn (SEQ ID NO: 6) | Peptide |
| 43 | CSU/CDC-009 | $C_{16}H_{35}N$ | — | — |
| 44 | CSU/CDC-017 | — | — | — |
| 45 | CSU/CDC-026 | $C_{35}H_{52}O_5$ | Furohyperforin | Endogenous metabolite - derived from food |
| 46 | CSU/CDC-030 | — | — | — |
| 47 | CSU/CDC-042 | — | — | — |
| 48 | CSU/CDC-052 | — | — | — |
| 49 | CSU/CDC-061 | — | — | — |
| 50 | CSU/CDC-070 | $C_{19}H_{32}O_8$ | — | — |
| 51 | CSU/CDC-074 | — | — | — |
| 52 | CSU/CDC-083 | — | — | — |
| 53 | CSU/CDC-084 | $C_{23}H_{28}N_6O_9$ | Asp His Phe Asp (SEQ ID NO: 7) | Peptide |
| 54 | CSU/CDC-087 | $C_{26}H_{43}NO_6$ | Glycocholic acid | Bile acid metabolism |
| 55 | CSU/CDC-091 | — | — | — |
| 56 | CSU/CDC-095 | $C_9H_{16}O_5$ | — | — |
| 57 | CSU/CDC-098 | $C_{10}H_{14}O_3$ | — | — |
| 58 | CSU/CDC-099 | $C_{26}H_{41}N_3O_5$ | — | — |
| 59 | CSU/CDC-112 | $C_{11}H_{18}O_4$ | alpha-Carboxy-delta-decalactone | Endogenous metabolite - derived from food |
| 60 | CSU/CDC-115 | $C_{20}H_{30}N_4O_{12}$ | Poly-g-D-glutamate | Poly D-glutamate metabolism |
| 61 | CSU/CDC-128 | — | — | — |
| 62 | CSU/CDC-133 | $C_{16}H_{28}O_4$ | — | — |
| 63 | CSU/CDC-134 | $C_{20}H_{20}O_6$ | Xanthoxylol | Endogenous metabolite - derived from food |
| 64 | CSU/CDC-136 | $C_{16}H_{26}O_5$ | Tetranor-PGE1 | Prostaglandin metabolism |
| 65 | CSU/CDC-137 | — | — | — |
| 66 | CSU/CDC-138 | — | — | — |
| 67 | CSU/CDC-141 | $C_{18}H_{34}O_5$ | 11,12,13-trihydroxy-9-octadecenoic acid | Fatty acid metabolism |
| 68 | CSU/CDC-144 | $C_{27}H_{46}N_6O_8$ | Leu Lys Glu Pro Pro (SEQ ID NO: 8) | Peptide |
| 69 | CSU/CDC-157 | $C_{34}H_{66}NO_8P$ | PE(29:1) | Glycerophospholipid metabolism |
| 70 | CSU/CDC-165 | $C_{45}H_{74}O_{15}$ | (3b,21b)-12-Oleanene-3,21,28-triol 28-[arabinosyl-(1->3)-arabinosyl-(1->3)-arabinoside] | Endogenous metabolite - derived from food |
| 71 | CSU/CDC-181 | — | — | — |
| 72 | CSU/CDC-183 | $C_{16}H_{28}O_4$ | Omphalotin A | Endogenous metabolite - derived from food |
| 73 | CSU/CDC-184 | $C21H4107P$ | Lyso-PA(18:1) | Glycerophospholipid metabolism |
| 74 | CSU/CDC-186 | — | — | — |
| 75 | CSU/CDC-188 | — | — | — |
| 76 | CSU/CDC-193 | — | — | — |
| 77 | CSU/CDC-194 | — | — | — |
| 78 | CSU/CDC-203 | — | — | — |
| 79 | CSU/CDC-206 | $C_{12}H_{24}N_4O_7$ | — | — |
| 80 | CSU/CDC-210 | $C_8H_9N_5O_2$ | 6-Amino-9H-purine-9-propanoic acid | Endogenous metabolite - derived from food |
| 81 | CSU/CDC-218 | — | — | — |
| 82 | CSU/CDC-222 | — | — | — |
| 83 | CSU/CDC-224 | — | — | — |
| 84 | CSU/CDC-237 | $C_{17}H_{35}NO_2$ | Pentadecanoyl ethanolamide | N-acyl ethanolamine metabolism |
| 85 | CSU/CDC-245 | — | — | — |
| 86 | CSU/CDC-250 | $C_{18}H_{35}NO_2$ | 3-Keto-spingosine | Sphingolipid metabolism |
| 87 | CSU/CDC-252 | — | — | — |
| 88 | CSU/CDC-005 | $C_{12}H_{14}O_4$ | — | — |
| 89 | CSU/CDC-007 | $C_{17}H_{19}NO_3$ | — | — |
| 90 | CSU/CDC-010 | — | — | — |
| 91 | CSU/CDC-011 | $C_{21}H_{44}NO_7P$ | Glycero-phospho-N-Palmitoyl Ethanolamine | N-acyl ethanolamine metabolism |
| 92 | CSU/CDC-015 | $C_{26}H_{52}NO_7P$ | PC(18:1) | Glycero-phospholipid metabolism |
| 93 | CSU/CDC-016 | $C_{21}H_{30}O_5$ | 4,5α-dihydro-cortisone | Sterol metabolism |
| 94 | CSU/CDC-018 | — | — | — |
| 95 | CSU/CDC-020 | $C_{16}H_{33}NO$ | Palmitic amide | Primary Fatty Acid Amide Metabolism |
| 96 | CSU/CDC-021 | — | — | — |
| 97 | CSU/CDC-022 | — | — | — |
| 98 | CSU/CDC-023 | $C_{18}H_{37}NO$ | Stearamide | Primary Fatty Acid Amide Metabolism |
| 99 | CSU/CDC-024 | $C_{22}H_{43}NO$ | 13Z-Docosenamide (Erucamide) | Primary Fatty Acid Amide Metabolism |
| 100 | CSU/CDC-025 | $C_{38}H_{77}N_2O_6P$ | SM(d18:1-15:0)/SM(d18:1/14:1-OH) | Sphingolipid metabolism |
| 101 | CSU/CDC-027 | $C_{25}H_{37}NO_5$ | Ala Ile Lys Thr (SEQ ID NO: 9) | Peptide |
| 102 | CSU/CDC-029 | $C_{16}H_{28}N_6O_5$ | Lys His Thr | Peptides |
| 103 | CSU/CDC-031 | $C_{46}H_{89}NO_{12}S$ | C22-OH Sulfatide | Sphingolipid metabolism |
| 104 | CSU/CDC-032 | $C_{24}H_{40}O_8$ | 2-glyceryl-6-keto-PGF1α | Prostaglandin metabolism |
| 105 | CSU/CDC-033 | $C_{44}H_{85}NO_{11}S$ | C20 Sulfatide | Sphingolipid metabolism |
| 106 | CSU/CDC-034 | $C_{42}H_{82}NO_{10}P$ | PS(36:0) | Glycero-phospholipid metabolism |
| 107 | CSU/CDC-035 | — | — | — |
| 108 | CSU/CDC-036 | $C_{43}H_{84}NO_{10}P$ | PS(37:0) | Glycero-phospholipid metabolism |
| 109 | CSU/CDC-037 | $C_{41}H_{80}NO_9P$ | PS-O(35:1) | Glycero-phospholipid metabolism |
| 110 | CSU/CDC-038 | $C_{39}H_{73}O_8P$ | PA(36:2) | Glycero-phospholipid metabolism |
| 111 | CSU/CDC-040 | — | — | — |
| 112 | CSU/CDC-041 | — | — | — |
| 113 | CSU/CDC-043 | $C_{83}H_{150}O_{17}P_2$ | CL(74:6) | Glycero-phospholipid metabolism |
| 114 | CSU/CDC-044 | $C_{46}H_{89}NO_{11}5$ | C22 Sulfatide | Sphingolipid metabolism |
| 115 | CSU/CDC-045 | — | — | — |
| 116 | CSU/CDC-046 | — | — | — |
| 117 | CSU/CDC-047 | — | — | — |
| 118 | CSU/CDC-048 | — | — | — |

TABLE D-continued

| | | | | |
|---|---|---|---|---|
| 119 | CSU/CDC-049 | — | — | — |
| 120 | CSU/CDC-050 | $C_{40}H_{75}O_8P$ | PA(37:2) | Glycerophospholipid metabolism |
| 121 | CSU/CDC-051 | — | — | — |
| 122 | CSU/CDC-053 | — | — | — |
| 123 | CSU/CDC-054 | — | — | — |
| 124 | CSU/CDC-055 | $C_{20}H_{32}N_4O_7$ | Pro Asp Pro Leu (SEQ ID NO: 10) | Peptide |
| 125 | CSU/CDC-056 | — | — | — |
| 126 | CSU/CDC-057 | C831-1144017P2 | CL(74:9) | Glycerophospholipid metabolism |
| 127 | CSU/CDC-058 | — | — | — |
| 128 | CSU/CDC-059 | — | — | — |
| 129 | CSU/CDC-060 | — | — | — |
| 130 | CSU/CDC-063 | $C_{18}H_{34}O_2$ | 13Z-octadecenoic acid | Fatty acid metabolism |
| 131 | CSU/CDC-064 | $C_{15}H_{16}O_7$ | — | — |
| 132 | CSU/CDC-065 | $C_{54}H_{88}O_{24}$ | Camellioside D | Endogenous metabolite - derived from food |
| 133 | CSU/CDC-068 | — | — | — |
| 134 | CSU/CDC-069 | $C_{15}H_{26}N_6O_7$ | His Ser Lys | Peptide |
| 135 | CSU/CDC-071 | $C_{19}H_{34}N_6O_6$ | Pro Gln Ala Lys (SEQ ID NO: 11) | Peptide |
| 136 | CSU/CDC-073 | $C_{48}H_{84}NO_9P$ | PS-O(42:6) | Glycerophospholipid metabolism |
| 137 | CSU/CDC-076 | — | — | — |
| 138 | CSU/CDC-077 | — | — | — |
| 139 | CSU/CDC-078 | — | — | — |
| 140 | CSU/CDC-079 | $C_{21}H_{39}O_7P$ | Lyso-PA(18:2) | Glycerophospholipid metabolism |
| 141 | CSU/CDC-080 | $C_{45}H_{88}NO_{10}P$ | PS(39:0) | Glycerophospholipid metabolism |
| 142 | CSU/CDC-081 | — | — | — |
| 143 | CSU/CDC-082 | — | — | — |
| 144 | CSU/CDC-085 | — | — | — |
| 145 | CSU/CDC-088 | — | — | — |
| 146 | CSU/CDC-089 | $C_{20}H_{32}O_7$ | Lys His Thr | Peptide |
| 147 | CSU/CDC-090 | C16H30N6O6 | Lys Gln Gln | Peptide |
| 148 | CSU/CDC-092 | — | — | — |
| 149 | CSU/CDC-093 | — | — | — |
| 150 | CSU/CDC-094 | — | — | — |
| 151 | CSU/CDC-177 | $C_9H_{14}O_4$ | Nonanedioic Acid | Fatty acid metabolism |
| 152 | CSU/CDC-097 | $C_9H_{12}O_3$ | 2,6-Dimethoxy-4-methylphenol | Endogenous metabolite - derived from food |
| 153 | CSU/CDC-100 | $C_{15}H_{17}NO_4$ | — | — |
| 154 | CSU/CDC-101 | $C_{10}H_{12}N_5O_5P$ | — | — |
| 155 | CSU/CDC-102 | $C_{10}H_{16}O_4$ | Decenedioic acid | Fatty acid metabolism |
| 156 | CSU/CDC-103 | $C_5H_6O_3$ | 2-Hydroxy-2,4-pentadienoate | Phenylalanine metabolism |
| 157 | CSU/CDC-104 | $C_{24}H_{26}O_{11}$ | — | — |
| 158 | CSU/CDC-105 | $C_{10}H_{18}O_5$ | 3-Hydroxy-sebacic acid | Fatty acid metabolism |
| 159 | CSU/CDC-106 | — | — | — |
| 160 | CSU/CDC-108 | $C_{18}H_{20}N_2O_4$ | Phe Tyr | Peptide |
| 161 | CSU/CDC-109 | — | — | — |
| 162 | CSU/CDC-110 | $C_9H_{12}O_3$ | 2,6-Dimethoxy-4-methylphenol | Endogenous metabolite - derived from food |
| 163 | CSU/CDC-111 | $C_9H_{14}O_4$ | — | — |
| 164 | CSU/CDC-113 | $C_{25}H_{22}N_4O_6$ | His Cys Asp Thr (SEQ ID NO: 12) | Peptide |
| 165 | CSU/CDC-114 | $C_6H_8O_3$ | (4E)-2-Oxo-hexenoic acid | Fatty acid metabolism |
| 166 | CSU/CDC-116 | $C_7H_8O_2$ | 4-Methyl-catechol | Catechol metabolism |
| 167 | CSU/CDC-117 | $C_{12}H_{22}O_5$ | 3-Hydroxy-dodecanedioic acid | Fatty acid metabolism |
| 168 | CSU/CDC-118 | $C_{21}H_{36}N_6O_9$ | Gln Glu Gln Ile (SEQ ID NO: 13) | Peptide |
| 169 | CSU/CDC-119 | $C_{16}H_{12}O_6$ | Chrysoeriol | Endogenous metabolite - derived from food |
| 170 | CSU/CDC-120 | $C_{16}H_{24}N_4O_2$ | — | — |
| 171 | CSU/CDC-121 | $C_{19}H_{30}O_8$ | Citroside A | Endogenous metabolite - derived from food |
| 172 | CSU/CDC-122 | — | — | — |
| 173 | CSU/CDC-123 | $C_{42}H_{73}O_8P$ | PA(39:5) | Glycerophospholipid metabolism |
| 174 | CSU/CDC-124 | — | — | — |
| 175 | CSU/CDC-125 | — | — | — |
| 176 | CSU/CDC-126 | — | — | — |
| 177 | CSU/CDC-127 | — | — | — |
| 178 | CSU/CDC-129 | $C_{97}H_{167}N_5O_{48}$ | NeuAcalpha2-3Galbeta1-3GalNAcbeta1-4(9-OAc-NeuAcalpha2-8NeuAcalpha2-3)Galbeta1-4Glcbeta-Cer(d18:1/18:0) | Sphingolipid metabolism |
| 179 | CSU/CDC-130 | — | — | — |
| 180 | CSU/CDC-131 | — | — | — |
| 181 | CSU/CDC-135 | $C_{12}H_{24}N_6O_4$ | Arg Ala Ala | Peptide |
| 182 | CSU/CDC-139 | $C_{17}H_{30}O_4$ | 8E-Heptadecenedioic acid | Fatty acid metabolism |
| 183 | CSU/CDC-140 | $C_{40}H_{78}NO_9P$ | PS-O(34:1) | Glycerophospholipid metabolism |
| 184 | CSU/CDC-142 | $C_{79}H_{140}O_{17}P_2$ | CL(70:7) | Glycerophospholipid metabolism |
| 185 | CSU/CDC-143 | $C_{37}H_{72}NO_7P$ | PE-P(32:1) | Glycerophospholipid metabolism |
| 186 | CSU/CDC-145 | — | — | — |
| 187 | CSU/CDC-146 | $C_{35}H_{46}O_4$ | — | — |
| 188 | CSU/CDC-147 | $C_{33}H_{36}N_4O_6$ | 15,16-Dihydrobiliverdin | Bilirubin breakdown products - Porphyrin metabolism |
| 189 | CSU/CDC-148 | — | — | — |
| 190 | CSU/CDC-149 | — | — | — |
| 191 | CSU/CDC-150 | — | — | — |
| 192 | CSU/CDC-151 | — | — | — |
| 193 | CSU/CDC-153 | $C_{40}H_{54}O_4$ | Isomytiloxanthin | Isoflavinoid |
| 194 | CSU/CDC-154 | $C_{43}H_{72}NO_8P$ | PE(38:7) | Glycerophospholipid metabolism |
| 195 | CSU/CDC-156 | $C_{40}H_{69}O_{10}P$ | PG(34:5) | Glycerophospholipid metabolism |
| 196 | CSU/CDC-159 | $C_{23}H_{42}N_6O_6$ | Ala Leu Ala Pro Lys (SEQ ID NO: 14) | Peptide |
| 197 | CSU/CDC-160 | $C_{42}H_{73}O_{10}P$ | PG(36:5) | Glycerophospholipid metabolism |

TABLE D-continued

| # | ID | Formula | Name | Pathway |
|---|---|---|---|---|
| 198 | CSU/CDC-161 | — | — | — |
| 199 | CSU/CDC-162 | $C_{53}H_{72}O_8$ | Amitenone | Endogenous metabolite - derived from food |
| 200 | CSU/CDC-163 | $C_{26}H_{48}N_6O_6$ | Leu Ala Pro Lys Ile (SEQ ID NO: 15) | Peptide |
| 201 | CSU/CDC-167 | — | — | — |
| 202 | CSU/CDC-168 | $C_{18}H_{16}O_6$ | 2-Oxo-3-phenylpropanoic acid | Phenylalanine metabolism |
| 203 | CSU/CDC-169 | — | — | — |
| 204 | CSU/CDC-170 | — | — | — |
| 205 | CSU/CDC-171 | $C_{37}H_{63}O_8P$ | PA(24:5) | Glycerophospholipid metabolism |
| 206 | CSU/CDC-172 | $C_5H_8O_4$ | 2-Acetolactic acid | Pantothenate and CoA Biosynthesis Pathway |
| 207 | CSU/CDC-173 | — | — | — |
| 208 | CSU/CDC-174 | $C_{10}H_{20}N_6O_4$ | Asn Arg | Dipeptide |
| 209 | CSU/CDC-175 | $C_6H_{10}O_4$ | α-Ketopantoic acid | Pantothenate and CoA Biosynthesis Pathway |
| 210 | CSU/CDC-176 | $C_9H_{12}O_3$ | Epoxyoxophorone | Endogenous metabolite - derived from food |
| 211 | CSU/CDC-096 | $C_9H_{14}O_4$ | 5-Butyltetrahydro-2-oxo-3-furancarboxylic acid | Endogenous metabolite - derived from food |
| 212 | CSU/CDC-178 | $C_9{14}O_4$ | 3,6-Nonadienal | Endogenous metabolite - derived from food |
| 213 | CSU/CDC-179 | $C_{26}H_{42}O_{10}$ | Cofaryloside | Endogenous metabolite - derived from food |
| 214 | CSU/CDC-180 | $C_{25}H_{42}N_2O_7S$ | Epidihydrophaseic acid | Endogenous metabolite - derived from food |
| 215 | CSU/CDC-185 | — | — | — |
| 216 | CSU/CDC-187 | — | — | — |
| 217 | CSU/CDC-189 | — | — | — |
| 218 | CSU/CDC-190 | — | — | — |
| 219 | CSU/CDC-191 | $C_{81}H_{144}O_{17}P_2$ | CL(72:7) | Glycerophospholipid metabolism |
| 220 | CSU/CDC-192 | — | — | — |
| 221 | CSU/CDC-195 | $C_{17}H_{24}O_3$ | Benzylsuccinate | Phenylpropanoic acid metabolism |
| 222 | CSU/CDC-196 | — | — | — |
| 223 | CSU/CDC-197 | — | — | — |
| 224 | CSU/CDC-198 | — | — | — |
| 225 | CSU/CDC-199 | — | — | — |
| 226 | CSU/CDC-200 | — | — | — |
| 227 | CSU/CDC-201 | — | — | — |
| 228 | CSU/CDC-202 | $C_{42}H_{67}O_8P$ | PA(39:8) | Glycerophospholipid metabolism |
| 229 | CSU/CDC-207 | $C_{20}H_{41}NO_2$ | Stearoyl ethanolamide | N-acyl ethanolamine metabolism |
| 230 | CSU/CDC-208 | $C_{56}H_{99}NO_{14}$ | 3-O-acetyl-sphingosine-2,3,4,6-tetra-O-acetyl-GalCer (d18:1/h22:0) | Sphingolipid metabolism |
| 231 | CSU/CDC-209 | — | — | — |
| 232 | CSU/CDC-214 | $C_{14}H_{29}NO_2$ | Lauroyl ethanolamide | N-acyl ethanolamine metabolism |
| 233 | CSU/CDC-215 | — | — | — |
| 234 | CSU/CDC-216 | $C_{31}H_{46}O_2$ | — | — |
| 235 | CSU/CDC-217 | — | — | — |
| 236 | CSU/CDC-220 | — | — | — |
| 237 | CSU/CDC-221 | — | — | — |
| 238 | CSU/CDC-223 | — | — | — |
| 239 | CSU/CDC-225 | — | — | — |
| 240 | CSU/CDC-226 | — | — | — |
| 241 | CSU/CDC-228 | $C_{23}H_{40}O_6$ | — | — |
| 242 | CSU/CDC-230 | $C_{19}H_{36}O_2$ | Methyl oleate | Oleic acid ester |
| 243 | CSU/CDC-231 | — | — | — |
| 244 | CSU/CDC-232 | — | — | — |
| 245 | CSU/CDC-233 | — | — | — |
| 246 | CSU/CDC-234 | $C_7H_{12}N_2O_6$ | L-beta-aspartyl-L-serine | Peptide |
| 247 | CSU/CDC-236 | $C_{19}H_{36}O_3$ | 2-oxo-nonadecanoic acid | Fatty acid metabolism |
| 248 | CSU/CDC-239 | $C_{19}H_{38}O_3$ | 2-Hydroxy-nonadecanoic acid | Fatty acid metabolism |
| 249 | CSU/CDC-240 | $C_{30}H_{48}O_2$ | 4,4-Dimethyl-14a-formyl-5a-cholesta-8,24-dien-3b-ol | Sterol metabolism |
| 250 | CSU/CDC-241 | $C_{30}H_{48}O$ | Butyrospermone | Sterol metabolism |
| 251 | CSU/CDC-242 | $C_{22}H_{45}NO_2$ | Eicosanoyl ethanolamide | N-acyl ethanolamine metabolism |
| 252 | CSU/CDC-243 | $C_{22}H_{42}O_4$ | — | — |
| 253 | CSU/CDC-246 | $C_7H_5NS_2$ | — | — |
| 254 | CSU/CDC-249 | $C_{47}H_{80}O_2$ | Cholesterol ester (20:2) | Sterol metabolism |
| 255 | CSU/CDC-251 | $C_{26}H_{37}NO_6$ | — | — |
| 256 | CSU/CDC-255 | — | — | — |
| 257 | CSU/CDC-256 | — | — | — |
| 258 | CSU/CDC-257 | — | — | — |
| 259 | CSU/CDC-259 | — | — | — |
| 260 | CSU/CDC-260 | $C_{83}H_{148}O_{17}P_2$ | CL(74:7) | Glycerophospholipid metabolism |
| 261 | CSU/CDC-261 | — | — | — | wherein each molecular feature is identified by its mass to charge ratio; and (iv) inputting the abundance values from step (iii) into a classification model trained with samples of metabolite extracts derived from suitable controls, wherein if the molecular features of Table A or Table C are provided, the classification model is Least Absolute Shrinkage and Selection Operator (LASSO) and if the molecular features of Table D are provided, the classification model is Random Forest (RF), and wherein the classification model produces a disease score and the disease score distinguishes subjects with Lyme disease.

2. The method of claim 1, wherein the subject is diagnosed with Stage 1 Lyme disease.

\* \* \* \* \*